(12) United States Patent
Barry et al.

(10) Patent No.: US 11,155,829 B2
(45) Date of Patent: Oct. 26, 2021

(54) INSECTICIDAL PROTEINS FROM PLANTS AND METHODS FOR THEIR USE

(71) Applicant: PIONEER HI-BRED INTERNATIONAL, INC., Johnston, IA (US)

(72) Inventors: Jennifer Barry, Ames, IA (US); Catherine Clark, Altoona, IA (US); Ryan Gerber, Apex, NC (US); Amy Lum, Hayward, CA (US); John Mathis, Johnston, IA (US); Azalea Ong, Castro Valley, CA (US); Brooke Peterson-Burch, Ankeny, IA (US); Thomas C. Wolfe, Des Moines, IA (US); Weiping Xie, East Palo Alto, CA (US); Nasser Yalpani, Kelowna (CA); Xiaohong Zhong, San Leandro, CA (US)

(73) Assignee: PIONEER HI-BRED INTERNATIONAL, INC.

( * ) Notice: Subject to any disclaimer, the term of this patent is extended or adjusted under 35 U.S.C. 154(b) by 225 days.

(21) Appl. No.: 16/311,765

(22) PCT Filed: Jun. 27, 2017

(86) PCT No.: PCT/US2017/039376
§ 371 (c)(1),
(2) Date: Dec. 20, 2018

(87) PCT Pub. No.: WO2018/005411
PCT Pub. Date: Jan. 4, 2018

(65) Prior Publication Data
US 2019/0211352 A1      Jul. 11, 2019

Related U.S. Application Data

(60) Provisional application No. 62/357,501, filed on Jul. 1, 2016.

(51) Int. Cl.
| | | |
|---|---|---|
| *C12N 15/82* | (2006.01) |
| *A01N 37/46* | (2006.01) |
| *C07K 14/415* | (2006.01) |
| *A01N 63/50* | (2020.01) |

(52) U.S. Cl.
CPC ......... *C12N 15/8286* (2013.01); *A01N 37/46* (2013.01); *A01N 63/50* (2020.01); *C07K 14/415* (2013.01); *Y02A 40/146* (2018.01)

(58) Field of Classification Search
None
See application file for complete search history.

(56) References Cited

U.S. PATENT DOCUMENTS

| | | |
|---|---|---|
| 5,024,837 A | 6/1991 | Donovan et al. |
| 2007/0044179 A1 | 2/2007 | Stewart et al. |
| 2011/0277180 A1 | 11/2011 | Romano |
| 2015/0139976 A1* | 5/2015 | Singh .................. A01N 37/46 424/94.61 |
| 2016/0040184 A1 | 2/2016 | Cong et al. |

FOREIGN PATENT DOCUMENTS

| | | |
|---|---|---|
| WO | 2012/006271 A1 | 1/2012 |
| WO | 2016/060949 A1 | 4/2016 |

OTHER PUBLICATIONS

International Search Report for International Application PCT/US2017/039376, dated Sep. 22, 2017.
Written Opinion for International Application PCT/US2017/039376, dated Sep. 22, 2017.

* cited by examiner

Primary Examiner — Stephen Uyeno

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

Figure 3:
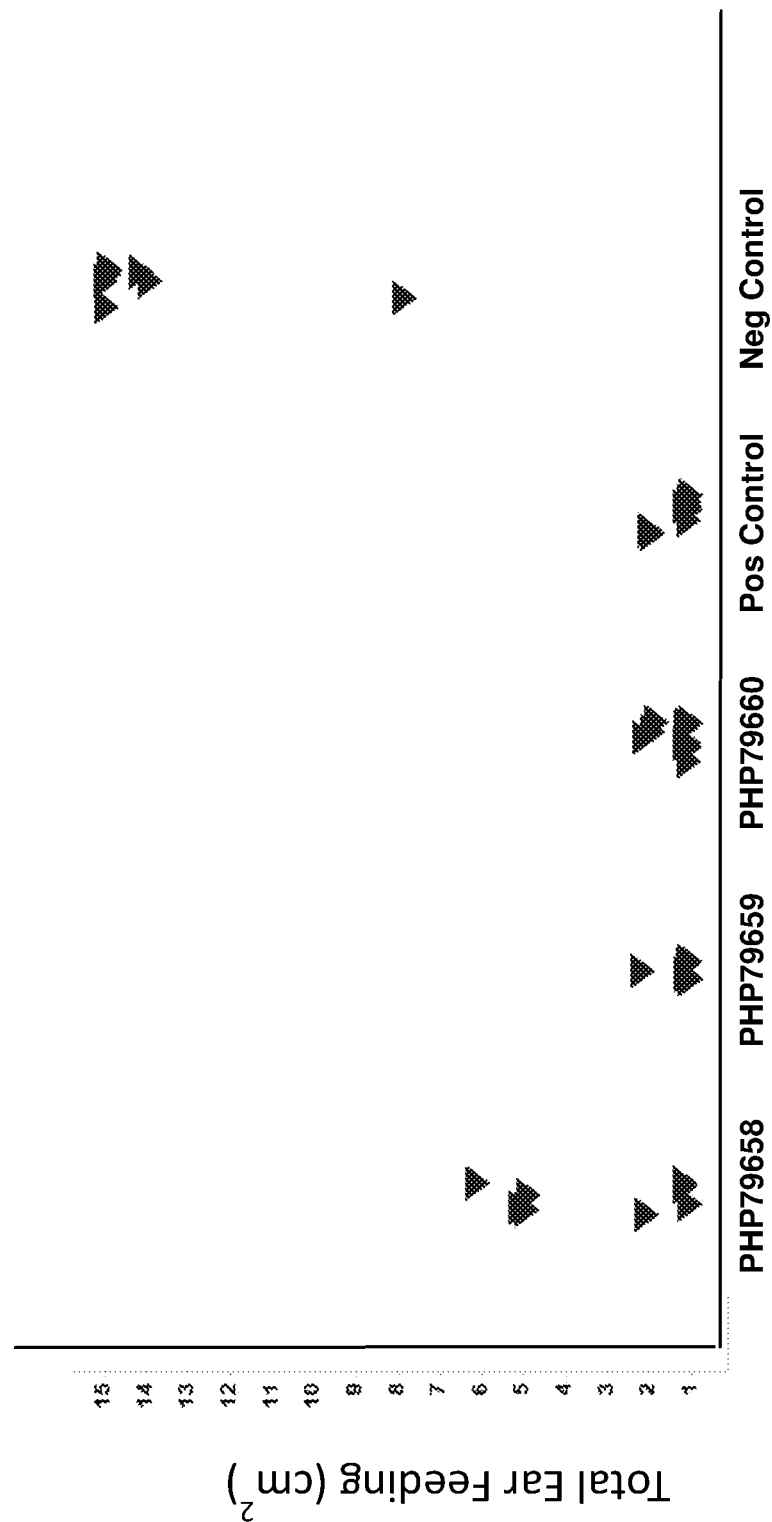

14 Claims, 5 Drawing Sheets
Specification includes a Sequence Listing.

Fig. 1A

|  |  | 1 | ▼ | • | 50 |
|---|---|---|---|---|---|
| IPD103Aa | (1) | ------------MADKAAAAAREAEEEVEITMDETEAVGTHLDFLGADVKL |
| IPD103Ab | (1) | ------------MADQAAAAREAEEEVEITMDETEAVGTHLDFLGADVKL |
| IPD103Ac | (1) | ------------MAEPAAAAREAEEEVEITMDETEAVGTHLDFLGADVKL |
| IPD103Ad | (1) | ------------MADQGAAAREAEEEVEITMDETEAVGTHLDFL-ADVKV |
| IPD103Ae | (1) | ------------MADQ-AAAREAEEEVEITMDETEAVGTHLDFL-ADVKV |
| IPD103Bd | (1) | ------------MADQVAAARGAEEEVEITMDETEAVGTHLDFL-ADVKV |
| IPD103Ba | (1) | MREREREREREMAEPAAAAAKKAEEEVEIFMDDTEAVGTHLDFL-AGLKV |
| IPD103Bb | (1) | ------------MAEPAAAAAKKAEEEVEIFMDDTEAVGTHLDFL-AGLKV |
| IPD103Ca | (1) | MREREREREREMAEPAAAAAKKAEEEVEIFMDDTEAVGTHLDFL-AGLKV |
| IPD103Be | (1) | ------------MADPATAAREAEEEVQETLMDETEAVGTHLDFV-AGLEV |
| IPD103Bf | (1) | ----MQREREREMADQAAAAAREAEEEVEVFMDETEAVGTHLDFL-AGLNV |
| IPD103Bk | (1) | ------------MADQAAAAAREAEEEVEVFMDETEAVGTHLDFL-AGLNV |
| IPD103Db | (1) | ------------------------------------------------- |
| IPD103Bi | (1) | ----------MADKVAAASRAQGAEEEVEDLMDETEAVGTHLDCMGGDVKV |
| IPD103Da | (1) | ----------MADEVAGHHGPACEEEEEEMLMDETEAVGVHAIDG---LPV |
| IPD103Bc | (1) | ----------MADKAPPPAREAEEEVEETMDETEAVGTHLDIIAHLSVQ |
| IPD103Bj | (1) | ----------MADKAPPPAREAEEEVEETMDETEAVGTHLDIIAHLSVQ |
| IPD103Bg | (1) | ---------MADKVAAAPPPAREAEEEVEETMDETEAVGTHLDIIATL--- |
| IPD103Bh | (1) | ---------MADKVAAAPPPAREAEEEVEETMDETEAVGTHLDIIATL--- |

|  |  | 51▼ | 100 |
|---|---|---|---|
| IPD103Aa | (40) | QPRNIITVEVDAAAVIQQIREIFQTMARHFNSTRVVRDEAIKGIRDHFRA |
| IPD103Ab | (39) | QPRNIITVEVDAAAVIQQIREIFQTMARHFNSTRVVRDEAIKGIRDHFRA |
| IPD103Ac | (39) | QPRNIITVEVDAAAVIQQIREIFQTMARHFNSTRVVRDEAIKGIRDHFRA |
| IPD103Ad | (38) | QPRNIITVEVDAAAVIQQIREIFQTMARHFNSTRVVRDEAIKGIRDHFRA |
| IPD103Ae | (37) | QPRNIITVEVDAAAVIQQIREIFQTMARHFNSTRVVRDEAIKGIRDHFRA |
| IPD103Bd | (38) | QPRSIITVEVDAAAVIQQIREIFQTMARHFNSTRVVRDEAIKGIRDHFRA |
| IPD103Ba | (50) | QPRKIITVEVDPAAVIQQIREIFQTMARHFNSTTVVRDEAIKGIRDHFRA |
| IPD103Bb | (39) | QPRKIITVEVDPAAVIQQIREIFQTLARHFNSTTVVRDEAIKGIRDHFRA |
| IPD103Ca | (50) | QPRKIITVEVDPAAVIQQIREIFQTLARHFNSTTVVRDEAIKGIRDHFRA |
| IPD103Be | (39) | QPRKVITVEVDAAAVIQQIREIFRTMASHFNSTRVVRDEAIKGIRDHFRA |
| IPD103Bf | (47) | QPRKVITVEVDAAAVIQQIREIFQTMARHFNSTRVVRDEAIKGIRDHFRA |
| IPD103Bk | (39) | QPRKVITVEVDAAAVIQQIREIFQTMARHFNSTRVVRDEAIKGIRDHFRA |
| IPD103Db | (1) | ---------MDAAAVIQQIREIFQSMADDFSSTKVVRDEAIKGIRDHFRA |
| IPD103Bi | (41) | QARGIITVEVDPAAVIQQIREIFQTLARHYNSTRVVRDAAIKAIRDHFRA |
| IPD103Da | (39) | QNRSIITVEVDAAAVIQQIREIFASMIKHYNSTRVVRDEAIKSIRDHFRL |
| IPD103Bc | (40) | -PRGIITVEVDPAAVIQQIREIFQTMARHFNSTRVVRDEAIKGIRDHFRA |
| IPD103Bj | (40) | -PRGIITVEVDPAAVIQQIREIFQTMARHFNSTRVVRDEAIKGIRDHFRA |
| IPD103Bg | (40) | -PRGIITVEVDSAAVIQQIREIFQTMARHFNSTRVVRDEAIKGIRDHFRA |
| IPD103Bh | (40) | -PRGIITVEVDGAAVIQQIREIFQTMARHFNSTRVVRDEAIKGIRDHFRA |

Fig. 1B

```
                 101                                                    150
IPD103Aa   (90)  AVPTRNVVVIHTQHVHT-LVGLEHTHLVLQTGIFKKVPVDIYVFKSGVFT
IPD103Ab   (89)  AVPTRNVVVIHTQHVHT-LVGLEHTHLVLQTGIFKKVPVDIYVFKSGVFT
IPD103Ac   (89)  AVPTRNVVVIHTQHVHT-LVGLEHTHLVLQTGIFKKVPVDIYVFKSGVFT
IPD103Ad   (88)  AVPTRNVVVIHTQHVQT-LVAVEHSIVLQTGIFKKVPVDIYVFKSGVFT
IPD103Ae   (87)  AVPTRNVVVIHTQHVQT-LVAVEHSIVLQTGIFKKVPVDIYVFKSGVFT
IPD103Bd   (88)  AVPTRNVVVVHTQHVHT-LVGLEHTNIVLQTGLFKKVPVDIYVFKSGVFT
IPD103Ba  (100)  AVPTRNVVVVHTQHIHT-LEGLEHTNLVLQTGLFRKVPVDIYVFKSGVFT
IPD103Bb   (89)  AVPTRNVVVVHTQHIHT-LEGLEHTNLVLQTGRFRKVPVDIYVFKSGVFT
IPD103Ca  (100)  AVPTRNVVVVHTQHIHT-LEGLEHTNLVLQTGRFRKVPVDIYVFKSGVFT
IPD103Be   (89)  AVPTRNVVVVHTQHIHT-LEGLEHTNLVLQTGLFKKVPVDIYVFKSGVFT
IPD103Bf   (97)  AVPTRNVVVVHTQHIHT-LVDVEHTNLVLQTGIFKKVPVDIYVFKSGVFT
IPD103Bk   (89)  AVPTRNVVVVHTQHIHT-LVDVEHTNLVLQTGIFKKVPVDIYVFKSGVFT
IPD103Db   (42)  AVPTRNVVVVHTPHIHTQLVDVEHTKLVLKTGIFEKVPVDIYVFKSGVFT
IPD103Bi   (91)  AVPTRNVVVIHTQHVHT-LADVEHSHLVLQTGIFKKVPVDIYVFKSGVFT
IPD103Da   (89)  AVPTRNVVVIHTQHVHT-LDAVESSHLVLRTGLFKKVPVDIFVFKSGVFT
IPD103Bc   (89)  AVPTRNVVVIHTQHVHT-LVGLEHTHLVLQTGIFRTVPVDIYVFKSGVFT
IPD103Bj   (89)  AVPTRNVVIHTQHVHT-LVGLEHTHLVLQTGIFRTVPVDIYVFKSGVLT
IPD103Bg   (89)  AIPTRNVVVIHTQHVHT-LVGLEHTHLVLQTGIFKKVPVDVYVFKSGVLT
IPD103Bh   (89)  AIPTRNVVVIHTQHVHT-LVGLEHTHLVLQTGIFKKVPVDVYVFKSGVLT 151                               184
IPD103Aa  (139)  NLGDGGFINWAWGGFVDQVVGKRIHFRLPPGALP
IPD103Ab  (138)  NLGDGGFINWAWGGFVDQVVGKRIHFRLPPGALP
IPD103Ac  (138)  NLGDGGFINWAWGGFVDQVVGKRIHFRLPPGALP
IPD103Ad  (137)  NLGDGGYINWAWGGFVDQVVGKRIHFRLPPGALP
IPD103Ae  (136)  NLGDGGYINWAWGGFVDQVVGKRIHFRLPPGALP
IPD103Bd  (137)  ILGDGGFINWAWGGFVDQVVGKRIHFRLPPGALP
IPD103Ba  (149)  ILGDGGFINWAWGGFVEQVVGKRIHFRLPPGALP
IPD103Bb  (138)  ILGDGGFINWAWGGFVEQVVGKRIHFRLPPGALP
IPD103Ca  (149)  ILGDGGFINWAWGGFVEQVVGKRIHFRLPPGALP
IPD103Be  (138)  ILGDGGFINWAWGGFVQEVAGKRIXFRLPPGALP
IPD103Bf  (146)  ILGDGGFINWAWGGFVDQVDGKRIHFRLPPGALP
IPD103Bk  (138)  ILGDGGFINWAWGGFVDQVDGKRIHFRLPPGALP
IPD103Db   (92)  ILGDGGYNNWAWGGFVDQVVGKRIHFRLPPGALP
IPD103Bi  (140)  NLGDGGFINWAWGGYVTEVVGKRIHFRLPPGALP
IPD103Da  (138)  NLGDGGFINWAWGGYGVNHTAKRVVFSRPPGALP
IPD103Bc  (138)  NLGDGGFINWAWGGFVTEVVGKRVHFRLPPGALP
IPD103Bj  (138)  NLGDGGFINWAWGGFVTEVVGKRVHFRLPPGALP
IPD103Bg  (138)  NLGDGGFINWAWGGFVTEVVGKRVHFRLPPGALP
IPD103Bh  (138)  NLGDGGFINWAWGGFVTEVVGKRVHFRLPPGALP
```

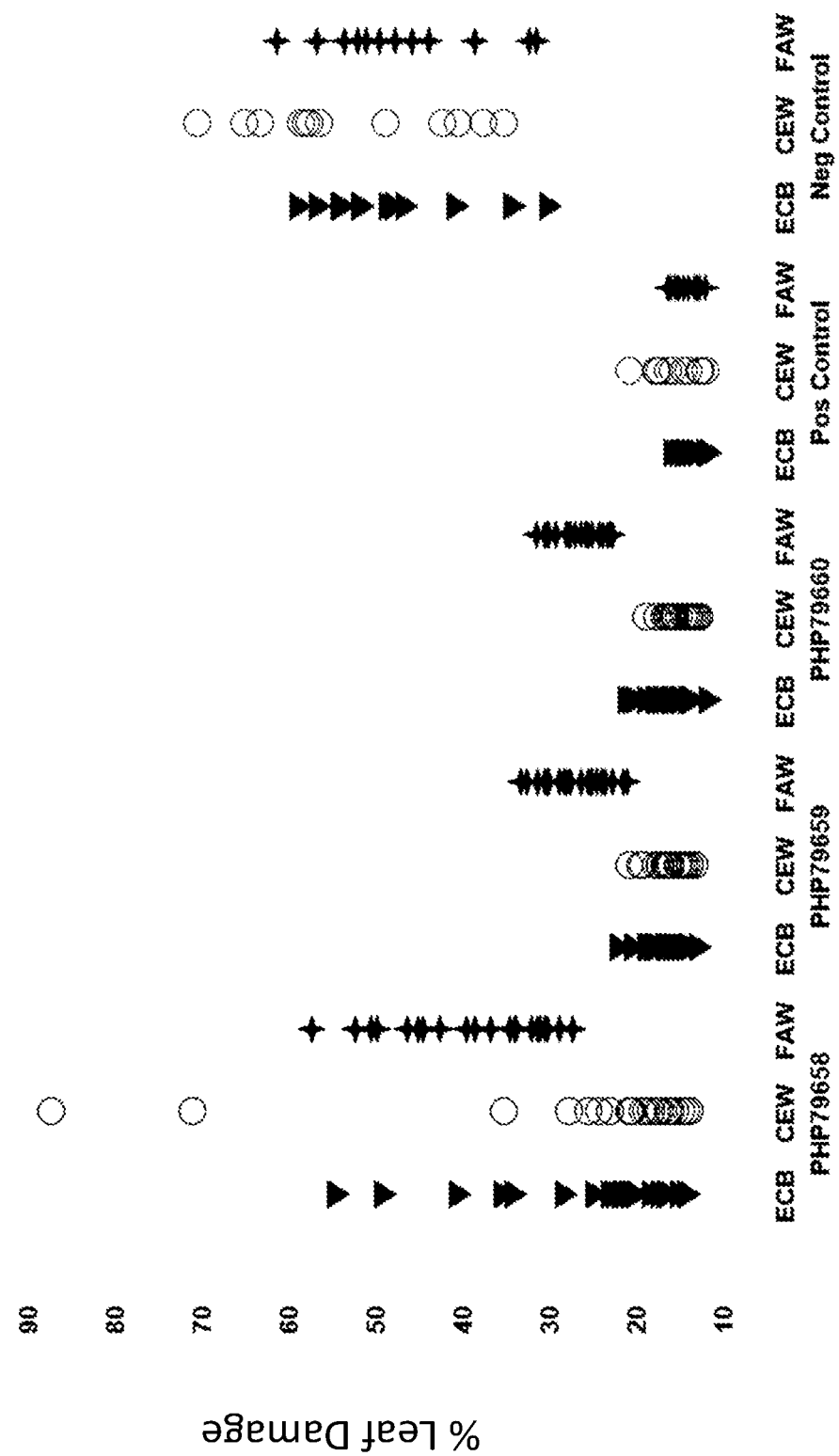

SEQUENCE LISTING

<160> NUMBER OF SEQ ID NOS: 508

<210> SEQ ID NO 1
<211> LENGTH: 516
<212> TYPE: DNA
<213> ORGANISM: Athyrium niponicum

<400> SEQUENCE: 1

```
atggcggaca aagcagcagc agcagctaga gaagctgaag agaggtggga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516
```

<210> SEQ ID NO 2
<211> LENGTH: 172
<212> TYPE: PRT
<213> ORGANISM: Athyrium niponicum

<400> SEQUENCE: 2

```
Met Ala Asp Lys Ala Ala Ala Ala Arg Glu Ala Glu Glu Val
 1               5                  10                  15

Glu Thr Thr Met Asp Glu Thr Glu Ala Val Gly Thr His Leu Asp Phe
                20                  25                  30

Leu Gly Ala Asp Val Lys Leu Gln Pro Arg Asn Ile Ile Thr Val Glu
            35                  40                  45

Val Asp Ala Ala Ala Val Ile Gln Gln Ile Arg Glu Ile Phe Gln Thr
        50                  55                  60

Met Ala Arg His Phe Asn Ser Thr Arg Val Val Arg Asp Glu Ala Ile
 65                 70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170
```

<210> SEQ ID NO 3
<211> LENGTH: 513
<212> TYPE: DNA
<213> ORGANISM: Athyrium niponicum

<400> SEQUENCE: 3

```
atggcggacc aagcagcagc agctagagaa gctgaagaag aggtggagac gacgatggac    60
```

```
gagactgagg cggtggggac gcacctggac ttcttgggcg cggacgtgaa gttgcaaccc    120
cgcaacatca tcaccgtgga ggtggacgcc gctgccgtaa tccaacagat cagagagatc    180
ttccagacaa tggcgcgtca cttcaactct acgagggtgg tgcgggatga agccatcaag    240
ggcattcgag accacttcag ggccgccgtc ccgactcgca acgtggtggt cattcacact    300
cagcacgttc acactggt  gggcttggag cacacccacc tcgtcttgca gaccggcatc    360
ttcaaaaagg tccccgtcga catctatgtc ttcaagtccg gcgtcttcac caaccttgga    420
gacggaggct tcatcaactg gcatggggt  ggcttcgtcg accaggtcgt cggcaagcgt    480
atccacttcc gcttgccccc cggggcgctc cct                                513
```

<210> SEQ ID NO 4
<211> LENGTH: 171
<212> TYPE: PRT
<213> ORGANISM: Athyrium niponicum
<400> SEQUENCE: 4

```
Met Ala Asp Gln Ala Ala Ala Ala Arg Glu Ala Glu Glu Val Glu
1               5                   10                  15

Thr Thr Met Asp Glu Thr Glu Ala Val Gly Thr His Leu Asp Phe Leu
            20                  25                  30

Gly Ala Asp Val Lys Leu Gln Pro Arg Asn Ile Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170
```

<210> SEQ ID NO 5
<211> LENGTH: 513
<212> TYPE: DNA
<213> ORGANISM: Platycerium wandae
<400> SEQUENCE: 5

```
atggccgaac cagcagcagc agctagagaa gctgaagaag aggtggagac gacgatggac     60
gagactgagg cggtggggac gcacctggac ttcttgggcg cggacgtgaa gttgcaaccc    120
cgcaacatca tcaccgtgga ggtggacgcg gctgccgtaa tccaacagat cagagagatc    180
ttccagacaa tggcgcgtca cttcaactct acgagggtgg tgcgggatga agccatcaag    240
ggcattcgag accacttcag ggccgccgtc ccgactcgca acgtggtggt cattcacact    300
cagcacgttc acactggt  gggcttggag cacacccacc tcgtcttgca gaccggcatc    360
ttcaaaaagg tccccgtcga catctatgtc ttcaagtccg gcgtcttcac caaccttgga    420
```

```
gacggaggct tcatcaactg ggcatggggt ggcttcgtcg accaggtcgt cggcaagcgt    480
atccacttcc gcttgccccc cggggcgctc cct                                 513
```

<210> SEQ ID NO 6
<211> LENGTH: 171
<212> TYPE: PRT
<213> ORGANISM: Platycerium wandae

<400> SEQUENCE: 6

```
Met Ala Glu Pro Ala Ala Ala Arg Glu Ala Glu Glu Val Glu
1               5                   10                  15

Thr Thr Met Asp Glu Thr Glu Ala Val Gly Thr His Leu Asp Phe Leu
            20                  25                  30

Gly Ala Asp Val Lys Leu Gln Pro Arg Asn Ile Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170
```

<210> SEQ ID NO 7
<211> LENGTH: 510
<212> TYPE: DNA
<213> ORGANISM: Pteris ensiformis

<400> SEQUENCE: 7

```
atggccgacc aaggagcagc agctagagaa gctgaggaag aggtggagac gacgatggac    60
gagacggagg cggtggggac gcacctggac tttttggcgg acgtgaaggt gcagccccgc   120
aacatcatca ccgtggaggt ggacgccgct gccgtaatcc aacagatcag agagatcttc   180
caaaccatgg cacgtcactt caactctacg agggtggtgc gggatgaagc cattaagggc   240
attcgagacc acttcagggc cgccgttccg actcgcaacg tggtggtcat tcacactcag   300
cacgttcaaa cactggtggc cgtggagcac agccacatcg tcttgcagac cggcatcttc   360
aagaaggtcc ccgtcgacat ctatgttttc aagtccggcg tcttcaccaa ccttggagac   420
ggaggctaca tcaactgggc atggggtggc ttcgtagacc aggtcgtcgg caagcgtatc   480
cacttccgct tgccccccgg ggcgctccct                                    510
```

<210> SEQ ID NO 8
<211> LENGTH: 170
<212> TYPE: PRT
<213> ORGANISM: Pteris ensiformis

<400> SEQUENCE: 8

```
Met Ala Asp Gln Gly Ala Ala Arg Glu Ala Glu Glu Val Glu
1               5                   10                  15

Thr Thr Met Asp Glu Thr Glu Ala Val Gly Thr His Leu Asp Phe Leu
            20                  25                  30

Ala Asp Val Lys Val Gln Pro Arg Asn Ile Ile Thr Val Glu Val Asp
        35                  40                  45

Ala Ala Ala Val Ile Gln Gln Ile Arg Glu Ile Phe Gln Thr Met Ala
    50                  55                  60

Arg His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val
                85                  90                  95

Ile His Thr Gln His Val Gln Thr Leu Val Ala Val Glu His Ser His
                100                 105                 110

Ile Val Leu Gln Thr Gly Ile Phe Lys Lys Val Pro Val Asp Ile Tyr
            115                 120                 125

Val Phe Lys Ser Gly Val Phe Thr Asn Leu Gly Asp Gly Gly Tyr Ile
        130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 9
<211> LENGTH: 507
<212> TYPE: DNA
<213> ORGANISM: Pteris ensiformis

<400> SEQUENCE: 9
atggccgacc aagctgcagc tagagaagct gaggaagagg tggagacgac gatggacgag      60
acggaggcgg tggggacgca cctggacttt ttggcggacg tgaaggtgca gccccgcaac     120
atcatcaccg tggaggtgga cgccgctgcc gtaatccaac agatcagaga gatcttccaa     180
accatggcac gtcacttcaa ctctacgagg gtggtgcggg atgaagccat taagggcatt     240
cgagaccact tcagggccgc cgttccgact cgcaacgtgg tggtcattca cactcagcac     300
gttcaaacac tggtggccgt ggagcacagc cacatcgtct gcagaccgg catcttcaag      360 aaggtccccg tcgacatcta tgttttcaag tccggcgtct tcaccaacct ggagacgga      420 ggctacatca actgggcatg gggtggcttc gtagaccagg tcgtcggcaa gcgtatccac     480
ttccgcttgc cccccggggc gctccct                                         507

<210> SEQ ID NO 10
<211> LENGTH: 169
<212> TYPE: PRT
<213> ORGANISM: Pteris ensiformis

<400> SEQUENCE: 10

Met Ala Asp Gln Ala Ala Ala Arg Glu Ala Glu Glu Val Glu Thr
1               5                   10                  15

Thr Met Asp Glu Thr Glu Ala Val Gly Thr His Leu Asp Phe Leu Ala
            20                  25                  30

Asp Val Lys Val Gln Pro Arg Asn Ile Ile Thr Val Glu Val Asp Ala
        35                  40                  45

Ala Ala Val Ile Gln Gln Ile Arg Glu Ile Phe Gln Thr Met Ala Arg
    50                  55                  60
```

His Phe Asn Ser Thr Arg Val Val Arg Asp Glu Ala Ile Lys Gly Ile
65                  70                  75                  80

Arg Asp His Phe Arg Ala Ala Val Pro Thr Arg Asn Val Val Ile
            85                  90                  95

His Thr Gln His Val Gln Thr Leu Val Ala Val Glu His Ser His Ile
            100                 105                 110

Val Leu Gln Thr Gly Ile Phe Lys Lys Val Pro Val Asp Ile Tyr Val
            115                 120                 125

Phe Lys Ser Gly Val Phe Thr Asn Leu Gly Asp Gly Gly Tyr Ile Asn
        130                 135                 140

Trp Ala Trp Gly Gly Phe Val Asp Gln Val Val Gly Lys Arg Ile His
145                 150                 155                 160

Phe Arg Leu Pro Pro Gly Ala Leu Pro
                165

<210> SEQ ID NO 11
<211> LENGTH: 546
<212> TYPE: DNA
<213> ORGANISM: Platycerium wandae

<400> SEQUENCE: 11
atgagagagc gagagcgaga gcgagagaga gagatggccg aaccagcagc agcagcagct      60
aaaaaagctg aagaagaggt ggagatattt atggacgaca ctgaggcggt ggggacgcat     120
ctggacttct tggcgggctt gaaggtgcag ccccgcaaga tcatcaccgt ggaggtggac     180
cccgctgccg taatccagca gatcagggag atcttccaaa ccatggcacg tcacttcaac     240
tcgacgacgg tggtgcggga tgaagccatc aagggcattc gagaccactt cagggccgcc     300
gttccgactc gcaacgtggt ggtcgttcac actcagcaca ttcacaccct ggagggcttg     360
gagcacacca accttgtctt gcagaccggc ctcttcagaa aggtccccgt cgacatctac     420
gtcttcaagt ctggcgtctt caccctcctt ggagatggag cttcatcaa ctgggcgtgg     480 ggtggcttcg tagagcaggt cgtcggcaag cgtatccact ccgcttacc ccctggggcg     540 ctccct                                                                546

<210> SEQ ID NO 12
<211> LENGTH: 182
<212> TYPE: PRT
<213> ORGANISM: Platycerium wandae

<400> SEQUENCE: 12

Met Arg Glu Arg Glu Arg Glu Arg Glu Arg Glu Met Ala Glu Pro Ala
1               5                   10                  15

Ala Ala Ala Lys Lys Ala Glu Glu Glu Val Glu Ile Phe Met Asp
            20                  25                  30

Asp Thr Glu Ala Val Gly Thr His Leu Asp Phe Leu Ala Gly Leu Lys
        35                  40                  45

Val Gln Pro Arg Lys Ile Ile Thr Val Glu Val Asp Pro Ala Ala Val
    50                  55                  60

Ile Gln Gln Ile Arg Glu Ile Phe Gln Thr Met Ala Arg His Phe Asn
65                  70                  75                  80

Ser Thr Thr Val Val Arg Asp Glu Ala Ile Lys Gly Ile Arg Asp His
                85                  90                  95

Phe Arg Ala Ala Val Pro Thr Arg Asn Val Val Val His Thr Gln
            100                 105                 110

His Ile His Thr Leu Glu Gly Leu Glu His Thr Asn Leu Val Leu Gln

```
                    115                 120                 125
Thr Gly Leu Phe Arg Lys Val Pro Val Asp Ile Tyr Val Phe Lys Ser
        130                 135                 140

Gly Val Phe Thr Leu Leu Gly Asp Gly Gly Phe Ile Asn Trp Ala Trp
145                 150                 155                 160

Gly Gly Phe Val Glu Gln Val Val Gly Lys Arg Ile His Phe Arg Leu
                165                 170                 175

Pro Pro Gly Ala Leu Pro
            180

<210> SEQ ID NO 13
<211> LENGTH: 513
<212> TYPE: DNA
<213> ORGANISM: Platycerium wandae

<400> SEQUENCE: 13
atggccgaac cagcagcagc agcagctaaa aaagctgaag aagaggtgga gatatttatg      60
gacgacactg aggcggtggg gacgcatctg gacttcttgg cgggcttgaa ggtgcagccc     120
cgcaagatca tcaccgtgga ggtggacccc gctgccgtaa tccagcagat aagagagatc     180
tttcaaaccc tggcacgtca cttcaactcg acgacggtgg tgcgggatga agccatcaag     240
ggcattcgag accacttcag ggccgccgtt ccgactcgca acgtggtggt cgttcacact     300
cagcacattc acaccctgga gggcttggag cacaccaacc ttgtcttgca gaccggccgc     360
ttcagaaagg tccccgtcga catctacgtc ttcaagtctg gcgtcttcac cctccttgga     420
gatggaggct tcatcaactg gcgtgggggt ggcttcgtag agcaggtcgt cggcaagcgt     480
atccacttcc gcttaccccc tggggcgctc cct                                  513

<210> SEQ ID NO 14
<211> LENGTH: 171
<212> TYPE: PRT
<213> ORGANISM: Platycerium wandae

<400> SEQUENCE: 14

Met Ala Glu Pro Ala Ala Ala Ala Lys Lys Ala Glu Glu Glu Val
1               5                   10                  15

Glu Ile Phe Met Asp Asp Thr Glu Ala Val Gly Thr His Leu Asp Phe
                20                  25                  30

Leu Ala Gly Leu Lys Val Gln Pro Arg Lys Ile Ile Thr Val Glu Val
            35                  40                  45

Asp Pro Ala Ala Val Ile Gln Gln Ile Arg Glu Ile Phe Gln Thr Leu
        50                  55                  60

Ala Arg His Phe Asn Ser Thr Thr Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
                100                 105                 110

Asn Leu Val Leu Gln Thr Gly Arg Phe Arg Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Glu Gln Val Val Gly Lys Arg
145                 150                 155                 160

Ile His Phe Arg Leu Pro Pro Gly Ala Leu Pro
                165                 170
```

<210> SEQ ID NO 15
<211> LENGTH: 513
<212> TYPE: DNA
<213> ORGANISM: Athyrium filix-femina

<400> SEQUENCE: 15

```
atggccgaca aagcgcctcc tcctgctaga gaagcagaag aagaggtgga ggagacgatg      60
gacgagactg aggcagtggg gacgcacctg gacttgatag cgcacctgag tgtgcaaccc     120
cgcggcatca tcaccgtgga ggtggacccc gccgctgtaa tccaacagat cagagagatc     180
ttccaaacca tggcacgtca tttcaactct acgagggtgg tacgggatga agccatcaag     240
ggcattcgag accacttcag ggccgccgtc ccgactcgca acgtggtggt cattcacact     300
caacacgttc acacactggt gggcttggag cacacccacc tcgtcttgca gaccggcatc     360
tttagaacgg tccccgtcga catctacgtc ttcaagtccg gcgtgttcac caacctcgga     420
gacggaggct tcatcaactg gcatgggggt ggcttcgtga ccgaggtcgt tgggaagcgt     480
gtccacttcc gcttgccccc cggggcactc cct                                  513
```

<210> SEQ ID NO 16
<211> LENGTH: 171
<212> TYPE: PRT
<213> ORGANISM: Athyrium filix-femina

<400> SEQUENCE: 16

```
Met Ala Asp Lys Ala Pro Pro Ala Arg Glu Ala Glu Glu Glu Val
1               5                   10                  15

Glu Glu Thr Met Asp Glu Thr Glu Ala Val Gly Thr His Leu Asp Leu
            20                  25                  30

Ile Ala His Leu Ser Val Gln Pro Arg Gly Ile Ile Thr Val Glu Val
        35                  40                  45

Asp Pro Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Arg Thr Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Thr Glu Val Val Gly Lys Arg
145                 150                 155                 160

Val His Phe Arg Leu Pro Pro Gly Ala Leu Pro
                165                 170
```

<210> SEQ ID NO 17
<211> LENGTH: 510
<212> TYPE: DNA
<213> ORGANISM: Colysis wrightii

<400> SEQUENCE: 17

```
atggccgacc aagtagcagc agcgagaggg gctgaagaag aggtggagac gacgatggac      60
```

-continued

| | |
|---|---|
| gagactgagg ctgtggggac gcacctggac ttcttggcgg acgtgaaggt gcaaccccgg | 120 |
| agcatcatca ccgtggaggt ggacgccgct gctgtaatcc aacagatcag agagatcttc | 180 |
| caaaccatgg cacgtcactt caactctacg agggtggtgc gggacgaagc catcaagggg | 240 |
| attcgagacc acttccgggc cgccgtcccg actcgcaacg tggtggtcgt tcacactcag | 300 |
| cacgttcaca cactggtggg cctggagcac accaacatcg tcttgcagac cggcctcttc | 360 |
| aaaaaggtcc ccgtcgacat ctatgtcttc aagtccggcg tcttcaccct ccttggagac | 420 |
| ggaggcttca tcaactgggc atggggtggc ttcgtagacc aggtcgtcgg caagcgtatc | 480 |
| cacttccgct tgcccccccgg ggcgctccct | 510 |

<210> SEQ ID NO 18
<211> LENGTH: 170
<212> TYPE: PRT
<213> ORGANISM: Colysis wrightii

<400> SEQUENCE: 18

Met Ala Asp Gln Val Ala Ala Arg Gly Ala Glu Glu Val Glu
1               5                   10                  15

Thr Thr Met Asp Glu Thr Glu Ala Val Gly Thr His Leu Asp Phe Leu
            20                  25                  30

Ala Asp Val Lys Val Gln Pro Arg Ser Ile Ile Thr Val Glu Val Asp
        35                  40                  45

Ala Ala Val Ile Gln Gln Ile Arg Glu Ile Phe Gln Thr Met Ala
    50                  55                  60

Arg His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val Val
                85                  90                  95

Val His Thr Gln His Val His Thr Leu Val Gly Leu Glu His Thr Asn
            100                 105                 110

Ile Val Leu Gln Thr Gly Leu Phe Lys Lys Val Pro Val Asp Ile Tyr
        115                 120                 125

Val Phe Lys Ser Gly Val Phe Thr Leu Leu Gly Asp Gly Gly Phe Ile
    130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 19
<211> LENGTH: 513
<212> TYPE: DNA
<213> ORGANISM: unknown
<220> FEATURE:
<223> OTHER INFORMATION: IPD103 variant
<220> FEATURE:
<221> NAME/KEY: misc_feature
<222> LOCATION: (484)..(484)
<223> OTHER INFORMATION: n is a, c, g, or t

<400> SEQUENCE: 19

| | |
|---|---|
| atggccgacc cagcaacagc agctagagaa gctgaagaag aggtgcagga gactttgatg | 60 |
| gacgagactg aggcggtggg gacgcacctg gacttcgtgg cgggcttgga ggtgcaaccc | 120 |
| cgcaaggtca tcaccgtgga ggtggacgcc gctgccgtaa tccagcagat cagagagatc | 180 |
| ttccgaacca tggcaagtca cttcaactcg acgagggtgg tgcgggatga agccatcaag | 240 |

```
ggcattcgag accacttcag ggccgccgtc ccgactcgca acgtggtggt cgttcacacc    300
cagcacattc acacactgga gggcttggag cacaccaacc tcgtcttgca gaccggcctc    360
ttcaaaaagg tccccgtcga catctacgtc ttcaagtccg gcgtcttcac cctccttgga    420
gacggaggct tcatcaactg gcatggggt ggcttcgtac aggaggtcgc cggcaagcgt     480
atcnacttcc gcttgccccc cggggcgctc cct                                 513
```

```
<210> SEQ ID NO 20
<211> LENGTH: 171
<212> TYPE: PRT
<213> ORGANISM: unknown
<220> FEATURE:
<223> OTHER INFORMATION: IPD103 variant
<220> FEATURE:
<221> NAME/KEY: misc_feature
<222> LOCATION: (162)..(162)
<223> OTHER INFORMATION: Xaa can be any naturally occurring amino acid

<400> SEQUENCE: 20

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile Xaa Phe Arg Leu Pro Pro Gly Ala Leu Pro
                165                 170
```

```
<210> SEQ ID NO 21
<211> LENGTH: 537
<212> TYPE: DNA
<213> ORGANISM: Nephrolepsis cordifolia

<400> SEQUENCE: 21
atgcagagag agagagagag agagatggcc gaccaagctg cagcagcagc tagagaagct    60
gaagaagagg tggaggtttt tatggacgag actgaggcgg tggggacgca cctggacttc   120
ttggcgggct tgaacgttca accccgcaag gtcatcaccg tggaggtgga cgccgctgcc   180
gtaatccaac agatcagaga gatcttccaa accatggcac gtcacttcaa ctcgacgagg   240
gtggtgcggg atgaagccat caagggcatt cgcgaccact tcagggccgc cgtcccgact   300
cgcaacgtgg tggtcgttca cactcagcac attcacactc tggtggacgt ggagcacacc   360
aacctcgtct tgcagaccgg catcttcaaa aaggtccccg tcgacatcta tgtcttcaag   420
```

```
tccggcgtct tcaccctcct tggagacggc ggcttcatca actgggcatg gggtggcttc      480
gtagaccagg ttgacggcaa gcgtatccac ttccgcttgc ccccggggc gctccct          537
```

<210> SEQ ID NO 22
<211> LENGTH: 179
<212> TYPE: PRT
<213> ORGANISM: Nephrolepsis cordifolia

<400> SEQUENCE: 22

```
Met Gln Arg Glu Arg Glu Arg Glu Met Ala Asp Gln Ala Ala Ala Ala
1               5                   10                  15

Ala Arg Glu Ala Glu Glu Val Gly Val Phe Met Asp Glu Thr Glu
            20                  25                  30

Ala Val Gly Thr His Leu Asp Phe Leu Ala Gly Leu Asn Val Gln Pro
        35                  40                  45

Arg Lys Val Ile Thr Val Glu Val Asp Ala Ala Ala Val Ile Gln Gln
    50                  55                  60

Ile Arg Glu Ile Phe Gln Thr Met Ala Arg His Phe Asn Ser Thr Arg
65                  70                  75                  80

Val Val Arg Asp Glu Ala Ile Lys Gly Ile Arg Asp His Phe Arg Ala
                85                  90                  95

Ala Val Pro Thr Arg Asn Val Val Val His Thr Gln His Ile His
            100                 105                 110

Thr Leu Val Asp Val Glu His Thr Asn Leu Val Leu Gln Thr Gly Ile
        115                 120                 125

Phe Lys Lys Val Pro Val Asp Ile Tyr Val Phe Lys Ser Gly Val Phe
    130                 135                 140

Thr Leu Leu Gly Asp Gly Gly Phe Ile Asn Trp Ala Trp Gly Gly Phe
145                 150                 155                 160

Val Asp Gln Val Asp Gly Lys Arg Ile His Phe Arg Leu Pro Pro Gly
                165                 170                 175

Ala Leu Pro
```

<210> SEQ ID NO 23
<211> LENGTH: 513
<212> TYPE: DNA
<213> ORGANISM: Polystichium tsus-simense

<400> SEQUENCE: 23

```
atggccgaca agtagcagc agcgcctcct cctgctagag aagcagaaga agaggtggag       60
gagacgatgg acgagactga ggcggtgggg acgcacctgg acttgatagc gaccctaccg     120
cgtggcatca tcaccgtgga ggtggactcc gccgccgtaa tccaacagat cagagagatc     180
ttccaaacca tggcacgtca tttcaactct acgagggtgg taaggatgag agccatcaag     240
ggcattcgag accacttcag ggccgccatc ccgactcgca acgtggtggt cattcacact     300
caacacgttc acacactggt gggcttggag cacacccacc tcgtcttgca gaccggcatc     360
tttaaaaagg tccccgtcga cgtctacgtc ttcaagtccg gcgtgctcac caacctcgga     420
gacggaggct tcatcaactg gcatgggggt ggcttcgtga ccgaggtcgt tgggaagcgt     480
gtccacttcc gcttgccccc cggggcgctc cct                                  513
```

<210> SEQ ID NO 24
<211> LENGTH: 171
<212> TYPE: PRT
<213> ORGANISM: Polystichium tsus-simense

<400> SEQUENCE: 24

Met Ala Asp Lys Val Ala Ala Pro Pro Ala Arg Glu Ala Glu
1               5                   10                  15

Glu Glu Val Glu Glu Thr Met Asp Glu Thr Glu Ala Val Gly Thr His
            20                  25                  30

Leu Asp Leu Ile Ala Thr Leu Pro Arg Gly Ile Ile Thr Val Glu Val
        35                  40                  45

Asp Ser Ala Ala Val Ile Gln Gln Ile Arg Glu Ile Phe Gln Thr Met
50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Ile Pro Thr Arg Asn Val Val
                85                  90                  95

Val Ile His Thr Gln His Val Thr Leu Val Gly Leu Glu His Thr
            100                 105                 110

His Leu Val Leu Gln Thr Gly Ile Phe Lys Lys Val Pro Val Asp Val
        115                 120                 125

Tyr Val Phe Lys Ser Gly Val Leu Thr Asn Leu Gly Asp Gly Gly Phe
130                 135                 140

Ile Asn Trp Ala Trp Gly Gly Phe Val Thr Glu Val Val Gly Lys Arg
145                 150                 155                 160

Val His Phe Arg Leu Pro Pro Gly Ala Leu Pro
                165                 170

<210> SEQ ID NO 25
<211> LENGTH: 513
<212> TYPE: DNA
<213> ORGANISM: Polystichium tsus-simense

<400> SEQUENCE: 25
atggccgaca aagtagcagc agcgcctcct cctgctagag aagcagaaga agaggtggag    60
gagacgatgg acgagactga ggcggtgggg acgcacctgg acttgatagc aaccctaccg   120
cgtggcatca tcaccgtgga ggtggacggc gccgccgtaa tccaacagat cagagagatc   180
ttccaaacca tggcacgtca tttcaactct acgagggtgg taagggatga agccatcaag   240
ggcattcgag accacttcag ggccgccatc ccgactcgca acgtggtggt cattcacact   300
caaacgttc acacactggt gggcttggag cacacccacc tcgtcttgca gaccggcatc   360
tttaaaaagg tccccgtcga cgtctacgtc ttcaagtccg gcgtgctcac caacctcgga   420
gacggaggct tcatcaactg gcatggggt ggcttcgtga ccgaggtcgt tgggaagcgt   480
gtccacttcc gcttgccccc cggggcgctc cct                               513

<210> SEQ ID NO 26
<211> LENGTH: 171
<212> TYPE: PRT
<213> ORGANISM: Polystichium tsus-simense

<400> SEQUENCE: 26

Met Ala Asp Lys Val Ala Ala Pro Pro Ala Arg Glu Ala Glu
1               5                   10                  15

Glu Glu Val Glu Glu Thr Met Asp Glu Thr Glu Ala Val Gly Thr His
            20                  25                  30

Leu Asp Leu Ile Ala Thr Leu Pro Arg Gly Ile Ile Thr Val Glu Val
        35                  40                  45

Asp Gly Ala Ala Val Ile Gln Gln Ile Arg Glu Ile Phe Gln Thr Met

```
                    50                  55                  60
Ala Arg His Phe Asn Ser Thr Arg Val Val Arg Asp Glu Ala Ile Lys
 65                  70                  75                  80

Gly Ile Arg Asp His Phe Arg Ala Ala Ile Pro Thr Arg Asn Val Val
                 85                  90                  95

Val Ile His Thr Gln His Val His Thr Leu Val Gly Leu Glu His Thr
                100                 105                 110

His Leu Val Leu Gln Thr Gly Ile Phe Lys Lys Val Pro Val Asp Val
            115                 120                 125

Tyr Val Phe Lys Ser Gly Val Leu Thr Asn Leu Gly Asp Gly Gly Phe
        130                 135                 140

Ile Asn Trp Ala Trp Gly Gly Phe Val Thr Glu Val Val Gly Lys Arg
145                 150                 155                 160

Val His Phe Arg Leu Pro Pro Gly Ala Leu Pro
                165                 170

<210> SEQ ID NO 27
<211> LENGTH: 519
<212> TYPE: DNA
<213> ORGANISM: Thelypteris palustris

<400> SEQUENCE: 27
atggccgaca aagtagcagc agcttctcgg gctcaaggag cagaagaggt ggaggatctg      60
atggacgaga cagaggcggt ggggacgcac ctggactgca tgggcggcga cgtgaaggtg     120
caagcacgcg gcatcatcac cgtggaggtg accccgccg ccgtaatcca acagatcaga     180
gagatcttcc aaaccctggc acgtcactac aactctacga gggtggtacg ggatgcagcc     240
atcaaggcca ttcgagacca cttcagggcc gccgtcccga ctcgcaacgt ggtggtcatc     300
cacactcaac acgttcacac actggcggac gtagagcaca gccacctcgt cttgcagacc     360
ggcatcttca gaaggqtccc cgtcgacatc tacgtcttca gtccggcgt gttcaccaac     420 ctcggcgacg gaggcttcat caactgggca tggggtggct acgtgacaga ggtcgttggg     480
aagcgtatcc acttccgctt gccccgggg gcactccct                            519

<210> SEQ ID NO 28
<211> LENGTH: 173
<212> TYPE: PRT
<213> ORGANISM: Thelypteris palustris

<400> SEQUENCE: 28

Met Ala Asp Lys Val Ala Ala Ala Ser Arg Ala Gln Gly Ala Glu Glu
 1               5                  10                  15

Val Glu Asp Leu Met Asp Glu Thr Glu Ala Val Gly Thr His Leu Asp
                20                  25                  30

Cys Met Gly Gly Asp Val Lys Val Gln Ala Arg Gly Ile Ile Thr Val
            35                  40                  45

Glu Val Asp Pro Ala Ala Val Ile Gln Gln Ile Arg Glu Ile Phe Gln
        50                  55                  60

Thr Leu Ala Arg His Tyr Asn Ser Thr Arg Val Val Arg Asp Ala Ala
 65                  70                  75                  80

Ile Lys Ala Ile Arg Asp His Phe Arg Ala Ala Val Pro Thr Arg Asn
                85                  90                  95

Val Val Val Ile His Thr Gln His Val His Thr Leu Ala Asp Val Glu
                100                 105                 110

His Ser His Leu Val Leu Gln Thr Gly Ile Phe Lys Lys Val Pro Val
```

|  | | 115 | | | 120 | | | 125 | | | |
|---|---|---|---|---|---|---|---|---|---|---|---|

Asp Ile Tyr Val Phe Lys Ser Gly Val Phe Thr Asn Leu Gly Asp Gly
       130              135             140

Gly Phe Ile Asn Trp Ala Trp Gly Gly Tyr Val Thr Glu Val Val Gly
145                 150               155             160

Lys Arg Ile His Phe Arg Leu Pro Pro Gly Ala Leu Pro
       165              170

<210> SEQ ID NO 29
<211> LENGTH: 513
<212> TYPE: DNA
<213> ORGANISM: Athyrium filix-femina

<400> SEQUENCE: 29

```
atggccgaca aagcgcctcc tcctgctaga gaagcagaag aagaggtgga ggagacgatg      60
gacgagactg aggcagtggg gacgcacctg gacttgatag cgcacctgag tgtgcaaccc     120
cgcggcatca tcaccgtgga ggtggacccc gccgctgtaa tccaacagat cagagagatc     180
ttccaaacca tggcacgtca tttcaactct acgagggtgg tacgggatga agccatcaag     240
ggcattcgag accacttcag ggccgccgtc ccgactcgca acgtggtggt cattcacact     300
caacacgttc acacactggt gggcttggag cacacccacc tcgtcttgca gaccggcatc     360
tttagaacgg tccccgtcga catctacgtc ttcaagtccg gcgtgctcac caacctcgga     420
gacggaggct tcatcaactg gcatggggt ggcttcgtga ccgaggtcgt tgggaagcgt     480
gtccacttcc gcttgccccc cggggcactc cct                                 513
```

<210> SEQ ID NO 30
<211> LENGTH: 171
<212> TYPE: PRT
<213> ORGANISM: Athyrium filix-femina

<400> SEQUENCE: 30

Met Ala Asp Lys Ala Pro Pro Ala Arg Glu Ala Glu Glu Glu Val
1             5                 10               15

Glu Glu Thr Met Asp Glu Thr Glu Ala Val Gly Thr His Leu Asp Leu
       20              25              30

Ile Ala His Leu Ser Val Gln Pro Arg Gly Ile Ile Thr Val Glu Val
        35              40              45

Asp Pro Ala Ala Val Ile Gln Gln Ile Arg Glu Ile Phe Gln Thr Met
    50              55              60

Ala Arg His Phe Asn Ser Thr Arg Val Val Arg Asp Glu Ala Ile Lys
65              70              75             80

Gly Ile Arg Asp His Phe Arg Ala Ala Val Pro Thr Arg Asn Val Val
         85             90              95

Val Ile His Thr Gln His Val His Thr Leu Val Gly Leu Glu His Thr
       100            105            110

His Leu Val Leu Gln Thr Gly Ile Phe Arg Thr Val Pro Val Asp Ile
       115            120            125

Tyr Val Phe Lys Ser Gly Val Leu Thr Asn Leu Gly Asp Gly Gly Phe
       130            135            140

Ile Asn Trp Ala Trp Gly Gly Phe Val Thr Glu Val Val Gly Lys Arg
145               150            155            160

Val His Phe Arg Leu Pro Pro Gly Ala Leu Pro
       165            170

<210> SEQ ID NO 31
<211> LENGTH: 513
<212> TYPE: DNA
<213> ORGANISM: Nephrolepis cordifolia

<400> SEQUENCE: 31

```
atggccgacc aagctgcagc agcagctaga gaagctgaag aagaggtgga ggttttatg      60 gacgagactg aggcggtggg gacgcacctg gacttcttgg cgggcttgaa cgttcaaccc     120
cgcaaggtca tcaccgtgga ggtggacgcc gctgccgtaa tccaacagat cagagagatc     180
ttccaaacca tggcacgtca cttcaactcg acgagggtgg tgcgggatga agccatcaag     240
ggcattcgcg accacttcag gccgccgtc ccgactcgca acgtggtggt cgttcacact      300
cagcacattc acactctggt ggacgtggag cacaccaacc tcgtcttgca gaccggcatc     360
ttcaaaaagg tccccgtcga catctatgtc ttcaagtccg gcgtcttcac cctccttgga    420
gacggcggct tcatcaactg gcatggggt ggcttcgtag accaggttga cggcaagcgt      480
atccacttcc gcttgccccc cggggcgctc cct                                  513
```

<210> SEQ ID NO 32
<211> LENGTH: 171
<212> TYPE: PRT
<213> ORGANISM: Nephrolepis cordifolia

<400> SEQUENCE: 32

```
Met Ala Asp Gln Ala Ala Ala Ala Arg Glu Ala Glu Glu Val
1               5                   10                  15

Glu Val Phe Met Asp Glu Thr Glu Ala Val Gly Thr His Leu Asp Phe
        20                  25                  30

Leu Ala Gly Leu Asn Val Gln Pro Arg Lys Val Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Val Asp Val Glu His Thr
                100                 105                 110

Asn Leu Val Leu Gln Thr Gly Ile Phe Lys Lys Val Pro Val Asp Ile
        115                 120                 125

Tyr Val Phe Lys Ser Gly Val Phe Thr Leu Leu Gly Asp Gly Phe
    130                 135                 140

Ile Asn Trp Ala Trp Gly Gly Phe Val Asp Gln Val Asp Gly Lys Arg
145                 150                 155                 160

Ile His Phe Arg Leu Pro Pro Gly Ala Leu Pro
                165                 170
```

<210> SEQ ID NO 33
<211> LENGTH: 546
<212> TYPE: DNA
<213> ORGANISM: Platycerium wandae

<400> SEQUENCE: 33

```
atgagagagc gagagcgaga gcgagagaga gagatggccg aaccagcagc agcagcagct      60
aaaaaagctg aagaagaggt ggagatattt atggacgaca ctgaggcggt ggggacgcat     120
ctggacttct tggcgggctt gaaggtgcag ccccgcaaga tcatcaccgt ggaggtggac     180
```

```
cccgctgccg taatccagca gataagagag atctttcaaa ccctggcacg tcacttcaac    240
tcgacgacgg tggtgcggga tgaagccatc aagggcattc agaccactt cagggccgcc    300 gttccgactc gcaacgtggt ggtcgttcac actcagcaca ttcacaccct ggagggcttg    360
gagcaccaca accttgtctt gcagaccggc cgcttcagaa aggtccccgt cgacatctac    420
gtcttcaagt ctggcgtctt caccctcctt ggagatggag cttcatcaa ctgggcgtgg    480 ggtggcttcg tggagcaggt cgtcggcaag cgtatccact ccgcttacc ccctggggcg    540 ctccct                                                              546
```

<210> SEQ ID NO 34
<211> LENGTH: 182
<212> TYPE: PRT
<213> ORGANISM: Platycerium wandae

<400> SEQUENCE: 34

```
Met Arg Glu Arg Glu Arg Glu Arg Glu Met Ala Glu Pro Ala
1               5                   10                  15

Ala Ala Ala Lys Lys Ala Glu Glu Val Glu Ile Phe Met Asp
                20                  25                  30

Asp Thr Glu Ala Val Gly Thr His Leu Asp Phe Leu Ala Gly Leu Lys
                35                  40                  45

Val Gln Pro Arg Lys Ile Ile Thr Val Glu Val Asp Pro Ala Ala Val
50                  55                  60

Ile Gln Gln Ile Arg Glu Ile Phe Gln Thr Leu Ala Arg His Phe Asn
65                  70                  75                  80

Ser Thr Thr Val Val Arg Asp Glu Ala Ile Lys Gly Ile Arg Asp His
                85                  90                  95

Phe Arg Ala Ala Val Pro Thr Arg Asn Val Val Val His Thr Gln
                100                 105                 110

His Ile His Thr Leu Glu Gly Leu Glu His Thr Asn Leu Val Leu Gln
            115                 120                 125

Thr Gly Arg Phe Arg Lys Val Pro Val Asp Ile Tyr Val Phe Lys Ser
        130                 135                 140

Gly Val Phe Thr Leu Leu Gly Asp Gly Phe Ile Asn Trp Ala Trp
145                 150                 155                 160

Gly Gly Phe Val Glu Gln Val Val Gly Lys Arg Ile His Phe Arg Leu
                165                 170                 175

Pro Pro Gly Ala Leu Pro
            180
```

<210> SEQ ID NO 35
<211> LENGTH: 513
<212> TYPE: DNA
<213> ORGANISM: Tectaria milnei

<400> SEQUENCE: 35

```
atggccgatg aggtagctgg tcatcacggt cctgcctgtg aagaagaaga agaagagatg    60
ctgatggatg agactgaggc ggtgggggtg catgcaatcg atggcctgcc ggtgcaaaac   120
cgtagcatca ttaccgtgga ggtggacgcc gcagccgtaa tccagcagat cagagagata   180
tttgcatcga tgatcaagca ctacaactcc acgcgagtgg tgcgggatga ggccatcaag   240
tccattcgag accacttcag gctcgccgtg cccactcgca acgtggtggt gattcacact   300
cagcacgttc acacactgga cgccgtggag agctcgcacc tggtcttgcg aaccggtcta   360
```

```
ttcaaaaagg tgccagtgga catcttcgtc ttcaagtctg gcgtgttcac caacctggga    420
gacgggggct tcatcaactg ggcatggggt ggctacggcg tcaaccacac tgccaagcgt    480
gttgtcttca gtcggccccc tggggcgctc cct                                 513
```

```
<210> SEQ ID NO 36
<211> LENGTH: 171
<212> TYPE: PRT
<213> ORGANISM: Tectaria milnei

<400> SEQUENCE: 36
```

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Ala Ser Met
    50                  55                  60

Ile Lys His Tyr Asn Ser Thr Arg Val Val Arg Asp Glu Ala Ile Lys
65                  70                  75                  80

Ser Ile Arg Asp His Phe Arg Leu Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Arg Thr Gly Leu Phe Lys Lys Val Pro Val Asp Ile
        115                 120                 125

Phe Val Phe Lys Ser Gly Val Phe Thr Asn Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

```
<210> SEQ ID NO 37
<211> LENGTH: 375
<212> TYPE: DNA
<213> ORGANISM: Davallia tyermannii

<400> SEQUENCE: 37
atggacgccg ctgccgtaat ccagcagatt agagagatct tccaatccat ggcagatgac     60
ttcagctcga cgaaggtggt gcgggatgaa gccatcaagg gcattcgaga ccacttcagg    120
gccgccgtcc cgactcgcaa cgtggtggtc gttcacaccc gcacattca cacacagctg    180 gtggacgtgg agcacaccaa actcgtcttg aagaccggca tcttcgaaaa ggtcccgtc    240 gacatctatg tcttcaagtc cggcgtcttc accctccttg agacggagg ctacaacaac    300 tgggcatggg gtggcttcgt agaccaggtc gtcggcaagc gtatccactt ccgcttgccc    360
cccggggcgc tccct                                                     375
```

```
<210> SEQ ID NO 38
<211> LENGTH: 125
<212> TYPE: PRT
<213> ORGANISM: Davallia tyermannii

<400> SEQUENCE: 38
```

Met Asp Ala Ala Ala Val Ile Gln Gln Ile Arg Glu Ile Phe Gln Ser
1               5                   10                  15

Met Ala Asp Asp Phe Ser Ser Thr Lys Val Val Arg Asp Glu Ala Ile
            20                  25                  30

Lys Gly Ile Arg Asp His Phe Arg Ala Ala Val Pro Thr Arg Asn Val
        35                  40                  45

Val Val Val His Thr Pro His Ile His Thr Gln Leu Val Asp Val Glu
 50                  55                  60

His Thr Lys Leu Val Leu Lys Thr Gly Ile Phe Glu Lys Val Pro Val
 65                  70                  75                  80

Asp Ile Tyr Val Phe Lys Ser Gly Val Phe Thr Leu Gly Asp Gly
                85                  90                  95

Gly Tyr Asn Asn Trp Ala Trp Gly Gly Phe Val Asp Gln Val Val Gly
            100                 105                 110

Lys Arg Ile His Phe Arg Leu Pro Pro Gly Ala Leu Pro
            115                 120                 125

<210> SEQ ID NO 39
<211> LENGTH: 579
<212> TYPE: DNA
<213> ORGANISM: Artificial Sequence
<220> FEATURE:
<223> OTHER INFORMATION: IPD103 variant

<400> SEQUENCE: 39
atgggcagca gccatcatca tcatcatcac agcagcggcc tggtgccgcg cggcagccat        60
atggcggaca agcagcagc agcagctaga gaagctgaag aagaggtgga gacgacgatg       120
gacgagactg aggcggtggg gacgcacctg gacttcttgg gcgcggacgt gaagttgcaa       180
ccccgcaaca tcatcaccgt ggaggtggac gcggctgccg taatccaaca gatcagagag       240
atcttccaga caatggcgcg tcacttcaac tctacgaggg tggtgcggga tgaagccatc       300
aagggcattc gagaccactt cagggccgcc gtcccgactc gcaacgtggt ggtcattcac       360
actcagcacg ttcacacact ggtgggcttg gagcacaccc acctcgtctt gcagaccggc       420
atcttcaaaa aggtccccgt cgacatctat gtcttcaagt ccggcgtctt caccaacctt       480
ggagacggag gcttcatcaa ctgggcatgg ggtggcttcg tcgaccaggt cgtcggcaag       540
cgtatccact ccgcttgcc ccccggggcg ctcccttga       579

<210> SEQ ID NO 40
<211> LENGTH: 192
<212> TYPE: PRT
<213> ORGANISM: Artificial Sequence
<220> FEATURE:
<223> OTHER INFORMATION: IPD103 variant

<400> SEQUENCE: 40

Met Gly Ser Ser His His His His His His Ser Gly Leu Val Pro
  1               5                   10                  15

Arg Gly Ser His Met Ala Asp Lys Ala Ala Ala Ala Arg Glu Ala
            20                  25                  30

Glu Glu Glu Val Glu Thr Thr Met Asp Glu Thr Glu Ala Val Gly Thr
        35                  40                  45

His Leu Asp Phe Leu Gly Ala Asp Val Lys Leu Gln Pro Arg Asn Ile
 50                  55                  60

Ile Thr Val Glu Val Asp Ala Ala Ala Val Ile Gln Gln Ile Arg Glu
 65                  70                  75                  80

Ile Phe Gln Thr Met Ala Arg His Phe Asn Ser Thr Arg Val Val Arg
            85                  90                  95

-continued

```
Asp Glu Ala Ile Lys Gly Ile Arg Asp His Phe Arg Ala Ala Val Pro
            100                 105                 110
Thr Arg Asn Val Val Ile His Thr Gln His Val His Thr Leu Val
        115                 120                 125
Gly Leu Glu His Thr His Leu Val Leu Gln Thr Gly Ile Phe Lys Lys
    130                 135                 140
Val Pro Val Asp Ile Tyr Val Phe Lys Ser Gly Val Phe Thr Asn Leu
145                 150                 155                 160
Gly Asp Gly Gly Phe Ile Asn Trp Ala Trp Gly Phe Val Asp Gln
                165                 170                 175
Val Val Gly Lys Arg Ile His Phe Arg Leu Pro Pro Gly Ala Leu Pro
        180                 185                 190

<210> SEQ ID NO 41
<211> LENGTH: 513
<212> TYPE: DNA
<213> ORGANISM: Artificial Sequence
<220> FEATURE:
<223> OTHER INFORMATION: IPD103 variant

<400> SEQUENCE: 41
atggccgacc cagcaacagc agctagagaa gctgaagaag aggtggagac gacgatggac      60
gagactgagg cggtggggac gcacctggac ttcttgggcg cggacgtgaa gttgcaaccc     120
cgcaacatca tcaccgtgga ggtggacgcc gctgccgtaa tccagcagat cagagagatc     180
ttccagacaa tggcgcgtca cttcaactct acgagggtgg tgcgggatga agccatcaag     240
ggcattcgag accacttcag ggccgccgtc ccgactcgca acgtggtggt cgttcacacc     300
cagcacattc acacactgga gggcttggag cacaccaacc tcgtcttgca gaccggcctc     360
ttcaaaaagg tccccgtcga catctacgtc ttcaagtccg gcgtcttcac cctccttgga     420
gacggaggct tcatcaactg gcatggggt ggcttcgtac aggaggtcgc cggcaagcgt      480
atccacttcc gcttgccccc cggggcgctc cct                                  513

<210> SEQ ID NO 42
<211> LENGTH: 510
<212> TYPE: DNA
<213> ORGANISM: Artificial Sequence
<220> FEATURE:
<223> OTHER INFORMATION: IPD103 variant

<400> SEQUENCE: 42
atggccgacc cagcagcagc agctagagaa gctgaagaag aggtggagac gacgatggac      60
gagactgagg cggtggggac gcacctggac ttcgtggcgg gcttggaggt gcaaccccgc     120
aaggtcatca ccgtggaggt ggacgccgct gccgtaatcc agcagatcag agagatcttc     180
cagacaatgg cgcgtcactt caactctacg agggtggtgc gggatgaagc catcaagggc     240
attcgagacc acttcagggc cgccgtcccg actcgcaacg tggtggtcgt tcacacccag     300
cacattcaca cactggtggg cttggagcac acccacctcg tcttgcagac cggcatcttc     360
aaaaaggtcc ccgtcgacat ctatgtcttc aagtccggcg tcttcaccaa ccttggagac     420
ggaggcttca tcaactgggc atggggtggc ttcgtacagg aggtcgccgg caagcgtatc     480
cacttccgct tgccccccgg ggcgctccct                                      510

<210> SEQ ID NO 43
<211> LENGTH: 516
<212> TYPE: DNA
```

<213> ORGANISM: Artificial Sequence
<220> FEATURE:
<223> OTHER INFORMATION: IPD103 variant

<400> SEQUENCE: 43

| | | | | | |
|---|---|---|---|---|---|
| atggccgacc | cagcaacagc | agctagagaa | gctgaagaag | aggtgcagga | gactttgatg | 60 |
| gacgagactg | aggcggtggg | gacgcacctg | gacttcttgg | gcgcggacgt | gaagttgcaa | 120 |
| ccccgcaaca | tcatcaccgt | ggaggtggac | gcggctgccg | taatccagca | gatcagagag | 180 |
| atcttccgaa | ccatggcaag | tcacttcaac | tcgacgaggg | tggtgcggga | tgaagccatc | 240 |
| aagggcattc | gagaccactt | cagggccgcc | gtcccgactc | gcaacgtggt | ggtcgttcac | 300 |
| actcagcacg | ttcacacact | ggtgggcttg | agcacaccc | acctcgtctt | gcagaccggc | 360 |
| ctcttcaaaa | aggtccccgt | cgacatctac | gtcttcaagt | ccggcgtctt | caccctcctt | 420 |
| ggagacggag | gcttcatcaa | ctgggcatgg | ggtggcttcg | tacaggaggt | cgccggcaag | 480 |
| cgtatccact | tccgcttgcc | ccccggggcg | ctccct | | | 516 |

<210> SEQ ID NO 44
<211> LENGTH: 516
<212> TYPE: DNA
<213> ORGANISM: Artificial Sequence
<220> FEATURE:
<223> OTHER INFORMATION: IPD103 variant

<400> SEQUENCE: 44

| | | | | | |
|---|---|---|---|---|---|
| atggcggaca | aaacagcagc | agcagctaga | gaagctgaag | aagaggtgca | ggagactttg | 60 |
| atggacgaga | ctgaggcggt | ggggacgcac | ctggacttcg | tggcgggctt | ggaggtgcaa | 120 |
| ccccgcaaca | tcatcaccgt | ggaggtggac | gccgctgccg | taatccagca | gatcagagag | 180 |
| atcttccgaa | ccatggcaag | tcacttcaac | tcgacgaggg | tggtgcggga | tgaagccatc | 240 |
| aagggcattc | gagaccactt | cagggccgcc | gtcccgactc | gcaacgtggt | ggtcgttcac | 300 |
| acccagcaca | ttcacacact | ggagggcttg | agcacacca | acctcgtctt | gcagaccggc | 360 |
| atcttcaaaa | aggtccccgt | cgacatctat | gtcttcaagt | ccggcgtctt | caccaacctt | 420 |
| ggagacggag | gcttcatcaa | ctgggcatgg | ggtggcttcg | tcgaccaggt | cgtcggcaag | 480 |
| cgtatccact | tccgcttgcc | ccccggggcg | ctccct | | | 516 |

<210> SEQ ID NO 45
<211> LENGTH: 513
<212> TYPE: DNA
<213> ORGANISM: Artificial Sequence
<220> FEATURE:
<223> OTHER INFORMATION: IPD103 variant

<400> SEQUENCE: 45

| | | | | | |
|---|---|---|---|---|---|
| atggcggaca | aagcagcagc | agcagctaga | gaagctgaag | aagaggtgga | gacgacgatg | 60 |
| gacgagactg | aggcggtggg | gacgcacctg | gacttcgtgg | cgggcttgga | ggtgcaaccc | 120 |
| cgcaaggtca | tcaccgtgga | ggtggacgcc | gctgccgtaa | tccagcagat | cagagagatc | 180 |
| ttccgaacca | tggcaagtca | cttcaactcg | acgaggtgg | tgcgggatga | agccatcaag | 240 |
| ggcattcgag | accacttcag | gccgccgtc | ccgactcgca | acgtggtggt | cgttcacacc | 300 |
| cagcacattc | acacactgga | gggcttggag | cacacccacc | tcgtcttgca | gaccggcctc | 360 |
| ttcaaaaagg | tccccgtcga | catctacgtc | ttcaagtccg | gcgtcttcac | cctccttgga | 420 |
| gacggaggct | tcatcaactg | gcatggggt | ggcttcgtac | aggaggtcgc | cggcaagcgt | 480 |
| atccacttcc | gcttgccccc | cggggcgctc | cct | | | 513 |

<210> SEQ ID NO 46
<211> LENGTH: 513
<212> TYPE: DNA
<213> ORGANISM: Artificial Sequence
<220> FEATURE:
<223> OTHER INFORMATION: IPD103 variant
<220> FEATURE:
<221> NAME/KEY: misc_feature
<222> LOCATION: (412)..(412)
<223> OTHER INFORMATION: n is a, c, g, or t

<400> SEQUENCE: 46

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactct acgagggtgg tgcgggatga acccatcaag   240
ggcattcgag accacttcag gccgccgtc ccgactcgca acgtggtggt cattcacact   300
cagcacgttc acacactggt gggcttggag cacacccacc tcgtattgca gaccggcatc   360
ttcaaaaagg tccccgtcga catttatgtc ttcaagtccg gtgttttcac cntcctcgga   420
gacggaggct tcatcaactg gcatggggt ggcttcgtcg accaggtcgt cggcaagcgt   480
atccacttcc gcttgccccc cggggcggtc cct                                513
```

<210> SEQ ID NO 47
<211> LENGTH: 513
<212> TYPE: DNA
<213> ORGANISM: Artificial Sequence
<220> FEATURE:
<223> OTHER INFORMATION: IPD103 variant

<400> SEQUENCE: 47

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaacatca tcaccgtgga ggtggacgcg gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtggt cgttcacacc   300
cagcacattc acacactggt gggcttggag cacacccacc tcgtcttgca gaccggcatc   360
ttcaaaaagg tccccgtcga catctacgtc ttcaagtccg gcgtcttcac cctccttgga   420
gacggaggct tcatcaactg gcatggggt ggcttcgtac aggaggtcgc cggcaagcgt   480
atccacttcc gcttgccccc cggggcgctc cct                                513
```

<210> SEQ ID NO 48
<211> LENGTH: 513
<212> TYPE: DNA
<213> ORGANISM: Artificial Sequence
<220> FEATURE:
<223> OTHER INFORMATION: IPD103 variant

<400> SEQUENCE: 48

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactct acgagggtgg tgcgggatga agccatcaag   240
```

```
ggcattcgag accacttcag ggccgccgtc ccgactcgca acgtggtggt cgttcacact        300
cagcacgttc acacactggt gggcttggag cacaccaacc tcgtcttgca gaccggcctc        360
ttcaaaaagg tccccgtcga catctacgtc ttcaagtccg gcgtcttcac cctccttgga        420
gacggaggct tcatcaactg gcatgggggt ggcttcgtac aggaggtcgc cggcaagcgt        480
atccacttcc gcttgccccc cggggcgctc cct                                    513
```

```
<210> SEQ ID NO 49
<211> LENGTH: 519
<212> TYPE: DNA
<213> ORGANISM: Artificial Sequence
<220> FEATURE:
<223> OTHER INFORMATION: IPD103 variant

<400> SEQUENCE: 49
atggcggaca aagcagcagc agcagctaga gaagctgaag aagaggtgca ggagactttg         60
atggacgaga ctgaggcggt ggggacgcac ctggacttct tgggcgcgga cgtgaagttg        120
caaccccgca acatcatcac cgtggaggtg gacgcggctg ccgtaatcca acagatcaga        180
gagatcttcc gaaccatggc aagtcacttc aactcgacga gggtggtgcg ggatgaagcc        240
atcaagggca ttcgagacca cttcaggccc gccgtcccga ctcgcaacgt ggtggtcgtt        300
cacacccagc acgttcacac actggtgggc ttggagcaca ccaacctcgt cttgcagacc        360
ggcctcttca aaaggtccc cgtcgacatc tatgtcttca gtccggcgt cttcaccctc         420 cttggagacg gaggcttcat caactgggca tggggtggct cgtacagga gtcgccggc         480 aagcgtatcc acttccgctt gccccccggg gcgctccct                              519
```

```
<210> SEQ ID NO 50
<211> LENGTH: 516
<212> TYPE: DNA
<213> ORGANISM: Artificial Sequence
<220> FEATURE:
<223> OTHER INFORMATION: IPD103 variant

<400> SEQUENCE: 50
atggcggaca aagcagcagc agcagctaga gaagctgaag aagaggtgga gacgacgatg         60
gacgagactg aggcggtggg gacgcacctg gacttcttgg gcgcggacgt gaagttgcaa        120
ccccgcaaca tcatcaccgt ggaggtggac gcggctgccg taatccagca gatcagagag        180
atcttccgaa ccatggcaag tcacttcaac tcgacgaggg tggtgcggga tgaagccatc        240
aagggcattc gagaccactt cagggccgcc gtcccgactc gcaacgtggt ggtcattcac        300
actcagcacg ttcacacact ggtgggcttg agcacaccc acctcgtctt gcagaccggc        360
ctcttcaaaa aggtccccgt cgacatctat gtcttcaagt ccggcgtctt caccctcctt        420
ggagacggag gcttcatcaa ctgggcatgg ggtggcttcg tcgaccaggt cgtcggcaag        480
cgtatccact tccgcttgcc ccccggggcg ctccct                                  516
```

```
<210> SEQ ID NO 51
<211> LENGTH: 513
<212> TYPE: DNA
<213> ORGANISM: Artificial Sequence
<220> FEATURE:
<223> OTHER INFORMATION: IPD103 variant

<400> SEQUENCE: 51
atggcggaca aagcagcagc agcagctaga gaagctgaag aagaggtgga gacgacgatg         60
gacgagactg aggcggtggg gacgcacctg gacttcgtgg cgggcttgga ggtgcaaccc        120
```

```
cgcaaggtca tcaccgtgga ggtggacgcg gctgccgtaa tccaacagat cagagagatc    180
ttccgaacca tggcaagtca cttcaactct acgagggtgg tgcggatgga agccatcaag    240
ggcattcgag accacttcag ggccgccgtc ccgactcgca acgtggtggt cgttcacacc    300
cagcacattc acacactgga gggcttggag cacacccacc tcgtcttgca gaccggcatc    360
ttcaaaaagg tccccgtcga catctacgtc ttcaagtccg gcgtcttcac cctccttgga    420 gacgaggct  tcatcaactg gcatgggggt ggcttcgtac aggaggtcgc cggcaagcgt    480
atccacttcc gcttgccccc cggggcgctc cct                                 513
```

<210> SEQ ID NO 52
<211> LENGTH: 513
<212> TYPE: DNA
<213> ORGANISM: Artificial Sequence
<220> FEATURE:
<223> OTHER INFORMATION: IPD103 variant

<400> SEQUENCE: 52

```
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaacatca tcaccgtgga ggtggacgcc gctgccgtaa tccagcagat cagagagatc    180
ttccagacaa tggcgcgtca cttcaactct acgagggtgg tgcggatgga agccatcaag    240
ggcattcgag accacttcag ggccgccgtc ccgactcgca acgtggtggt cgttcacacc    300
cagcacgttc acacactggt gggcttggag cacacccacc tcgtcttgca gaccggcatc    360
ttcaaaaagg tccccgtcga catctacgtc ttcaagtccg gcgtcttcac cctccttgga    420 gacgaggct  tcatcaactg gcatgggggt ggcttcgtcg accaggtcgt cggcaagcgt    480
atccacttcc gcttgccccc cggggcgctc cct                                 513
```

<210> SEQ ID NO 53
<211> LENGTH: 516
<212> TYPE: DNA
<213> ORGANISM: Artificial Sequence
<220> FEATURE:
<223> OTHER INFORMATION: IPD103 variant

<400> SEQUENCE: 53

```
atggcggaca aagcagcagc agcagctaga gaagctgaag aagaggtgca ggagactttg     60
atggacgaga ctgaggcggt ggggacgcac ctggacttcg tggcgggctt ggaggtgcaa    120
ccccgcaagg tcatcaccgt ggaggtggac gccgctgccg taatccagca gatcagagag    180
atcttccgaa ccatggcaag tcacttcaac tcgacgaggg tggtgcggga tgaagccatc    240
aagggcattc gagaccactt cagggccgcc gtcccgactc gcaacgtggt ggtcattcac    300
actcagcacg ttcacacact ggtgggcttg agcacacccc acctcgtctt gcagaccggc    360
atcttcaaaa aggtccccgt cgacatctac gtcttcaagt ccggcgtctt caccctcctt    420
ggagacggag gcttcatcaa ctgggcatgg ggtggcttcg tcgaccaggt cgtcggcaag    480
cgtatccact tccgcttgcc ccccggggcg ctccct                              516
```

<210> SEQ ID NO 54
<211> LENGTH: 513
<212> TYPE: DNA
<213> ORGANISM: Artificial Sequence
<220> FEATURE:
<223> OTHER INFORMATION: IPD103 variant

<400> SEQUENCE: 54

```
acggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaacatca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag ggccgccgtc ccgactcgca acgtggtggt cgttcacact     300
cagcacgttc acacactggt gggcttggag cacacccacc tcgtcttgca gaccggcatc     360
ttcaaaaagg tccccgtcga catctacgtc ttcaagtccg gcgtcttcac cctccttgga     420
gacggaggct tcatcaactg gcatggggt ggcttcgtac aggaggtcgc cggcaagcgt     480
atccacttcc gcttgccccc cggggcgctc cct                                  513
```

<210> SEQ ID NO 55
<211> LENGTH: 510
<212> TYPE: DNA
<213> ORGANISM: Artificial Sequence
<220> FEATURE:
<223> OTHER INFORMATION: IPD103 variant

<400> SEQUENCE: 55

```
atggccgacc cagcaacagc agctagagaa gctgaagaag aggtggagac gacgatggac      60
gagactgagg cggtggggac gcacctggac ttcgtggcgg gcttggaggt gcaacccgc     120 aaggtcatca ccgtggaggt ggacgccgct gccgtaatcc agcagatcag agagatcttc     180
cgaaccatgg caagtcactt caactcgacg agggtggtgc gggatgaagc catcaagggc     240
attcgagacc acttcagggc cgccgtcccg actcgcaacg tggtggtcgt tcacactcag     300
cacgttcaca cactggtggg cttggagcac acccacctcg tcttgcagac cggcctcttc     360
aaaaaggtcc ccgtcgacat ctacgtcttc aagtccggcg tcttcaccct ccttggagac     420
ggaggcttca tcaactgggc atggggtggc ttcgtcgacc aggtcgtcgg caagcgtatc     480
cacttccgct tgccccccgg ggcgctccct                                      510
```

<210> SEQ ID NO 56
<211> LENGTH: 513
<212> TYPE: DNA
<213> ORGANISM: Artificial Sequence
<220> FEATURE:
<223> OTHER INFORMATION: IPD103 variant

<400> SEQUENCE: 56

```
atggccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaacatca tcaccgtgga ggtggacgcg gctgccgtaa tccagcagat cagagagatc     180
ttccgaacca tggcaagtca cttcaactcg acgagggtgg tgcgggatga agccatcaag     240
ggcattcgag accacttcag ggccgccgtc ccgactcgca acgtggtggt cgttcacacc     300
cagcacgttc acacactggt gggcttggag cacacccacc tcgtcttgca gaccggcatc     360
ttcaaaaagg tccccgtcga catctacgtc ttcaagtccg gcgtcttcac cctccttgga     420
gacggaggct tcatcaactg gcatggggt ggcttcgtcg accaggtcgt cggcaagcgt     480
atccacttcc gcttgccccc cggggcgctc cct                                  513
```

<210> SEQ ID NO 57
<211> LENGTH: 513

```
<212> TYPE: DNA
<213> ORGANISM: Artificial Sequence
<220> FEATURE:
<223> OTHER INFORMATION: IPD103 variant

<400> SEQUENCE: 57
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag gccgccgtc ccgactcgca acgtggtggt cgttcacacc    300
cagcacattc acacactggt gggcttggag cacacccacc tcgtcttgca gaccggcctc   360
ttcaaaaagg tccccgtcga catctacgtc ttcaagtccg cgtcttcac cctccttgga    420 gacggaggct tcatcaactg gcatggggt ggcttcgtac aggaggtcgc cggcaagcgt    480
atccacttcc gcttgccccc cggggcgctc cct                                513

<210> SEQ ID NO 58
<211> LENGTH: 516
<212> TYPE: DNA
<213> ORGANISM: Artificial Sequence
<220> FEATURE:
<223> OTHER INFORMATION: IPD103 variant

<400> SEQUENCE: 58
atggcggaca aaacagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gccgctgccg taatccagca gatcagagag   180
atcttccgaa ccatggcaag tcacttcaac tcgacgaggg tggtgcggga tgaagccatc   240 aaggcattc gagaccactt cagggccgcc gtcccgactc gcaacgtggt ggtcgttcac    300
acccagcaca ttcacacact ggagggcttg agcacaccc acctcgtctt gcagaccggc    360
atcttcaaaa aggtccccgt cgacatctat gtcttcaagt ccggcgtctt caccctcctt   420
ggagacggag gcttcatcaa ctgggcatgg ggtggcttcg tacaggaggt cgccggcaag   480
cgtatccact tccgcttgcc ccccggggcg ctccct                             516

<210> SEQ ID NO 59
<211> LENGTH: 513
<212> TYPE: DNA
<213> ORGANISM: Artificial Sequence
<220> FEATURE:
<223> OTHER INFORMATION: IPD103 variant

<400> SEQUENCE: 59
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaacatca tcaccgtgga ggtggacgcc gctgccgtaa tccagcagat cagagagatc   180
ttccgaacca tggcaagtca cttcaactct acgagggtgg tgcgggatga agccatcaag   240
ggcattcgag accacttcag gccgccgtc ccgactcgca acgtggtggt cattcacacc    300
cagcacgttc acacactggt gggcttggag cacacccacc tcgtcttgca gaccggcatc   360
ttcaaaaagg tccccgtcga catctacgtc ttcaagtccg cgtcttcac cctccttgga    420 gacggaggct tcatcaactg gcatggggt ggcttcgtcg accaggtcgt cggcaagcgt    480
```
atccacttcc gcttgccccc cggggcgctc cct                                513

<210> SEQ ID NO 60
<211> LENGTH: 516
<212> TYPE: DNA
<213> ORGANISM: Artificial Sequence
<220> FEATURE:
<223> OTHER INFORMATION: IPD103 variant

<400> SEQUENCE: 60
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gcggctgccg taatccaaca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcgttcac     300
acccagcaca ttcacacact ggtgggcttg gagcacaccc acctcgtctt gcagaccggc     360
atcttcaaaa aggtccccgt cgacatctat gtcttcaagt ccggcgtctt caccaacctt     420
ggagacggag gcttcatcaa ctgggcatgg ggtggcttcg tcgaccaggt cgtcggcaag     480
cgtatccact ccgcttgcc ccccggggcg ctccct                               516

<210> SEQ ID NO 61
<211> LENGTH: 513
<212> TYPE: DNA
<213> ORGANISM: Artificial Sequence
<220> FEATURE:
<223> OTHER INFORMATION: IPD103 variant

<400> SEQUENCE: 61
atggccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag gccgccgtc ccgactcgca acgtggtggt cgttcacacc      300
cagcacattc acacactgga gggcttggag cacaccaacc tcgtcttgca gaccggcctc     360
ttcaaaaagg tccccgtcga catctatgtc ttcaagtccg gcgtcttcac caaccttgga     420
gacggaggct tcatcaactg gcatggggt ggcttcgtcg accaggtcgt cggcaagcgt      480
atccacttcc gcttgccccc cggggcgctc cct                                513

<210> SEQ ID NO 62
<211> LENGTH: 516
<212> TYPE: DNA
<213> ORGANISM: Artificial Sequence
<220> FEATURE:
<223> OTHER INFORMATION: IPD103 variant

<400> SEQUENCE: 62
atggcggaca aagcagcagc agcagctaga gaagctgaag aagaggtgga gactttgatg      60
gacgagactg aggcggtggg gacgcacctg gacttcttgg gcgcggacgt gaagttgcaa     120
ccccgcaaca tcatcaccgt ggaggtggac gccgctgccg taatccagca gatcagagag     180
atcttccgaa ccatggcaaa tcacttcaac tcgacgaggg tggtgcggga tgaagccatc     240
aagggcattc gagaccactt cagggccgcc gtcccgactc gcaacgtggt ggtcgttcac     300
acccagcaca ttcacacact ggagggcttg gagcacacca acctcgtctt gcagaccggc     360

```
ctcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact ccgcttgcc ccccggggcg ctccct                              516
```

```
<210> SEQ ID NO 63
<211> LENGTH: 510
<212> TYPE: DNA
<213> ORGANISM: Artificial Sequence
<220> FEATURE:
<223> OTHER INFORMATION: IPD103 variant

<400> SEQUENCE: 63
atggccgacc cagcagcagc agctagagaa gctgaagaag aggtggagac gacgatggac     60
gagactgagg cggtggggac gcacctggac ttcgtggcgg gcttggaggt gcaaccccgc   120
aaggtcatca ccgtggaggt ggacgcggct gccgtaatcc aacagatcag agagatcttc   180
cagacaatgg cgcgtcactt caactcgacg agggtggtgc gggatgaagc catcaagggc   240
attcgagacc acttcagggc cgccgtcccg actcgcaacg tggtggtcgt tcacactcag   300
cacgttcaca cactggtggg cttggagcac accaacctcg tcttgcagac cggcctcttc   360
aaaaaggtcc ccgtcgacat ctacgtcttc aagtccggcg tcttcaccct ccttggagac   420
ggaggcttca tcaactgggc atggggtggc ttcgtacagg aggtcgccgg caagcgtatc   480
cacttccgct tgcccccgg ggcgctccct                                     510
```

```
<210> SEQ ID NO 64
<211> LENGTH: 513
<212> TYPE: DNA
<213> ORGANISM: Artificial Sequence
<220> FEATURE:
<223> OTHER INFORMATION: IPD103 variant

<400> SEQUENCE: 64
atggcggaca agcagcagc agcagctaga gaagctgaag aagaggtgga gacgacgatg     60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtggt cgttcacacc    300
cagcacattc acacactgga gggcttggag cacaccaacc tcgtcttgca gaccggcatc   360
ttcaaaaagg tccccgtcga catctatgtc ttcaagtccg cgtcttcac caaccttgga    420 gacggaggct tcatcaactg ggcatggggt ggcttcgtac aggaggtcgc cggcaagcgt   480
atccacttcc gcttgccccc cggggcgctc cct                                513
```

```
<210> SEQ ID NO 65
<211> LENGTH: 516
<212> TYPE: DNA
<213> ORGANISM: Artificial Sequence
<220> FEATURE:
<223> OTHER INFORMATION: IPD103 variant

<400> SEQUENCE: 65
atggcggaca agcagcagc agcagctaga gaagctgaag aagaggtgga gacgacgatg     60
gacgagactg aggcggtggg gacgcacctg gacttcttgg cgcggacgt gaagttgcaa    120 ccccgcaagg tcatcaccgt ggaggtggac gccgctgccg taatccaaca gatcagagag   180
```

```
atcttccaga caatggcgcg tcacttcaac tctacgaggg tggtgcggga tgaagccatc    240
aagggcattc gagaccactt cagggccgcc gtcccgactc gcaacgtggt ggtcgttcac    300
actcagcaca ttcacacact ggagggcttg agcacaccc acctcgtctt gcagaccggc    360
ctcttcaaaa aggtccccgt cgacatctac gtcttcaagt ccggcgtctt cacccctctt    420
ggagacggag gcttcatcaa ctgggcatgg ggtggcttcg tacaggaggt cgccggcaag    480
cgtatccact ccgcttgcc ccccggggcg ctccct                              516
```

```
<210> SEQ ID NO 66
<211> LENGTH: 519
<212> TYPE: DNA
<213> ORGANISM: Artificial Sequence
<220> FEATURE:
<223> OTHER INFORMATION: IPD103 variant

<400> SEQUENCE: 66
atggcggaca aagcagcagc agcagctaga gaagctgaag aagaggtgca ggagactttg    60
atggacgaga ctgaggcggt ggggacgcac ctggacttct tgggcgcgga cgtgaagttg    120
caaccccgca aggtcatcac cgtggaggtg gacgccgctg ccgtaatcca acagatcaga    180
gagatcttcc agacaatggc gcgtcacttc aactctacga gggtggtgcg ggatgaagcc    240
atcaagggca ttcgagacca cttcagggcc gccgtcccga ctcgcaacgt ggtagtcgtt    300
cacacccagc acattcacac actggagggc ttggagcaca cccacctcgt cttgcagacc    360
ggcatcttca aaaggtccc cgtcgacatc tacgtcttca gtccggcgt cttcaccaac     420 cttggagacg gaggcttcat caactgggca tggggtggct tcgtacagga ggtcgccggc    480
aagcgtatcc acttccgctt gccccccggg gcgctccct                          519
```

```
<210> SEQ ID NO 67
<211> LENGTH: 513
<212> TYPE: DNA
<213> ORGANISM: Artificial Sequence
<220> FEATURE:
<223> OTHER INFORMATION: IPD103 variant

<400> SEQUENCE: 67
atggcggaca aagcagcagc agcagctaga gaagctgaag aagaggtgga gacgacgatg    60
gacgaaactg aggcggtggg gacgcacctg gacttcgtgg cgggcttgga ggtgcaaccc    120
cgcaaggtca tcaccgtgga ggtggacgcg gctgccgtaa tccagcagat cagagagatc    180
ttccgaacca tggcaagtca cttcaactcg acgaggtgg tgcgggatga agccatcaag    240
ggcattcgag accacttcag gccgccgtc ccgactcgca acgtggtggt cgttcacacc     300
cagcacgttc acacactggt gggctcggag cacacccacc tcgtcttgca gaccggcatc    360
ttcaaaaagg tccccgtcga catctatgtc ttcaagtccg gcgtcttcac cctccttgga    420
gacggaggct tcatcaactg gcatggggt ggcttcgtcg accaggtcgt cggcaagcgt    480
atccacttcc gcttgccccc cggggcgctc cct                               513
```

```
<210> SEQ ID NO 68
<211> LENGTH: 513
<212> TYPE: DNA
<213> ORGANISM: Artificial Sequence
<220> FEATURE:
<223> OTHER INFORMATION: IPD103 variant

<400> SEQUENCE: 68
atggcggaca aagcagcagc agcagctaga gaagctgaag aagaggtgga gacgacgatg    60
```

-continued

```
gacgagactg aggcggtggg gacgcacctg gacttcgtgg cgggcttgga ggtgcaaccc      120
cgcaaggtca tcaccgtgga ggtggacgcc gctgccgtaa tccagcagat cagagagatc      180
ttccgaacca tggcaagtca cttcaactcg acgaggtgg tgcgggatga agccatcaag       240
ggcattcgag accacttcag gccgccgtc ccgactcgca acgtggtggt cgttcacact       300
cagcacgttc acacactggt gggcttggag cacaccaacc tcgtcttgca gaccggcctc      360
ttcaaaaagg tccccgtcga catctacgtc ttcaagtccg gcgtcttcac cctccttgga      420
gacggaggct tcatcaactg ggcatggggt ggcttcgtcg accaggtcgt cggcaagcgt      480
atccacttcc gcttgccccc cggggcgctc cct                                   513
```

<210> SEQ ID NO 69
<211> LENGTH: 516
<212> TYPE: DNA
<213> ORGANISM: Artificial Sequence
<220> FEATURE:
<223> OTHER INFORMATION: IPD103 variant

<400> SEQUENCE: 69

```
atggcggaca aagcagcagc agcagctaga gaagctgaag aagaggtgga gacgacgatg       60
gacgagactg aggcggtggg gacgcacctg gacttcttgg gcgcggacgt gaagttgcaa      120
ccccgcaagg tcatcaccgt ggaggtggac gccgctgccg taatccaaca gatcagagag      180
atcttccaga caatggcgcg tcacttcaac tcgacgaggg tggtgcggga tgaagccatc      240
aagggcattc gagaccactt cagggccgcc gtcccgactc gcaacgtggt ggtcgttcac      300
acccagcaca ttcacacact ggtgggcttg agcacaccc acctcgtctt gcagaccggc      360
atcttcaaaa aggtccccgt cgacatctat gtcttcaagt ccggcgtctt caccaacctt      420
ggagacggag gcttcatcaa ctgggcatgg ggtggcttcg tacaggaggt cgccggcaag      480
cgtatccact tccgcttgcc ccccggggcg ctccca                                516
```

<210> SEQ ID NO 70
<211> LENGTH: 513
<212> TYPE: DNA
<213> ORGANISM: Artificial Sequence
<220> FEATURE:
<223> OTHER INFORMATION: IPD103 variant

<400> SEQUENCE: 70

```
atggccgacc cagcaacagc ggctagagaa gctgaagaag aggtgcagga gactttgatg       60
gacgagactg aggcggtggg gacgcacctg gacttcgtgg cgggcttgga ggtgcaaccc      120
cgcaaggtca tcaccgtgga ggtggacgcc gctgccgtaa tccagcagat cagagagatc      180
ttccgaacca tggcaagtca cttcaactcg acgaggtgg tgcgggatga agccatcaag       240
ggcattcgag accacttcag gccgccgtc ccgactcgca acgtggtggt cgttcacacc       300
cagcacattc acacactgga gggcttggag cacacccacc tcgtcttgca gaccggcatc      360
ttcaaaaagg tccccgtcga catctacgtc ttcaagtccg gcgtcttcac caaccttgga      420
gacggaggct tcatcaactg ggcatggggt ggcttcgtac aggaggtcgc cggcaagcgt      480
atccacttcc gcttgccccc cggggcgctc cct                                   513
```

<210> SEQ ID NO 71
<211> LENGTH: 513
<212> TYPE: DNA
<213> ORGANISM: Artificial Sequence
<220> FEATURE:

<223> OTHER INFORMATION: IPD103 variant

<400> SEQUENCE: 71

```
atggccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgaggtgg tgcgggatga agccatcaag      240
ggcattcgag accacttcag gccgccgtc ccgactcgca acgtggtggt cattcacact      300
cagcacgttc acacactggt gggcttggag cacaccaacc tcgtcttgca gaccggcatc     360
ttcaaaaagg tccccgtcga catctatgtc ttcaagtccg gcgtcttcac caaccttgga     420
gacggaggct tcatcaactg gcatggggt ggcttcgtac aggaggtcgc cggcaagcgt      480
atccacttcc gcttgccccc cggggcgctc cct                                  513
```

<210> SEQ ID NO 72
<211> LENGTH: 513
<212> TYPE: DNA
<213> ORGANISM: Artificial Sequence
<220> FEATURE:
<223> OTHER INFORMATION: IPD103 variant

<400> SEQUENCE: 72

```
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcg gctgccgtaa tccaacagat cagagagatc     180
ttccagacaa tggcgcgtca cttcaactct acgaggtgg tgcgggatga agccatcaag      240
ggcattcgag accacttcag gccgccgtc ccgactcgca acgtggtggt cgttcacacc      300
cagcacattc acacactgga gggcttggag cacaccaacc tcgtcttgca gaccggcctc     360
ttcaaaaagg tccccgtcga catctacgtc ttcaagtccg gcgtcttcac cctccttgga     420
gacggaggct tcatcaactg gcatggggt ggcttcgtcg accaggtcgt cggcaagcgt      480
atccacttcc gcttgccccc cggggcgctc cct                                  513
```

<210> SEQ ID NO 73
<211> LENGTH: 513
<212> TYPE: DNA
<213> ORGANISM: Artificial Sequence
<220> FEATURE:
<223> OTHER INFORMATION: IPD103 variant

<400> SEQUENCE: 73

```
atggccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaaggtca tcaccgtgga ggtggacgcg gctgccgtaa tccagcagat cagagagatc     180
ttccgaacca tggcaagtca cttcaactcg acgaggtgg tgcgggatga agccatcaag      240
ggcattcgag accacttcag gccgccgtc ccgactcgca acgtggtggt cgttcacacc      300
cagcacattc acacactgga gggcttggag cacacccacc tcgtcttgca gaccggcatc     360
ttcaaaaagg tccccgtcga catctatgtc ttcaagtccg gcgtcttcac cctccttgga     420
gacggaggct tcatcaactg gcatggggt ggcttcgtac aggaggtcgc cggcaagcgt      480
atccacttcc gcttgccccc cggggcgctc cct                                  513
```

<210> SEQ ID NO 74
<211> LENGTH: 513
<212> TYPE: DNA
<213> ORGANISM: Artificial Sequence
<220> FEATURE:
<223> OTHER INFORMATION: IPD103 variant

<400> SEQUENCE: 74

```
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgaggtgg tgcgggatga agccatcaag      240
ggcattcgag accacttcag gccgccgtc ccgactcgca acgtggtggt cgttcacact      300
cagcacgttc acacactgga gggcttggag cacacccacc tcgtcttgca gaccggcctc    360
ttcaaaaagg tccccgtcga catctacgtc ttcaagtccg gcgtcttcac cctccttgga    420
gacggaggct tcatcaactg gcatggggt ggcttcgtcg accaggtcgt cggcaagcgt     480
atccacttcc gcttgccccc cggggcgctc cct                                 513
```

<210> SEQ ID NO 75
<211> LENGTH: 189
<212> TYPE: DNA
<213> ORGANISM: Artificial Sequence
<220> FEATURE:
<223> OTHER INFORMATION: IPD103 variant

<400> SEQUENCE: 75

```
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccaacagat cagagagatc     180
ttccagaca                                                            189
```

<210> SEQ ID NO 76
<211> LENGTH: 513
<212> TYPE: DNA
<213> ORGANISM: Artificial Sequence
<220> FEATURE:
<223> OTHER INFORMATION: IPD103 variant

<400> SEQUENCE: 76

```
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgaggtgg tgcgggatga agccatcaag      240
ggcattcgag accacttcag gccgccgtc ccgactcgca acgtggtggt cgttcacact      300
cagcacgttc acacactgga gggcttggag cacacccacc tcgtcttgca gaccggcatc    360
ttcaaaaagg tccccgtcga catctacgtc ttcaagtccg gcgtcttcac cctccttgga    420
gacggaggct tcatcaactg gcatggggt ggcttcgtac aggaggtcgc cggcaagcgt     480
atccacttcc gcttgccccc cggggcgctc cct                                 513
```

<210> SEQ ID NO 77
<211> LENGTH: 513
<212> TYPE: DNA
<213> ORGANISM: Artificial Sequence
<220> FEATURE:

<223> OTHER INFORMATION: IPD103 variant

<400> SEQUENCE: 77

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag gccgccgtc ccgactcgca acgtggtggt cgttcacact   300
cagcacgttc acacactggt gggcttggag cacacccacc tcgtcttgca gaccggcctc   360
ttcaaaaagg tccccgtcga catctatgtc ttcaagtccg gcgtcttcac caaccttgga   420
gacggaggct tcatcaactg gcatggggt ggcttcgtac aggaggtcgc cggcaagcgt   480
atccacttcc gcttgccccc cggggcgctc cct                                513
```

<210> SEQ ID NO 78
<211> LENGTH: 513
<212> TYPE: DNA
<213> ORGANISM: Artificial Sequence
<220> FEATURE:
<223> OTHER INFORMATION: IPD103 variant
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (195)..(196)
<223> OTHER INFORMATION: n is a, c, g, or t

<400> SEQUENCE: 78

```
atggcggaca cagcagcagc agctgctaga gaagatgaag aagagctgga gacgnngatg    60
gacgagactg aggcggtggg gacgcacctg gacttcgtgg cgggcttgga ggtgcaaccc   120
cgcaaggtca tcaccgtgga ggtggacgcg gctgccgtaa tccancagat cagagagatc   180
ttccggacca tggcnngtca cttcaactct acgagggtgg tgcgggatga agccatcaag   240
ggcattcgag accacttcag gccgccgtc ccgactcgca acgtggtggt cgttcacacc   300
cagcacgttc acacactgga gggcttggag cacacccacc tcgtcttgca gaccggcatc   360
ttcaaaaagg tccccgtcga catctacgtc ttcaagtccg gcgtcttcac catccttgga   420
gacggaggct tcatcaactg gcatggggt ggcttcgtcg accaggtcgt cggcaagcgt   480
atccacttcc gcttgccccc cggggcgctc cct                                513
```

<210> SEQ ID NO 79
<211> LENGTH: 510
<212> TYPE: DNA
<213> ORGANISM: Artificial Sequence
<220> FEATURE:
<223> OTHER INFORMATION: IPD103 variant

<400> SEQUENCE: 79

```
atggcggaca aagcagcagc agctagagaa gctgaagaag aggtggagac gacgatggac    60
gagactgagg cggtggggac gcacctggac ttcgtggcgg gcttggaggt gcaacccgc   120
aacatcatca ccgtggaggt ggacgcgct gccgtaatcc aacagatcag agagatcttc   180
cagacaatgg cgcgtcactt caactctacg agggtggtgc gggatgaagc catcaagggc   240
```

```
attcgagacc acttcagggc cgccgtcccg actcgcaacg tggtggtcgt tcacacccag    300
cacattcaca cactggaggg cttggagcac accaacctcg tcttgcagac cggcctcttc    360
aaaaaggtcc ccgtcgacat ctacgtcttc aagtccggcg tcttcaccaa cctgggagac    420
ggaggcttca tcaactgggc atggggtggc ttcgtacagg aggtcgccgg caagcgtatc    480
cacttccgct tgccccccgg ggcgctccct                                     510
```

<210> SEQ ID NO 80
<211> LENGTH: 510
<212> TYPE: DNA
<213> ORGANISM: Artificial Sequence
<220> FEATURE:
<223> OTHER INFORMATION: IPD103 variant

<400> SEQUENCE: 80

```
atggcggaca aagcagcagc agcagctaga gaagctgaag aagaggagga ggaaatgctg     60
atggacgaga ctgaggcggt gggggtgcac gcgatcgacg tctgccggt gcaaaaccgc    120 agcatcatca ccgtggaggt ggacgcggct gccgtaatcc agcagatcag agagatcttc    180
cgaaccatgg caagtcactt caactcgacg agggtggtgc gggatgaagc catcaagagc    240
attcgagacc acttcaggct cgccgtcccg actcgcaacg tggtggtcgt tcacacccag    300
cacgttcaca cactggtggg cttggagcac acccacctcg tcttgcagac cggcatcttc    360
aaaaaggtcc ccgtcgacat ctatgtcttc aagtccggcg tcttcaccaa ccttggagac    420
ggaggcttca tcaactgggc atggggtggc ttcgtcgacc aggtcgtcgg caagcgtatc    480
cacttccgct tgccccccgg ggcgctccct                                     510
```

<210> SEQ ID NO 81
<211> LENGTH: 513
<212> TYPE: DNA
<213> ORGANISM: Artificial Sequence
<220> FEATURE:
<223> OTHER INFORMATION: IPD103 variant

<400> SEQUENCE: 81

```
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaaggtca tcaccgtgga ggtggacgcg gctgccgtaa tccaacagat cagagagatc    180
ttccagacaa tggcgcgtca cttcaactcg acgagggtgg tgcgggatga agccatcaag    240
ggcattcgag accacttcag ggccgccgtc ccgactcgca acgtggtggt cattcacacc    300
cagcacgttc acacactggt gggcttggag cacacccacc tcgtcttgcg gaccggcctg    360
ttcaaaaagg tccctgtcga catctacgtc ttcaagtccg gcgtcttcac caaccttgga    420
gacggaggct tcatcaactg gcatgggggt ggcttcgtcg accaggtcgt cggcaagcgt    480
atccacttcc gcttgccccc cggggcgctc cct                                 513
```

<210> SEQ ID NO 82
<211> LENGTH: 510
<212> TYPE: DNA
<213> ORGANISM: Artificial Sequence
<220> FEATURE:
<223> OTHER INFORMATION: IPD103 variant

<400> SEQUENCE: 82

```
atggcggaca aagcagcagc agcagctaga gaagctgaag aagaggagga ggaaatgctg     60
```

-continued

| | |
|---|---|
| atggacgaga ctgaggcggt gggggtgcac gcgatcgacg gtctgccggt gcaaaaccgc | 120 |
| agcatcatca ccgtggaggt ggacgccgct gccgtaatcc agcagatcag agagatcttc | 180 |
| cgaaccatgg caagtcactt caactcgacg agggtggtgc gggatgaagc catcaagggc | 240 |
| attcgagacc acttcaggct cgccgtcccg actcgcaacg tggtggtcat tcacactcag | 300 |
| cacgttcaca cactggtggg cttggagcac acccacctcg tcttgcagac cggcctcttc | 360 |
| aaaaaggtcc ccgtcgacat ctacgtcttc aagtccggcg tcttcaccaa cctgggagac | 420 |
| ggaggcttca tcaactgggc atggggtggc ttcgtacagg aggtcgccgg caagcgtatc | 480 |
| cacttccgct tgccccccgg ggcgctccct | 510 |

<210> SEQ ID NO 83
<211> LENGTH: 513
<212> TYPE: DNA
<213> ORGANISM: Artificial Sequence
<220> FEATURE:
<223> OTHER INFORMATION: IPD103 variant

<400> SEQUENCE: 83

| | |
|---|---|
| atggcggaca aagcagcagc agcagctaga gaagctgaag aagaggtgga gacgacgatg | 60 |
| gacgagactg aggcggtggg gacgcacctg gacttcgtgg cgggcttgga ggtgcaaccc | 120 |
| cgcaaggtca tcaccgtgga ggtggacgcc gctgccgtaa tccaacagat cagagagatc | 180 |
| ttccagacaa tggcgcgtca cttcaactct acgaggtgg tgcggatga agccatcaag | 240 |
| agcattcgag accacttcag ggccgccgtc ccgactcgca acgtggtggt cgttcacacc | 300 |
| cagcacattc acacactgga gggcttggag cacacccacc tcgtcttgca gaccggcctc | 360 |
| ttcaaaaagg tccccgtcga catctacgtc ttcaagtccg gcgtcttcac caaccttgga | 420 |
| gacggaggct tcatcaactg gcatggggt ggcttcgtcg accaggtcgt cggcaagcgt | 480 |
| atccacttcc gcttgccccc cggggcgctc cct | 513 |

<210> SEQ ID NO 84
<211> LENGTH: 513
<212> TYPE: DNA
<213> ORGANISM: Artificial Sequence
<220> FEATURE:
<223> OTHER INFORMATION: IPD103 variant

<400> SEQUENCE: 84

| | |
|---|---|
| atggcggacg aagtagcagg tcaccatggt ccagcatgtg aagaagagga ggaggaaatg | 60 |
| ctgatggacg agactgaggc ggtggggggtg cacgcgatcg acgtctgcc ggtgcaaaac | 120 |
| cgcagcatca tcaccgtgga ggtggacgcc gctgccgtaa tccaacagat cagagagatc | 180 |
| ttcgcgtcaa tgatcaaaca ctacaactct acgaggtgg tgcgggatga agccatcaag | 240 |
| ggcattcgag accacttcag ggccgccgtc ccgactcgca acgtggtggt cgttcacact | 300 |
| cagcacgttc acacactggt gggcttggag cacacccacc tcgtcttgca gaccggcctc | 360 |
| ttcaaaaagg tccccgtcga catctacgtc ttcaagtccg gcgtcttcac cctccttgga | 420 |
| gacggaggct tcatcaactg gcatggggt ggctacggcg tcaaccacac cgccaagcgt | 480 |
| gtcgtcttca gccggccccc cggggcgctc cct | 513 |

<210> SEQ ID NO 85
<211> LENGTH: 519
<212> TYPE: DNA
<213> ORGANISM: Artificial Sequence
<220> FEATURE:
<223> OTHER INFORMATION: IPD103 variant

<400> SEQUENCE: 85

```
atggcggacg aagtagcagg tcaccatggt ccagcatgtg aagaagagga ggaggaaatg     60
ctgatggacg agactgaggc ggtggggacg cacctggact tcgtggcggg cttggaggtg    120
caaccccgca aggtcatcac cgtggaggtg gacgccgctg ccgtaatcca gcagatcaga    180
gagatcttcc gaaccatggc aagtcacttc aactctacga gggtggtgcg ggatgaagcc    240
atcaagggca ttcgagacca cttcagggcc gccgtcccga ctcgcaacgt ggtggtcgtt    300
cacacccagc acattcacac actggagggc ttggagcaca cccacctcgt cttgcggacc    360
ggcctgttca aaaggtccc tgtcgacatc tttgtcttca gtccggcgt cttcaccaac    420
cttggagacg gaggcttcat caactgggca tggggtggct acgtacagga ggtcgccggc    480
aagcgtatcc acttccgctt gccccccggg gcgctccct                           519
```

<210> SEQ ID NO 86
<211> LENGTH: 522
<212> TYPE: DNA
<213> ORGANISM: Artificial Sequence
<220> FEATURE:
<223> OTHER INFORMATION: IPD103 variant

<400> SEQUENCE: 86

```
atggcggacg aagtagcagg tcaccatggt ccagcatgtg aagaagagga ggaggaaatg     60
ctgatggacg agactgaggc ggtggggacg cacctggact tcttgggcgc ggacgtgaag    120
ttgcaacccc gcaacatcat caccgtggag gtggacgcgg ctgccgtaat ccaacagatc    180
agagagatct ccagacaat ggcgcgtcac ttcaactcga cgagggtggt gcgggatgaa    240
gccatcaagg gcattcgaga ccacttcagg gccgccgtcc cgactcgcaa cgtggtggtc    300
gttcacaccc agcacattca cactggag ggcttggagc acaccaacct cgtcttgcag     360
accggcctct tcaaaaaggt ccccgtcgac atctatgtct tcaagtccgg cgtcttcacc    420
aaccttggag acggaggctt catcaactgg gcatggggtg gcttcgtaca ggaggtcgcc    480
ggcaagcgta tccacttccg cttgccccc ggggcgctcc ct                        522
```

<210> SEQ ID NO 87
<211> LENGTH: 516
<212> TYPE: DNA
<213> ORGANISM: Artificial Sequence
<220> FEATURE:
<223> OTHER INFORMATION: IPD103 variant

<400> SEQUENCE: 87

```
atggcggaca aagcagcagc agcagctaga gaagctgaag aagaggtgca ggagactttg     60
atggacgaga ctgaggcggt ggggacgcac ctggacttcg tggcgggctt ggaggtgcaa    120
ccccgcaagg tcatcaccgt ggaggtggac gcggctgccg taatccaaca gatcagagag    180
atcttccaga caatggcgcg tcacttcaac tcgacgaggg tggtgcggga tgaagccatc    240
aagggcattc gagaccactt cagggccgcc gtcccgactc gcaacgtggt ggtcattcac    300
actcagcacg ttcacacact ggacgccgtg gagtcctccc acctcgtctt gcggaccggc    360
ctgttcaaaa aggtccctgt cgacatctat gtcttcaagt ccggcgtctt caccaacctt    420
ggagacggag gcttcatcaa ctgggcatgg ggtggctacg tcgaccaggt cgtcggcaag    480
cgtatccact tccgcttgcc cccggggcg ctccct                               516
```

<210> SEQ ID NO 88

<211> LENGTH: 513
<212> TYPE: DNA
<213> ORGANISM: Artificial Sequence
<220> FEATURE:
<223> OTHER INFORMATION: IPD103 variant

<400> SEQUENCE: 88

| | | | | | |
|---|---|---|---|---|---|
| atggcggaca | aagcagcagc | agcagctaga | gaagctgaag | aagaggtgga | gacgacgatg | 60 |
| gacgagactg | aggcggtggg | gacgcacctg | gacttcgtgg | cgggcttgga | ggtgcaaccc | 120 |
| cgcaaggtca | tcaccgtgga | ggtggacgcc | gctgccgtaa | tccaacagat | cagagagatc | 180 |
| ttccagacaa | tggcgcgtca | cttcaactct | acgagggtgg | tgcgggatga | agccatcaag | 240 |
| agcattcgag | accacttcag | ggccgccgtc | ccgactcgca | acgtggtggt | cattcacact | 300 |
| cagcacgttc | acacactggt | gggcttggag | cacacccacc | tcgtcttgca | gaccggcctc | 360 |
| ttcaaaaagg | tccccgtcga | catctatgtc | ttcaagtccg | gcgtcttcac | caacctggga | 420 |
| gacggaggct | tcatcaactg | gcatggggt  | ggcttcgtac | aggaggtcgt | cggcaagcgt | 480 |
| atccacttcc | gcttgccccc | cggggcgctc | cct | | | 513 |

<210> SEQ ID NO 89
<211> LENGTH: 513
<212> TYPE: DNA
<213> ORGANISM: Artificial Sequence
<220> FEATURE:
<223> OTHER INFORMATION: IPD103 variant

<400> SEQUENCE: 89

| | | | | | |
|---|---|---|---|---|---|
| atggccgacc | agcaacagc  | agctagagaa | gctgaagaag | aggtgcagga | gactttgatg | 60 |
| gacgagactg | aggcggtggg | gacgcacctg | gacttcgtgg | cgggcttgga | ggtgcaaccc | 120 |
| cgcaaggtca | tcaccgtgga | ggtggacgcg | gctgccgtaa | tccaacagat | cagagagatc | 180 |
| ttccgaacca | tggcaagtca | cttcaactcg | acgagggtgg | tgcgggatga | agccatcaag | 240 |
| ggcattcgag | accacttcag | ggccgccgtc | ccgactcgca | acgtggtggt | cattcacact | 300 |
| cagcacgttc | acacactgga | cgccgtggag | tcctcccacc | tcgtcttgca | gaccggcctc | 360 |
| ttcaaaaagg | tccccgtcga | catctatgtc | ttcaagtccg | gcgtcttcac | caaccttgga | 420 |
| gacggaggct | tcatcaactg | gcatggggt  | ggcttcgtcg | accaggtcgt | cggcaagcgt | 480 |
| atccacttcc | gcttgccccc | cggggcgctc | cct | | | 513 |

<210> SEQ ID NO 90
<211> LENGTH: 519
<212> TYPE: DNA
<213> ORGANISM: Artificial Sequence
<220> FEATURE:
<223> OTHER INFORMATION: IPD103 variant

<400> SEQUENCE: 90

| | | | | | |
|---|---|---|---|---|---|
| atggcggacg | aagtagcagg | tcaccatggt | ccagcatgtg | aagaagaggt | gcaggagact | 60 |
| ttgatggacg | agactgaggc | ggtggggacg | cacctggact | tcgtggcggg | cttggaggtg | 120 |
| caaccccgca | gcatcatcac | cgtggaggtg | gacgccgctg | ccgtaatcca | acagatcaga | 180 |
| gagatcttcc | agacaatggc | gcgtcacttc | aactctacga | gggtggtgcg | ggatgaagcc | 240 |
| atcaagggca | ttcgagacca | cttcaggctc | gccgtcccga | ctcgcaacgt | ggtggtcgtt | 300 |
| cacacccagc | acgttcacac | actggtgggc | ttggagcaca | cccacctcgt | cttgcagacc | 360 |
| ggcatcttca | aaaggtccc  | cgtcgacatc | tatgtcttca | agtccggcgt | cttcaccaac | 420 |
| ctgggagacg | gaggcttcat | caactgggca | tggggtggct | tcgtcgacca | ggtcgtcggc | 480 |

```
aagcgtatcc acttccgctt gccccccggg gcgctccct                          519
```

<210> SEQ ID NO 91
<211> LENGTH: 519
<212> TYPE: DNA
<213> ORGANISM: Artificial Sequence
<220> FEATURE:
<223> OTHER INFORMATION: IPD103 variant

<400> SEQUENCE: 91

```
aaggcggacg aagtagcagg tcaccatggt ccagcatgtg aagaagagga ggaggaaatg   60
ctgatggacg agactgaggc ggtggggacg cacctggact tcgtggcggg cttggaggtg  120
caaccccgca aggtcatcac cgtggaggtg gacgccgctg ccgtaatcca acagatcaga  180
gagatcttcc gaaccatggc aagtcactac aactctacga gggtggtgcg ggatgaagcc  240
atcaagggca ttcgagacca cttcagggcc gccgtcccga ctcgcaacgt ggtggtcatt  300
cacactcagc acgttcacac actggacgcc gtggagtcct cccacctcgt cttgcagacc  360
ggcatcttca aaaaggtccc cgtcgacatc tacgtcttca gtccggcgt cttcaccaac  420
ctgggagacg gaggcttcat caactgggca tggggtggct tcgtcgacca ggtcgtcggc  480
aagcgtatcc acttccgctt gccccccggg gcgctccct                          519
```

<210> SEQ ID NO 92
<211> LENGTH: 522
<212> TYPE: DNA
<213> ORGANISM: Artificial Sequence
<220> FEATURE:
<223> OTHER INFORMATION: IPD103 variant

<400> SEQUENCE: 92

```
atggcggacg aagtagcagg tcaccatggt ccagcatgtg aagaagagga ggaggaaatg   60
ctgatggacg agactgaggc ggtggggacg cacctggact tcttgggcgc ggacgtgaag  120
ttgcaacccc gcaacatcat caccgtggag gtggacgcgg ctgccgtaat ccagcagatc  180
agagagatct tccagacaat ggcgcgtcac ttcaactcta cgagggtggt gcggatgaa   240
gccatcaagg gcattcgaga ccacttcagg gccgccgtcc cgactcgcaa cgtggtggtc  300
attcacactc agcacgttca cacactggac gccgtggagt cctcccacct cgtcttgcgg  360
accggcctgt tcaaaaaggt ccctgtcgac atctatgtct tcaagtccgg cgtcttcacc  420
aacctgggag acggaggctt catcaactgg gcatggggtg gcttcgtcga ccaggtcgtc  480
ggcaagcgta tccacttccg cttgccccc ggggcgctcc ct                      522
```

<210> SEQ ID NO 93
<211> LENGTH: 513
<212> TYPE: DNA
<213> ORGANISM: Artificial Sequence
<220> FEATURE:
<223> OTHER INFORMATION: IPD103 variant

<400> SEQUENCE: 93

```
atggcggacg aagtagcagg tcaccatggt ccagcatgtg aagaagagga ggaggaaatg   60
ctgatggacg agactgaggc ggtggggtg cacgcgatcg acggtctgcc ggtgcaaaac  120
cgcagcatca tcaccgtgga ggtggacgcc gctgccgtaa tccagcagat cagagagatc  180
ttccgaacca tggcaagtca cttcaactcg acgagggtgg tgcggatga agccatcaag  240
agcattcgag accacttcag gctcgccgtc ccgactcgca acgtggtggt cgttcacact  300
```

-continued

```
cagcacgttc acacactggt gggcttggag cacacccacc tcgtcttgcg gaccggcctc    360
ttcaaaaagg tccccgtcga catctacgtc ttcaagtccg gcgtcttcac cctccttgga    420
gacggaggct tcatcaactg gcatggggt ggcttcgtac aggaggtcgc cggcaagcgt    480
atccacttcc gcttgccccc cggggcgctc cct                                 513
```

<210> SEQ ID NO 94
<211> LENGTH: 516
<212> TYPE: DNA
<213> ORGANISM: Artificial Sequence
<220> FEATURE:
<223> OTHER INFORMATION: IPD103 variant

<400> SEQUENCE: 94

```
atggcggacg aagtagcagg tcaccatggt ccagcatgtg aagaagaggt ggagacgacg    60
atggacgaga ctgaggcggt ggggacgcac ctggacttcg tggcgggctt ggaggtgcaa   120
ccccgcaagg tcatcaccgt ggaggtggac gcggctgccg taatccaaca gatcagagag   180
atcttccaga caatggcgcg tcacttcaac tctacgaggg tggtgcggga tgaagccatc   240
aagagcattc gagaccactt cagggccgcc gtcccgactc gcaacgtggt ggtcattcac   300
actcagcacg ttcacacact ggagggcttg gagcacacca acctcgtctt gcagaccggc   360
atcttcaaaa aggtccccgt cgacatctac gtcttcaagt ccggcgtctt caccaacctg   420
ggagacggag gcttcatcaa ctgggcatgg ggtggcttcg tcgaccaggt cgtcggcaag   480
cgtatccact tccgcttgcc ccccggggcg ctccct                              516
```

<210> SEQ ID NO 95
<211> LENGTH: 513
<212> TYPE: DNA
<213> ORGANISM: Artificial Sequence
<220> FEATURE:
<223> OTHER INFORMATION: IPD103 variant

<400> SEQUENCE: 95

```
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgaggtgg tgcgggatga agccatcaag   240
agcattcgag accacttcag ggccgccgtc ccgactcgca acgtggtggt cgttcacact   300
cagcacgttc acacactgga cgccgtggag tcctcccacc tcgtcttgcg gaccggcctg   360
ttcaaaaagg tccctgtcga catctacgtc ttcaagtccg gcgtcttcac caaccttgga   420
gacggaggct tcatcaactg gcatggggt ggcttcgtcg accaggtcgt cggcaagcgt    480
atccacttcc gcttgccccc cggggcgctc cct                                 513
```

<210> SEQ ID NO 96
<211> LENGTH: 517
<212> TYPE: DNA
<213> ORGANISM: Artificial Sequence
<220> FEATURE:
<223> OTHER INFORMATION: IPD103 variant
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t

<400> SEQUENCE: 96

```
atggcggacg aagtagcagg tcaccatggt ccagcactga agaagaggag agagagatgg      60
atgatggacg agacgagacg aggcggtgca cctgcacgtg atcgccggtc tggaggtgca     120
accccgcagc atcatcaccg tggaggtgga cgccgctgcc gtaatccagc agatcagaga     180
gatcttccag acaatggcga gtcacttcaa ctctacgagg gtggtgcggg atgaagccat     240
caagggcatt cgagaccact caggggccgc cgtcccgact cgcaacgtgg tggtcattca     300
cactcagcac gttcacacac tggaggccgt ggagtcctcc cacctcgtct tgcggaccgg     360
cctgttcaaa aaggtccctg tcgacatcta cgtcttcaag tccggcgtct tcaccctcct     420
tggagacgga ggcttcatca actgggcatg gggtggcttc gtcgtccang tcgtcggcaa     480
gcgtgtccac ttcngccggc ccccgggggc gctccct                              517
```

<210> SEQ ID NO 97
<211> LENGTH: 513
<212> TYPE: DNA
<213> ORGANISM: Artificial Sequence
<220> FEATURE:
<223> OTHER INFORMATION: IPD103 variant
<220> FEATURE:
<221> NAME/KEY: misc_feature
<222> LOCATION: (412)..(412)
<223> OTHER INFORMATION: n is a, c, g, or t

<400> SEQUENCE: 97

```
atggcggacc cagcaacagc agctagagaa gctgaagaag aggtgcagga gactttgatg      60
gacgagagtg aggcggtggg gacgcacctg gacttcgtgg cgggcttgga ggtgcaaccc     120
cgcaaggtca tcaccgtgga ggtggacgcc gctgccgtaa tccatcagat cagagagatc     180
ttccagacaa tggcgcgtca cttcaactct acgagggtgg tgcgggatga agccatcaag     240
ggcatttgag accacttcag ggccgctgtc ccgactcgca acgtggtggt cattcactcc     300
cagcacattc acacactgga gggcttggag cacaccaacc tcgtcttgca gaccggcatg     360
ttcaaaaagg tccccgtcga catctttgtc ttcaagtccg gcgtcttcac cntccttgga     420
gacggaggct tcatcaactg gcatgggggt ggcttcgtac aggaggtcgt cggcaagcgt     480
atccacttcc gcttgccccc cggggcgctc cct                                  513
```

<210> SEQ ID NO 98
<211> LENGTH: 513
<212> TYPE: DNA
<213> ORGANISM: Artificial Sequence
<220> FEATURE:
<223> OTHER INFORMATION: IPD103 variant

<400> SEQUENCE: 98

```
atggcggacg aagtagcagg tcaccatggt ccagcatgtg aagaagagga ggaggaaatg      60
ctgatggacg agactgaggc ggtgggggtg cacgcgatcg acgtctgcc ggtgcaaaac     120
cgcagcatca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag ggccgccgtc ccgactcgca acgtggtggt cgttcacacc     300
cagcacattc acacactgga gggcttggag cacaccaacc tcgtcttgca gaccggcctc     360
ttcaaaaagg tccccgtcga catctacgtc ttcaagtccg gcgtcttcac cctccttgga     420
gacggaggct tcatcaactg gcatgggggt ggcttcggcg tcaaccacac cgccaagcgt     480
```

```
gtcgtcttca gccggccccc cggggcgctc cct                                513
```

<210> SEQ ID NO 99
<211> LENGTH: 513
<212> TYPE: DNA
<213> ORGANISM: Artificial Sequence
<220> FEATURE:
<223> OTHER INFORMATION: IPD103 variant

<400> SEQUENCE: 99

```
atggcggacg aagtagcagg tcaccatggt ccagcatgtg aagaagagga ggaggaaatg    60
ctgatggacg agactgaggc ggtggggtg cacgcgatcg acggtctgcc ggtgcaaaac    120
cgcagcatca tcaccgtgga ggtggacgcc gctgccgtaa tccagcagat cagagagatc   180
ttccgaacca tggcaagtca cttcaactcg acgaggtgg tgcgggatga agccatcaag    240
agcattcgag accacttcag ggccgccgtc ccgactcgca acgtggtggt cattcacact   300
cagcacgttc acacactgga cgccgtggag tcctcccacc tcgtcttgca gaccggcctc   360
ttcaaaaagg tccccgtcga catctttgtc ttcaagtccg gcgtcttcac caacctggga   420
gacggaggct tcatcaactg gcatggggt ggctacggcg tcaaccacac cgccaagcgt   480
gtcgtcttca gccggccccc cggggcgctc cct                                513
```

<210> SEQ ID NO 100
<211> LENGTH: 513
<212> TYPE: DNA
<213> ORGANISM: Artificial Sequence
<220> FEATURE:
<223> OTHER INFORMATION: IPD103 variant

<400> SEQUENCE: 100

```
atggcggacg aagtagcagg tcaccatggt ccagcatgtg aagaagagga ggaggaaatg    60
ctgatggacg agactgaggc ggtggggtg cacgcgatcg acggtctgcc ggtgcaaaac    120
cgcagcatca tcaccgtgga ggtggacgcc gctgccgtaa tccagcagat cagagagatc   180
ttccgaacca tggcaagtca cttcaactcg acgaggtgg tgcgggatga agccatcaag    240
agcattcgag accacttcag ggccgccgtc ccgactcgca acgtggtggt cattcacact   300
cagcacgttc acacactgga cgccgtggag tcctcccacc tcgtcttgcg gaccggcctg   360
ttcaaaaagg tccccgtcga catctatgtc ttcaagtccg gcgtcttcac caacctggga   420
gacggaggct tcatcaactg gcatggggt ggcttcgtcg accaggtcgt cggcaagcgt   480
atccacttcc gcttgccccc cggggcgctc cct                                513
```

<210> SEQ ID NO 101
<211> LENGTH: 519
<212> TYPE: DNA
<213> ORGANISM: Artificial Sequence
<220> FEATURE:
<223> OTHER INFORMATION: IPD103 variant

<400> SEQUENCE: 101

```
atggcggaca agcagcagc agcagctaga gaagctgaag aagaggtgca ggagactttg    60
atggacgaga ctgaggcggt ggggacgcac ctggacttct tgggcgcgga cgtgaagttg   120
caaccccgca aggtcatcac cgtggaggtg gacgccgctg ccgtaatcca acagatcaga   180
gagatcttcc gaaccatggc aagtcacttc aactcgacga gggtggtgcg ggatgaagcc   240
atcaagggca ttcgagacca cttcagggcc gccgtcccga ctcgcaacgt ggtggtcgtt   300
cacacccagc acattcacac actggagggc ttggagcaca ccaacctcgt cttgcagacc   360
```

```
ggcatcttca aaaaggtccc cgtcgacatc tacgtcttca agtccggcgt cttcaccctc    420
cttggagacg gaggcttcat caactgggca tggggtggct tcgtacagga ggtcgccggc    480
aagcgtatcc acttccgctt gccccccggg gcgctccct                          519
```

<210> SEQ ID NO 102
<211> LENGTH: 513
<212> TYPE: DNA
<213> ORGANISM: Artificial Sequence
<220> FEATURE:
<223> OTHER INFORMATION: IPD103 variant

<400> SEQUENCE: 102

```
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac    120
cgcagcatca tcaccgtgga ggtggacgcc gctgccgtaa tccagcagat cagagagatc    180
ttccgaacca tggcaagtca cttcaactcg acgaggtgg tgcgggatga agccatcaag    240
agcattcgag accacttcag gctcgccgtc ccgactcgca acgtggtggt cattcacact    300
cagcacgttc acacactgga cgccgtggag tcctcccacc tcgtcttgcg gaccggcctg    360
ttcaaaaagg tccctgtcga catctttgtc ttcaagtccg gcgtcttcac caacctggga    420
gacggaggct tcatcaactg gcatgggt ggcttcgtac aggaggtcgc cggcaagcgt    480
atccacttcc gcttgccccc cggggcgctc cct                                513
```

<210> SEQ ID NO 103
<211> LENGTH: 522
<212> TYPE: DNA
<213> ORGANISM: Artificial Sequence
<220> FEATURE:
<223> OTHER INFORMATION: IPD103 variant

<400> SEQUENCE: 103

```
atggcggacg aagtagcagg tcaccatggt ccagcatgtg aagaagagga ggaggaaatg    60
ctgatggacg agactgaggc ggtggggacg cacctggact tcttgggcgc ggacgtgaag    120
ttgcaacccc gcaaggtcat caccgtggag gtggacgccg ctgccgtaat ccaacagatc    180
agagagatct tccgaaccat ggcaagtcac ttcaactcga cgaggtggt gcgggatgaa    240 gccatcaagg gcattcgaga ccacttcagg ccgccgtcc cgactcgcaa cgtggtggtc    300
gttcacactc agcacgttca cacactggtg gcttggagc acacccacct cgtcttgcag    360
accggcctct tcaaaaaggt ccccgtcgac atctatgtct tcaagtccgg cgtcttcacc    420
aacctgggag acggaggctt catcaactgg gcatgggtg gcttcgtcga ccaggtcgtc    480
ggcaagcgta tccacttccg cttgccccc ggggcgctcc ct                      522
```

<210> SEQ ID NO 104
<211> LENGTH: 507
<212> TYPE: DNA
<213> ORGANISM: Artificial Sequence
<220> FEATURE:
<223> OTHER INFORMATION: IPD103 variant

<400> SEQUENCE: 104

```
atggcggacg aagtagcagc agcagctaga gaagctgaag aagaggtgga gacgacgatg    60
gacgagactg aggcggtggg ggtgcacgcg atcgacggtc tgccggtgca aaaccgcagc    120
atcatcaccg tggaggtgga cgccgctgcc gtaatccagc agatcagaga gatcttccga    180
```

```
accatggcaa gtcacttcaa ctcgacgagg gtggtgcggg atgaagccat caagggcatt    240
cgagaccact tcaggctcgc cgtcccgact cgcaacgtgg tggtcattca cactcagcac    300
gttcacacac tggtgggctt ggagcacacc cacctcgtct tgcagaccgg catcttcaaa    360
aaggtccccg tcgacatcta tgtcttcaag tccggcgtct tcaccaacct tggagacgga    420
ggcttcatca actgggcatg gggtggcttc gtcgaccagg tcgtcggcaa gcgtatccac    480
ttccgcttgc ccccggggc gctccct                                        507
```

```
<210> SEQ ID NO 105
<211> LENGTH: 513
<212> TYPE: DNA
<213> ORGANISM: Artificial Sequence
<220> FEATURE:
<223> OTHER INFORMATION: IPD103 variant

<400> SEQUENCE: 105
atggcggaca aagcagcagc agcagctaga gaagctgaag aagaggtgga gacgacgatg    60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgaggtgg tgcgggatga agccatcaag    240
ggcattcgag accacttcag ggccgccgtc ccgactcgca acgtggtggt cattcacact    300
cagcacgttc acacactgga cgccgtggag tcctcccacc tcgtcttgcg gaccggcctg    360
ttcaaaaagg tccccgtcga catctacgtc ttcaagtccg gcgtcttcac caacctggga    420 gacgaggct tcatcaactg ggcatggggt ggcttcggcg tcaaccacac cgccaagcgt    480
gtcgtcttca gccggccccc cggggcgctc cct                                513
```

```
<210> SEQ ID NO 106
<211> LENGTH: 516
<212> TYPE: DNA
<213> ORGANISM: Artificial Sequence
<220> FEATURE:
<223> OTHER INFORMATION: IPD103 variant

<400> SEQUENCE: 106
atggcggaca aagcagcagc agcagctaga gaagctgaag aagaggtgga gacgacgatg    60
gacgagactg aggcggtggg gacgcacctg gacttcttgg gcgcggacgt gaagttgcaa    120
ccccgcaagg tcatcaccgt ggaggtggac gccgctgccg taatccagca gatcagagag    180
atcttccgaa ccatggcaag tcacttcaac tcgacgaggg tggtgcggga tgaagccatc    240
aagggcattt gagaccactt cagggccgcc gtcccgactc gcaacgtggt ggtcgttcac    300
acccagcaca ttcacacact ggagggcttg gagcacacca acctcgtctt gcagaccggc    360
ctcttcaaaa aggtccccgt cgacatctat gtcttcaagt ccggcgtctt caccaacctt    420
ggagacggag gcttcatcaa ctgggcatgg gtggcttcg tacaggaggt cgccggcaag    480
cgtatccact tccgcttgcc ccccggggcg ctccct                             516
```

```
<210> SEQ ID NO 107
<211> LENGTH: 516
<212> TYPE: DNA
<213> ORGANISM: Artificial Sequence
<220> FEATURE:
<223> OTHER INFORMATION: IPD103 variant

<400> SEQUENCE: 107
atggcggacg aagtagcagg tcaccatggt ccagcatgtg aagaagaggt ggagacgacg    60
```

```
atggacgaga ctgaggcggt ggggacgcac ctggacttcg tggcgggctt ggaggtgcaa    120
ccccgcaagg tcatcaccgt ggaggtggac gccgctgccg taatccagca gatcagagag    180
atcttccgaa ccatggcaag tcacttcaac tctacgaggg tggtgcggga tgaagccatc    240
aagagcattc gagaccactt cagggccgcc gtcccgactc gcaacgtggt ggtcgttcac    300
actcagcacg ttcacacact ggtgggcttg gagcacacca acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tacaggaggc cgccggcaag    480
cgtatccact ccgcttgcc ccccggggcg ctccct                              516
```

<210> SEQ ID NO 108
<211> LENGTH: 513
<212> TYPE: DNA
<213> ORGANISM: Artificial Sequence
<220> FEATURE:
<223> OTHER INFORMATION: IPD103 variant

<400> SEQUENCE: 108

```
atggcggaca aagcagcagc agcagctaga gaagctgaag aagaggcgga gacgacgatg     60
gacgagactg aggcggtggg gacgcacctg gagttgatgg cgggcttgga ggtgcaaccc    120
cgcagcatca tcaccgtgga ggtggacgcc gctgccgtaa tccagcagat cagagagatc    180
ttccgaacca tggcaagtca cttcaactcg acgagggtgg tgcgggatga agccatcaag    240
ggcattcgag accccttcag ggccgccgtc ccgactcgca acgtggtggt cgttcactcc    300
cagcacattc acacactggt gggcttggag cacacccacc tcgtgttgca gaccggcatg    360
ttcaaaaagg tccccgtcga catctatctc ttcaagtccg gcgtcttcac cctccttgga    420
gacggaggct tcatcaactg gcatggggt ggcttcgtac agcaggtcgc cggcaagcgt    480
atccacttcc gcttgccccc cggggcggtc ccc                                513
```

<210> SEQ ID NO 109
<211> LENGTH: 513
<212> TYPE: DNA
<213> ORGANISM: Artificial Sequence
<220> FEATURE:
<223> OTHER INFORMATION: IPD103 variant

<400> SEQUENCE: 109

```
atagccgacc cagcaacagc agctagagaa gctgaagaag aggtgcagga gactttgatg     60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgagggtgg tgcgggatga agccatcaag    240
ggcattcgag accacttcag ggccgccgtc ccgactcgca acgtggtggt cattcacact    300
cagcacgttc acacactggt gggcttggag cacacccacc tcgtcttgca gaccggcctc    360
ttcaaaaagg tccccgtcga catctacgtc ttcaagtccg gcgtcttcac cctccttgga    420
gacggaggct tcatcaactg gcatggggt ggcttcgtac aggaggtcgc cggcaagcgt    480
atccacttcc gcttgccccc cggggcgctc cct                                513
```

<210> SEQ ID NO 110
<211> LENGTH: 513
<212> TYPE: DNA
<213> ORGANISM: Artificial Sequence
<220> FEATURE:

<223> OTHER INFORMATION: IPD103 variant

<400> SEQUENCE: 110

| | | |
|---|---|---|
| atggccgacc cagcaacagc agcagctaga gaagatgaag aagaggtgga gactttgatg | 60 | |
| gacgagactg aggcggtggg gacgcacctg gacttcgtgg cgggcttgga ggtgcaaccc | 120 | |
| cgcaacatca tcaccgtgga ggtggacgcc gctgccgtaa tccaacagat cagagagatc | 180 | |
| ttccgaacca tggcaagtca cttcaactct acgagggtgg tgcgggatga agccatcaag | 240 | |
| ggcattcgag accacttcag gccgccgtc ccgactcgca acgtggtggt cattcacact | 300 | |
| cagcacgttc acacactggt gggcttggag cacacccacc tcgttttgca gaccggcatc | 360 | |
| ttcaaaaagg tccccgtcga catctatgtc ttcaagtccg gcgtcttcac caaccttgga | 420 | |
| gacggaggct tcatcaactg gcatgggggt ggcttcgtac aggaggtcgc cggcaagcgt | 480 | |
| gtcctcttca gccggccccc cggggcgctc cct | 513 | |

<210> SEQ ID NO 111
<211> LENGTH: 513
<212> TYPE: DNA
<213> ORGANISM: Artificial Sequence
<220> FEATURE:
<223> OTHER INFORMATION: IPD103 variant

<400> SEQUENCE: 111

| | | |
|---|---|---|
| atggcggacg aagtagcagg tcaccatggt ccagcatgtg aagaagagga ggaggaaatg | 60 | |
| ctgatggacg agactgaggc ggtgggggtg cacgcgatcg acggtctgcc ggtgcaaccc | 120 | |
| cgcaaggtca tcaccgtgga ggtggacgcc gctgccgtaa tccagcagat cagagagatc | 180 | |
| ttccgaacca tggcaagtca cttcaactcg acgagggtgg tgcgggatga agccatcaag | 240 | |
| ggcattcgag accacttcag gccgccgtc ccgactcgca acgtggtggt cattcacact | 300 | |
| cagcacgttc acacactgga cgccgtggag tcctcccacc tcgtcttgcg gaccggcctg | 360 | |
| ttcaaaaagg tccctgtcga catctttgtc ttcaagtccg gcgtcttcac caaccttgga | 420 | |
| gacggaggct tcatcaactg gcatgggggt ggctacggcg tcaaccacac cgccaagcgt | 480 | |
| gtcgtcttca gccggccccc cggggcgctc cct | 513 | |

<210> SEQ ID NO 112
<211> LENGTH: 513
<212> TYPE: DNA
<213> ORGANISM: Artificial Sequence
<220> FEATURE:
<223> OTHER INFORMATION: IPD103 variant

<400> SEQUENCE: 112

| | | |
|---|---|---|
| atggccgacc cagcaacagc agctagagaa gctgaagaag aggtgcagga gactttgatg | 60 | |
| gacgagactg aggcggtggg gacgcacctg gacttcgtgg cgggcttgga ggtgcaaccc | 120 | |
| cgcaaggtca tcaccgtgga ggtggacgcc gctgccgtaa tccagcagat cagagagatc | 180 | |
| ttccagacaa tggcgcgtca cttcaactct acgagggtgg tgcgggatga agccatcaag | 240 | |
| ggcattcgag accacttcag gccgccgtc ccgactcgca acgtggtggt cgttcacacc | 300 | |
| cagcacattc acacactggt gggcttggag cacaccaacc tcgtcttgca gaccggcctc | 360 | |
| ttcaaaaagg tccccgtcga catctacgtc ttcaagtccg gcgtcttcac cctccttgga | 420 | |
| gacggaggct tcatcaactg gcatgggggt ggcttcgtac aggaggtcgc cggcaagcgt | 480 | |
| atccacttcc gcttgccccc cggggcgctc cct | 513 | |

```
<210> SEQ ID NO 113
<211> LENGTH: 513
<212> TYPE: DNA
<213> ORGANISM: Artificial Sequence
<220> FEATURE:
<223> OTHER INFORMATION: IPD103 variant

<400> SEQUENCE: 113
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgaggtgg tgcgggatga agccatcaag      240
ggcattcgag accacttcag ggccgccgtc ccgactcgca acgtggtggt cgttcacacc     300
cagcacattc acacactgga gggcttggag cacaccaacc tcgtcttgca gaccggcctc     360
ttcaaaaagg tccccgtcga catctacgtc ttcaagtccg gcgtcttcac cctccttgga     420
gacggaggct tcatcaactg ggcatggggt ggcttcgtac aggaggtcgc cggcaagcgt     480
atccacttcc gcttgccccc cggggcgctc cct                                  513

<210> SEQ ID NO 114
<211> LENGTH: 516
<212> TYPE: DNA
<213> ORGANISM: Artificial Sequence
<220> FEATURE:
<223> OTHER INFORMATION: IPD103 variant

<400> SEQUENCE: 114
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaagg tcatcaccgt ggaggtggac gccgctgccg taatccagca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcgttcac     300
acccagcacg ttcacacact ggtgggcttg gagcacacca acctcgtctt gcagaccggc     360
atcttcaaaa aggtccccgt cgacatctac gtcttcaagt ccggcgtctt caccaacctt     420
ggagacggag gcttcatcaa ctgggcatgg ggtggcttcg tacaggaggt cgccggcaag     480
cgtatccact ccgcttgcc ccgggcg ctccct                                    516

<210> SEQ ID NO 115
<211> LENGTH: 513
<212> TYPE: DNA
<213> ORGANISM: Artificial Sequence
<220> FEATURE:
<223> OTHER INFORMATION: IPD103 variant

<400> SEQUENCE: 115
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcg gctgccgtaa tccaacagat cagagagatc     180
ttccagacaa tggcgcgtca cttcaactct acgaggtgg tgcgggatga agccatcaag      240
ggcattcgag accacttcag ggccgccgtc ccgactcgca acgtggtggt cgttcacacc     300
cagcacattc acacactgga gggcttggag cacacccacc tcgtcttgca gaccggcctc     360
ttcaaaaagg tccccgtcga catctatgtc ttcaagtccg gcgtcttcac caaccttgga     420
```

```
gacggaggct tcatcaactg ggcatggggt ggcttcgtcg accaggtcgt cggcaagcgt      480
atccacttcc gcttgccccc cggggcgctc cct                                   513

<210> SEQ ID NO 116
<211> LENGTH: 510
<212> TYPE: DNA
<213> ORGANISM: Artificial Sequence
<220> FEATURE:
<223> OTHER INFORMATION: IPD103 variant

<400> SEQUENCE: 116
atggccgacc cagcaacagc agctagagaa gctgaagaag aggtggagac gacgatggac       60
gagactgagg cggtggggac gcacctggac ttcgtggcgg gcttggaggt gcaaccccgc      120
aaggtcatca ccgtggaggt ggacgccgct gccgtaatcc aacagatcag agagatcttc      180
cagacaatgg cgcgtcactt caactctacg agggtggtgc gggatgaagc catcaagggc      240
attcgagacc acttcagggc cgccgtcccg actcgcaacg tggtggtcat tcacactcag      300
cacgttcaca cactggaggg cttggagcac accaacctcg tcttgcagac cggcatcttc      360
aaaaaggtcc ccgtcgacat ctacgtcttc aagtccggcg tcttcaccct ccttggagac      420
ggaggcttca tcaactgggc atggggtggc ttcgtacagg aggtcgccgg caagcgtatc      480
cacttccgct tgccccccgg ggcgctccct                                       510

<210> SEQ ID NO 117
<211> LENGTH: 516
<212> TYPE: DNA
<213> ORGANISM: Artificial Sequence
<220> FEATURE:
<223> OTHER INFORMATION: IPD103 variant

<400> SEQUENCE: 117
atggcggaca aagcagcagc agcagctaga gaagctgaag aagaggtgca ggagactttg       60
atggacgaga ctgaggcggt ggggacgcac ctggacttcg tggcgggctt ggaggtgcaa      120
ccccgcaagg tcatcaccgt ggaggtggac gccgctgccg taatccaaca gatcagagag      180
atcttccgaa ccatggcaag tcacttcaac tcgacgaggg tggtgcggga tgaagccatc      240
aagggcattc gagaccactt cagggccgcc gtcccgactc gcaacgtggt ggtcgttcac      300
actcagcacg ttcacacatt ggagggcttg gagcacaccc acctcgtctt gcagaccggc      360
ctcttcaaaa aggtccccgt cgacatctat gtcttcaagt ccggcgtctt caccaaccct      420
tggagacgga ggcttcatca actgggcatg ggtggcttcg tacaggaggt cgccggcaag      480
cgtatccact tccgcttgcc ccccggggcg ctccct                                516

<210> SEQ ID NO 118
<211> LENGTH: 510
<212> TYPE: DNA
<213> ORGANISM: Artificial Sequence
<220> FEATURE:
<223> OTHER INFORMATION: IPD103 variant

<400> SEQUENCE: 118
atggccgacc cagcaacagc agctagagaa gctgaagaag aggtggagac gacgatggac       60
gagactgagg cggtggggac gcacctggac ttcgtggcgg gcttggaggt gcaaccccgc      120
aacatcatca ccgtggaggt ggacgcggct gccgtaatcc agcagatcag agagatcttc      180
cagacaatgg cgagtcactt caactcgacg agggtggtgc gggatgaagc catcaagggc      240
attcgagacc acttcagggc cgccgtcccg actcgcaacg tggtggtcgt tcacacccag      300
```

```
cacattccaca cactggtggg cttggagcac acccacctcg tcttgcagac cggcctcttc    360
aaaaaggtcc ccgtcgacat ctacgtcttc aagtccggcg tcttcaccct ccttggagac    420
ggaggcttca tcaactgggc atggggtggc ttcgtacagg aggtcgccgg caagcgtatc    480
cacttccgct tgccccccgg ggcgctccct                                     510
```

<210> SEQ ID NO 119
<211> LENGTH: 516
<212> TYPE: DNA
<213> ORGANISM: Artificial Sequence
<220> FEATURE:
<223> OTHER INFORMATION: IPD103 variant

<400> SEQUENCE: 119

```
atggccgacc cagcaacagc agctagagaa gctgaagaag aggtgcagga gactttgatg     60
gacgagactg aggcggtggg gacgcacctg gacttcttgg gcgcggacgt gaagttgcaa    120
ccccgcaaca tcataccgt ggaggtggac gccgctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcgttcac    300
actcagcacg ttcacacact ggtgggcttg agcacaccc acctcgtctt gcagaccggc    360
ctcttcaaaa aggtccccgt cgacatctac gtcttcaagt ccggcgtctt caccctcctt    420
ggagacggag gcttcatcaa ctgggcatgg ggtggcttcg tacaggaggt cgccggcaag    480
cgtatccact ccgcttgcc ccccggggcg ctccct                                516
```

<210> SEQ ID NO 120
<211> LENGTH: 513
<212> TYPE: DNA
<213> ORGANISM: Artificial Sequence
<220> FEATURE:
<223> OTHER INFORMATION: IPD103 variant

<400> SEQUENCE: 120

```
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgagggtgg tgcgggatga agccatcaag    240
ggcattcgag accacttcag ggccgccgtc ccgactcgca acgtggtggt cattcacacc    300
cagcacgttc acacactggt gggcttggag cacacccacc tcgtcttgca gaccggcctc    360
ttcaaaaagg tccccgtcga catctatgtc ttcaagtccg gcgtcttcac cctccttgga    420
gacggaggct tcatcaactg gcatgggt ggcttcgtcg accaggtcgt cggcaagcgt     480
atccacttcc gcttgccccc cggggcgctc cct                                 513
```

<210> SEQ ID NO 121
<211> LENGTH: 510
<212> TYPE: DNA
<213> ORGANISM: Artificial Sequence
<220> FEATURE:
<223> OTHER INFORMATION: IPD103 variant

<400> SEQUENCE: 121

```
atggccgacc cagcagcagc agctagagaa gctgaagaag aggtggagac gacgatggac     60
gagactgagg cggtggggac gcacctggac ttcgtggcgg gcttggaggt gcaaccccgc    120
```

| | | |
|---|---|---|
| aacatcatca ccgtggaggt ggacgcggct gccgtaatcc aacagatcag cgagatcttc | 180 | |
| cgaaccatgg caagtcactt caactcgacg agggtggtgc gggatgaagc catcaagggc | 240 | |
| attcgagacc acttcagggc cgccgtcccg actcgcaacg tggtggtcgt tcacacccag | 300 | |
| cacattcaca cactggaggg cttggagcac acccacctcg tcttgcagac cggcatcttc | 360 | |
| aaaaaggtcc ccgtcgacat ctacgtcttc aagtccggcg tcttcaccct ccttggagac | 420 | |
| ggaggcttca tcaactgggc atggggtggc ttcgtcgacc aggtcgtcgg caagcgtatc | 480 | |
| cacttccgct tgccccccgg ggcgctccct | 510 | |

<210> SEQ ID NO 122
<211> LENGTH: 516
<212> TYPE: DNA
<213> ORGANISM: Artificial Sequence
<220> FEATURE:
<223> OTHER INFORMATION: IPD103 variant

<400> SEQUENCE: 122

| | | |
|---|---|---|
| atggcggaca aagcagcagc agcagctaga gaagctgaag aagaggtgga gacgacgatg | 60 | |
| gacgagactg aggcggtggg gacgcacctg gacttcttgg gcgcggacgt gaagttgcaa | 120 | |
| ccccgcaaca tcatcaccgt ggaggtggac gcggctgccg taatccaaca gatcagagag | 180 | |
| atcttccaga caatggcgcg tcacttcaac tcgacgaggg tggtgcggga tgaagccatc | 240 | |
| aagggcattc gagaccactt cagggccgcc gtcccgactc gcaacgtggt ggtcgttcac | 300 | |
| acccagcaca ttcacacact ggagggcttg gagcacacca acctcgtctt gcagaccggc | 360 | |
| ctcttcaaaa aggtccccgt cgacatctac gtcttcaagt ccggcgtctt caccctcctt | 420 | |
| ggagacggag gcttcatcaa ctgggcatgg ggtggcttcg tcgaccaggt cgtcggcaag | 480 | |
| cgtatccact ccgcttgcc cccggggcg ctccct | 516 | |

<210> SEQ ID NO 123
<211> LENGTH: 516
<212> TYPE: DNA
<213> ORGANISM: Artificial Sequence
<220> FEATURE:
<223> OTHER INFORMATION: IPD103 variant

<400> SEQUENCE: 123

| | | |
|---|---|---|
| atggcggaca aagcagcagc agcagctaga gaagctgaag aagaggtgca ggagactttg | 60 | |
| atggacgaga ctgaggcggt ggggacgcac ctggacttcg tggcgggctt ggaggtgcaa | 120 | |
| ccccgcaagg tcatcaccgt ggaggtggac gccgctgccg taatccagca gatcagagag | 180 | |
| atcttccgaa ccatggcaag tcacttcaac tcgacgaggg tggtgcggga tgaagccatc | 240 | |
| aagggcattc gagaccactt cagggccgcc gtcccgactc gcaacgtggt ggtcattcac | 300 | |
| actcagcacg ttcacacact ggagggcttg gagcacaccc acctcgtctt gcagaccggc | 360 | |
| ctcttcaaaa aggtccccgt cgacatctac gtcttcaagt ccggcgtctt caccctcctt | 420 | |
| ggagacggag gcttcatcaa ctgggcatgg ggtggcttcg tcgaccaggt cgtcggcaag | 480 | |
| cgtatccact ccgcttgcc cccggggcg ctccct | 516 | |

<210> SEQ ID NO 124
<211> LENGTH: 513
<212> TYPE: DNA
<213> ORGANISM: Artificial Sequence
<220> FEATURE:
<223> OTHER INFORMATION: IPD103 variant

<400> SEQUENCE: 124

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgaggtgg tgcgggatga agccatcaag   240
ggcattcgag accacttcag ggccgccgtc ccgactcgca acgtggtggt cgttcacacc   300
cagcacattc acacactggt gggcttggag cacacccacc tcgtcttgca gaccggcatc   360
ttcaaaaagg tccccgtcga catctacgtc ttcaagtccg gcgtcttcac caaccttgga   420
gacggaggct tcatcaactg gcatggggt ggcttcgtac aggaggtcgc cggcaagcgt   480
atccacttcc gcttgccccc cggggcgctc cct                                513
```

<210> SEQ ID NO 125
<211> LENGTH: 516
<212> TYPE: DNA
<213> ORGANISM: Artificial Sequence
<220> FEATURE:
<223> OTHER INFORMATION: IPD103 variant

<400> SEQUENCE: 125

```
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccagca gatcagagag   180
atcttccgaa ccatggcaag tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tacaggaggt cgccggcaag   480
cgtatccact tccgcttgcc ccccggggcg ctccct                              516
```

<210> SEQ ID NO 126
<211> LENGTH: 516
<212> TYPE: DNA
<213> ORGANISM: Artificial Sequence
<220> FEATURE:
<223> OTHER INFORMATION: IPD103 variant

<400> SEQUENCE: 126

```
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctac gtcttcaagt ccggcgtctt caccctcctt   420
ggagacggag gcttcatcaa ctgggcatgg ggtggcttcg tacaggaggt cgccggcaag   480
cgtatccact tccgcttgcc ccccggggcg ctccct                              516
```

<210> SEQ ID NO 127
<211> LENGTH: 513
<212> TYPE: DNA

```
<213> ORGANISM: Artificial Sequence
<220> FEATURE:
<223> OTHER INFORMATION: IPD103 variant

<400> SEQUENCE: 127
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgaggtgg tgcgggatga agccatcaag      240
ggcattcgag accacttcag gccgccgtc ccgactcgca acgtggtggt cgttcacacc      300
cagcacattc acacactgga gggcttggag cacacccacc tcgtcttgca gaccggcctc     360
ttcaaaaagg tccccgtcga catctacgtc ttcaagtccg gcgtcttcac caaccttgga     420
gacggaggct tcatcaactg gcatggggt ggcttcgtac aggaggtcgc cggcaagcgt      480
atccacttcc gcttgccccc cggggcgctc cct                                  513

<210> SEQ ID NO 128
<211> LENGTH: 519
<212> TYPE: DNA
<213> ORGANISM: Artificial Sequence
<220> FEATURE:
<223> OTHER INFORMATION: IPD103 variant

<400> SEQUENCE: 128
atggcggaca aagcagcagc agcagctaga gaagctgaag aagaggtgca ggagactttg      60
atggacgaga ctgaggcggt ggggacgcac ctggacttct ggcgcggga cgtgaagttg      120
caaccccgca acatcatcac cgtggaggtg gacgccgctg ccgtaatcca gcagatcaga     180
gagatcttcc gaaccatggc aagtcacttc aactctacga gggtggtgcg ggatgaagcc     240
atcaagggca ttcgagacca cttcagggcc gccgtcccga ctcgcaacgt ggtggtcgtt     300
cacacccagc acattcacac actggagggc ttggagcaca cccacctcgt cttgcagacc     360
ggcctcttca aaaggtccc cgtcgacatc tacgtcttca gtccggcgt cttcaccctc      420
cttggagacg gaggcttcat caactgggca tggggtggct tcgtacagga ggtcgccggc     480
aagcgtatcc acttccgctt gccccccggg gcgctccct                            519

<210> SEQ ID NO 129
<211> LENGTH: 510
<212> TYPE: DNA
<213> ORGANISM: Artificial Sequence
<220> FEATURE:
<223> OTHER INFORMATION: IPD103 variant

<400> SEQUENCE: 129
atggccgacc cagcaacagc agctagagaa gctgaagaag aggtggagac gacgatggac      60
gagactgagg cggtggggac gcacctggac ttcgtggcgg gcttggaggt gcaaccccgc     120
aaggtcatca ccgtggaggt ggacgccgct gccgtaatcc aacagatcag agagatcttc     180
cagacaatgg cgcgtcactt caactcgacg agggtggtgc gggatgaagc catcaagggc     240
attcgagacc acttcagggc gccgtcccg actcgcaacg tggtggtcgt tcacacccag      300
cacattcaca cactggaggg cttggagcac accaacctcg tcttgcagac cggcctcttc     360
aaaaaggtcc ccgtcgacat ctacgtcttc aagtccggcg tcttcaccct ccttggagac     420
ggaggcttca tcaactgggc atggggtggc ttcgtacagg aggtcgccgg caagcgtatc     480
cacttccgct tgccccccgg ggcgctccct                                      510
```

<210> SEQ ID NO 130
<211> LENGTH: 513
<212> TYPE: DNA
<213> ORGANISM: Artificial Sequence
<220> FEATURE:
<223> OTHER INFORMATION: IPD103 variant

<400> SEQUENCE: 130

| | | | | | |
|---|---|---|---|---|---|
| atggcggaca | aagcagcagc | agcagctaga | gaagctgaag | aagaggtgga | gacgacgatg | 60 |
| gacgagactg | aggcggtggg | gacgcacctg | gacttcgtgg | cgggcttgga | ggtgcaaccc | 120 |
| cgcaaggtca | tcaccgtgga | ggtggacgcc | gctgccgtaa | tccagcagat | cagagagatc | 180 |
| ttccgaacca | tggcaagtca | cttcaactct | acgagggtgg | tgcgggatga | agccatcaag | 240 |
| ggcattcgag | accacttcag | ggccgccgtc | ccgactcgca | acgtggtggt | cattcacacc | 300 |
| cagcacattc | acacactgga | gggcttggag | cacaccaacc | tcgtcttgca | gaccggcatc | 360 |
| ttcaaaaagg | tccccgtcga | catctatgtc | ttcaagtccg | gcgtcttcac | cctccttgga | 420 |
| gacggaggct | tcatcaactg | gcatggggt | ggcttcgtcg | accaggtcgt | cggcaagcgt | 480 |
| atccacttcc | gcttgccccc | cggggcgctc | cct | | | 513 |

<210> SEQ ID NO 131
<211> LENGTH: 513
<212> TYPE: DNA
<213> ORGANISM: Artificial Sequence
<220> FEATURE:
<223> OTHER INFORMATION: IPD103 variant

<400> SEQUENCE: 131

| | | | | | |
|---|---|---|---|---|---|
| atggcggaca | aagcagcagc | agcagctaga | gaagctgaag | aagaggtgga | gacgacgatg | 60 |
| gacgagactg | aggcggtggg | gacgcacctg | gacttcgtgg | cgggcttgga | ggtgcaaccc | 120 |
| cgcaaggtca | tcaccgtgga | ggtggacgcc | gctgccgtaa | tccagcagat | cagagagatc | 180 |
| ttccgaacca | tggcaagtca | cttcaactcg | acgagggtgg | tgcgggatga | agccatcaag | 240 |
| ggcattcgag | accacttcag | ggccgccgtc | ccgactcgca | acgtggtggt | cattcacact | 300 |
| cagcacgttc | acacactggt | gggcttggag | cacacccacc | tcgtcttgca | gaccggcatc | 360 |
| ttcaaaaagg | tccccgtcga | catctacgtc | ttcaagtccg | gcgtcttcac | cctccttgga | 420 |
| gacggaggct | tcatcaactg | gcatggggt | ggcttcgtac | aggaggtcgc | cggcaagcgt | 480 |
| atccacttcc | gcttgccccc | cggggcgctc | cct | | | 513 |

<210> SEQ ID NO 132
<211> LENGTH: 516
<212> TYPE: DNA
<213> ORGANISM: Artificial Sequence
<220> FEATURE:
<223> OTHER INFORMATION: IPD103 variant

<400> SEQUENCE: 132

| | | | | | |
|---|---|---|---|---|---|
| atggcggaca | aagcagcagc | agcagctaga | gaagctgaag | aagaggtgca | ggagactttg | 60 |
| atggacgaga | ctgaggcggt | ggggacgcac | ctggacttcg | tggcgggctt | ggaggtgcaa | 120 |
| ccccgcaagg | tcatcaccgt | ggaggtggac | gccgctgccg | taatccagca | gatcagagag | 180 |
| atcttccaga | caatggcgcg | tcacttcaac | tctacgaggg | tggtgcggga | tgaagccatc | 240 |
| aagggcattc | gagaccactt | cagggccgcc | gtcccgactc | gcaacgtggt | ggtcattcac | 300 |
| actcagcacg | ttcacacact | ggagggcttg | gagcacacca | acctcgtctt | gcagaccggc | 360 |

-continued

| | | |
|---|---|---|
| atcttcaaaa aggtccccgt cgacatctat gtcttcaagt ccggcgtctt caccaacctt | 420 | |
| ggagacggag gcttcatcaa ctgggcatgg ggtggcttcg tacaggaggt cgccggcaag | 480 | |
| cgtatccact tccgcttgcc ccccggggcg ctccct | 516 | |

<210> SEQ ID NO 133
<211> LENGTH: 513
<212> TYPE: DNA
<213> ORGANISM: Artificial Sequence
<220> FEATURE:
<223> OTHER INFORMATION: IPD103 variant

<400> SEQUENCE: 133

| | | |
|---|---|---|
| atggcggaca aagcagcagc agcagctaga gaagctgaag aagaggtgga gacgacgatg | 60 | |
| gacgagactg aggcggtggg gacgcacctg gacttcgtgg cgggcttgga ggtgcaaccc | 120 | |
| cgcaaggtca tcaccgtgga ggtggacgcc gctgccgtaa tccagcagat cagagagatc | 180 | |
| ttccgaacca tggcaagtca cttcaactcg acgagggtgg tgcgggatga agccatcaag | 240 | |
| ggcattcgag accacttcag ggccgccgtc ccgactcgca acgtggtggt cattcacacc | 300 | |
| cagcacattc acacactgga gggcttggag cacacccacc tcgtcttgca gaccggcctc | 360 | |
| ttcaaaaagg tccccgtcga catctacgtc ttcaagtccg cgtcttcac cctccttgga | 420 | |
| gacggaggct tcatcaactg gcatggggt ggcttcgtac aggaggtcgc cggcaagcgt | 480 | |
| atccacttcc gcttgccccc cggggcgctc cct | 513 | |

<210> SEQ ID NO 134
<211> LENGTH: 516
<212> TYPE: DNA
<213> ORGANISM: Artificial Sequence
<220> FEATURE:
<223> OTHER INFORMATION: IPD103 variant

<400> SEQUENCE: 134

| | | |
|---|---|---|
| atggcggaca aagcagcagc agctagagaa gctgaagaag aggtgcagga gactttgatg | 60 | |
| gacgagactg aggcggtggg gacgcacctg gacttcttgg gcgcggacgt gaagttgcaa | 120 | |
| ccccgcaaca tcatcaccgt ggaggtggac gccgctgccg taatccagca gatcagagag | 180 | |
| atcttccgaa ccatggcaag tcacttcaac tctacgaggg tggtgcggga tgaagccatc | 240 | |
| aagggcattc gagaccactt cagggccgcc gtcccgactc gcaacgtggt ggtcgttcac | 300 | |
| acccagcaca ttcacacact ggagggcttg agcacacca acctcgtctt gcagaccggc | 360 | |
| ctcttcaaaa aggtccccgt cgacatctac gtcttcaagt ccggcgtctt caccctcctt | 420 | |
| ggagacggag gcttcatcaa ctgggcatgg ggtggcttcg tacaggaggt cgccggcaag | 480 | |
| cgtatccact tccgcttgcc ccccggggcg ctccct | 516 | |

<210> SEQ ID NO 135
<211> LENGTH: 513
<212> TYPE: DNA
<213> ORGANISM: Artificial Sequence
<220> FEATURE:
<223> OTHER INFORMATION: IPD103 variant

<400> SEQUENCE: 135

| | | |
|---|---|---|
| atggcggaca aagcagcagc agcagctaga gaagctgaag aagaggtgga gacgacgatg | 60 | |
| gacgagactg aggcggtggg gacgcacctg gacttcgtgg cgggcttgga ggtgcaaccc | 120 | |
| cgcaaggtca tcaccgtgga ggtggacgcc gctgccgtaa tccagcagat cagagagatc | 180 | |
| ttccgaacca tggcaagtca cttcaactcg acgagggtgg tgcgggatga agccatcaag | 240 | |

```
ggcattcgag accacttcag ggccgccgtc ccgactcgca acgtggtggt cgttcacact      300
cagcacgttc acacactgga gggcttggag cacaccaacc tcgtcttgca gaccggcctc      360
ttcaaaaagg tccccgtcga catctatgtc ttcaagtccg gcgtcttcac cctccttgga      420
gacggaggct tcatcaactg gcatgggggt ggcttcgtac aggaggtcgc cggcaagcgt      480
atccacttcc gcttgccccc cggggcgctc cct                                   513

<210> SEQ ID NO 136
<211> LENGTH: 513
<212> TYPE: DNA
<213> ORGANISM: Artificial Sequence
<220> FEATURE:
<223> OTHER INFORMATION: IPD103 variant

<400> SEQUENCE: 136
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactct acgagggtgg tgcgggatga agccatcaag     240
ggcattcgag accacttcag ggccgccgtc ccgactcgca acgtggtggt cgttcacacc     300
cagcacattc acacactgga gggcttggag cacacccacc tcgtcttgca gaccggcatc      360
ttcaaaaagg tccccgtcga catctacgtc ttcaagtccg gcgtcttcac cctccttgga      420
gacggaggct tcatcaactg gcatgggggt ggcttcgtcg accaggtcgt cggcaagcgt      480
atccacttcc gcttgccccc cggggcgctc cct                                   513

<210> SEQ ID NO 137
<211> LENGTH: 513
<212> TYPE: DNA
<213> ORGANISM: Artificial Sequence
<220> FEATURE:
<223> OTHER INFORMATION: IPD103 variant

<400> SEQUENCE: 137
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag ggccgccgtc ccgactcgca acgtggtggt cattcacacc     300
cagcacattc acacactgga gggcttggag cacaccaacc tcgtcttgca gaccggcctc      360
ttcaaaaagg tccccgtcga catctatgtc ttcaagtccg gcgtcttcac cctccttgga      420
gacggaggct tcatcaactg gcatgggggt ggcttcgtcg accaggtcgt cggcaagcgt      480
atccacttcc gcttgccccc cggggcgctc cct                                   513

<210> SEQ ID NO 138
<211> LENGTH: 513
<212> TYPE: DNA
<213> ORGANISM: Artificial Sequence
<220> FEATURE:
<223> OTHER INFORMATION: IPD103 variant

<400> SEQUENCE: 138
atggccgacc cagcaacagc agctagagaa gctgaagaag aggtgcagga gactttgatg      60
```

-continued

```
gacgagactg aggcggtggg gacgcacctg gacttcgtgg cgggcttgga ggtgcaaccc      120
cgcaacatca tcaccgtgga ggtggacgcg gctgccgtaa tccagcagat cagagagatc      180
ttccgaacca tggcaagtca cttcaactcg acgagggtgg tgcgggatga agccatcaag      240
ggcattcgag accacttcag ggccgccgtc ccgactcgca acgtggtggt cattcacacc      300
cagcacattc acacactgga gggcttggag cacaccaacc tcgtcttgca gaccggcatc      360
ttcaaaaagg tccccgtcga catctacgtc ttcaagtccg gcgtcttcac cctccttgga      420
gacggaggct tcatcaactg ggcatggggt ggcttcgtcg accaggtcgt cggcaagcgt      480
atccacttcc gcttgccccc cggggcgctc cct                                   513
```

```
<210> SEQ ID NO 139
<211> LENGTH: 516
<212> TYPE: DNA
<213> ORGANISM: Artificial Sequence
<220> FEATURE:
<223> OTHER INFORMATION: IPD103 variant

<400> SEQUENCE: 139
atggcggaca aagcagcagc agcagctaga gaagctgaag aagaggtgca ggagactttg      60
atggacgaga ctgaggcggt ggggacgcac ctggacttcg tggcgggctt ggaggtgcaa      120
ccccgcaagg tcatcaccgt ggaggtggac gccgctgccg taatccagca gatcagagag      180
atcttccgaa ccatggcaag tcacttcaac tctacgaggg tggtgcggga tgaagccatc      240
aagggcattc gagaccactt cagggccgcc gtcccgactc gcaacgtggt ggtcattcac      300
actcagcacg ttcacacact ggtgggcttg gagcacaccc acctcgtctt gcagaccggc      360
atcttcaaaa aggtccccgt cgacatctac gtcttcaagt ccggcgtctt caccctcctt      420
ggagacggag gcttcatcaa ctgggcatgg ggtggcttcg tcgaccaggt cgtcggcaag      480
cgtatccact tccgcttgcc ccccggggcg ctccct                                516
```

```
<210> SEQ ID NO 140
<211> LENGTH: 516
<212> TYPE: DNA
<213> ORGANISM: Artificial Sequence
<220> FEATURE:
<223> OTHER INFORMATION: IPD103 variant

<400> SEQUENCE: 140
atggcggaca aagcagcagc agcagctaga gaagctgaag aagaggtgca ggagactttg      60
atggacgaga ctgaggcggt ggggacgcac ctggacttcg tggcgggctt ggaggtgcaa      120
ccccgcaagg tcatcaccgt ggaggtggac gccgctgccg taatccagca gatcagagag      180
atcttccaga caatggcgcg tcacttcaac tctacgaggg tggtgcggga tgaagccatc      240
aagggcattc gagaccactt cagggccgcc gtcccgactc gcaacgtggt ggtcgttcac      300
actcagcacg ttcacacact ggtgggcttg gagcacaccc acctcgtctt gcagaccggc      360
atcttcaaaa aggtccccgt cgacatctac gtcttcaagt ccggcgtctt caccaacctt      420
ggagacggag gcttcatcaa ctgggcatgg ggtggcttcg tacaggaggt cgccggcaag      480
cgtatccact tccgcttgcc ccccggggcg ctccct                                516
```

```
<210> SEQ ID NO 141
<211> LENGTH: 513
<212> TYPE: DNA
<213> ORGANISM: Artificial Sequence
<220> FEATURE:
<223> OTHER INFORMATION: IPD103 variant
```

<400> SEQUENCE: 141

```
atggccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag ggccgccgtc ccgactcgca acgtggtggt cgttcacact     300
cagcacgttc acacactgga gggcttggag cacaccaacc tcgtcttgca gaccggcatc     360
ttcaaaaagg tccccgtcga catctatgtc ttcaagtccg gcgtcttcac cctccttgga     420
gacggaggct tcatcaactg gcatggggt ggcttcgtcg accaggtcgt cggcaagcgt      480
atccacttcc gcttgccccc cggggcgctc cct                                  513
```

<210> SEQ ID NO 142
<211> LENGTH: 516
<212> TYPE: DNA
<213> ORGANISM: Artificial Sequence
<220> FEATURE:
<223> OTHER INFORMATION: IPD103 variant

<400> SEQUENCE: 142

```
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gcggctgccg taatccagca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcgttcac     300
acccagcaca ttcacacact ggagggcttg agcacaccaa cctcgtcttg cagaccggc     360
ctcttcaaaa aggtccccgt cgacatctac gtcttcaagt ccggcgtctt caccctcctt     420
ggagacggag gcttcatcaa ctgggcatgg ggtggcttcg tacaggaggt cgccggcaag     480
cgtatccact ccgcttgcc ccccggggcg ctccct                                516
```

<210> SEQ ID NO 143
<211> LENGTH: 516
<212> TYPE: DNA
<213> ORGANISM: Artificial Sequence
<220> FEATURE:
<223> OTHER INFORMATION: IPD103 variant

<400> SEQUENCE: 143

```
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gcggctgccg taatccaaca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcattcac     300
actcagcacg ttcacacact ggtgggcttg agcacaccc acctcgtctt gcagaccggc      360
ctcttcaaaa aggtccccgt cgacatctac gtcttcaagt ccggcgtctt caccctcctt     420
ggagacggag gcttcatcaa ctgggcatgg ggtggcttcg tacaggaggt cgccggcaag     480
cgtatccact ccgcttgcc ccccggggcg ctccct                                516
```

<210> SEQ ID NO 144

<211> LENGTH: 516
<212> TYPE: DNA
<213> ORGANISM: Artificial Sequence
<220> FEATURE:
<223> OTHER INFORMATION: IPD103 variant

<400> SEQUENCE: 144

| | |
|---|---|
| atggcggaca aagcagcagc agcagctaga gaagctgaag aagaggtgga gacgacgatg | 60 |
| gacgagactg aggcggtggg gacgcacctg gacttcttgg gcgcggacgt gaagttgcaa | 120 |
| ccccgcaaca tcatcaccgt ggaggtggac gcggctgccg taatccagca gatcagagag | 180 |
| atcttccaga caatggcgcg tcacttcaac tcgacgaggg tggtgcggga tgaagccatc | 240 |
| aagggcattc gagaccactt cagggccgcc gtcccgactc gcaacgtggt ggtcgttcac | 300 |
| actcagcacg ttcacacact ggtgggcttg agcacacccc acctcgtctt gcagaccggc | 360 |
| ctcttcaaaa aggtccccgt cgacatctac gtcttcaagt ccggcgtctt caccctcctt | 420 |
| ggagacggag gcttcatcaa ctgggcatgg ggtggcttcg tcgaccaggt cgccggcaag | 480 |
| cgtatccact tccgcttgcc ccccggggcg ctccct | 516 |

<210> SEQ ID NO 145
<211> LENGTH: 516
<212> TYPE: DNA
<213> ORGANISM: Artificial Sequence
<220> FEATURE:
<223> OTHER INFORMATION: IPD103 variant

<400> SEQUENCE: 145

| | |
|---|---|
| atggccgacc cagcaacagc agctagagaa gctgaagaag aggtgcagga gactttgatg | 60 |
| gacgagactg aggcggtggg gacgcacctg gacttcttgg gcgcggacgt gaagttgcaa | 120 |
| ccccgcaaca tcatcaccgt ggaggtggac gcggctgccg taatccagca gatcagagag | 180 |
| atcttccgaa ccatggcaag tcacttcaac tcgacgaggg tggtgcggga tgaagccatc | 240 |
| aagggcattc gagaccactt cagggccgcc gtcccgactc gcaacgtggt ggtcgttcac | 300 |
| acccagcaca ttcacacact ggagggcttg agcacacccc acctcgtctt gcagaccggc | 360 |
| ctcttcaaaa aggtccccgt cgacatctac gtcttcaagt ccggcgtctt caccctcctt | 420 |
| ggagacggag gcttcatcaa ctgggcatgg ggtggcttcg tacaggaggt cgccggcaag | 480 |
| cgtatccact tccgcttgcc ccccggggcg ctccct | 516 |

<210> SEQ ID NO 146
<211> LENGTH: 510
<212> TYPE: DNA
<213> ORGANISM: Artificial Sequence
<220> FEATURE:
<223> OTHER INFORMATION: IPD103 variant

<400> SEQUENCE: 146

| | |
|---|---|
| atggccgacc cagcaacagc agctagagaa gctgaagaag aggtggagac gacgatggac | 60 |
| gagactgagg cggtggggac gcacctggac ttcgtggcgg gcttggaggt gcaaccccgc | 120 |
| aaggtcatca ccgtggaggt ggacgccgct gccgtaatcc agcagatcag agagatcttc | 180 |
| cgaaccatgg caagtcactt caactcgacg agggtggtgc gggatgaagc catcaagggc | 240 |
| attcgagacc acttcagggc cgccgtcccg actcgcaacg tggtggtcat tcacactcag | 300 |
| cacattcaca cactggaggg cttgagcaca ccaacctcg tcttgcagac cggcctcttc | 360 |
| aaaaaggtcc ccgtcgacat ctatgtcttc aagtccggcg tcttcaccct ccttggagac | 420 |
| ggaggcttca tcaactgggc atggggtggc ttcgtacagg aggtcgccgg caagcgtatc | 480 | cacttccgct tgcccccggg ggcgctccct                                          510

<210> SEQ ID NO 147
<211> LENGTH: 513
<212> TYPE: DNA
<213> ORGANISM: Artificial Sequence
<220> FEATURE:
<223> OTHER INFORMATION: IPD103 variant

<400> SEQUENCE: 147
atggcggaca aagcagcagc agcagctaga gaagctgaag aagaggtgga gacgacgatg          60
gacgagactg aggcggtggg gacgcacctg gacttcgtgg cgggcttgga ggtgcaaccc         120
cgcaaggtca tcaccgtgga ggtggacgcc gctgccgtaa tccaacagat cagagagatc         180
ttccagacaa tggcgcgtca cttcaactct acgagggtgg tgcggatgaa agccatcaag         240
ggcattcgag accacttcag gccgccgtc ccgactcgca acgtggtggt cattcacact          300
cagcacgttc acacactggt gggcttggag cacaccacc tcgtcttgca gaccggcctc          360
ttcaaaaagg tccccgtcga catctatgtc ttcaagtccg gcgtcttcac caaccttgga         420
gacggaggct tcatcaactg gcatggggt ggcttcgtcg accaggtcgt cggcaagcgt          480
atccacttcc gcttgccccc cggggcgctc cct                                      513

<210> SEQ ID NO 148
<211> LENGTH: 513
<212> TYPE: DNA
<213> ORGANISM: Artificial Sequence
<220> FEATURE:
<223> OTHER INFORMATION: IPD103 variant
<220> FEATURE:
<221> NAME/KEY: misc_feature
<222> LOCATION: (127)..(127)
<223> OTHER INFORMATION: n is a, c, g, or t

<400> SEQUENCE: 148
atggcggaca aagcagcagc agcagctaga gaagctgaag aagaggtgga gacgacgatg          60
gacgagactg aggcggtggg gacgcacctg gacttcgtgg cgggcttgga ggtgcaaccc         120
cgcaagntca tcaccgtgga ggtggacgcc gctgccgtaa tccagcagat cagagagatc         180
ttccgaacca tggcaagtca cttcaactcg acgagggtgg tgcggatgaa agccatcaag         240
ggcattcgag accacttcag gccgccgtc ccgactcgca acgtggtggt cgttcacacc          300
cagcacattc acacactggt gggcttggag cacaccaacc tcgtcttgca gaccggcatc         360
ttcaaaaagg tccccgtcga catctatgtc ttcaagtccg gcgtcttcac catccttgga         420
gacggaggct tcatcaactg gcatggggt ggcttcgtac aggaggtcgt cggcaagcgt          480
atccacttcc gcttgccccc cggggcgctc cct                                      513

<210> SEQ ID NO 149
<211> LENGTH: 516
<212> TYPE: DNA
<213> ORGANISM: Artificial Sequence
<220> FEATURE:
<223> OTHER INFORMATION: IPD103 variant

<400> SEQUENCE: 149
atggcggaca aagcagcagc agcagctaga gaagctgaag aagaggtgca ggagactttg          60
atggacgaga ctgaggcggt ggggacgcac ctggacttcg tggcgggctt ggaggtgcaa         120
ccccgcaagg tcatcaccgt ggaggtggac gcggctgccg taatccaaca gatcagagag         180

```
atcttccgaa ccatggcaag tcacttcaac tcgacgaggg tggtgcggga tgaagccatc      240
aagggcattc gagaccactt cagggccgcc gtcccgactc gcaacgtggt ggtcgttcac      300
acccagcaca ttcacacact ggagggcttg gagcacacca acctcgtctt gcagaccggc      360
atcttcaaaa aggtccccgt cgacatctac gtcttcaagt ccggcgtctt caccctcctt      420
ggagacggag gcttcatcaa ctgggcatgg ggtggcttcg tacaggaggt cgccggcaag      480
cgtatccact ccgcttgcc ccccggggcg ctccct                                  516
```

<210> SEQ ID NO 150
<211> LENGTH: 513
<212> TYPE: DNA
<213> ORGANISM: Artificial Sequence
<220> FEATURE:
<223> OTHER INFORMATION: IPD103 variant

<400> SEQUENCE: 150

```
atggccgacc cagcaacagc agctagagaa gctgaagaag aggtgcagga gactttgatg       60
gacgagactg aggcggtggg gacgcacctg gacttcgtgg cgggcttgga ggtgcaaccc      120
cgcaaggtca tcaccgtgga ggtggacgcc gctgccgtaa tccagcagat cagagagatc      180
ttccgaacca tggcaagtca cttcaactcg acgaggtgg tgcgggatga agccatcaag       240
ggcattcgag accacttcag ggccgccgtc ccgactcgca acgtggtggt cattcacact      300
cagcacgttc acacactggt gggcttggag cacaccaacc tcgtcttgca gaccggcctc      360
ttcaaaaagg tccccgtcga catctacgtc ttcaagtccg gcgtcttcac caaccttgga      420
gacggaggct tcatcaactg gcatggggt ggcttcgtac aggaggtcgc cggcaagcgt      480
atccacttcc gcttgccccc cggggcgctc cct                                   513
```

<210> SEQ ID NO 151
<211> LENGTH: 510
<212> TYPE: DNA
<213> ORGANISM: Artificial Sequence
<220> FEATURE:
<223> OTHER INFORMATION: IPD103 variant
<220> FEATURE:
<221> NAME/KEY: misc_feature
<222> LOCATION: (32)..(32)
<223> OTHER INFORMATION: n is a, c, g, or t

<400> SEQUENCE: 151

```
atggccgacc cagcaacagc agctagagaa gntgaagaag aggtggagac gacgatggac       60
gagactgagg cggtggggac gcacctggac ttcgtggcgg gcttggaggt gcaaccccgc      120
aaggtcatca ccgtggaggt ggacgccgct gccgtaatcc agcagatcag agagatcttc      180
cgaaccatgg caagtcactt caactcgacg agggtggtgc gggatgaagc catcaagggc      240
attcgagacc acttcagggc cgccgtcccg actcgcaacg tggtggtcgt tcacacccag      300
cacattcaca cactggtggg cttggagcac acccacctcg tcttgcagac cggcatcttc      360
aaaaaggtcc ccgtcgacat ttatgtcttc aagtccggcg tcttcaccct ccttggagac      420
ggaggcttca tcaactgggc atggggtggc ttcgtcgacc aggtcgtcgg caagcgtatc      480
cacttccgct tgccccccgg ggcgctccct                                        510
```

<210> SEQ ID NO 152
<211> LENGTH: 513
<212> TYPE: DNA
<213> ORGANISM: Artificial Sequence
<220> FEATURE:
<223> OTHER INFORMATION: IPD103 variant

<400> SEQUENCE: 152

```
atggccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaaggtca tcaccgtgga ggtggacgcg gctgccgtaa tccaacagat cagagagatc     180
ttccagacaa tggcgcgtca cttcaactcg acgaggtgg tgcgggatga agccatcaag      240
ggcattcgag accacttcag ggccgccgtc ccgactcgca acgtggtggt cgttcacact     300
cagcacgttc acacactgga gggcttggag cacacccacc tcgtcttgca gaccggcatc     360
ttcaaaaagg tccccgtcga catctacgtc ttcaagtccg cgtcttcac cctccttgga      420
gacggaggct tcatcaactg gcatgggggt ggcttcgtcg accaggtcgt cggcaagcgt     480
atccacttcc gcttgccccc cggggcgctc cct                                  513
```

<210> SEQ ID NO 153
<211> LENGTH: 516
<212> TYPE: DNA
<213> ORGANISM: Artificial Sequence
<220> FEATURE:
<223> OTHER INFORMATION: IPD103 variant

<400> SEQUENCE: 153

```
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gccgctgccg taatccagca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcgttcac     300
acccagcaca ttcacacact ggagggcttg agcacaccca acctcgtctt gcagaccggc     360
ctcttcaaaa aggtccccgt cgacatctac gtcttcaagt ccggcgtctt caccctcctt     420
ggagacggag gcttcatcaa ctgggcatgg ggtggcttcg tcgaccaggt cgtcggcaag     480
cgtatccact ccgcttgcc cccgggcg ctccct                                  516
```

<210> SEQ ID NO 154
<211> LENGTH: 516
<212> TYPE: DNA
<213> ORGANISM: Artificial Sequence
<220> FEATURE:
<223> OTHER INFORMATION: IPD103 variant

<400> SEQUENCE: 154

```
atggcggaca aagcagcagc agcagctaga gaagctgaag aagaggtgca ggagactttg      60
atggacgaga ctgaggcggt ggggacgcac ctggacttcg tggcgggctt ggaggtgcaa     120
ccccgcaaca tcatcaccgt ggaggtggac gccgctgccg taatccagca gatcagagag     180
atcttccgaa ccatggcaag tcacttcaac tctacgaggg tggtgcggga tgaagccatc     240
aagggcattc gagaccactt cagggccgcc gtcccgactc gcaacgtggt ggtcgttcac     300
acccagcaca ttcacacact ggtgggcttg agcacaccc acctcgtctt gcagaccggc      360
ctcttcaaaa aggtccccgt cgacatctac gtcttcaagt ccggcgtctt caccctcctt     420
ggagacggag gcttcatcaa ctgggcatgg ggtggcttcg tacaggaggt cgccggcaag     480
cgtatccact ccgcttgcc cccgggcg ctccct                                  516
```

<210> SEQ ID NO 155

<211> LENGTH: 513
<212> TYPE: DNA
<213> ORGANISM: Artificial Sequence
<220> FEATURE:
<223> OTHER INFORMATION: IPD103 variant

<400> SEQUENCE: 155

```
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccaacagat cagagagatc     180
ttccagacaa tggcgcgtca cttcaactcg acgaggtgg tgcgggatga agccatcaag     240
ggcattcgag accacttcag gccgccgtc ccgactcgca acgtggtggt cgttcacacc      300
cagcacattc acacactgga gggcttggag cacaccaacc tcgtcttgca gaccggcctc     360
ttcaaaaagg tccccgtcga catctacgtc ttcaagtccg gcgtcttcac caaccttgga     420
gacggaggct tcatcaactg gcatggggt ggcttcgtcg accaggtcgt cggcaagcgt      480
atccacttcc gcttgccccc cggggcgctc cct                                  513
```

<210> SEQ ID NO 156
<211> LENGTH: 516
<212> TYPE: DNA
<213> ORGANISM: Artificial Sequence
<220> FEATURE:
<223> OTHER INFORMATION: IPD103 variant

<400> SEQUENCE: 156

```
atggcggaca aagcagcagc agcagctaga gaagctgaag aagaggtgca ggagactttg      60
atggacgaga ctgaggcggt ggggacgcac ctggacttcg tggcgggctt ggaggtgcaa     120
ccccgcaagg tcatcaccgt ggaggtggac gccgctgccg taatccagca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcattcac      300
actcagcacg ttcacacact ggtgggcttg agcacaccc acctcgtctt gcagaccggc      360
ctcttcaaaa aggtccccgt cgacatctac gtcttcaagt ccggcgtctt caccctcctt     420
ggagacggag gcttcatcaa ctgggcatgg ggtggcttcg tacaggaggt cgtcggcaag     480
cgtatccact ccgcttgcc cccggggcg ctccct                                 516
```

<210> SEQ ID NO 157
<211> LENGTH: 513
<212> TYPE: DNA
<213> ORGANISM: Artificial Sequence
<220> FEATURE:
<223> OTHER INFORMATION: IPD103 variant

<400> SEQUENCE: 157

```
atggccgacc agcaacagc agctagaaa gctgaagaag aggtgcagga ctttgatg         60
gacgagactg aggcggtggg gacgcacctg gacttcgtgg cgggcttgga ggtgcaaccc     120
cgcaaggtca tcaccgtgga ggtggacgcg gctgccgtaa tccaacagat cagagagatc     180
ttccagacaa tggcgcgtca cttcaactct acgaggtgg tgcgggatga agccatcaag      240
ggcattcgag accacttcag gccgccgtc ccgactcgca acgtggtggt cgttcacact      300
cagcacgttc acacactggt gggcttggag cacaccacc tcgtcttgca gaccggcatt      360
ttcaaaaagg tccccgtcga catctacgtc ttcaagtccg gcgtcttcac cctccttgga     420
gacggaggct tcatcaactg gcatggggt ggcttcgtac aggaggtcgc cggcaagcgt      480
```

```
atccacttcc gcttgccccc cggggcgctc cct                                  513
```

<210> SEQ ID NO 158
<211> LENGTH: 519
<212> TYPE: DNA
<213> ORGANISM: Artificial Sequence
<220> FEATURE:
<223> OTHER INFORMATION: IPD103 variant

<400> SEQUENCE: 158

```
atggccgaca aagcagcagc agcagctaga gaagctgaag aagaggtgga gacgacgatg     60
gacgagactg aggcggtggg gacgcacctg gacttcttgg gcgcggacgt gaagttgcaa    120
ccccgcaaca tcatcaccgt ggaggtggac gcggctgccg taatccaaca gatcagagag    180
atcttccgaa ccacggcaag tcacttcaac tcgacgaggg tggtgcggga tgaagccatc    240
aagggcattc gagaccactt cagggccgcc gtcccgactc gcaacgtggt ggtcattcac    300
tcccagcaca ttcacacatt ggagggcttg gagcacaccc acctcgtctt gcagaccggc    360
atcttcaaaa aggtccccgt cgacatgtac gtcttcaagt ccggcgtctt caccaacctt    420
ggagacggag gcttcatcaa ctgggcatgg ggtggcttcg tcgaccaggt cgtcggcaag    480
cgtatccact ccgcttgcc ccccggggcg ctcccccga                            519
```

<210> SEQ ID NO 159
<211> LENGTH: 513
<212> TYPE: DNA
<213> ORGANISM: Artificial Sequence
<220> FEATURE:
<223> OTHER INFORMATION: IPD103 variant

<400> SEQUENCE: 159

```
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaaggtca tcaccgtgga ggtggacgcc gctgccgtaa tccaacagat cagagagatc    180
ttccagacaa tggcgcgtca cttcaactcg acgaggtgg tgcgggatga agccatcaag    240
ggcattcgag accacttcag gccgccgtc ccgactcgca acgtggtggt cgttcacacc    300
cagcacgttc acacactggt gggcttggag cacacccacc tcgtcttgca gaccggcctc    360
ttcaaaaagg tccccgtcga catctacgtc ttcaagtccg gcgtcttcac cctccttgga    420
gacggaggct tcatcaactg gcatggggt ggcttcgtac aggaggtcgc cggcaagcgt    480
atccacttcc gcttgccccc cggggcgctc cct                                  513
```

<210> SEQ ID NO 160
<211> LENGTH: 516
<212> TYPE: DNA
<213> ORGANISM: Artificial Sequence
<220> FEATURE:
<223> OTHER INFORMATION: IPD103 variant

<400> SEQUENCE: 160

```
atggccgacc cagcaacagc agctagagaa gctgaagaag aggtgcagga gactttgatg     60
gacgagactg aggcggtggg gacgcacctg gacttcttgg gcgcggacgt gaagttgcaa    120
ccccgcaaca tcatcaccgt ggaggtggac gccgctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
```

```
actcagcacg ttcacacact ggtgggcttg agcacacca acctcgtctt gcagaccggc    360
ctcttcaaaa aggtccccgt cgacatctac gtcttcaagt ccggcgtctt caccctcctt    420
ggagacggag gcttcatcaa ctgggcatgg ggtggcttcg tacaggaggt cgccggcaag    480
cgtatccact ccgcttgcc ccccggggcg ctccct                               516
```

<210> SEQ ID NO 161
<211> LENGTH: 513
<212> TYPE: DNA
<213> ORGANISM: Artificial Sequence
<220> FEATURE:
<223> OTHER INFORMATION: IPD103 variant

<400> SEQUENCE: 161

```
atggccgacc cagcaacagc agctagagaa gctgaagaag aggtggagac gacgatggac    60
gagactgagg cggtggggac gcacctggac ttcttgggcg cggacgtgaa gttgcaaccc   120
cgcaacatca tcaccgtgga ggtggacgcg gctgccgtaa tccatcagat cagagagatc   180
ttccagacaa tggcgcgtca cttcaactct acgagggtgg tgcggatgaa agccatcaag   240
ggcattcgag accacttcag ggccgccgtc ccgactcgca acgtggtggt cgttcactcc   300
cagcacattc acacattggt gggcttggag cacacccacc tcgtcttgca gaccggcctc   360
ttcaaaaagg tccccgtcga catgtacgta ttcaagtccg gcgtcttcac caaccttgga   420
gacggaggct tcatcaactg gcatgggg gccttcgtac aggaggtcgc cggcaagcgt    480
atccacttcc gcttgccccc cggggcgctc cct                                513
```

<210> SEQ ID NO 162
<211> LENGTH: 516
<212> TYPE: DNA
<213> ORGANISM: Artificial Sequence
<220> FEATURE:
<223> OTHER INFORMATION: IPD103 variant

<400> SEQUENCE: 162

```
atggcggacc cagcaacagc agctagagaa gatgaagaag aggtgcagga gactttgatg    60
gacgagactg aggcggtggg gacgcacctg gacttcttgg gcgcggacgt gaagttgcaa   120
ccccgcaaca tcatcaccgt ggaggtggac gcggctgccg taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggagggcttg agcacaccc acctcgtctt gcagaccggc   360
ctcttcaaaa aggtccccgt cgacatctac gtcttcaagt ccggcgtctt caccctcctt    420
ggagacggag gcttcatcaa ctgggcatgg ggtggtttcg tacaggaggt cgccggcaag    480
cgtatccact ccgcttgcc ccccggggcg ctccct                               516
```

<210> SEQ ID NO 163
<211> LENGTH: 513
<212> TYPE: DNA
<213> ORGANISM: Artificial Sequence
<220> FEATURE:
<223> OTHER INFORMATION: IPD103 variant

<400> SEQUENCE: 163

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaacatca tcaccgtgga ggtggacgcc gctgccgtaa tccagcagat cagagagatc   180
```

```
ttccgaacca tggcaagtca cttcaactcg acgagggtgg tgcgggatga agccatcaag      240
ggcattcgag accacttcag ggccgccgtc ccgactcgca acgtggtggt cgttcacacc      300
cagcacattc acacactgga gggcttggag cacacccacc tcgtcttgca gaccggcatc      360
ttcaaaaagg tccccgtcga catctatgtc ttcaagtccg gcgtcttcac cctccttgga      420
gacggaggct tcatcaactg gcatggggt ggcttcgtac aggaggtcgc cggcaagcgt       480
atccacttcc gcttgccccc cggggcgctc cct                                   513
```

<210> SEQ ID NO 164
<211> LENGTH: 516
<212> TYPE: DNA
<213> ORGANISM: Artificial Sequence
<220> FEATURE:
<223> OTHER INFORMATION: IPD103 variant

<400> SEQUENCE: 164

```
atggcggaca aagcagcaac agcagctaga gaagctgaag aagaggtgca ggagactttg       60
atggacgaga ctgaggcggt ggggacgcac ctggacttcg tggcgggctt ggaggtgcaa      120
ccccgcaaca tcatcaccgt ggaggtggac gccgctgccg taatccaaca gatcagagag      180
atcttccgga ccatggcaag tcacttcaac tctacgaggg tggtgcggga tgaagccatc      240
aagggcattc gagaccactt cagggccgcc gtcccgactc gcaacgtggt ggtcgttcac      300
acccagcaca ttcacacact ggagggcttg agcacaccca cctcgtcttg cagaccggc      360 atcttcaaaa aggtccccgt cgacatctac gtcttcaagt ccggcgtctt caccctcctt      420
ggagacggag gcttcatcaa ctgggcatgg ggtggcttcg tacagcaggt cgtcggcaag      480
cgtatccact ccgcttgcc ccccggggcg ctccct                                 516
```

<210> SEQ ID NO 165
<211> LENGTH: 516
<212> TYPE: DNA
<213> ORGANISM: Artificial Sequence
<220> FEATURE:
<223> OTHER INFORMATION: IPD103 variant

<400> SEQUENCE: 165

```
atggcggaca aagcagcagc agcagctaga gaagctgaag aagaggtgga gacgacgatg       60
gacgagactg aggcggtggg gacgcacctg gacttcttgg gcgcggacgt gaagttgcaa      120
ccccgcaagg tcatcaccgt ggaggtggac gccgctgccg taatccaaca gatcagagag      180
atcttccaga caatggcgcg tcacttcaac tcgacgaggg tggtgcggga tgaagccatc      240
aagggcattc gagaccactt cagggccgcc gtcccgactc gcaacgtggt ggtcattcac      300
actcagcaca ttcacacact ggagggcttg agcacaccca cctcgtcttg cagaccggc      360 ctcttcaaaa aggtccccgt cgacatctac gtcttcaagt ccggcgtctt caccctcctt      420
ggagacggag gcttcatcaa ctgggcatgg ggtggcttcg tcgacgaggt cgtcggcaag      480
cgtatccact ccgcttgcc ccccggggcg ctccct                                 516
```

<210> SEQ ID NO 166
<211> LENGTH: 519
<212> TYPE: DNA
<213> ORGANISM: Artificial Sequence
<220> FEATURE:
<223> OTHER INFORMATION: IPD103 variant

<400> SEQUENCE: 166

```
atggcggaca aagcagcagc agcagctaga gaagctgaag aagaggtgca ggagactttg      60
atggacgaga ctgaggcggt ggggacgcac ctggacttct tgggcgcgga cgtgaagttg     120
caaccccgca acatcatcac cgtggaggtg gacgcggctg ccgtaatcca gcagatcaga     180
gagatcttcc gaaccatggc aagtcacttc aactcgacga gggtggtgcg ggatgaagcc     240
atcaagggca ttcgagacca cttcagggcc gccgtcccga ctcgcaacgt ggtggtcatt     300
cacactcagc acgttcacac actggtgggc ttggagcaca cccacctcgt cttgctgacc     360
ggcatcttca aaaggtccc cgtcgacatc tatgtcttca agtccggcgt cttcaccaac      420
cttggagacg gaggcttcat caactgggca tggggtggct tcgtacagga ggtcgccggc     480
aagcgtatcc acttccgctt gcccccccggg gcgctccct                           519
```

<210> SEQ ID NO 167
<211> LENGTH: 516
<212> TYPE: DNA
<213> ORGANISM: Artificial Sequence
<220> FEATURE:
<223> OTHER INFORMATION: IPD103 variant

<400> SEQUENCE: 167

```
atggcggaca aagcagcagc agcagctaga gaagctgaag aagaggtgca ggagactttg      60
atggacgaga ctgaggcggt ggggacgcac ctggacttcg tggcgggctt ggaggtgcaa     120
ccccgcaaca tcatcaccgt ggaggtggac gcggctgccg taatccaaca gatcagagag     180
atcttccaga caatggcgcg tcacttcaac tcgacgaggg tggtgcggga tgaagccatc     240
aagggcattc gagaccactt cagggccgcc gtcccgactc gcaacgtggt ggtcattcac     300
actcagcacg ttcacacact ggtgggcttg agcacaccc acctcgtctt gcagaccggc     360
atcttcaaaa aggtccccgt cgacatctat gtcttcaagt ccggcgtctt caccaacctt     420
ggagacggag gcttcatcaa ctgggcatgg gtggcttcg tacaggaggt cgccggcaag     480
cgtatccact tccgcttgcc cccggggcg ctccct                                516
```

<210> SEQ ID NO 168
<211> LENGTH: 513
<212> TYPE: DNA
<213> ORGANISM: Artificial Sequence
<220> FEATURE:
<223> OTHER INFORMATION: IPD103 variant

<400> SEQUENCE: 168

```
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag gccgccgtc ccgactcgca acgtggtggt cattcacact      300
cagcacgttc acacactggt gggcttggag cacacccacc tcgtcttgca gaccggcctc     360
ttcaaaaagg tccccgtcga catctatgtc ttcaagtccg gcgtcttcac cctccttgga     420
gacggaggct tcatcaactg gcatggggt ggcttcgtcg accaggtcgt cggcaagcgt      480
atccacttcc gcttgccccc cggggcgctc cct                                  513
```

<210> SEQ ID NO 169
<211> LENGTH: 516
<212> TYPE: DNA
<213> ORGANISM: Artificial Sequence

```
<220> FEATURE:
<223> OTHER INFORMATION: IPD103 variant

<400> SEQUENCE: 169
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gccgctgccg taatccagca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcgttcac     300
acccagcaca ttcacacact ggagggcttg gagcacacca acctcgtctt gcagaccggc     360
ctcttcaaaa aggtccccgt cgacatctac gtcttcaagt ccggcgtctt caccctcctt     420
ggagacggag gcttcatcaa ctgggcatgg ggtggcttcg tcgaccaggt cgtcggcaag     480
cgtatccact tccgcttgcc ccccggggcg ctccct                               516

<210> SEQ ID NO 170
<211> LENGTH: 516
<212> TYPE: DNA
<213> ORGANISM: Artificial Sequence
<220> FEATURE:
<223> OTHER INFORMATION: IPD103 variant

<400> SEQUENCE: 170
atggcggaca aagcagcagc agcagctaga gaagctgaag aagaggtgca ggagactttg      60
atggacgaga ctgaggcggt ggggacgcac ctggacttcg tggcgggctt ggaggtgcaa     120
ccccgcaaca tcatcaccgt ggaggtggac gcggctgccg taatccaaca gatcagagag     180
atcttccgaa ccatggcaag tcacttcaac tctacgaggg tggtgcggga tgaagccatc     240
aagggcattc gagaccactt cagggccgcc gtcccgactc gcaacgtggt ggtcattcac     300
acccagcaca ttcacacact ggtgggcttg gagcacacca acctcgtctt gcagaccggc     360
ctcttcaaaa aggtccccgt cgacatctat gtcttcaagt ccggcgtctt caccaacctt     420
ggagacggag gcttcatcaa ctgggcatgg ggtggcttcg tcgaccaggt cgtcggcaag     480
cgtatccact tccgcttgcc ccccggggcg ctccct                               516

<210> SEQ ID NO 171
<211> LENGTH: 516
<212> TYPE: DNA
<213> ORGANISM: Artificial Sequence
<220> FEATURE:
<223> OTHER INFORMATION: IPD103 variant

<400> SEQUENCE: 171
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gccgctgccg taatccaaca gatcagagag     180
atcttccaga caatggcgcg tcacttcaac tctacgaggg tggtgcggga tgaagccatc     240
aagggcattc gagaccactt cagggccgcc gtcccgactc gcaacgtggt ggtcgttcac     300
acccagcacg ttcacacact ggagggcttg gagcacacca acctcgtctt gcagaccggc     360
atcttcaaaa aggtccccgt cgacatctat gtcttcaagt ccggcgtctt caccaacctt     420
ggagacggag gcttcatcaa ctgggcatgg ggtggcttcg tacaggaggt cgccggcaag     480
cgtatccact tccgcttgcc ccccggggcg ctccct                               516
```

<210> SEQ ID NO 172
<211> LENGTH: 513
<212> TYPE: DNA
<213> ORGANISM: Artificial Sequence
<220> FEATURE:
<223> OTHER INFORMATION: IPD103 variant

<400> SEQUENCE: 172

```
atggccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag gccgccgtc ccgactcgca acgtggtggt cgttcacacc     300
cagcacattc acacactgga gggcttggag cacacccacc tcgtcttgca gaccggcatc     360
ttcaaaaagg tccccgtcga catctacgtc ttcaagtccg gcgtcttcac caaccttgga     420
gacggaggct tcatcaactg gcatgggggt ggcttcgtcg accaggtcgt cggcaagcgt     480
atccacttcc gcttgcccc cggggcgctc cct                                    513
```

<210> SEQ ID NO 173
<211> LENGTH: 516
<212> TYPE: DNA
<213> ORGANISM: Artificial Sequence
<220> FEATURE:
<223> OTHER INFORMATION: IPD103 variant

<400> SEQUENCE: 173

```
atggcggaca aagcagcagc agcagctaga gaagctgaag aagaggtgca ggagactttg      60
atggacgaga ctgaggcggt ggggacgcac ctggacttcg tggcgggctt ggaggtgcaa     120
ccccgcaagg tcatcaccgt ggaggtggac gccgctgccg taatccagca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcgttcac     300
acccagcaca ttcacacact ggtgggcttg agcacaccc acctcgtctt gcagaccggc     360
ctcttcaaaa aggtccccgt cgacatctac gtcttcaagt ccggcgtctt caccctcctt     420
ggagacggag gcttcatcaa ctgggcatgg ggtggcttcg tacaggaggt cgccggcaag     480
cgtatccact tccgcttgcc ccccgggggcg ctccct                              516
```

<210> SEQ ID NO 174
<211> LENGTH: 510
<212> TYPE: DNA
<213> ORGANISM: Artificial Sequence
<220> FEATURE:
<223> OTHER INFORMATION: IPD103 variant

<400> SEQUENCE: 174

```
atggccgacc cagcaacagc agctagagaa gctgaagaag aggtggagac gacgatggac      60
gagactgagg cggtggggac gcacctggac ttcgtggcgg gcttggaggt gcaaccccgc     120
aaggtcatca ccgtggaggt ggacgccgct gccgtaatcc agcagatcag agagatcttc     180
gaaccatgg caagtcactt caactcgacg agggtggtgc gggatgaagc catcaagggc     240
attcgagacc acttcagggc cgccgtcccg actcgcaacg tggtggtcgt tcacacccag     300
cacattcaca cactgagggg cttggaacac accaacctcg tcttgcagac cggcctcttc     360
aaaaaggtcc ccgtcgacat ctacgtcttc aagtccggcg tcttcaccaa ccttggagac     420
```

```
ggaggcttca tcaactgggc atggggtggc ttcgtcgacc aggtcgtcgg caagcgtatc    480
cacttccgct tgccccccgg ggcgctccct                                     510
```

<210> SEQ ID NO 175
<211> LENGTH: 513
<212> TYPE: DNA
<213> ORGANISM: Artificial Sequence
<220> FEATURE:
<223> OTHER INFORMATION: IPD103 variant

<400> SEQUENCE: 175

```
atggccgacc cagcaacagc agctagagaa gctgaagaag aggtgcagga gactttgatg     60
gacgagactg aggcggtggg gacgcacctg gacttcgtgg cgggcttgga ggtgcaaccc    120
cgcaacatca tcaccgtgga ggtggacgcg gctgccgtaa tccaacagat cagagagatc    180
ttccagacaa tggcgcgtca cttcaactct acgagggtgg tgcgggatga agccatcaag    240
ggcattcgag accacttcag gccgccgtc ccgactcgca acgtggtggt cattcacgcc     300
cagcacattc acacactgga gggcttggag cacaccaacc tcgtcttgca gaccggcatc    360
ttcaaaaagg tccccgtcga catctacgtc ttcaagtccg gcgtcttcac cctccttgga    420
gacggaggct tcatcaactg gcatggggt ggcttcgtac aggaggtcgc cggcaagcgt     480
atccacttcc gcttgccccc cggggcgctc cct                                 513
```

<210> SEQ ID NO 176
<211> LENGTH: 519
<212> TYPE: DNA
<213> ORGANISM: Artificial Sequence
<220> FEATURE:
<223> OTHER INFORMATION: IPD103 variant

<400> SEQUENCE: 176

```
atggcggaca aagcagcagc agcagctaga gaagctgaag aagaggtgca ggagactttg     60
atggacgaga ctgaggcggt ggggacgcac ctggacttct gggcgcgga cgtgaagttg     120 caaccccgca acatcatcac cgtggaggtg gacgccgctg ccgtaatcca gcagatcaga    180
gagatcttcc gaaccatggc aagtcacttc aactcgacga gggtggtgcg ggatgaagcc    240
atcaagggca ttcgagacca cttcagggcc gccgtcccga ctcgcaacgt ggtggtcatt    300
cacactcagc acgttcacac actggtgggc ttggagcaca cccacctcgt cttgcagacc    360
ggcatcttca aaaaggtccc cgtcgacatc tatgtcttca gtccggcgt cttcacccctc    420 cttggagacg gaggcttcat caactgggca tggggtggct tcgtacagga ggtcgccggc    480
aagcgtatcc acttccgctt gccccccggg gcgctccct                           519
```

<210> SEQ ID NO 177
<211> LENGTH: 513
<212> TYPE: DNA
<213> ORGANISM: Artificial Sequence
<220> FEATURE:
<223> OTHER INFORMATION: IPD103 variant

<400> SEQUENCE: 177

```
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaacatca tcaccgtgga ggtggacgcg gctgccgtaa tccagcagat cagagagatc    180
ttccgaacca tggcaagtca cttcaactcg acgagggtgg tgcgggatga agccatcaag    240
```

```
ggcattcgag accacttcag ggccgccgtc ccgactcgca acgtggtggt cgttcacacc    300
cagcacgttc acacactgga gggcttggag cacaccaacc tcgtcttgca gaccggcctc    360
ttcaaaaagg tccccgtcga catctatgtc ttcaagtccg gcgtcttcac cctccttgga    420
gacggaggct tcatcaactg gcatggggt ggcttcgtac aggaggtcgc cggcaagcgt     480
atccacttcc gcttgccccc cggggcgctc cct                                 513

<210> SEQ ID NO 178
<211> LENGTH: 513
<212> TYPE: DNA
<213> ORGANISM: Artificial Sequence
<220> FEATURE:
<223> OTHER INFORMATION: IPD103 variant

<400> SEQUENCE: 178
ataaccgacc cagcaacagc agctagagaa gctgaagaag aggtggagac gacgatggac     60
gagactgagg cggtggggac gcacctggac ttcttgggcg cggacgtgaa gttgcaaccc    120
cgcaaggtca tcaccgtgga ggtggacgcc gctgccgtaa tccaacagat cagagagatc    180
ttccgaacca tggcaagtca cttcaactcg acgagggtgg tgcgggatga agccatcaag    240
ggcattcgag accacttcag ggccgccgtc ccgactcgca acgtggtggt cattcacact    300
cagcacgttc acacactggt gggcttggag cacaccaacc tcgtcttgca gaccggcctc    360
ttcaaaaagg tccccgtcga catctacgtc ttcaagtccg gcgtcttcac cctccttgga    420
gacggaggct tcatcaactg gcatggggt ggcttcgtac aggaggtcgc cggcaagcgt     480
atccacttcc gcttgccccc cggggcgctc cct                                 513

<210> SEQ ID NO 179
<211> LENGTH: 519
<212> TYPE: DNA
<213> ORGANISM: Artificial Sequence
<220> FEATURE:
<223> OTHER INFORMATION: IPD103 variant

<400> SEQUENCE: 179
atggcggaca aagcagcagc agcagctaga gaagctgaag aagaggtgca ggagactttg     60
atggacgaga gtgaggcggt ggggacgcac ctggacttcg tggcgggctt ggaggtgcaa    120
ccccgcaagg tcatcacctt ggaggtggac gccgctgccg taatccagca gatcagagag    180
atcttccgaa ccatggcaag tcccttcaac tcgacgaggg tggtgcggga tgaagccatc    240
aagggcattc gagaccactt cagggccgcc gtcccgactc gcaacgtggt ggtcgttcac    300
tcccagcaca ttcacacatt ggagggattg gagcacacca acttcgtctt gcagaccggc    360
ctcttcaaaa aggtccccgt ggacatgtac gtattcaagt ccggcgtctt caccaacctt    420
ggagacggag gcttcatcaa ctgggcatgg ggtggcttcg tacaggaggt cgccggcaag    480
cgtatccact ccgcttgcc ccccggggcg ctccctcga                            519

<210> SEQ ID NO 180
<211> LENGTH: 513
<212> TYPE: DNA
<213> ORGANISM: Artificial Sequence
<220> FEATURE:
<223> OTHER INFORMATION: IPD103 variant

<400> SEQUENCE: 180
atggcggaca aagcagcagc agcaggtaga gaagatgaag aagaggtgga gacgacgatg     60
gacgagactg aggcggtggg gacgcacctg gacttcgtgg cgggcttgga ggtgcaaccc    120
```

```
cgcaacatca tcaccgtgga ggtggacgcg gctgccgtaa tccaacagat cagagagatc    180
ttccgaacca tggcaagcca cttcaactct acgagggtgg tgcgggatga agccatcaag    240
ggcattcgag accacttcag ggccgccgtc ccgactcgca acgtggtggt cattcacact    300
cagcacgttc acacactggt gggcttggag cacacccacc tcgtcttgca gaccggcctc    360
ttcaaaaagg tccccgtcga catctacgtc ttcaagtccg gcgtcttcac cctccttgga    420
gacggaggct tcatcaactg gcatgggggt ggcttcgtcg accaggtcgt cggcaagcgt    480
atccacttcc gcttgccccc cggggcgctc cct                                 513
```

<210> SEQ ID NO 181
<211> LENGTH: 513
<212> TYPE: DNA
<213> ORGANISM: Artificial Sequence
<220> FEATURE:
<223> OTHER INFORMATION: IPD103 variant

<400> SEQUENCE: 181

```
atggccgacc cagcaacagc agctagagaa gctgaagaag aggtgcagga gactttgatg     60
gacgagactg aggcggtggg gacgcacctg gacttcgtgg cgggcttgga ggtgcaaccc    120
cgcaaggtca tcaccgtgga ggtggacgcg gctgccgtaa tccaacagat cagagagatc    180
ttccagacaa tggcgcgtca cttcaactct acgagggtgg tgcgggatga agccatcaag    240
ggcattcgag accacttcag ggccgccgtc ccgactcgca acgtggtggt cgttcacact    300
cagcacgttc acacactagt gggcttggag cacacccacc tcgtcttgca gaccggcctc    360
ttcaaaaagg tccccgtcga catctatgtc ttcaagtccg gcgtcttcac caaccttgga    420
gacggaggct tcatcaactg gcatgggggt ggcttcgtac aggaggtcgc cggcaagcgt    480
atccacttcc gcttgccccc cggggcgctc cct                                 513
```

<210> SEQ ID NO 182
<211> LENGTH: 513
<212> TYPE: DNA
<213> ORGANISM: Artificial Sequence
<220> FEATURE:
<223> OTHER INFORMATION: IPD103 variant

<400> SEQUENCE: 182

```
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaacatca tcaccgtgga ggtggacgcg gctgccgtaa tccaacagat cagagagatc    180
ttccagacaa tggcgcgtca cttcaactct acgagggtgg tgcgggatga agccatcaag    240
ggcattcgag accacttcag ggccgccgtc ccgactcgca acgtggtggt cgttcacacc    300
cagcacattc acacactgga gggcttggag cacacccacc tcgtcttgca gaccggcatc    360
ttcaaaaagg tccccgtcga catctatgtc ttcaagtccg gcgtcttcac cctccttgga    420
gacggaggct tcatcaactg gcatgggggt ggcttcgtcg accaggtcgt cggcaagcgt    480
atccacttcc gcttgccccc cggggcgctc cct                                 513
```

<210> SEQ ID NO 183
<211> LENGTH: 519
<212> TYPE: DNA
<213> ORGANISM: Artificial Sequence
<220> FEATURE:
<223> OTHER INFORMATION: IPD103 variant

<400> SEQUENCE: 183

```
atggcggaca aagcagcagc agcagctaga gaagctgaag aagaggtgca ggagactttg      60
atggacgaga ctgaggcggt ggggacgcac ctggacttct tgggcgcgga cgtgaagttg     120
caaccccgca acatcatcac cgtggaggtg gacgcggctg ccgtaatcca gcagatcaga     180
gagatcttcc agacaatggc gcgtcacttc aactctacga gggtggtgcg ggatgaagcc     240
atcaagggca ttcgagacca cttcagggcc gccgtcccga ctcgcaacgt ggtggtcgtt     300
cacacccagc acattcacac actggagggc ttggagcaca cccacctcgt cttgcagacc     360
ggcctcttca aaaaggtccc cgtcgacatc tacgtcttca gtccggcgt cttcaccctc      420
cttggagacg gaggcttcat caactgggca tggggtggct cgtcgacca ggtcgtcggc      480
aagcgtatcc acttccgctt gccccccggg gcgctccct                           519
```

<210> SEQ ID NO 184
<211> LENGTH: 513
<212> TYPE: DNA
<213> ORGANISM: Artificial Sequence
<220> FEATURE:
<223> OTHER INFORMATION: IPD103 variant

<400> SEQUENCE: 184

```
atggcggacg aagtagcagg tcaccatggt ccagcatgtg aagaagagga ggaggaaatg      60
ctgatggacg agactgaggc ggtgggggtg cacgcgatcg acggtctgcc ggtgcaaaac     120
cgcagcatca tcaccgtgga ggtggacgcg gctgccgtaa tccagcagat cagagagatc     180
ttccgaacca tggcaagtca cttcaactcg acgaggtgg tgcgggatga agccatcaag      240
ggcattcgag accacttcag gctcgccgtc ccgactcgca acgtggtggt cgttcacact     300
cagcacgttc acacactggt gggcttggag cacacccacc tcgtcttgca gaccggcatc     360
ttcaaaaagg tccccgtcga catctatgtc ttcaagtccg gcgtcttcac cctccttgga     420
gacgaggct tcatcaactg gcatggggt ggctacggcg tcaaccacac cgccaagcgt       480
gtcgtcttca gccggccccc cggggcgctc cct                                 513
```

<210> SEQ ID NO 185
<211> LENGTH: 516
<212> TYPE: DNA
<213> ORGANISM: Artificial Sequence
<220> FEATURE:
<223> OTHER INFORMATION: IPD103 variant

<400> SEQUENCE: 185

```
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gccgctgccg taatccaaca gatcagagag     180
atcttccaga caatggcgcg tcacttcaac tctacgaggg tggtgcggga tgaagccatc     240
aagggcattc gagaccactt cagggccgcc gtcccgactc gcaacgtggt ggtcattcac     300
actcagcacg ttcacacact ggacgccgtg gagtcctccc acctcgtctt gcggaccggc     360
ctgttcaaaa aggtccctgt cgacatcttt gtcttcaagt ccggcgtctt caccaacctt     420
ggagacggag gcttcatcaa ctgggcatgg ggtggcttcg tacaggaggt cgccggcaag     480
cgtatccact tccgcttgcc cccggggcg ctccct                              516
```

<210> SEQ ID NO 186
<211> LENGTH: 507

```
<212> TYPE: DNA
<213> ORGANISM: Artificial Sequence
<220> FEATURE:
<223> OTHER INFORMATION: IPD103 variant

<400> SEQUENCE: 186
atggcggaca aagcagcagc agcagctaga gaagctgaag aagaggtgga gacgacgatg      60
gacgagactg aggcggtggg ggtgcacgcg atcgacggtc tgccggtgca aaaccgcagc     120
atcatcaccg tggaggtgga cgccgctgcc gtaatccagc agatcagaga gatcttccga     180
accatggcaa gtcacttcaa ctcgacgagg gtggtgcggg atgaagccat caagagcatt     240
cgagaccact tcaggctcgc cgtcccgact cgcaacgtgg tggtcgttca cacccagcac     300
gttcacacac tggacgccgt ggagtcctcc cacctcgtct tgcggaccgg cctgttcaaa     360
aaggtccctg tcgacatctt tgtcttcaag tccggcgtct tcaccaacct gggagacgga     420
ggcttcatca actgggcatg gggtggcttc gtacaggagg tcgccggcaa gcgtatccac     480
ttccgcttgc ccccggggc gctccct                                          507

<210> SEQ ID NO 187
<211> LENGTH: 516
<212> TYPE: DNA
<213> ORGANISM: Artificial Sequence
<220> FEATURE:
<223> OTHER INFORMATION: IPD103 variant

<400> SEQUENCE: 187
atggcggacg aagtagcagg tcaccatggt ccagcatgtg aagaagagga ggagacgacg      60
atggacgaga ctgaggcggt ggggacgcac ctggacttcg tggcgggctt ggaggtgcaa     120
ccccgcaagg tcatcaccgt ggaggtggac gccgctgccg taatccagca gatcagagag     180
atcttccgaa ccatggcaag tcacttcaac tcgacgaggg tggtgcggga tgaagccatc     240
aagggcattc gagaccactt cagggccgcc gtcccgactc gcaacgtggt ggtcgttcac     300
actcagcacg ttcacacact ggacgccgtg gagtcctccc acctcgtctt gcggaccggc     360
ctgttcaaaa aggtccctgt cgacatcttt gtcttcaagt ccggcgtctt caccaacctg     420
ggagacggag gcttcatcaa ctgggcatgg gtggctacg tacaggaggt cgtcggcaag     480
cgtatccact tccgcttgcc ccccggggcg ctccct                               516

<210> SEQ ID NO 188
<211> LENGTH: 513
<212> TYPE: DNA
<213> ORGANISM: Artificial Sequence
<220> FEATURE:
<223> OTHER INFORMATION: IPD103 variant

<400> SEQUENCE: 188
atggcggacg aagtagcagg tcaccatggt ccagcatgtg aagaagagga ggaggaaatg      60
ctgatggacg agactgaggc ggtggggtg cacgcgatcg acgtctgcc ggtgcaaaac       120 cgcagcatca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accttcag gctcgccgtc ccgactcgca acgtggtggt cattcacact      300
cagcacgttc acacactgga cgccgtggag tcctcccacc tcgtcttgcg gaccggcctg     360
ttcaaaaagg tccctgtcga catctttgtc ttcaagtccg gcgtcttcac caacctggga     420
gacggaggct tcatcaactg ggcatggggt ggctacggcg tcaaccacac cgccaagcgt     480
```

```
gtcgtcttca gccggccccc cggggcgctc cct                                  513
```

<210> SEQ ID NO 189
<211> LENGTH: 510
<212> TYPE: DNA
<213> ORGANISM: Artificial Sequence
<220> FEATURE:
<223> OTHER INFORMATION: IPD103 variant

<400> SEQUENCE: 189

```
atggccgacc cagcaacagc agctagagaa gctgaagaag aggtggagac gacgatggac    60
gagactgagg cggtggggac gcacctggac ttcgtggcgg gcttggaggt gcaacccgc    120
aaggtcatca ccgtggaggt ggacgccgct gccgtaatcc agcagatcag agagatcttc   180
cagacaatgg cgcgtcactt caactctacg agggtggtgc gggatgaagc catcaagggc   240
attcgagacc acttcagggc cgccgtcccg actcgcaacg tggtggtcat tcacactcag   300
cacgttcaca cactggacgc cgtggagtcc tcccacctcg tcttgcggac cggcctgttc   360
aaaaaggtcc ctgtcgacat ctttgtcttc aagtccggcg tcttcaccaa cctgggagac   420
ggaggcttca tcaactgggc atggggtggc tacgtcgacc aggtcgtcgg caagcgtatc   480
cacttccgct gcccccccgg ggcgctccct                                    510
```

<210> SEQ ID NO 190
<211> LENGTH: 516
<212> TYPE: DNA
<213> ORGANISM: Artificial Sequence
<220> FEATURE:
<223> OTHER INFORMATION: IPD103 variant

<400> SEQUENCE: 190

```
atggcggacg aagtagcagg tcaccatggt ccagcatgtg aagaagagga ggagaggacg    60
atggacgaga ctgaggcggt ggggacgcac ctggacttcg tggcgggctt ggaggtgcaa   120
ccccgcaagg tcatcaccgt ggaggtggac gccgctgccg taatccagca tatcagagag   180
atcttcggaa ccatggcaag tcacttcaac tcgacgaggg tggtgcggga tgaagccatc   240
aagggcattc gagaccactt cagggccgcc gtcccgactc gcaacgtggt ggtcgttcac   300
actcagcacg ttcacacact ggacgccgtg gagtcctccc acctcgtctt gcggaccggc   360
ctgttcaaaa aggtccctgt cgacatcttt gtcttcaagt ccggcgtctt caccaacctg   420
ggagacggag gcttcatcaa ctgggcatgg ggtggctacg tacaggaggt cgtcggcaag   480
cgtatccact ccgcctgcc ccccggggcg ctccct                              516
```

<210> SEQ ID NO 191
<211> LENGTH: 519
<212> TYPE: DNA
<213> ORGANISM: Artificial Sequence
<220> FEATURE:
<223> OTHER INFORMATION: IPD103 variant

<400> SEQUENCE: 191

```
atggcggacg aagtagcagg tcaccatggt ccagcatgtg aagaagagga ggaggaaatg    60
ctgatggacg agactgaggc ggtggggacg cacctggact tcgtggcggg cttggaggtg   120
caaccccgca aggtcatcac cgtggaggtg gacgccgctg ccgtaatcca gcagatcaga   180
gagatcttcc gaaccatggc aagtcacttc aactcgacga gggtggtgcg ggatgaagcc   240
atcaagggca ttcgagacca cttcaggctc gccgtcccga ctcgcaacgt ggtggtcgtt   300
cacactcagc acgttcacac actggacgcc gtggagtcct cccacctcgt cttgcggacc   360
```

```
ggcctgttca aaaaggtccc tgtcgacatc tttgtcttca agtccggcgt cttcaccaac    420
ctgggagacg gaggcttcat caactgggca tggggtggct acggcgtcaa ccacaccgcc    480
aagcgtgtcg tcttcagccg gccccccggg gcgctccct                           519
```

<210> SEQ ID NO 192
<211> LENGTH: 513
<212> TYPE: DNA
<213> ORGANISM: Artificial Sequence
<220> FEATURE:
<223> OTHER INFORMATION: IPD103 variant

<400> SEQUENCE: 192

```
atggcggacg cagcagcagc agctgctaga agaagaagaa gagagcagga gacgacgatg    60
gacgagactg aggcggtggg gacgcacctg gacttcgtgg cgggcttgga ggtgcaaccc   120
cgcaacatca tcaccgtgga ggtggacgcg gctgccgtaa tccaacagat cagagagatc   180
ttccagtcaa tgatcagtca cttcaactcg acgagggtgg tgcggatga agccatcaag    240 ggcattcgag accacttcag ggtcgccgtc ccgactcgca acgtggtggt cattcacact   300
cagcacgttc acacactgga gggcgtggag tcctcccacc tcgtcttgca gaccggcatg   360
ttcaaaaagg tccccgtcga catctatgtc ttcaagtccg gcgtcttcac catcctggga   420
gacggaggct tcatcaactg gcatgggggt ggcttcggcg accaggtcgt cggcaagcgt   480
gtccacttcc gcctgccccc cggggcgctc cct                                513
```

<210> SEQ ID NO 193
<211> LENGTH: 513
<212> TYPE: DNA
<213> ORGANISM: Artificial Sequence
<220> FEATURE:
<223> OTHER INFORMATION: IPD103 variant

<400> SEQUENCE: 193

```
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctttgtc ttcaagtccg gcgtcttcac caacctggga   420
gacggaggct tcatcaactg gcatgggggt ggctacggcg tcaaccacac cgccaagcgt   480
gtcgtcttca gccggccccc cggggcgctc cct                                513
```

<210> SEQ ID NO 194
<211> LENGTH: 519
<212> TYPE: DNA
<213> ORGANISM: Artificial Sequence
<220> FEATURE:
<223> OTHER INFORMATION: IPD103 variant

<400> SEQUENCE: 194

```
atggcggacg aagtagcagg tcaccatggt ccagcatgtg aagaagagga ggaggaaatg    60
ctgatggacg agactgaggc ggtgggggacg cacctggact tcgtggcggg cttggaggtg   120
caaccccgca acatcatcac cgtggaggtg gacgccgctg ccgtaatcca acagatcaga   180
```

```
gagatcttcc agacaatggc gcgtcacttc aactctacga gggtggtgcg ggatgaagcc    240
atcaagggca ttcgagacca cttcagggcc gccgtcccga ctcgcaacgt ggtggtcatt    300
cacactcagc acgttcacac actggacgcc gtggagtcct cccacctcgt cttgcggacc    360
ggcctgttca aaaaggtccc tgtcgacatc tttgtcttca agtccggcgt cttcaccaac    420
ctgggagacg gaggcttcat caactgggca tggggtggct tcgtacagga ggtcgccggc    480
aagcgtatcc acttccgctt gccccccggg gcgctccct                           519
```

<210> SEQ ID NO 195
<211> LENGTH: 513
<212> TYPE: DNA
<213> ORGANISM: Artificial Sequence
<220> FEATURE:
<223> OTHER INFORMATION: IPD103 variant

<400> SEQUENCE: 195

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgaggtgg tgcgggatga agccatcaag    240
agcattcgag accacttcag ggccgccgtc ccgactcgca acgtggtggt cattcacact    300
cagcacgttc acacactgga gggcttggag cacaccaacc tcgtcttgca gaccggcctc    360
ttcaaaaagg tccccgtcga catctatgtc ttcaagtccg gcgtcttcac caacctggga    420
gacggaggct tcatcaactg gcgtggggt ggcttcgtac aggaggtcgc cggcaagcgt    480
atccacttcc gcttgccccc cggggcgctc cct                                 513
```

<210> SEQ ID NO 196
<211> LENGTH: 510
<212> TYPE: DNA
<213> ORGANISM: Artificial Sequence
<220> FEATURE:
<223> OTHER INFORMATION: IPD103 variant

<400> SEQUENCE: 196

```
atggcggacg aagcagcagc agcagctaga gaagctgaag aagaggagga ggaaatgctg    60
atggacgaga ctgaggcggt gggggtgcac gcgatcgacg tctgccggt gcaaaaccgc    120 agcatcatca ccgtggaggt ggacgccgct gccgtaatcc aacagatcag agagatcttc    180
cgaaccatgg caagtcactt caactcgacg agggtggtgc gggatgaagc catcaagggc    240
attcgagacc acttcaggct cgccgtcccg actcgcaacg tggtggtcat tcacactcag    300
cacattcaca cactggtggg cttggagtcc tcccacctcg ccttgcggac cggcctgttc    360
aaaaaggtcc ctgtcgacat ctacgtcttc aagtccggcg tcttcaccct ccttggagac    420
ggaggcttca tcaactgggc atggggtggc ttcgtcgacc aggtcgtcgg caagcgtatc    480
cacttccgct tgccccccgg ggcgctccct                                     510
```

<210> SEQ ID NO 197
<211> LENGTH: 516
<212> TYPE: DNA
<213> ORGANISM: Artificial Sequence
<220> FEATURE:
<223> OTHER INFORMATION: IPD103 variant

<400> SEQUENCE: 197

```
atggcggaca aagcagcagc agcagctaga gaagctgaag aagaggtgga gacgacgatg    60
```

```
gacgagactg aggcggtggg gacgcacctg gacttcttgg gcgcggacgt gaagttgcaa      120
ccccgcaaca tcatcaccgt ggaggtggac gccgctgccg taatccaaca gatcagagag      180
atcttccaga caatggcgcg tcacttcaac tctacgaggg tggtgcggga tgaagccatc      240
aagggcattc gagaccactt cagggccgcc gtcccgactc gcaacgtggt ggtcattcac      300
actcagcacg ttcacacact ggtgggcttg gagcacacca acctcgtctt gcggaccggc      360
ctgttcaaaa aggtccccgt cgacatctac gtcttcaagt ccggcgtctt caccctcctt      420
ggagacggag gcttcatcaa ctgggcatgg ggtggcttcg tacaggaggt cgccggcaag      480
cgtatccact ccgcttgcc ccccggggcg ctccct                                 516
```

<210> SEQ ID NO 198
<211> LENGTH: 510
<212> TYPE: DNA
<213> ORGANISM: Artificial Sequence
<220> FEATURE:
<223> OTHER INFORMATION: IPD103 variant

<400> SEQUENCE: 198

```
atggcggacg aagtagcagg tcaccatggt ccagcatgtg aagaagaggt ggagacgacg       60
atggacgaga ctgaggcggt gggggtgcac gcgatcgacg tctgccggt gcaaaaccgc       120 agcatcatca ccgtggaggt ggacgccgct gccgtaatcc agcagatcag agagatcttc      180
cgaaccatgg caagtcactt caactcgacg agggtggtgc gggatgaagc catcaagggc      240
attcgagacc acttcaggct cgccgtcccg actcgcaacg tggtggtcgt tcacacccag      300
cacgttcaca cactggaggg cttggagcac accaacctcg tcttgcagac cggcctcttc      360
aaaaaggtcc ccgtcgacat ctacgtcttc aagtccggcg tcttcaccct ccttggagac      420
ggaggcttca tcaactgggc atgggtggc ttcgtacagg aggtcgccgg caagcgtatc       480
cacttccgct tgccccccgg ggcgctccct                                       510
```

<210> SEQ ID NO 199
<211> LENGTH: 513
<212> TYPE: DNA
<213> ORGANISM: Artificial Sequence
<220> FEATURE:
<223> OTHER INFORMATION: IPD103 variant

<400> SEQUENCE: 199

```
atggcggacg aagtagcagg tcaccatggt ccagcatgtg aagaagagga ggaggaaatg       60
ctgatggacg agactgaggc ggtgggggtg cacgcgatcg acggtctgcc ggtgcaaccc      120
cgcaaggtca tcaccgtgga ggtggacgcc gctgccgtaa tccaacagat cagagagatc      180
ttccagacaa tggcgcgtca cttcaactct acgaggtgg tgcgggatga agccatcaag       240
ggcattcgag accacttcag ggccgccgtc ccgactcgca acgtggtggt cgttcacacc      300
cagcacattc acacactggt gggcttggag cacacccacc tcgtcttgca gaccggcctc      360
ttcaaaaagg tccccgtcga catctacgtc ttcaagtccg gcgtcttcac cctccttgga      420
gacggaggct tcatcaactg ggcatggggt ggcttcgtcg accaggtcgt cggcaagcgt      480
atccacttcc gcttgccccc cggggcgctc cct                                   513
```

<210> SEQ ID NO 200
<211> LENGTH: 513
<212> TYPE: DNA
<213> ORGANISM: Artificial Sequence
<220> FEATURE:

<223> OTHER INFORMATION: IPD103 variant

<400> SEQUENCE: 200

```
atggcggacg aagtagcagg tcaccatggt ccagcatgtg aagaagagga ggaggaaatg      60
ctgatggacg agactgaggc ggtggggtg cacgcgatcg acggtctgcc ggtgcaaaac      120
cgcagcatca tcaccgtgga ggtggacgcc gctgccgtaa tccagcagat cagagagatc     180
ttccgaacca tggcaagtca cttcaactcg acgaggtgg tgcgggatga agccatcaag      240
agcattcgag accacttcag gctcgccgtc ccgactcgca acgtggtggt cattcacacc     300
cagcacgttc acacactgga gggcttggag tcctcccacc tcgtcttgcg gaccggcctg     360
ttcaaaaagg tccctgtcga catctttgtc ttcaagtccg gcgtcttcac caacctggga    420
gacggaggct tcatcaactg gcatgggggt ggctacggcg tcaaccacac cgccaagcgt     480
gtcgtcttca gccggcccc cggggcgctc cct                                   513
```

<210> SEQ ID NO 201
<211> LENGTH: 513
<212> TYPE: DNA
<213> ORGANISM: Artificial Sequence
<220> FEATURE:
<223> OTHER INFORMATION: IPD103 variant

<400> SEQUENCE: 201

```
atggcggacg aagtagcagg tcaccatggt ccagcatgtg aagaagagga ggaggaaatg      60
ctgatggacg agactgaggc ggtggggtg cacgcgatcg acggtctgcc ggtgcaaaac      120
cgcagcatca tcaccgtgga ggtggacgcc gctgccgtaa tccaacagat cagagagatc     180
ttcgcgtcaa tgatcaaaca cttcaactcg acgaggtgg tgcgggatga agccatcaag      240
ggcattcgag accacttcag ggccgccgtc ccgactcgca acgtggtggt cattcacact     300
cagcacgttc acacactgga cgccgtggag tcctcccacc tcgtcttgcg gaccggcctg     360
ttcaaaaagg tccctgtcga catctttgtc ttcaagtccg gcgtcttcac caacctggga    420
gacggaggct tcatcaactg gcatgggggt ggctacggcg tcaaccacac cgccaagcgt     480
gtcgtcttca gccggcccc cggggcgctc cct                                   513
```

<210> SEQ ID NO 202
<211> LENGTH: 513
<212> TYPE: DNA
<213> ORGANISM: Artificial Sequence
<220> FEATURE:
<223> OTHER INFORMATION: IPD103 variant

<400> SEQUENCE: 202

```
atggcggacg aagtagcagg tcaccatggt ccagcatgtg aagaagagga ggaggaaatg      60
ctgatggacg agactgaggc ggtggggtg cacgcgatcg acggtctgcc ggtgcaaaac      120
cgcagcatca tcaccgtgga ggtggacgcc gctgccgtaa tccagcagat cagagagatc     180
ttccgaacca tggcaagtca cttcaactcg acgaggtgg tgcgggatga agccatcaag      240
agcattcgag accacttcag ggccgccgtc ccgactcgca acgtggtggt cgttcacacc     300
cagcacattc acacactgga gggcttggag cacaccaacc tcgtcttgca gaccggcctg     360
ttcaaaaagg tccctgtcga catctacgtc ttcaagtccg gcgtcttcac caacctggga    420
gacggaggct tcatcaactg gcatgggggt ggcttcgtac aggaggtcgc cggcaagcgt     480
atccacttcc gcttgccccc cggggcgctc cct                                  513
```

<210> SEQ ID NO 203
<211> LENGTH: 513
<212> TYPE: DNA
<213> ORGANISM: Artificial Sequence
<220> FEATURE:
<223> OTHER INFORMATION: IPD103 variant

<400> SEQUENCE: 203

```
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcc gctgccgtaa tccaacagat cagagagatc   180
ttccgaacca tggcaagtca cttcaactcg acgaggtgg tgcgggatga agccatcaag    240
ggcattcgag accacttcag gccgccgtc ccgactcgca acgtggtggt cattcacact    300
cagcacgttc acacactgga cgccgtggag tcctcccacc tcgtcttgcg gaccggcctg   360
ttcaaaaagg tccctgtcga catctttgtc ttcaagtccg gcgtcttcac cctccttgga   420
gacggaggct tcatcaactg gcatgggggt ggctacggcg tcaaccacac cgccaagcgt   480
gtcgtcttca gccggccccc cggggcgctc cct                                513
```

<210> SEQ ID NO 204
<211> LENGTH: 513
<212> TYPE: DNA
<213> ORGANISM: Artificial Sequence
<220> FEATURE:
<223> OTHER INFORMATION: IPD103 variant

<400> SEQUENCE: 204

```
atggcggacg aagtagcagg tcaccatggt ccagcatgtg aagaagagga ggaggaaatg    60
ctgatggacg agactgaggc ggtggggtg cacgcgatcg acgtctgcc ggtgcaaaac    120
cgcagcatca tcaccgtgga ggtggacgcg gctgccgtaa tccaacagat cagagagatc   180
ttccgaacca tggcaagtca cttcaactcg acgaggtgg tgcgggatga agccatcaag    240
ggcattcgag accacttcag gctcgccgtc ccgactcgca acgtggtggt cattcacact    300
cagcacgttc acacactgga cgccgtggag tcctcccacc tcgtcttgcg gaccggcctg   360
ttcaaaaagg tccctgtcga cattttgtc ttcaagtccg gtgttttcac caacctggga   420
gacggaggct tcatcaactg gcatgggggt ggctacggcg tcaaccacac cgccaagcgt   480
gtcgtcttca gccggccccc cggggcgctc cct                                513
```

<210> SEQ ID NO 205
<211> LENGTH: 516
<212> TYPE: DNA
<213> ORGANISM: Artificial Sequence
<220> FEATURE:
<223> OTHER INFORMATION: IPD103 variant

<400> SEQUENCE: 205

```
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gccgctgccg taatccagca gatcagagag   180
atcttccgaa ccatggcaag tcacttcaac tcgacgaggt ggtgcggga tgaagccatc    240
aagggcattc gagaccactt cagggccgcc gtcccgactc gcaacgtggt ggtcgttcac   300
actcagcacg ttcacacact ggtgggcttg agcacaccc acctcgtctt gcagaccggc   360
ctcttcaaaa aggtccccgt cgacatctac gtcttcaagt ccggcgtctt caccctcctt   420
```

| | |
|---|---|
| ggagacggag gcttcatcaa ctgggcatgg ggtggcttcg tcgaccaggt cgtcggcaag | 480 |
| cgtatccact tccgcttgcc ccccggggcg ctccct | 516 |

<210> SEQ ID NO 206
<211> LENGTH: 519
<212> TYPE: DNA
<213> ORGANISM: Artificial Sequence
<220> FEATURE:
<223> OTHER INFORMATION: IPD103 variant

<400> SEQUENCE: 206

| | |
|---|---|
| atggcggacg aagtagcagg tcaccatggt ccagcatgtg aagaagagga ggaggaaatg | 60 |
| ctgatggacg agactgaggc ggtggggacg cacctggact tcgtggcggg cttggaggtg | 120 |
| caaaaccgca gcatcatcac cgtggaggtg gacgccgctg ccgtaatcca acagatcaga | 180 |
| gagatcttcc gaaccatggc aagtcacttc aactcgacga gggtggtgcg ggatgaagcc | 240 |
| atcaagggca ttcgagacca cttcaggctc gccgtcccga ctcgcaacgt ggtggtcgtt | 300 |
| cacactcagc acgttcacac actggacgcc gtggagtcct cccacctcgt cttgcggacc | 360 |
| ggcctgttca aaaaggtccc tgtcgacatc tttgtcttca gtccggcgt cttcaccaac | 420 |
| ctgggagacg gaggcttcat caactgggca tggggtggct acggcgtcaa ccacaccgcc | 480 |
| aagcgtgtcg tcttcagccg gcccccccggg gcgctccct | 519 |

<210> SEQ ID NO 207
<211> LENGTH: 513
<212> TYPE: DNA
<213> ORGANISM: Artificial Sequence
<220> FEATURE:
<223> OTHER INFORMATION: IPD103 variant

<400> SEQUENCE: 207

| | |
|---|---|
| atggcggacg aagtagcagg tcaccatggt ccagcatgtg aagaagagga ggaggaaatg | 60 |
| ctgatggacg agactgaggc ggtggggtg cacgcgatcg acgtctgcc ggtgcaaaac | 120 |
| cgcagcatca tcaccgtgga ggtggacgcc gctgccgtaa tccaacagat cagagagatc | 180 |
| ttccgaacca tggcaagtca cttcaactcg acgagggtgg tgcgggatga agccatcaag | 240 |
| agcattcgag accacttcag gctcgccgtc ccgactcgca acgtggtggt cattcacact | 300 |
| cagcacgttc acacactgga cgccgtggag tcctcccacc tcgtcttgca gaccggcctc | 360 |
| ttcaaaaagg tccccgtcga catctacgtc ttcaagtccg gcgtcttcac caacctggga | 420 |
| gacggaggct tcatcaactg gcatgggggt ggctacggcg tcaaccacac cgccaagcgt | 480 |
| gtcgtcttca gccggccccc cggggcgctc cct | 513 |

<210> SEQ ID NO 208
<211> LENGTH: 516
<212> TYPE: DNA
<213> ORGANISM: Artificial Sequence
<220> FEATURE:
<223> OTHER INFORMATION: IPD103 variant

<400> SEQUENCE: 208

| | |
|---|---|
| atggcggaca agcagcagc agcagctaga gaagctgaag aagaggtgga gacgacgatg | 60 |
| gacgagactg aggcggtggg gacgcacctg gacttcttgg gcgcggacgt gaagttgcaa | 120 |
| ccccgcaaca tcatcaccgt ggaggtggac gccgctgccg taatccaaca gatcagagag | 180 |
| atcttccgaa ccatggcaag tcacttcaac tctacgaggg tggtgcggga tgaagccatc | 240 |
| aagggcattc gagaccactt cagggccgcc gtcccgactc gcaacgtggt ggtcattcac | 300 |

```
actcagcacg ttcacacact ggtgggcttg gagcacaccc acctcgtctt gcagaccggc    360
ctcttcaaaa aggtccccgt cgacatctat gtcttcaagt ccggcgtctt caccaacctg    420
ggagacggag gcttcatcaa ctgggcatgg ggtggcttcg tacaggaggt cgccggcaag    480
cgtatccact ccgccggcc ccccggggcg ctccct                               516
```

<210> SEQ ID NO 209
<211> LENGTH: 513
<212> TYPE: DNA
<213> ORGANISM: Artificial Sequence
<220> FEATURE:
<223> OTHER INFORMATION: IPD103 variant

<400> SEQUENCE: 209

```
atggcggacg aagtagcagg tcaccatggt ccagcatgtg aagaagagga ggaggaaatg     60
ctgatggacg agactgaggc ggtgggggtg cacgcgatcg acggtctgcc ggtgcaaaac    120
cgcagcatca tcaccgtgga ggtggacgcc gctgccgtaa tccaacagat cagagagatc    180
ttcgcgtcaa tgatcaaaca ctacaactct acgagggtgg tgcgggatga agccatcaag    240
agcattcgag accacttcag ggccgccgtc ccgactcgca acgtggtggt cattcacacc    300
cagcacgttc acacactgga gggcttggag cacaccaacc tcgtcttgca gaccggcctg    360
ttcaaaaagg tccctgtcga catctttgtc ttcaagtccg gcgtcttcac caacctggga    420
gacggaggct tcatcaactg gcatggggt ggctacggcg tcaaccacac cgccaagcgt    480
gtcgtcttca gccggccccc cggggcgctc cct                                 513
```

<210> SEQ ID NO 210
<211> LENGTH: 513
<212> TYPE: DNA
<213> ORGANISM: Artificial Sequence
<220> FEATURE:
<223> OTHER INFORMATION: IPD103 variant

<400> SEQUENCE: 210

```
atggcggacg aagtagcagg tcaccatggt ccagcatgtg aagaagagga ggaggaaatg     60
ctgatggacg agactgaggc ggtgggggtg cacgcgatcg acggtctgcc ggtgcaaaac    120
cgcagcatca tcaccgtgga ggtggacgcc gctgccgtaa tccaacagat cagagagatc    180
ttccagacaa tggcgcgtca cttcaactct acgagggtgg tgcgggatga agccatcaag    240
ggcattcgag accacttcag ggccgccgtc ccgactcgca acgtggtggt cattcacact    300
cagcacgttc acacactgga cgccgtggag tcctcccacc tcgtcttgca gaccggcctc    360
ttcaaaaagg tccccgtcga catctatgtc ttcaagtccg gcgtcttcac caaccttgga    420
gacggaggct tcatcaactg gcatggggt ggctacggcg tcaaccacac cgccaagcgt    480
gtcgtcttca gccggccccc cggggcgctc cct                                 513
```

<210> SEQ ID NO 211
<211> LENGTH: 513
<212> TYPE: DNA
<213> ORGANISM: Artificial Sequence
<220> FEATURE:
<223> OTHER INFORMATION: IPD103 variant

<400> SEQUENCE: 211

```
atggccgacc cagcaacagc agctagagaa gctgaagaag aggtggagac gacgatggac     60
gagactgagg cggtggggac gcacctggac ttcttgggcg cggacgtgaa gttgcaaccc    120
```

```
cgcaacatca tcaccgtgga ggtggacgcg gctgccgtaa tccagcagat cagagagatc    180
ttccagacaa tggcgcgtca cttcaactct acgagggtgg tgcgggatga agccatcaag    240
ggcattcgag accacttcag gctcgccgtc ccgactcgca acgtggtggt cattcacacc    300
cagcacgttc acacactgga cgccgtggag tcctcccgcc tcgtcttgcg gaccggcctg    360
ttcaaaaagg tccctgtcga catctttgtc ttcaagtccg gcgtcttcac caacctggga    420
gacggaggct tcatcaactg gcatgggggt ggcttcgtcg accaggtcgt cggcaagcgt    480
atccacttcc gcttgccccc cggggcgctc cct                                 513
```

<210> SEQ ID NO 212
<211> LENGTH: 519
<212> TYPE: DNA
<213> ORGANISM: Artificial Sequence
<220> FEATURE:
<223> OTHER INFORMATION: IPD103 variant

<400> SEQUENCE: 212

```
atggcggaca aagcagcagc agcagctaga gaagctgaag aagaggtgca ggagactttg     60
atggacgaga ctgaggcggt ggggacgcac ctggacttct tgggcgcgga cgtgaagttg    120
caaccccgca aggtcatcac cgtggaggtg acgcggctg ccgtaatcca gcagatcaga    180
gagatcttcc gaaccatggc aagtcacttc aactctacga gggtggtgcg ggatgaagcc    240
atcaagggca ttcgagacca cttcagggcc gccgtcccga ctcgcaacgt ggtggtcgtt    300
cacactcagc acgttcacac actggacgcc gtggagtcct cccacctcgt cttgcggacc    360
ggcctgttca aaaaggtccc cgtcgacatc tacgtcttca gtccggcgt cttcaccctc    420 cttggagacg ggggcttcat caactgggca tggggtggct tcgtcgacca ggtcgtcggc    480
aagcgtatcc acttccgctt gccccccggg gcgctccct                            519
```

<210> SEQ ID NO 213
<211> LENGTH: 513
<212> TYPE: DNA
<213> ORGANISM: Artificial Sequence
<220> FEATURE:
<223> OTHER INFORMATION: IPD103 variant

<400> SEQUENCE: 213

```
atggcggacg aagtagcagg tcaccatggt ccagcatgtg aagaagagga ggaggaaatg     60
ctgatggacg agactgaggc ggtgggggtg cacgcgatcg acggtctgcc ggtgcaaaac    120
cgcagcatca tcaccgtgga ggtggacgcc gctgccgtaa tccaacagat cagagagatc    180
ttcgcgtcaa tgatcaaaca ctacaactct acgagggtgg tgcgggatga agccatcaag    240
ggcattcgag accacttcag ggccgccgtc ccgactcgca acgtggtggt cgttcacacc    300
cagcacgttc acacactgga cgccgtggag tcctcccacc tcgtcttgcg gaccggcctg    360
ttcaaaaagg tccctgtcga catctacgtc ttcaagtccg gcgtcttcac cctccttgga    420
gacggaggct tcatcaactg gcatgggggt ggctacggcg tcaaccacac cgccaagcgt    480
gtcgtcttca gccggccccc cggggcgctc cct                                 513
```

<210> SEQ ID NO 214
<211> LENGTH: 519
<212> TYPE: DNA
<213> ORGANISM: Artificial Sequence
<220> FEATURE:
<223> OTHER INFORMATION: IPD103 variant

<400> SEQUENCE: 214

```
atggcggacg aagtagcagg tcaccatggt ccagcatgtg aagaagagga ggaggaaatg      60
ctgatggacg agactgaggc ggtggggacg cacctggact tcgtggcggg cttggaggtg     120 caacccgca aggtcatcac cgtggaggtg gacgccgctg ccgtaatcca acagatcaga     180
gagatcttcc agacaatggc gcgtcactac aactctacga gggtggtgcg ggatgaagcc     240
atcaagagca ttcgagacca cttcagggcc gccgtcccga ctcgcaacgt ggtggtcgtt     300
cacacccagc acattcacac actggacgcc gtggagtcct cccacctcgt cttgcggacc     360
ggcctgttca aaaaggtccc tgtcgacatc tttgtcttca agtccggcgt cttcaccaac     420
ctgggagacg gaggcttcat caactgggca tggggtggct cgtacagga ggtcgccggc     480 aagcgtatcc acttccgctt gccccccggg gcgctccct                            519
```

<210> SEQ ID NO 215
<211> LENGTH: 513
<212> TYPE: DNA
<213> ORGANISM: Artificial Sequence
<220> FEATURE:
<223> OTHER INFORMATION: IPD103 variant

<400> SEQUENCE: 215

```
atggcggaca agcagcagc agcagctaga gaagctgaag aagaggtgga gacgacgatg       60
gacgagactg aggcggtggg ggtgcacctg gacttcgtgg cgggcttgga ggtgcaaccc     120
cgcaaggtca tcaccgtgga ggtggacgcc gctgccgtaa tccaacagat cagagagatc     180
ttcgggtcca tgatcaatca cttcaactct acgagggtgg tgcggatga agccatcaag     240 ggcattcgag accacttcag ggccgccgtc ccgactcgca acgtggtggt cattcacact     300
cagcacgttc acacactggt ggccgtggag tcctccccacc tcgtcttgca gaccggcctc     360
ttcaaaaagg tccccgtcga catctacgtc ttcaagtccg gcgtcttcac cctccttgga     420
gacggaggct tcatcaactg gcatgggt ggcttcggac tcgagctcgc cggcaagcgt      480
gtccacttcc gccggccccc cggggcgctc cct                                  513
```

<210> SEQ ID NO 216
<211> LENGTH: 513
<212> TYPE: DNA
<213> ORGANISM: Artificial Sequence
<220> FEATURE:
<223> OTHER INFORMATION: IPD103 variant

<400> SEQUENCE: 216

```
atggcggacg aagtagcagg tcaccatggt ccagcatgtg aagaagagga ggaggaaatg      60
ctgatggacg agactgaggc ggtggggtg cacgcgatcg acggtctgcc ggtgcaaaac     120
cgcagcatca tcaccgtgga ggtggacgcc gctgccgtaa tccaacagat cagagagatc     180
ttccgaacca tggcaagtca cttcaactcg acgaggtgg tgcgggatga agccatcaag     240
agcattcgag accacttcag gctcgccgtc ccgactcgca acgtggtggt cgttcacacc     300
cagcacattc acacactgga gggcttggag cacaccaacc tcgtcttgca gaccggcctc     360
ttcaaaaagg tccccgtcga catctacgtc ttcaagtccg gcgtcttcac caacctggga     420
gacggaggct tcatcaactg gcatgggt ggctacggcg tcaaccacac cgccaagcgt      480
gtcgtcttca gccggccccc cggggcgctc cct                                  513
```

<210> SEQ ID NO 217
<211> LENGTH: 510
<212> TYPE: DNA

```
<213> ORGANISM: Artificial Sequence
<220> FEATURE:
<223> OTHER INFORMATION: IPD103 variant

<400> SEQUENCE: 217
atggcggaca aagcagcagc agcagctaga gaagctgaag aagaggtgca ggagactttg      60
atggacgaga ctgaggcggt gggggtgcac gcgatcgacg tctgccggt  gcaaaaccgc     120
agcatcatca ccgtggaggt ggacgccgct gccgtaatcc agcagatcag agagatcttc    180
gcgtcaatga tcaaacacta caactctacg agggtggtgc gggatgaagc catcaagagc    240
attcgagacc acttcaggct cgccgtcccg actcgcaacg tggtggtcat tcacactcag    300
cacgttcaca cactggtggg cttggagcac acccacctcg tcttgcagac cggcctcttc    360
aaaaaggtcc ccgtcgacat ctacgtcttc aagtccggcg tcttcaccct ccttggagac    420
ggaggcttca tcaactgggc atggggtggc ttcgtcgacc aggtcgtcgg caagcgtatc    480
cacttccgct tgcccccgg  ggcgctccct                                     510

<210> SEQ ID NO 218
<211> LENGTH: 513
<212> TYPE: DNA
<213> ORGANISM: Artificial Sequence
<220> FEATURE:
<223> OTHER INFORMATION: IPD103 variant

<400> SEQUENCE: 218
atggcggacg aagtagcagg tcaccatggt ccagcatgtg aagaagagga ggaggaaatg     60
ctgatggacg agactgaggc ggtgggggtg cacgcgatcg acgtctgcc  ggtgcaaaac    120
cgcagcatca tcaccgtgga ggtggacgcc gctgccgtaa tccagcagat cagagagatc    180
ttccgaacca tggcaagtca cttcaactcg acgagggtgg tgcgggatga agccatcaag    240
agcattcgag accacttcag gctcgccgtc ccgactcgca acgtggtggt cgttcacact    300
cagcacgttc acacactgga cgccgtggag tcctcccacc tcgtcttgcg gaccggcctg    360
ttcaaaaagg tccctgtcga catctttgtc ttcaagtccg gcgtcttcac cctccttgga    420
gacggaggct tcatcaactg gcatggggt  ggctacggcg tcaaccacac cgccaagcgt    480
gtcgtcttca gccggccccc cggggcgctc cct                                 513

<210> SEQ ID NO 219
<211> LENGTH: 519
<212> TYPE: DNA
<213> ORGANISM: Artificial Sequence
<220> FEATURE:
<223> OTHER INFORMATION: IPD103 variant

<400> SEQUENCE: 219
atggcggacg aagtagcagg tcaccatggt ccagcatgtg aagaagagga ggaggaaatg     60
ctgatgacg  agactgaggc ggtggggacg cacctggact tcgtggcggg cttggaggtg    120
caaccccgca aggtcatcac cgtggaggtg gacgccgctg ccgtaatcca gcagatcaga    180
gagatcttcc gaaccatggc aagtcacttc aactcgacga gggtggtgcg ggatgaagcc    240
atcaaggca  ttcgagacca cttcaggcc  gccgtcccga ctcgcaacgt ggtggtcatt    300
cacactcagc acgttcacac actggacgcc gtggagtcct cccacctcgt cttgcggacc    360
ggcctgttca aaaaggtccc tgtcgacatc tttgtcttca gtccggcgt  cttcaccctc    420
cttggagacg gaggcttcat caactgggca tggggtggct acgtacagga ggtcgtcggc    480
aagcgtatcc acttccgctt gccccccggg gcgctccct                           519
```

<210> SEQ ID NO 220
<211> LENGTH: 513
<212> TYPE: DNA
<213> ORGANISM: Artificial Sequence
<220> FEATURE:
<223> OTHER INFORMATION: IPD103 variant

<400> SEQUENCE: 220

| | | | | | |
|---|---|---|---|---|---|
| atggcggacg | aagtagcagg | tcaccatggt | ccagcatgtg | aagaagagga | ggaggaaatg | 60 |
| ctgatggacg | agactgaggc | ggtgggggtg | cacgcgatcg | acggtctgcc | ggtgcaaccc | 120 |
| cgcaaggtca | tcaccgtgga | ggtggacgcc | gctgccgtaa | tccaacagat | cagagagatc | 180 |
| ttcgcgtcaa | tgatcaaaca | ctacaactct | acgagggtgg | tgcgggatga | agccatcaag | 240 |
| ggcattcgag | accacttcag | gctcgccgtc | ccgactcgca | acgtggtggt | cgttcacacc | 300 |
| cagcacattc | acacactgga | gggcttggag | cacaccaacc | tcgtcttgcg | gaccggcctg | 360 |
| ttcaaaaagg | tccctgtcga | catctacgtc | ttcaagtccg | gcgtcttcac | cctccttgga | 420 |
| gacggaggct | tcatcaactg | gcatggggt | ggctacggcg | tcaaccacac | cgccaagcgt | 480 |
| gtcgtcttca | gccggcccc | cggggcgctc | cct | | | 513 |

<210> SEQ ID NO 221
<211> LENGTH: 513
<212> TYPE: DNA
<213> ORGANISM: Artificial Sequence
<220> FEATURE:
<223> OTHER INFORMATION: IPD103 variant

<400> SEQUENCE: 221

| | | | | | |
|---|---|---|---|---|---|
| atggcggaca | agcagcagc | agcagctaga | gaagctgaag | aagaggtgga | gacgacgatg | 60 |
| gacgagactg | aggcggtggg | gacgcacctg | gacttcgtgg | cgggcttgga | ggtgcaaccc | 120 |
| cgcaaggtca | tcaccgtgga | ggtggacgcc | gctgccgtaa | tccaacagat | cagagagatc | 180 |
| ttccgaacca | tggcaagtca | cttcaactcg | acgagggtgg | tgcgggatga | agccatcaag | 240 |
| ggcattcgag | accacttcag | ggccgccgtc | ccgactcgca | acgtggtggt | cgttcacacc | 300 |
| cagcacattc | acacactgga | cgccgtggag | tcctcccacc | tcgtcttgcg | gaccggcctc | 360 |
| ttcaaaaagg | tccccgtcga | catctatgtc | ttcaagtccg | gcgtcttcac | cctccttgga | 420 |
| gacggaggct | tcatcaactg | gcatggggt | ggcttcgtcg | accaggtcgt | cggcaagcgt | 480 |
| atccacttcc | gcttgccccc | cggggcgctc | cct | | | 513 |

<210> SEQ ID NO 222
<211> LENGTH: 513
<212> TYPE: DNA
<213> ORGANISM: Artificial Sequence
<220> FEATURE:
<223> OTHER INFORMATION: IPD103 variant

<400> SEQUENCE: 222

| | | | | | |
|---|---|---|---|---|---|
| atggcggacg | aagtagcagg | tcaccatggt | ccagcatgtg | aagaagagga | ggaggaaatg | 60 |
| ctgatggacg | agactgaggc | ggtgggggtg | cacgcgatcg | acggtctgcc | ggtgcaaaac | 120 |
| cgcagcatca | tcaccgtgga | ggtggacgcc | gctgccgtaa | tccagcagat | cagagagatc | 180 |
| ttccaaacca | tggcaagtca | cttcaactcg | acgagggtgg | tgcgggatga | agccatcaag | 240 |
| agcattcgag | accacttcag | gctcgccgtc | ccgactcgca | acgtggtggt | cattcacact | 300 |
| cagcacgttc | acacactgga | cgccgtggag | tcctcccacc | tcgtcttgcg | gaccggcctg | 360 |

| | |
|---|---:|
| ttcaaaaagg tccccgtcga catctacgtc ttcaagtccg gcgtcttcac caacctggga | 420 |
| gacggaggct tcatcaactg gcatggggt ggctacggcg tcaaccacac cgccaagcgt | 480 |
| gtcgtcttca gccggccccc cggggcgctc cct | 513 |

<210> SEQ ID NO 223
<211> LENGTH: 522
<212> TYPE: DNA
<213> ORGANISM: Artificial Sequence
<220> FEATURE:
<223> OTHER INFORMATION: IPD103 variant

<400> SEQUENCE: 223

| | |
|---|---:|
| atggcggacg aagtagcagg tcaccatggt ccagcatgtg aagaagagga ggaggaaatg | 60 |
| ctgatggacg agactgaggc ggtggggacg cacctggact tcttgggcgc ggacgtgaag | 120 |
| ttgcaacccc gcaacatcat caccgtggag gtggacgcgg ctgccgtaat ccaacagatc | 180 |
| agagagatct tccagacaat ggcgcgtcac ttcaactcga cgagggtggt gcgggatgaa | 240 |
| gccatcaagg gcattcgaga ccacttcagg gccgccgtcc cgactcgcaa cgtggtggtc | 300 |
| gttcacaccc agcacattca cactggagg ggcttggagc acaccaacct cgtcttgcag | 360 |
| accggcctct tcaaaaaggt ccccgtcgac atctatgtct tcaagtccgg cgtcttcacc | 420 |
| aaccttggag acggaggctt catcaactgg gcatggggtg cttcgtaca ggaggtcgcc | 480 |
| ggcaagcgta tccacttccg cttgccccc ggggcgctcc ct | 522 |

<210> SEQ ID NO 224
<211> LENGTH: 511
<212> TYPE: DNA
<213> ORGANISM: Artificial Sequence
<220> FEATURE:
<223> OTHER INFORMATION: IPD103 variant

<400> SEQUENCE: 224

| | |
|---|---:|
| atggcggacg aagtagcagg tcaccatggt ccagcatgtg aagaagagga ggaggaaatg | 60 |
| ctgatggacg agactgaggc ggtgggggtg cacgcgatcg acggtctgcc ggtgcaaaac | 120 |
| cgcagcatca tcaccgtgga ggtggacgcc ctgccgtaat ccaacagatc agagagatct | 180 |
| tcgaaccatg gcaagtcact tcaactcgac gagggtggtg cgggatgaag ccatcaagag | 240 |
| cattcgagac cacttcaggc tcgccgtccc gactcgcaac gtggtggtca ttcacactca | 300 |
| gcacgttcac acactggacg ccgtggagtc ctcccacctc gtcttgcgga ccggcctgtt | 360 |
| caaaaaggtc cctgtcgaca tctacgtctt caagtccggc gtcttcacca accttggaga | 420 |
| cggaggcttc atcaactggg catggggtgg ctacggcgtc aaccacaccg ccaagcgtgt | 480 |
| cgtcttcagc cggcccccg gggcgctccc t | 511 |

<210> SEQ ID NO 225
<211> LENGTH: 513
<212> TYPE: DNA
<213> ORGANISM: Artificial Sequence
<220> FEATURE:
<223> OTHER INFORMATION: IPD103 variant

<400> SEQUENCE: 225

| | |
|---|---:|
| atggcggacg aagtagcagg tcaccatggt ccagcatgtg aagaagagga ggaggaaatg | 60 |
| ctgatggacg agactgaggc ggtgggggtg cacgcgatcg acggtctgcc ggtgcaaaac | 120 |
| cgcagcatca tcaccgtgga ggtggacgcc gctgccgtaa tccaacagat cagagagatc | 180 |
| ttcgcgtcaa tgatcaaaca ctacaactct acgagggtgg tgcgggatga agccatcaag | 240 |

```
agcattcgag accacttcag gctcgccgtc ccgactcgca acgtggtggt cattcacact    300
cagcacgttc acacactgga cgccgtggag tcctcccacc tcgtcttgcg gaccggcctg    360
ttcaaaaagg tccccgtcga catctacgtc ttcaagtccg gcgtcttcac taacctggga    420
gacggaggct tcatcaactg gcatggggt ggctacggcg tcaaccacac cgccaagcgt    480
gtcgtcttca gccggccccc cggggcgctc cct                                 513
```

```
<210> SEQ ID NO 226
<211> LENGTH: 510
<212> TYPE: DNA
<213> ORGANISM: Artificial Sequence
<220> FEATURE:
<223> OTHER INFORMATION: IPD103 variant

<400> SEQUENCE: 226
atggcggaca aagcagcagc agcagctaga gaagctgaag aagaggtgca ggagactttg    60
atggacgaga ctgaggcggt gggggtgcac gcgatcgacg tctgccggt gcaacccgc    120 aacatcatca ccgtggaggt ggacgcggct gccgtaatcc aacagatcag agagatcttc    180
cgaaccatgg caagtcactt caactcgacg agggtggtgc gggatgaagc catcaagggc    240
attcgagacc acttcagggc cgccgtcccg actcgcaacg tggtggtcgt tcacactcag    300
cacgttcaca cactggtggg cttggagcac acccacctcg tcttgcagac cggcctcttc    360
ataaaggtcc ccgtcgacat ctacgtcttc aagtccggcg tcttcaccct ccttggagac    420
ggaggcttca tcaactgggc atgggtggc ttcgtcgacc aggtcgtcgg caagcgtatc    480
cacttccgct tgcccccgg ggcgctccct                                      510
```

```
<210> SEQ ID NO 227
<211> LENGTH: 513
<212> TYPE: DNA
<213> ORGANISM: Artificial Sequence
<220> FEATURE:
<223> OTHER INFORMATION: IPD103 variant

<400> SEQUENCE: 227
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac    120
cgcagcatca tcaccgtgga ggtggacgcc gctgccgtaa tccaacagat cagagagatc    180
ttcgcgtcaa tgatcaaaca ctacaactct acgagggtgg tgcgggatga agccatcaag    240
agcattcgag accacttcag gctcgccgtc ccgactcgca acgtggtggt cattcacact    300
cagcacgttc acacactgga cgccgtggag tcctcccacc tcgtcttgca gaccggcctg    360
ttcaaaaagg tccccgtcga catctacgtc ttcaagtccg gcgtcttcac cctccttgga    420
gacggaggct tcatcaactg gcatggggt ggctacggcg tcaaccacac cgccaagcgt    480
gtcgtcttca gccggccccc cggggcgctc cct                                 513
```

```
<210> SEQ ID NO 228
<211> LENGTH: 513
<212> TYPE: DNA
<213> ORGANISM: Artificial Sequence
<220> FEATURE:
<223> OTHER INFORMATION: IPD103 variant

<400> SEQUENCE: 228
atggcggacg aagtagcagg tcaccatggt ccagcatgtg aagaagagga ggaggaaatg    60
```

```
ctgatggacg agactgaggc ggtggggtg cacgcgatcg acggtctgcc ggtgcaaaac      120
cgcagcatca tcaccgtgga ggtggacgcc gctgccgtaa tccagcagat cagagagatc      180
ttccgaacca tggcaagtca cttcaactcg acgagggtgg tgcgggatga agccatcaag      240
agcattcgag accacttcag gctcgccgtc ccgactcgca acgtggtggt cgttcacact      300
cagcacgttc acacactgga cgccgtggag tcctcccacc tcgtcttgcg gaccggcctg      360
ttcaaaaagg tccctgtcga catctttgtc ttcaagtccg gcgtcttcac caaccttgga      420
gacggaggct tcatcaactg gcatggggt ggctacggcg tcaaccacac cgccaagcgt      480
gtcgtcttca gccggccccc cggggcgctc cct                                  513
```

<210> SEQ ID NO 229
<211> LENGTH: 171
<212> TYPE: PRT
<213> ORGANISM: Artificial Sequence
<220> FEATURE:
<223> OTHER INFORMATION: IPD103 variant

<400> SEQUENCE: 229

```
Met Ala Asp Pro Ala Thr Ala Ala Arg Glu Ala Glu Glu Val Glu
1               5                   10                  15

Thr Thr Met Asp Glu Thr Glu Ala Val Gly Thr His Leu Asp Phe Leu
                20                  25                  30

Gly Ala Asp Val Lys Leu Gln Pro Arg Asn Ile Ile Thr Val Glu Val
            35                  40                  45

Asp Ala Ala Ala Val Ile Gln Gln Ile Arg Glu Ile Phe Gln Thr Met
        50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170
```

<210> SEQ ID NO 230
<211> LENGTH: 170
<212> TYPE: PRT
<213> ORGANISM: Artificial Sequence
<220> FEATURE:
<223> OTHER INFORMATION: IPD103 variant

<400> SEQUENCE: 230

```
Met Ala Asp Pro Ala Ala Ala Arg Glu Ala Glu Glu Val Glu
1               5                   10                  15

Thr Thr Met Asp Glu Thr Glu Ala Val Gly Thr His Leu Asp Phe Val
                20                  25                  30

Ala Gly Leu Glu Val Gln Pro Arg Lys Val Ile Thr Val Glu Val Asp
            35                  40                  45

Ala Ala Ala Val Ile Gln Gln Ile Arg Glu Ile Phe Gln Thr Met Ala
```

```
                50                  55                  60
Arg His Phe Asn Ser Thr Arg Val Val Arg Asp Glu Ala Ile Lys Gly
 65                  70                  75                  80

Ile Arg Asp His Phe Arg Ala Ala Val Pro Thr Arg Asn Val Val Val
                 85                  90                  95

Val His Thr Gln His Ile His Thr Leu Val Gly Leu Glu His Thr His
                100                 105                 110

Leu Val Leu Gln Thr Gly Ile Phe Lys Lys Val Pro Val Asp Ile Tyr
            115                 120                 125

Val Phe Lys Ser Gly Val Phe Thr Asn Leu Gly Asp Gly Gly Phe Ile
        130                 135                 140

Asn Trp Ala Trp Gly Gly Phe Val Gln Glu Val Ala Gly Lys Arg Ile
145                 150                 155                 160

His Phe Arg Leu Pro Pro Gly Ala Leu Pro
                165                 170

<210> SEQ ID NO 231
<211> LENGTH: 172
<212> TYPE: PRT
<213> ORGANISM: Artificial Sequence
<220> FEATURE:
<223> OTHER INFORMATION: IPD103 variant

<400> SEQUENCE: 231

Met Ala Asp Pro Ala Thr Ala Ala Arg Glu Ala Glu Glu Glu Val Gln
  1               5                  10                  15

Glu Thr Leu Met Asp Glu Thr Glu Ala Val Gly Thr His Leu Asp Phe
             20                  25                  30

Leu Gly Ala Asp Val Lys Leu Gln Pro Arg Asn Ile Ile Thr Val Glu
         35                  40                  45

Val Asp Ala Ala Val Ile Gln Gln Ile Arg Glu Ile Phe Arg Thr
     50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Val His Thr Gln His Val His Thr Leu Val Gly Leu Glu His
                100                 105                 110

Thr His Leu Val Leu Gln Thr Gly Leu Phe Lys Lys Val Pro Val Asp
            115                 120                 125

Ile Tyr Val Phe Lys Ser Gly Val Phe Thr Leu Leu Gly Asp Gly Gly
        130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 232
<211> LENGTH: 172
<212> TYPE: PRT
<213> ORGANISM: Artificial Sequence
<220> FEATURE:
<223> OTHER INFORMATION: IPD103 variant

<400> SEQUENCE: 232

Met Ala Asp Lys Thr Ala Ala Ala Arg Glu Ala Glu Glu Glu Val
  1               5                  10                  15
```

Gln Glu Thr Leu Met Asp Glu Thr Glu Ala Val Gly Thr His Leu Asp
            20                  25                  30

Phe Val Ala Gly Leu Glu Val Gln Pro Arg Asn Ile Ile Thr Val Glu
        35                  40                  45

Val Asp Ala Ala Val Ile Gln Gln Ile Arg Glu Ile Phe Arg Thr
 50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
                100                 105                 110

Thr Asn Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 233
<211> LENGTH: 171
<212> TYPE: PRT
<213> ORGANISM: Artificial Sequence
<220> FEATURE:
<223> OTHER INFORMATION: IPD103 variant

<400> SEQUENCE: 233

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
 50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
                100                 105                 110

His Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 234
<211> LENGTH: 171
<212> TYPE: PRT
<213> ORGANISM: Artificial Sequence
<220> FEATURE:

```
<223> OTHER INFORMATION: IPD103 variant
<220> FEATURE:
<221> NAME/KEY: misc_feature
<222> LOCATION: (138)..(138)
<223> OTHER INFORMATION: Xaa can be any naturally occurring amino acid

<400> SEQUENCE: 234

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Pro Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Xaa Leu Gly Asp Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Val Pro
                165                 170

<210> SEQ ID NO 235
<211> LENGTH: 171
<212> TYPE: PRT
<213> ORGANISM: Artificial Sequence
<220> FEATURE:
<223> OTHER INFORMATION: IPD103 variant

<400> SEQUENCE: 235

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Val Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Leu Leu Gly Asp Gly Phe
    130                 135                 140

Ile Asn Trp Ala Trp Gly Gly Phe Val Gln Glu Val Ala Gly Lys Arg
```

```
145                 150                 155                 160

Ile His Phe Arg Leu Pro Pro Gly Ala Leu Pro
                165                 170

<210> SEQ ID NO 236
<211> LENGTH: 171
<212> TYPE: PRT
<213> ORGANISM: Artificial Sequence
<220> FEATURE:
<223> OTHER INFORMATION: IPD103 variant

<400> SEQUENCE: 236

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Val Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 237
<211> LENGTH: 173
<212> TYPE: PRT
<213> ORGANISM: Artificial Sequence
<220> FEATURE:
<223> OTHER INFORMATION: IPD103 variant

<400> SEQUENCE: 237

Met Ala Asp Lys Ala Ala Ala Ala Arg Glu Ala Glu Glu Val
1               5                   10                  15

Gln Glu Thr Leu Met Asp Glu Thr Glu Ala Val Gly Thr His Leu Asp
            20                  25                  30

Phe Leu Gly Ala Asp Val Lys Leu Gln Pro Arg Asn Ile Ile Thr Val
        35                  40                  45

Glu Val Asp Ala Ala Val Ile Gln Gln Ile Arg Glu Ile Phe Arg
    50                  55                  60

Thr Met Ala Ser His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Val His Thr Gln His Val His Thr Leu Val Gly Leu Glu
            100                 105                 110
```

His Thr Asn Leu Val Leu Gln Thr Gly Leu Phe Lys Lys Val Pro Val
            115                 120                 125

Asp Ile Tyr Val Phe Lys Ser Gly Val Phe Thr Leu Leu Gly Asp Gly
        130                 135                 140

Gly Phe Ile Asn Trp Ala Trp Gly Gly Phe Val Gln Glu Val Ala Gly
145                 150                 155                 160

Lys Arg Ile His Phe Arg Leu Pro Pro Gly Ala Leu Pro
                165                 170

<210> SEQ ID NO 238
<211> LENGTH: 172
<212> TYPE: PRT
<213> ORGANISM: Artificial Sequence
<220> FEATURE:
<223> OTHER INFORMATION: IPD103 variant

<400> SEQUENCE: 238

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 239
<211> LENGTH: 171
<212> TYPE: PRT
<213> ORGANISM: Artificial Sequence
<220> FEATURE:
<223> OTHER INFORMATION: IPD103 variant

<400> SEQUENCE: 239

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

```
Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 240
<211> LENGTH: 171
<212> TYPE: PRT
<213> ORGANISM: Artificial Sequence
<220> FEATURE:
<223> OTHER INFORMATION: IPD103 variant

<400> SEQUENCE: 240

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Val Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 241
<211> LENGTH: 172
<212> TYPE: PRT
<213> ORGANISM: Artificial Sequence
<220> FEATURE:
<223> OTHER INFORMATION: IPD103 variant

<400> SEQUENCE: 241

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
            20                  25                  30

Phe Val Ala Gly Leu Glu Val Gln Pro Arg Lys Val Ile Thr Val Glu
```

```
            35                  40                  45
Val Asp Ala Ala Val Ile Gln Gln Ile Arg Glu Ile Phe Arg Thr
 50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
             100                 105                 110

Thr His Leu Val Leu Gln Thr Gly Ile Phe Lys Lys Val Pro Val Asp
             115                 120                 125

Ile Tyr Val Phe Lys Ser Gly Val Phe Thr Leu Leu Gly Asp Gly Gly
         130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                 165                 170
```

<210> SEQ ID NO 242
<211> LENGTH: 171
<212> TYPE: PRT
<213> ORGANISM: Artificial Sequence
<220> FEATURE:
<223> OTHER INFORMATION: IPD103 variant

<400> SEQUENCE: 242

```
Thr Ala Asp Lys Ala Ala Ala Ala Arg Glu Ala Glu Glu Val
 1               5                  10                  15

Glu Thr Thr Met Asp Glu Thr Glu Ala Val Gly Thr His Leu Asp Phe
                 20                  25                  30

Val Ala Gly Leu Glu Val Gln Pro Arg Asn Ile Ile Thr Val Glu Val
             35                  40                  45

Asp Ala Ala Ala Val Ile Gln Gln Ile Arg Glu Ile Phe Arg Thr Met
 50                  55                  60

Ala Ser His Phe Asn Ser Thr Arg Val Val Arg Asp Glu Ala Ile Lys
 65                  70                  75                  80

Gly Ile Arg Asp His Phe Arg Ala Ala Val Pro Thr Arg Asn Val Val
                 85                  90                  95

Val Val His Thr Gln His Val His Thr Leu Val Gly Leu Glu His Thr
             100                 105                 110

His Leu Val Leu Gln Thr Gly Ile Phe Lys Lys Val Pro Val Asp Ile
             115                 120                 125

Tyr Val Phe Lys Ser Gly Val Phe Thr Leu Leu Gly Asp Gly Gly Phe
         130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                 165                 170
```

<210> SEQ ID NO 243
<211> LENGTH: 170
<212> TYPE: PRT
<213> ORGANISM: Artificial Sequence
<220> FEATURE:
<223> OTHER INFORMATION: IPD103 variant

<400> SEQUENCE: 243

```
Met Ala Asp Pro Ala Thr Ala Ala Arg Glu Ala Glu Glu Val Glu
1               5                   10                  15

Thr Thr Met Asp Glu Thr Glu Ala Val Gly Thr His Leu Asp Phe Val
            20                  25                  30

Ala Gly Leu Glu Val Gln Pro Arg Lys Val Ile Thr Val Glu Val Asp
                35                  40                  45

Ala Ala Ala Val Ile Gln Gln Ile Arg Glu Ile Phe Arg Thr Met Ala
            50                  55                  60

Ser His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val
                85                  90                  95

Val His Thr Gln His Val His Thr Leu Val Gly Leu Glu His Thr His
                100                 105                 110

Leu Val Leu Gln Thr Gly Leu Phe Lys Lys Val Pro Val Asp Ile Tyr
            115                 120                 125

Val Phe Lys Ser Gly Val Phe Thr Leu Leu Gly Asp Gly Gly Phe Ile
            130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 244
<211> LENGTH: 171
<212> TYPE: PRT
<213> ORGANISM: Artificial Sequence
<220> FEATURE:
<223> OTHER INFORMATION: IPD103 variant

<400> SEQUENCE: 244

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
                35                  40                  45

Asp Ala Ala Ala Val Ile Gln Gln Ile Arg Glu Ile Phe Arg Thr Met
            50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Val Gly Leu Glu His Thr
                100                 105                 110

His Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
            130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 245
<211> LENGTH: 171
```

```
<212> TYPE: PRT
<213> ORGANISM: Artificial Sequence
<220> FEATURE:
<223> OTHER INFORMATION: IPD103 variant

<400> SEQUENCE: 245
```

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Val Gly Leu Glu His Thr
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

```
<210> SEQ ID NO 246
<211> LENGTH: 172
<212> TYPE: PRT
<213> ORGANISM: Artificial Sequence
<220> FEATURE:
<223> OTHER INFORMATION: IPD103 variant

<400> SEQUENCE: 246
```

Met Ala Asp Lys Thr Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Val Ile Gln Gln Ile Arg Glu Ile Phe Arg Thr
    50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 247
<211> LENGTH: 171
<212> TYPE: PRT
<213> ORGANISM: Artificial Sequence
<220> FEATURE:
<223> OTHER INFORMATION: IPD103 variant

<400> SEQUENCE: 247

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Asn Ile Ile Thr Val Glu Val
                35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65              70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
                100                 105                 110

His Leu Val Leu Gln Thr Gly Ile Phe Lys Lys Val Pro Val Asp Ile
                115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 248
<211> LENGTH: 172
<212> TYPE: PRT
<213> ORGANISM: Artificial Sequence
<220> FEATURE:
<223> OTHER INFORMATION: IPD103 variant

<400> SEQUENCE: 248

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Arg Asn Ile Ile Thr Val Glu
                35                  40                  45

Val Asp Ala Ala Ala Val Ile Gln Gln Ile Arg Glu Ile Phe Arg Thr
    50                  55                  60

Met Ala Ser His Phe Asn Ser Thr Arg Val Val Arg Asp Glu Ala Ile
65              70                  75                  80

Lys Gly Ile Arg Asp His Phe Arg Ala Ala Val Pro Thr Arg Asn Val
                85                  90                  95

Val Val Val His Thr Gln His Ile His Thr Leu Val Gly Leu Glu His
                100                 105                 110

Thr His Leu Val Leu Gln Thr Gly Ile Phe Lys Lys Val Pro Val Asp

```
                115                 120                 125
Ile Tyr Val Phe Lys Ser Gly Val Phe Thr Asn Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170
```

<210> SEQ ID NO 249
<211> LENGTH: 171
<212> TYPE: PRT
<213> ORGANISM: Artificial Sequence
<220> FEATURE:
<223> OTHER INFORMATION: IPD103 variant

<400> SEQUENCE: 249

```
Met Ala Asp Pro Ala Thr Ala Ala Arg Glu Ala Glu Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
        50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170
```

<210> SEQ ID NO 250
<211> LENGTH: 172
<212> TYPE: PRT
<213> ORGANISM: Artificial Sequence
<220> FEATURE:
<223> OTHER INFORMATION: IPD103 variant

<400> SEQUENCE: 250

```
Met Ala Asp Lys Ala Ala Ala Ala Arg Glu Ala Glu Glu Glu Val
1               5                   10                  15

Glu Thr Leu Met Asp Glu Thr Glu Ala Val Gly Thr His Leu Asp Phe
                20                  25                  30

Leu Gly Ala Asp Val Lys Leu Gln Pro Arg Asn Ile Ile Thr Val Glu
            35                  40                  45

Val Asp Ala Ala Ala Val Ile Gln Gln Ile Arg Glu Ile Phe Arg Thr
        50                  55                  60

Met Ala Asn His Phe Asn Ser Thr Arg Val Val Arg Asp Glu Ala Ile
65                  70                  75                  80
```

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
            100                 105                 110

Thr Asn Leu Val Leu Gln Thr Gly Leu Phe Lys Lys Val Pro Val Asp
        115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 251
<211> LENGTH: 170
<212> TYPE: PRT
<213> ORGANISM: Artificial Sequence
<220> FEATURE:
<223> OTHER INFORMATION: IPD103 variant

<400> SEQUENCE: 251

Met Ala Asp Pro Ala Ala Ala Arg Glu Ala Glu Glu Val Glu
1               5                   10                  15

Thr Thr Met Asp Glu Thr Glu Ala Val Gly Thr His Leu Asp Phe Val
            20                  25                  30

Ala Gly Leu Glu Val Gln Pro Arg Lys Val Ile Thr Val Glu Val Asp
        35                  40                  45

Ala Ala Val Ile Gln Gln Ile Arg Glu Ile Phe Gln Thr Met Ala
    50                  55                  60

Arg His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val
                85                  90                  95

Val His Thr Gln His Val His Thr Leu Val Gly Leu Glu His Thr Asn
            100                 105                 110

Leu Val Leu Gln Thr Gly Leu Phe Lys Lys Val Pro Val Asp Ile Tyr
        115                 120                 125

Val Phe Lys Ser Gly Val Phe Thr Leu Leu Gly Asp Gly Gly Phe Ile
    130                 135                 140

Asn Trp Ala Trp Gly Gly Phe Val Gln Glu Val Ala Gly Lys Arg Ile
145                 150                 155                 160

His Phe Arg Leu Pro Pro Gly Ala Leu Pro
                165                 170

<210> SEQ ID NO 252
<211> LENGTH: 171
<212> TYPE: PRT
<213> ORGANISM: Artificial Sequence
<220> FEATURE:
<223> OTHER INFORMATION: IPD103 variant

<400> SEQUENCE: 252

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Ala Val Ile Gln Gln Ile Arg Glu Ile Phe Arg Thr Met
            50                  55                  60

Ala Ser His Phe Asn Ser Thr Arg Val Val Arg Asp Glu Ala Ile Lys
 65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

Asn Leu Val Leu Gln Thr Gly Ile Phe Lys Lys Val Pro Val Asp Ile
            115                 120                 125

Tyr Val Phe Lys Ser Gly Val Phe Thr Asn Leu Gly Asp Gly Gly Phe
            130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 253
<211> LENGTH: 172
<212> TYPE: PRT
<213> ORGANISM: Artificial Sequence
<220> FEATURE:
<223> OTHER INFORMATION: IPD103 variant

<400> SEQUENCE: 253

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Lys Val Ile Thr Val Glu
            35                  40                  45

Val Asp Ala Ala Val Ile Gln Gln Ile Arg Glu Ile Phe Gln Thr
        50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
            100                 105                 110

Thr His Leu Val Leu Gln Thr Gly Leu Phe Lys Lys Val Pro Val Asp
            115                 120                 125

Ile Tyr Val Phe Lys Ser Gly Val Phe Thr Leu Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 254
<211> LENGTH: 173
<212> TYPE: PRT
<213> ORGANISM: Artificial Sequence
<220> FEATURE:
<223> OTHER INFORMATION: IPD103 variant

<400> SEQUENCE: 254

Met Ala Asp Lys Ala Ala Ala Ala Ala Arg Glu Ala Glu Glu Glu Val

-continued

```
              1               5                  10                 15
              Gln Glu Thr Leu Met Asp Glu Thr Ala Val Gly Thr His Leu Asp
                              20                 25                 30

Phe Leu Gly Ala Asp Val Lys Leu Gln Pro Arg Lys Val Ile Thr Val
                              35                 40                 45

Glu Val Asp Ala Ala Val Ile Gln Gln Ile Arg Glu Ile Phe Gln
              50                                 55                 60

Thr Met Ala Arg His Phe Asn Ser Thr Arg Val Val Arg Asp Glu Ala
              65                              70                 75                 80

Ile Lys Gly Ile Arg Asp His Phe Arg Ala Ala Val Pro Thr Arg Asn
                                              85                 90                 95

Val Val Val Val His Thr Gln His Ile His Thr Leu Glu Gly Leu Glu
                                              100                105                110

His Thr His Leu Val Leu Gln Thr Gly Ile Phe Lys Lys Val Pro Val
                                              115                120                125

Asp Ile Tyr Val Phe Lys Ser Gly Val Phe Thr Asn Leu Gly Asp Gly
                              130                135                140

Gly Phe Ile Asn Trp Ala Trp Gly Gly Phe Val Gln Glu Val Ala Gly
              145                             150                155                160

Lys Arg Ile His Phe Arg Leu Pro Pro Gly Ala Leu Pro
                                              165                170
```

<210> SEQ ID NO 255
<211> LENGTH: 171
<212> TYPE: PRT
<213> ORGANISM: Artificial Sequence
<220> FEATURE:
<223> OTHER INFORMATION: IPD103 variant

<400> SEQUENCE: 255

```
Met Ala Asp Lys Ala Ala Ala Ala Arg Glu Ala Glu Glu Val
1                5                  10                 15

Glu Thr Thr Met Asp Glu Thr Glu Ala Val Gly Thr His Leu Asp Phe
                 20                 25                 30

Val Ala Gly Leu Glu Val Gln Pro Arg Lys Val Ile Thr Val Glu Val
                 35                 40                 45

Asp Ala Ala Ala Val Ile Gln Gln Ile Arg Glu Ile Phe Arg Thr Met
                 50                 55                 60

Ala Ser His Phe Asn Ser Thr Arg Val Val Arg Asp Glu Ala Ile Lys
65                              70                 75                 80

Gly Ile Arg Asp His Phe Arg Ala Ala Val Pro Thr Arg Asn Val Val
                                85                 90                 95

Val Val His Thr Gln His Val His Thr Leu Val Gly Ser Glu His Thr
                                100                105                110

His Leu Val Leu Gln Thr Gly Ile Phe Lys Lys Val Pro Val Asp Ile
                 115                120                125

Tyr Val Phe Lys Ser Gly Val Phe Thr Leu Leu Gly Asp Gly Gly Phe
                 130                135                140

Ile Asn Trp Ala Trp Gly Gly Phe Val Asp Gln Val Val Gly Lys Arg
145                             150                155                160

Ile His Phe Arg Leu Pro Pro Gly Ala Leu Pro
                                165                170
```

<210> SEQ ID NO 256
<211> LENGTH: 171
<212> TYPE: PRT

```
<213> ORGANISM: Artificial Sequence
<220> FEATURE:
<223> OTHER INFORMATION: IPD103 variant

<400> SEQUENCE: 256

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65              70                  75                  80

Gly Ile Arg Asp His Phe Arg Ala Ala Val Pro Thr Arg Asn Val Val
                85                  90                  95

Val Val His Thr Gln His Val Thr Leu Val Gly Leu Glu His Thr
            100                 105                 110

Asn Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 257
<211> LENGTH: 172
<212> TYPE: PRT
<213> ORGANISM: Artificial Sequence
<220> FEATURE:
<223> OTHER INFORMATION: IPD103 variant

<400> SEQUENCE: 257

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Lys Val Ile Thr Val Glu
            35                  40                  45

Val Asp Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65              70                  75                  80

Lys Gly Ile Arg Asp His Phe Arg Ala Ala Val Pro Thr Arg Asn Val
                85                  90                  95

Val Val Val His Thr Gln His Ile His Thr Leu Val Gly Leu Glu His
            100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Val Gln Glu Val Ala Gly Lys
145                 150                 155                 160
```

```
Arg Ile His Phe Arg Leu Pro Pro Gly Ala Leu Pro
            165                 170
```

<210> SEQ ID NO 258
<211> LENGTH: 171
<212> TYPE: PRT
<213> ORGANISM: Artificial Sequence
<220> FEATURE:
<223> OTHER INFORMATION: IPD103 variant

<400> SEQUENCE: 258

```
Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
        50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
            165                 170
```

<210> SEQ ID NO 259
<211> LENGTH: 171
<212> TYPE: PRT
<213> ORGANISM: Artificial Sequence
<220> FEATURE:
<223> OTHER INFORMATION: IPD103 variant

<400> SEQUENCE: 259

```
Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
        50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

Asn Leu Val Leu Gln Thr Gly Ile Phe Lys Lys Val Pro Val Asp Ile
        115                 120                 125
```

```
Tyr Val Phe Lys Ser Gly Val Phe Thr Asn Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 260
<211> LENGTH: 171
<212> TYPE: PRT
<213> ORGANISM: Artificial Sequence
<220> FEATURE:
<223> OTHER INFORMATION: IPD103 variant

<400> SEQUENCE: 260

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 261
<211> LENGTH: 171
<212> TYPE: PRT
<213> ORGANISM: Artificial Sequence
<220> FEATURE:
<223> OTHER INFORMATION: IPD103 variant

<400> SEQUENCE: 261

Met Ala Asp Pro Ala Thr Ala Ala Arg Glu Ala Glu Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
```

```
                85                  90                  95
Val Val His Thr Gln His Ile His Thr Leu Glu Gly Leu Glu His Thr
               100                 105                 110

His Leu Val Leu Gln Thr Gly Ile Phe Lys Lys Val Pro Val Asp Ile
               115                 120                 125

Tyr Val Phe Lys Ser Gly Val Phe Thr Leu Leu Gly Asp Gly Gly Phe
               130                 135                 140

Ile Asn Trp Ala Trp Gly Gly Phe Val Gln Glu Val Ala Gly Lys Arg
145                150                 155                 160

Ile His Phe Arg Leu Pro Pro Gly Ala Leu Pro
               165                 170

<210> SEQ ID NO 262
<211> LENGTH: 171
<212> TYPE: PRT
<213> ORGANISM: Artificial Sequence
<220> FEATURE:
<223> OTHER INFORMATION: IPD103 variant

<400> SEQUENCE: 262

Met Ala Asp Lys Ala Ala Ala Ala Arg Glu Ala Glu Glu Glu Val
1               5                  10                  15

Glu Thr Thr Met Asp Glu Thr Glu Ala Val Gly Thr His Leu Asp Phe
               20                  25                  30

Val Ala Gly Leu Glu Val Gln Pro Arg Lys Val Ile Thr Val Glu Val
               35                  40                  45

Asp Ala Ala Ala Val Ile Gln Gln Ile Arg Glu Ile Phe Arg Thr Met
               50                  55                  60

Ala Ser His Phe Asn Ser Thr Arg Val Val Arg Asp Glu Ala Ile Lys
65                 70                  75                  80

Gly Ile Arg Asp His Phe Arg Ala Ala Val Pro Thr Arg Asn Val Val
               85                  90                  95

Val Val His Thr Gln His Val His Thr Leu Glu Gly Leu Glu His Thr
               100                 105                 110

His Leu Val Leu Gln Thr Gly Leu Phe Lys Lys Val Pro Val Asp Ile
               115                 120                 125

Tyr Val Phe Lys Ser Gly Val Phe Thr Leu Leu Gly Asp Gly Gly Phe
               130                 135                 140

Ile Asn Trp Ala Trp Gly Gly Phe Val Asp Gln Val Val Gly Lys Arg
145                150                 155                 160

Ile His Phe Arg Leu Pro Pro Gly Ala Leu Pro
               165                 170

<210> SEQ ID NO 263
<211> LENGTH: 171
<212> TYPE: PRT
<213> ORGANISM: Artificial Sequence
<220> FEATURE:
<223> OTHER INFORMATION: IPD103 variant

<400> SEQUENCE: 263

Met Ala Asp Lys Ala Ala Ala Ala Arg Glu Ala Glu Glu Glu Val
1               5                  10                  15

Glu Thr Thr Met Asp Glu Thr Glu Ala Val Gly Thr His Leu Asp Phe
               20                  25                  30

Val Ala Gly Leu Glu Val Gln Pro Arg Lys Val Ile Thr Val Glu Val
               35                  40                  45
```

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Glu Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 264
<211> LENGTH: 171
<212> TYPE: PRT
<213> ORGANISM: Artificial Sequence
<220> FEATURE:
<223> OTHER INFORMATION: IPD103 variant

<400> SEQUENCE: 264

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Glu Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Val Ala Gly Lys Arg
145                 150                 155                 160

Ile His Phe Arg Leu Pro Pro Gly Ala Leu Pro
                165                 170

<210> SEQ ID NO 265
<211> LENGTH: 171
<212> TYPE: PRT
<213> ORGANISM: Artificial Sequence
<220> FEATURE:
<223> OTHER INFORMATION: IPD103 variant

<400> SEQUENCE: 265

Met Ala Asp Lys Ala Ala Ala Ala Arg Glu Ala Glu Glu Glu Val
1               5                   10                  15

```
Glu Thr Thr Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
         35                  40                  45

Asp Ala Ala Val Ile Gln Gln Ile Arg Glu Ile Phe Gln Thr Met
     50                  55                  60

Ala Arg His Phe Asn Ser Thr Arg Val Val Arg Asp Glu Ala Ile Lys
 65                  70                  75                  80

Gly Ile Arg Asp His Phe Arg Ala Ala Val Pro Thr Arg Asn Val Val
                 85                  90                  95

Val Val His Thr Gln His Val His Thr Leu Val Gly Leu Glu His Thr
            100                 105                 110

His Leu Val Leu Gln Thr Gly Leu Phe Lys Lys Val Pro Val Asp Ile
            115                 120                 125

Tyr Val Phe Lys Ser Gly Val Phe Thr Asn Leu Gly Asp Gly Gly Phe
            130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 266
<211> LENGTH: 171
<212> TYPE: PRT
<213> ORGANISM: Artificial Sequence
<220> FEATURE:
<223> OTHER INFORMATION: IPD103 variant
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid

<400> SEQUENCE: 266

Met Ala Asp Thr Ala Ala Ala Ala Arg Glu Asp Glu Glu Glu Leu
 1               5                  10                  15

Glu Thr Xaa Met Asp Glu Thr Glu Ala Val Gly Thr His Leu Asp Phe
            20                  25                  30

Val Ala Gly Leu Glu Val Gln Pro Arg Lys Val Ile Thr Val Glu Val
         35                  40                  45

Asp Ala Ala Val Ile Xaa Gln Ile Arg Glu Ile Phe Arg Thr Met
     50                  55                  60

Ala Xaa His Phe Asn Ser Thr Arg Val Val Arg Asp Glu Ala Ile Lys
 65                  70                  75                  80

Gly Ile Arg Asp His Phe Arg Ala Ala Val Pro Thr Arg Asn Val Val
                 85                  90                  95

Val Val His Thr Gln His Val His Thr Leu Glu Gly Leu Glu His Thr
            100                 105                 110

His Leu Val Leu Gln Thr Gly Ile Phe Lys Lys Val Pro Val Asp Ile
            115                 120                 125

Tyr Val Phe Lys Ser Gly Val Phe Thr Ile Leu Gly Asp Gly Gly Phe
            130                 135                 140
```

```
Ile Asn Trp Ala Trp Gly Gly Phe Val Asp Gln Val Val Gly Lys Arg
145                 150                 155                 160

Ile His Phe Arg Leu Pro Pro Gly Ala Leu Pro
            165                 170
```

<210> SEQ ID NO 267
<211> LENGTH: 170
<212> TYPE: PRT
<213> ORGANISM: Artificial Sequence
<220> FEATURE:
<223> OTHER INFORMATION: IPD103 variant

<400> SEQUENCE: 267

```
Met Ala Asp Lys Ala Ala Ala Ala Arg Glu Ala Glu Glu Val Glu
1               5                   10                  15

Thr Thr Met Asp Glu Thr Glu Ala Val Gly Thr His Leu Asp Phe Val
                20                  25                  30

Ala Gly Leu Glu Val Gln Pro Arg Asn Ile Ile Thr Val Glu Val Asp
            35                  40                  45

Ala Ala Ala Val Ile Gln Gln Ile Arg Glu Ile Phe Gln Thr Met Ala
        50                  55                  60

Arg His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val Val
                85                  90                  95

Val His Thr Gln His Ile His Thr Leu Glu Gly Leu Glu His Thr Asn
            100                 105                 110

Leu Val Leu Gln Thr Gly Leu Phe Lys Lys Val Pro Val Asp Ile Tyr
        115                 120                 125

Val Phe Lys Ser Gly Val Phe Thr Asn Leu Gly Asp Gly Gly Phe Ile
    130                 135                 140

Asn Trp Ala Trp Gly Gly Phe Val Gln Glu Val Ala Gly Lys Arg Ile
145                 150                 155                 160

His Phe Arg Leu Pro Pro Gly Ala Leu Pro
            165                 170
```

<210> SEQ ID NO 268
<211> LENGTH: 170
<212> TYPE: PRT
<213> ORGANISM: Artificial Sequence
<220> FEATURE:
<223> OTHER INFORMATION: IPD103 variant

<400> SEQUENCE: 268

```
Met Ala Asp Lys Ala Ala Ala Ala Arg Glu Ala Glu Glu Glu
1               5                   10                  15

Glu Glu Met Leu Met Asp Glu Thr Glu Ala Val Gly Val His Ala Ile
                20                  25                  30

Asp Gly Leu Pro Val Gln Asn Arg Ser Ile Ile Thr Val Glu Val Asp
            35                  40                  45

Ala Ala Ala Val Ile Gln Gln Ile Arg Glu Ile Phe Arg Thr Met Ala
        50                  55                  60

Ser His Phe Asn Ser Thr Arg Val Val Arg Asp Glu Ala Ile Lys Ser
65                  70                  75                  80

Ile Arg Asp His Phe Arg Leu Ala Val Pro Thr Arg Asn Val Val Val
                85                  90                  95

Val His Thr Gln His Val His Thr Leu Val Gly Leu Glu His Thr His
```

```
            100                 105                 110
Leu Val Leu Gln Thr Gly Ile Phe Lys Lys Val Pro Val Asp Ile Tyr
            115                 120                 125

Val Phe Lys Ser Gly Val Phe Thr Asn Leu Gly Asp Gly Gly Phe Ile
        130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 269
<211> LENGTH: 171
<212> TYPE: PRT
<213> ORGANISM: Artificial Sequence
<220> FEATURE:
<223> OTHER INFORMATION: IPD103 variant

<400> SEQUENCE: 269

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Arg Thr Gly Leu Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 270
<211> LENGTH: 170
<212> TYPE: PRT
<213> ORGANISM: Artificial Sequence
<220> FEATURE:
<223> OTHER INFORMATION: IPD103 variant

<400> SEQUENCE: 270

Met Ala Asp Lys Ala Ala Ala Ala Arg Glu Ala Glu Glu Glu Glu
1               5                   10                  15

Glu Glu Met Leu Met Asp Glu Thr Glu Ala Val Gly Val His Ala Ile
            20                  25                  30

Asp Gly Leu Pro Val Gln Asn Arg Ser Ile Ile Thr Val Glu Val Asp
        35                  40                  45

Ala Ala Ala Val Ile Gln Gln Ile Arg Glu Ile Phe Arg Thr Met Ala
    50                  55                  60
```

Ser His Phe Asn Ser Thr Arg Val Val Arg Asp Glu Ala Ile Lys Gly
65                  70                  75                  80

Ile Arg Asp His Phe Arg Leu Ala Val Pro Thr Arg Asn Val Val Val
                85                  90                  95

Ile His Thr Gln His Val His Thr Leu Val Gly Leu Glu His Thr His
            100                 105                 110

Leu Val Leu Gln Thr Gly Leu Phe Lys Lys Val Pro Val Asp Ile Tyr
        115                 120                 125

Val Phe Lys Ser Gly Val Phe Thr Asn Leu Gly Asp Gly Gly Phe Ile
    130                 135                 140

Asn Trp Ala Trp Gly Gly Phe Val Gln Glu Val Ala Gly Lys Arg Ile
145                 150                 155                 160

His Phe Arg Leu Pro Pro Gly Ala Leu Pro
                165                 170

<210> SEQ ID NO 271
<211> LENGTH: 171
<212> TYPE: PRT
<213> ORGANISM: Artificial Sequence
<220> FEATURE:
<223> OTHER INFORMATION: IPD103 variant

<400> SEQUENCE: 271

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Gln Thr Met
        50                  55                  60

Ala Arg His Phe Asn Ser Thr Arg Val Val Arg Asp Glu Ala Ile Lys
65                  70                  75                  80

Ser Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 272
<211> LENGTH: 171
<212> TYPE: PRT
<213> ORGANISM: Artificial Sequence
<220> FEATURE:
<223> OTHER INFORMATION: IPD103 variant

<400> SEQUENCE: 272

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
                20                  25                  30

```
Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Ala Ser Met
    50                  55                  60

Ile Lys His Tyr Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Val Gly Leu Glu His Thr
            100                 105                 110

His Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
            130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 273
<211> LENGTH: 173
<212> TYPE: PRT
<213> ORGANISM: Artificial Sequence
<220> FEATURE:
<223> OTHER INFORMATION: IPD103 variant

<400> SEQUENCE: 273

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
            20                  25                  30

Asp Phe Val Ala Gly Leu Glu Val Gln Pro Arg Lys Val Ile Thr Val
        35                  40                  45

Glu Val Asp Ala Ala Val Ile Gln Gln Ile Arg Glu Ile Phe Arg
    50                  55                  60

Thr Met Ala Ser His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Val His Thr Gln His Ile His Thr Leu Glu Gly Leu Glu
            100                 105                 110

His Thr His Leu Val Leu Arg Thr Gly Leu Phe Lys Lys Val Pro Val
            115                 120                 125

Asp Ile Phe Val Phe Lys Ser Gly Val Phe Thr Asn Leu Gly Asp Gly
            130                 135                 140

Gly Phe Ile Asn Trp Ala Trp Gly Gly Tyr Val Gln Glu Val Ala Gly
145                 150                 155                 160

Lys Arg Ile His Phe Arg Leu Pro Pro Gly Ala Leu Pro
                165                 170

<210> SEQ ID NO 274
<211> LENGTH: 174
<212> TYPE: PRT
<213> ORGANISM: Artificial Sequence
<220> FEATURE:
<223> OTHER INFORMATION: IPD103 variant
```

-continued

```
<400> SEQUENCE: 274

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
            20                  25                  30

Asp Phe Leu Gly Ala Asp Val Lys Leu Gln Pro Arg Asn Ile Ile Thr
        35                  40                  45

Val Glu Val Asp Ala Ala Ala Val Ile Gln Gln Ile Arg Glu Ile Phe
50                  55                  60

Gln Thr Met Ala Arg His Phe Asn Ser Thr Arg Val Val Arg Asp Glu
65                  70                  75                  80

Ala Ile Lys Gly Ile Arg Asp His Phe Arg Ala Ala Val Pro Thr Arg
                85                  90                  95

Asn Val Val Val Val His Thr Gln His Ile His Thr Leu Glu Gly Leu
            100                 105                 110

Glu His Thr Asn Leu Val Leu Gln Thr Gly Leu Phe Lys Lys Val Pro
        115                 120                 125

Val Asp Ile Tyr Val Phe Lys Ser Gly Val Phe Thr Asn Leu Gly Asp
130                 135                 140

Gly Gly Phe Ile Asn Trp Ala Trp Gly Gly Phe Val Gln Glu Val Ala
145                 150                 155                 160

Gly Lys Arg Ile His Phe Arg Leu Pro Pro Gly Ala Leu Pro
                165                 170

<210> SEQ ID NO 275
<211> LENGTH: 172
<212> TYPE: PRT
<213> ORGANISM: Artificial Sequence
<220> FEATURE:
<223> OTHER INFORMATION: IPD103 variant

<400> SEQUENCE: 275

Met Ala Asp Lys Ala Ala Ala Ala Arg Glu Ala Glu Glu Glu Glu Val
1               5                   10                  15

Gln Glu Thr Leu Met Asp Glu Thr Glu Ala Val Gly Thr His Leu Asp
            20                  25                  30

Phe Val Ala Gly Leu Glu Val Gln Pro Arg Lys Val Ile Thr Val Glu
        35                  40                  45

Val Asp Ala Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Asp Ala Val Glu Ser
            100                 105                 110

Ser His Leu Val Leu Arg Thr Gly Leu Phe Lys Lys Val Pro Val Asp
        115                 120                 125

Ile Tyr Val Phe Lys Ser Gly Val Phe Thr Asn Leu Gly Asp Gly Gly
130                 135                 140

Phe Ile Asn Trp Ala Trp Gly Gly Tyr Val Asp Gln Val Val Gly Lys
145                 150                 155                 160

Arg Ile His Phe Arg Leu Pro Pro Gly Ala Leu Pro
                165                 170
```

```
<210> SEQ ID NO 276
<211> LENGTH: 171
<212> TYPE: PRT
<213> ORGANISM: Artificial Sequence
<220> FEATURE:
<223> OTHER INFORMATION: IPD103 variant

<400> SEQUENCE: 276
```

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Ser Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Gln Glu Val Val Gly Lys Arg
145                 150                 155                 160

Ile His Phe Arg Leu Pro Pro Gly Ala Leu Pro
                165                 170

```
<210> SEQ ID NO 277
<211> LENGTH: 171
<212> TYPE: PRT
<213> ORGANISM: Artificial Sequence
<220> FEATURE:
<223> OTHER INFORMATION: IPD103 variant

<400> SEQUENCE: 277
```

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
            165                 170

<210> SEQ ID NO 278
<211> LENGTH: 173
<212> TYPE: PRT
<213> ORGANISM: Artificial Sequence
<220> FEATURE:
<223> OTHER INFORMATION: IPD103 variant

<400> SEQUENCE: 278

Met Ala Asp Glu Val Ala Gly His His Gly Pro Ala Cys Glu Glu Glu
1               5                   10                  15

Val Gln Glu Thr Leu Met Asp Glu Thr Glu Ala Val Gly Thr His Leu
            20                  25                  30

Asp Phe Val Ala Gly Leu Glu Val Gln Pro Arg Ser Ile Ile Thr Val
        35                  40                  45

Glu Val Asp Ala Ala Ala Val Ile Gln Gln Ile Arg Glu Ile Phe Gln
    50                  55                  60

Thr Met Ala Arg His Phe Asn Ser Thr Arg Val Val Arg Asp Glu Ala
65                  70                  75                  80

Ile Lys Gly Ile Arg Asp His Phe Arg Leu Ala Val Pro Thr Arg Asn
                85                  90                  95

Val Val Val Val His Thr Gln His Val His Thr Leu Val Gly Leu Glu
            100                 105                 110

His Thr His Leu Val Leu Gln Thr Gly Ile Phe Lys Lys Val Pro Val
        115                 120                 125

Asp Ile Tyr Val Phe Lys Ser Gly Val Phe Thr Asn Leu Gly Asp Gly
    130                 135                 140

Gly Phe Ile Asn Trp Ala Trp Gly Gly Phe Val Asp Gln Val Val Gly
145                 150                 155                 160

Lys Arg Ile His Phe Arg Leu Pro Pro Gly Ala Leu Pro
                165                 170

<210> SEQ ID NO 279
<211> LENGTH: 173
<212> TYPE: PRT
<213> ORGANISM: Artificial Sequence
<220> FEATURE:
<223> OTHER INFORMATION: IPD103 variant

<400> SEQUENCE: 279

Lys Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
            20                  25                  30

Asp Phe Val Ala Gly Leu Glu Val Gln Pro Arg Lys Val Ile Thr Val
        35                  40                  45

Glu Val Asp Ala Ala Ala Val Ile Gln Gln Ile Arg Glu Ile Phe Arg
    50                  55                  60

Thr Met Ala Ser His Tyr Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Ile His Thr Gln His Val His Thr Leu Asp Ala Val Glu
            100                 105                 110

```
Ser Ser His Leu Val Leu Gln Thr Gly Ile Phe Lys Lys Val Pro Val
        115                 120                 125

Asp Ile Tyr Val Phe Lys Ser Gly Val Phe Thr Asn Leu Gly Asp Gly
    130                 135                 140

Gly Phe Ile Asn Trp Ala Trp Gly Gly Phe Val Asp Gln Val Val Gly
145                 150                 155                 160

Lys Arg Ile His Phe Arg Leu Pro Pro Gly Ala Leu Pro
                165                 170

<210> SEQ ID NO 280
<211> LENGTH: 174
<212> TYPE: PRT
<213> ORGANISM: Artificial Sequence
<220> FEATURE:
<223> OTHER INFORMATION: IPD103 variant

<400> SEQUENCE: 280

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
            20                  25                  30

Asp Phe Leu Gly Ala Asp Val Lys Leu Gln Pro Arg Asn Ile Ile Thr
        35                  40                  45

Val Glu Val Asp Ala Ala Ala Val Ile Gln Gln Ile Arg Glu Ile Phe
    50                  55                  60

Gln Thr Met Ala Arg His Phe Asn Ser Thr Arg Val Val Arg Asp Glu
65                  70                  75                  80

Ala Ile Lys Gly Ile Arg Asp His Phe Arg Ala Ala Val Pro Thr Arg
                85                  90                  95

Asn Val Val Ile His Thr Gln His Val His Thr Leu Asp Ala Val
            100                 105                 110

Glu Ser Ser His Leu Val Leu Arg Thr Gly Leu Phe Lys Lys Val Pro
        115                 120                 125

Val Asp Ile Tyr Val Phe Lys Ser Gly Val Phe Thr Asn Leu Gly Asp
    130                 135                 140

Gly Gly Phe Ile Asn Trp Ala Trp Gly Gly Phe Val Asp Gln Val Val
145                 150                 155                 160

Gly Lys Arg Ile His Phe Arg Leu Pro Pro Gly Ala Leu Pro
                165                 170

<210> SEQ ID NO 281
<211> LENGTH: 171
<212> TYPE: PRT
<213> ORGANISM: Artificial Sequence
<220> FEATURE:
<223> OTHER INFORMATION: IPD103 variant

<400> SEQUENCE: 281

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
```

```
                65                  70                  75                  80
Ser Ile Arg Asp His Phe Arg Leu Ala Val Pro Thr Arg Asn Val Val
                85                  90                  95

Val Val His Thr Gln His Val His Thr Leu Val Gly Leu Glu His Thr
            100                 105                 110

His Leu Val Leu Arg Thr Gly Leu Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 282
<211> LENGTH: 172
<212> TYPE: PRT
<213> ORGANISM: Artificial Sequence
<220> FEATURE:
<223> OTHER INFORMATION: IPD103 variant

<400> SEQUENCE: 282

Met Ala Asp Glu Val Ala Gly His His Gly Pro Ala Cys Glu Glu Glu
1               5                   10                  15

Val Glu Thr Thr Met Asp Glu Thr Glu Ala Val Gly Thr His Leu Asp
            20                  25                  30

Phe Val Ala Gly Leu Glu Val Gln Pro Arg Lys Val Ile Thr Val Glu
        35                  40                  45

Val Asp Ala Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Ser Ile Arg Asp His Phe Arg Ala Ala Val Pro Thr Arg Asn Val
                85                  90                  95

Val Val Ile His Thr Gln His Val His Thr Leu Glu Gly Leu Glu His
            100                 105                 110

Thr Asn Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 283
<211> LENGTH: 171
<212> TYPE: PRT
<213> ORGANISM: Artificial Sequence
<220> FEATURE:
<223> OTHER INFORMATION: IPD103 variant

<400> SEQUENCE: 283

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30
```

```
Ile Asp Gly Leu Pro Val Gln Asn Arg Ser Ile Ile Thr Val Glu Val
            35                  40                  45

Asp Ala Ala Val Ile Gln Gln Ile Arg Glu Ile Phe Arg Thr Met
 50                  55                  60

Ala Ser His Phe Asn Ser Thr Arg Val Val Arg Asp Glu Ala Ile Lys
 65                  70                  75                  80

Ser Ile Arg Asp His Phe Arg Ala Ala Val Pro Thr Arg Asn Val Val
                 85                  90                  95

Val Val His Thr Gln His Val His Thr Leu Asp Ala Val Glu Ser Ser
                100                 105                 110

His Leu Val Leu Arg Thr Gly Leu Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 284
<211> LENGTH: 172
<212> TYPE: PRT
<213> ORGANISM: Artificial Sequence
<220> FEATURE:
<223> OTHER INFORMATION: IPD103 variant

<400> SEQUENCE: 284

Met Ala Asp Glu Val Ala Gly His His Gly Pro Ala Ser Glu Glu Glu
  1               5                  10                  15

Glu Glu Arg Met Met Asp Glu Thr Glu Thr Glu Ala Val His Leu His
             20                  25                  30

Val Ile Ala Gly Leu Glu Val Gln Pro Arg Ser Ile Ile Thr Val Glu
         35                  40                  45

Val Asp Ala Ala Val Ile Gln Gln Ile Arg Glu Ile Phe Gln Thr
 50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Glu Ala Val Glu Ser
                100                 105                 110

Ser His Leu Val Leu Arg Thr Gly Leu Phe Lys Lys Val Pro Val Asp
            115                 120                 125

Ile Tyr Val Phe Lys Ser Gly Val Phe Thr Leu Leu Gly Asp Gly Gly
        130                 135                 140

Phe Ile Asn Trp Ala Trp Gly Gly Phe Val Val His Val Val Gly Lys
145                 150                 155                 160

Arg Val His Phe Ser Arg Pro Pro Gly Ala Leu Pro
                165                 170

<210> SEQ ID NO 285
<211> LENGTH: 171
<212> TYPE: PRT
<213> ORGANISM: Artificial Sequence
<220> FEATURE:
<223> OTHER INFORMATION: IPD103 variant

<400> SEQUENCE: 285
```

-continued

```
Met Ala Asp Pro Ala Thr Ala Ala Arg Glu Ala Glu Glu Val Gln
1               5                   10                  15

Glu Thr Leu Met Asp Glu Ser Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile His Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Ser Gln His Ile His Thr Leu Glu Gly Leu Glu His Thr
                100                 105                 110

Asn Leu Val Leu Gln Thr Gly Met Phe Lys Lys Val Pro Val Asp Ile
                115                 120                 125

Phe Val Phe Lys Ser Gly Val Phe Thr Leu Leu Gly Asp Gly Gly Phe
130                 135                 140

Ile Asn Trp Ala Trp Gly Gly Phe Val Gln Glu Val Val Gly Lys Arg
145                 150                 155                 160

Ile His Phe Arg Leu Pro Pro Gly Ala Leu Pro
                165                 170
```

<210> SEQ ID NO 286
<211> LENGTH: 171
<212> TYPE: PRT
<213> ORGANISM: Artificial Sequence
<220> FEATURE:
<223> OTHER INFORMATION: IPD103 variant

<400> SEQUENCE: 286

```
Met Ala Asp Glu Val Ala Gly His His Gly Pro Ala Cys Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
                100                 105                 110

Asn Leu Val Leu Gln Thr Gly Leu Phe Lys Lys Val Pro Val Asp Ile
                115                 120                 125

Tyr Val Phe Lys Ser Gly Val Phe Thr Leu Leu Gly Asp Gly Gly Phe
130                 135                 140

Ile Asn Trp Ala Trp Gly Gly Phe Gly Val Asn His Thr Ala Lys Arg
145                 150                 155                 160

Val Val Phe Ser Arg Pro Pro Gly Ala Leu Pro
                165                 170
```

<210> SEQ ID NO 287

<211> LENGTH: 171
<212> TYPE: PRT
<213> ORGANISM: Artificial Sequence
<220> FEATURE:
<223> OTHER INFORMATION: IPD103 variant

<400> SEQUENCE: 287

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Ser Ile Arg Asp His Phe Arg Ala Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Gln Thr Gly Leu Phe Lys Lys Val Pro Val Asp Ile
        115                 120                 125

Phe Val Phe Lys Ser Gly Val Phe Thr Asn Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 288
<211> LENGTH: 171
<212> TYPE: PRT
<213> ORGANISM: Artificial Sequence
<220> FEATURE:
<223> OTHER INFORMATION: IPD103 variant

<400> SEQUENCE: 288

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Ser Ile Arg Asp His Phe Arg Ala Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Arg Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg

```
145                 150                 155                 160
Ile His Phe Arg Leu Pro Pro Gly Ala Leu Pro
                165                 170

<210> SEQ ID NO 289
<211> LENGTH: 173
<212> TYPE: PRT
<213> ORGANISM: Artificial Sequence
<220> FEATURE:
<223> OTHER INFORMATION: IPD103 variant

<400> SEQUENCE: 289

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
                20                  25                  30

Phe Leu Gly Ala Asp Val Lys Leu Gln Pro Arg Lys Val Ile Thr Val
            35                  40                  45

Glu Val Asp Ala Ala Val Ile Gln Gln Ile Arg Glu Ile Phe Arg
    50                  55                  60

Thr Met Ala Ser His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Val His Thr Gln His Ile His Thr Leu Glu Gly Leu Glu
            100                 105                 110

His Thr Asn Leu Val Leu Gln Thr Gly Ile Phe Lys Lys Val Pro Val
        115                 120                 125

Asp Ile Tyr Val Phe Lys Ser Gly Val Phe Thr Leu Leu Gly Asp Gly
    130                 135                 140

Gly Phe Ile Asn Trp Ala Trp Gly Gly Phe Val Gln Glu Val Ala Gly
145                 150                 155                 160

Lys Arg Ile His Phe Arg Leu Pro Pro Gly Ala Leu Pro
                165                 170

<210> SEQ ID NO 290
<211> LENGTH: 171
<212> TYPE: PRT
<213> ORGANISM: Artificial Sequence
<220> FEATURE:
<223> OTHER INFORMATION: IPD103 variant

<400> SEQUENCE: 290

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
                20                  25                  30

Ile Asp Gly Leu Pro Val Gln Asn Arg Ser Ile Ile Thr Val Glu Val
            35                  40                  45

Asp Ala Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Ser Ile Arg Asp His Phe Arg Leu Ala Val Pro Thr Arg Asn Val Val
                85                  90                  95

Val Ile His Thr Gln His Val His Thr Leu Asp Ala Val Glu Ser Ser
            100                 105                 110
```

```
His Leu Val Leu Arg Thr Gly Leu Phe Lys Lys Val Pro Val Asp Ile
            115                 120                 125

Phe Val Phe Lys Ser Gly Val Phe Thr Asn Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 291
<211> LENGTH: 174
<212> TYPE: PRT
<213> ORGANISM: Artificial Sequence
<220> FEATURE:
<223> OTHER INFORMATION: IPD103 variant

<400> SEQUENCE: 291

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
            20                  25                  30

Asp Phe Leu Gly Ala Asp Val Lys Leu Gln Pro Arg Lys Val Ile Thr
        35                  40                  45

Val Glu Val Asp Ala Ala Val Ile Gln Gln Ile Arg Glu Ile Phe
50                  55                  60

Arg Thr Met Ala Ser His Phe Asn Ser Thr Arg Val Val Arg Asp Glu
65                  70                  75                  80

Ala Ile Lys Gly Ile Arg Asp His Phe Arg Ala Ala Val Pro Thr Arg
                85                  90                  95

Asn Val Val Val His Thr Gln His Val His Thr Leu Val Gly Leu
            100                 105                 110

Glu His Thr His Leu Val Leu Gln Thr Gly Leu Phe Lys Lys Val Pro
            115                 120                 125

Val Asp Ile Tyr Val Phe Lys Ser Gly Val Phe Thr Asn Leu Gly Asp
        130                 135                 140

Gly Gly Phe Ile Asn Trp Ala Trp Gly Gly Phe Val Gln Val Val
145                 150                 155                 160

Gly Lys Arg Ile His Phe Arg Leu Pro Pro Gly Ala Leu Pro
                165                 170

<210> SEQ ID NO 292
<211> LENGTH: 169
<212> TYPE: PRT
<213> ORGANISM: Artificial Sequence
<220> FEATURE:
<223> OTHER INFORMATION: IPD103 variant

<400> SEQUENCE: 292

Met Ala Asp Glu Val Ala Ala Ala Ala Arg Glu Ala Glu Glu Glu Val
1               5                   10                  15

Glu Thr Thr Met Asp Glu Thr Glu Ala Val Gly Val His Ala Ile Asp
            20                  25                  30

Gly Leu Pro Val Gln Asn Arg Ser Ile Ile Thr Val Glu Val Asp Ala
        35                  40                  45

Ala Ala Val Ile Gln Gln Ile Arg Glu Ile Phe Arg Thr Met Ala Ser
    50                  55                  60

His Phe Asn Ser Thr Arg Val Val Arg Asp Glu Ala Ile Lys Gly Ile
65                  70                  75                  80
```

```
Arg Asp His Phe Arg Leu Ala Val Pro Thr Arg Asn Val Val Ile
                85                  90                  95

His Thr Gln His Val His Thr Leu Val Gly Leu Glu His Thr His Leu
            100                 105                 110

Val Leu Gln Thr Gly Ile Phe Lys Lys Val Pro Val Asp Ile Tyr Val
        115                 120                 125

Phe Lys Ser Gly Val Phe Thr Asn Leu Gly Asp Gly Phe Ile Asn
    130                 135                 140

Trp Ala Trp Gly Gly Phe Val Asp Gln Val Val Gly Lys Arg Ile His
145                 150                 155                 160

Phe Arg Leu Pro Pro Gly Ala Leu Pro
                165
```

<210> SEQ ID NO 293
<211> LENGTH: 171
<212> TYPE: PRT
<213> ORGANISM: Artificial Sequence
<220> FEATURE:
<223> OTHER INFORMATION: IPD103 variant

<400> SEQUENCE: 293

```
Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Arg Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Gly Val Asn His Thr Ala Lys Arg
145                 150                 155                 160

Val Val Phe Ser Arg Pro Pro Gly Ala Leu Pro
                165                 170
```

<210> SEQ ID NO 294
<211> LENGTH: 172
<212> TYPE: PRT
<213> ORGANISM: Artificial Sequence
<220> FEATURE:
<223> OTHER INFORMATION: IPD103 variant

<400> SEQUENCE: 294

```
Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Lys Val Ile Thr Val Glu
```

```
                  35                  40                  45
Val Asp Ala Ala Val Ile Gln Gln Ile Arg Glu Ile Phe Arg Thr
 50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Val His Thr Gln His Ile His Thr Leu Glu Gly Leu Glu His
                100                 105                 110

Thr Asn Leu Val Leu Gln Thr Gly Leu Phe Lys Lys Val Pro Val Asp
                115                 120                 125

Ile Tyr Val Phe Lys Ser Gly Val Phe Thr Asn Leu Gly Asp Gly Gly
                130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170
```

<210> SEQ ID NO 295
<211> LENGTH: 172
<212> TYPE: PRT
<213> ORGANISM: Artificial Sequence
<220> FEATURE:
<223> OTHER INFORMATION: IPD103 variant

<400> SEQUENCE: 295

```
Met Ala Asp Glu Val Ala Gly His His Gly Pro Ala Cys Glu Glu
 1               5                  10                  15

Val Glu Thr Thr Met Asp Glu Thr Glu Ala Val Gly Thr His Leu Asp
                 20                  25                  30

Phe Val Ala Gly Leu Glu Val Gln Pro Arg Lys Val Ile Thr Val Glu
                 35                  40                  45

Val Asp Ala Ala Ala Val Ile Gln Gln Ile Arg Glu Ile Phe Arg Thr
 50                  55                  60

Met Ala Ser His Phe Asn Ser Thr Arg Val Val Arg Asp Glu Ala Ile
 65                  70                  75                  80

Lys Ser Ile Arg Asp His Phe Arg Ala Ala Val Pro Thr Arg Asn Val
                 85                  90                  95

Val Val Val His Thr Gln His Val His Thr Leu Val Gly Leu Glu His
                100                 105                 110

Thr Asn Leu Val Leu Gln Thr Gly Ile Phe Lys Lys Val Pro Val Asp
                115                 120                 125

Ile Tyr Val Phe Lys Ser Gly Val Phe Thr Asn Leu Gly Asp Gly Gly
                130                 135                 140

Phe Ile Asn Trp Ala Trp Gly Gly Phe Val Gln Glu Ala Ala Gly Lys
145                 150                 155                 160

Arg Ile His Phe Arg Leu Pro Pro Gly Ala Leu Pro
                165                 170
```

<210> SEQ ID NO 296
<211> LENGTH: 171
<212> TYPE: PRT
<213> ORGANISM: Artificial Sequence
<220> FEATURE:
<223> OTHER INFORMATION: IPD103 variant

<400> SEQUENCE: 296

```
Met Ala Asp Lys Ala Ala Ala Ala Arg Glu Ala Glu Glu Glu Ala
1               5                   10                  15

Glu Thr Thr Met Asp Glu Thr Glu Ala Val Gly Thr His Leu Glu Leu
            20                  25                  30

Met Ala Gly Leu Glu Val Gln Pro Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp Pro Phe Arg Ala Ala Val Pro Thr Arg Asn Val Val
                85                  90                  95

Val Val His Ser Gln His Ile His Thr Leu Val Gly Leu Glu His Thr
            100                 105                 110

His Leu Val Leu Gln Thr Gly Met Phe Lys Lys Val Pro Val Asp Ile
        115                 120                 125

Tyr Leu Phe Lys Ser Gly Val Phe Thr Leu Leu Gly Asp Gly Gly Phe
    130                 135                 140

Ile Asn Trp Ala Trp Gly Gly Phe Val Gln Gln Val Ala Gly Lys Arg
145                 150                 155                 160

Ile His Phe Arg Leu Pro Pro Gly Ala Val Pro
                165                 170

<210> SEQ ID NO 297
<211> LENGTH: 171
<212> TYPE: PRT
<213> ORGANISM: Artificial Sequence
<220> FEATURE:
<223> OTHER INFORMATION: IPD103 variant

<400> SEQUENCE: 297

Ile Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 298
<211> LENGTH: 171
```

```
<212> TYPE: PRT
<213> ORGANISM: Artificial Sequence
<220> FEATURE:
<223> OTHER INFORMATION: IPD103 variant

<400> SEQUENCE: 298

Met Ala Asp Pro Ala Thr Ala Ala Arg Glu Asp Glu Glu Val
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
                100                 105                 110

His Leu Val Leu Gln Thr Gly Ile Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Gln Glu Val Ala Gly Lys Arg
145                 150                 155                 160

Val Leu Phe Ser Arg Pro Pro Gly Ala Leu Pro
                165                 170

<210> SEQ ID NO 299
<211> LENGTH: 171
<212> TYPE: PRT
<213> ORGANISM: Artificial Sequence
<220> FEATURE:
<223> OTHER INFORMATION: IPD103 variant

<400> SEQUENCE: 299

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Asp Ala Val Glu Ser Ser
                100                 105                 110

His Leu Val Leu Arg Thr Gly Leu Phe Lys Lys Val Pro Val Asp Ile
            115                 120                 125

Phe Val Phe Lys Ser Gly Val Phe Thr Asn Leu Gly Asp Gly Gly Phe
        130                 135                 140

Ile Asn Trp Ala Trp Gly Gly Tyr Gly Val Asn His Thr Ala Lys Arg
145                 150                 155                 160
```

-continued

```
Val Val Phe Ser Arg Pro Pro Gly Ala Leu Pro
            165             170

<210> SEQ ID NO 300
<211> LENGTH: 171
<212> TYPE: PRT
<213> ORGANISM: Artificial Sequence
<220> FEATURE:
<223> OTHER INFORMATION: IPD103 variant

<400> SEQUENCE: 300

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Val Gly Leu Glu His Thr
                100                 105                 110

Asn Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Val Ala Gly Lys Arg
145                 150                 155                 160

Ile His Phe Arg Leu Pro Pro Gly Ala Leu Pro
                165             170

<210> SEQ ID NO 301
<211> LENGTH: 171
<212> TYPE: PRT
<213> ORGANISM: Artificial Sequence
<220> FEATURE:
<223> OTHER INFORMATION: IPD103 variant

<400> SEQUENCE: 301

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
                100                 105                 110

Asn Leu Val Leu Gln Thr Gly Leu Phe Lys Lys Val Pro Val Asp Ile
```

```
                115                 120                 125
Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 302
<211> LENGTH: 172
<212> TYPE: PRT
<213> ORGANISM: Artificial Sequence
<220> FEATURE:
<223> OTHER INFORMATION: IPD103 variant

<400> SEQUENCE: 302

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Arg Lys Val Ile Thr Val Glu
            35                  40                  45

Val Asp Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Val Pro Thr Arg Asn Val
                85                  90                  95

Val Val His Thr Gln His Val His Thr Leu Val Gly Leu Glu His
            100                 105                 110

Thr Asn Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 303
<211> LENGTH: 171
<212> TYPE: PRT
<213> ORGANISM: Artificial Sequence
<220> FEATURE:
<223> OTHER INFORMATION: IPD103 variant

<400> SEQUENCE: 303

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Gln Thr Met
50                  55                  60

Ala Arg His Phe Asn Ser Thr Arg Val Val Arg Asp Glu Ala Ile Lys
65                  70                  75                  80
```

```
Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 304
<211> LENGTH: 170
<212> TYPE: PRT
<213> ORGANISM: Artificial Sequence
<220> FEATURE:
<223> OTHER INFORMATION: IPD103 variant

<400> SEQUENCE: 304

Met Ala Asp Pro Ala Thr Ala Ala Arg Glu Ala Glu Glu Val Glu
1               5                   10                  15

Thr Thr Met Asp Glu Thr Glu Ala Val Gly Thr His Leu Asp Phe Val
            20                  25                  30

Ala Gly Leu Glu Val Gln Pro Arg Lys Val Ile Thr Val Glu Val Asp
        35                  40                  45

Ala Ala Ala Val Ile Gln Gln Ile Arg Glu Ile Phe Gln Thr Met Ala
    50                  55                  60

Arg His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val
                85                  90                  95

Ile His Thr Gln His Val His Thr Leu Glu Gly Leu Glu His Thr Asn
            100                 105                 110

Leu Val Leu Gln Thr Gly Ile Phe Lys Lys Val Pro Val Asp Ile Tyr
        115                 120                 125

Val Phe Lys Ser Gly Val Phe Thr Leu Leu Gly Asp Gly Gly Phe Ile
    130                 135                 140

Asn Trp Ala Trp Gly Gly Phe Val Gln Glu Val Ala Gly Lys Arg Ile
145                 150                 155                 160

His Phe Arg Leu Pro Pro Gly Ala Leu Pro
                165                 170

<210> SEQ ID NO 305
<211> LENGTH: 172
<212> TYPE: PRT
<213> ORGANISM: Artificial Sequence
<220> FEATURE:
<223> OTHER INFORMATION: IPD103 variant

<400> SEQUENCE: 305

Met Ala Asp Lys Ala Ala Ala Ala Arg Glu Ala Glu Glu Val
1               5                   10                  15

Gln Glu Thr Leu Met Asp Glu Thr Glu Ala Val Gly Thr His Leu Asp
            20                  25                  30

Phe Val Ala Gly Leu Glu Val Gln Pro Arg Lys Val Ile Thr Val Glu
        35                  40                  45
```

Val Asp Ala Ala Val Ile Gln Gln Ile Arg Glu Ile Phe Arg Thr
    50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Val His Thr Gln His Val His Thr Leu Glu Gly Leu Glu His
                100                 105                 110

Thr His Leu Val Leu Gln Thr Gly Leu Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 306
<211> LENGTH: 170
<212> TYPE: PRT
<213> ORGANISM: Artificial Sequence
<220> FEATURE:
<223> OTHER INFORMATION: IPD103 variant

<400> SEQUENCE: 306

Met Ala Asp Pro Ala Thr Ala Ala Arg Glu Ala Glu Glu Val Glu
 1               5                  10                  15

Thr Thr Met Asp Glu Thr Glu Ala Val Gly Thr His Leu Asp Phe Val
             20                  25                  30

Ala Gly Leu Glu Val Gln Pro Arg Asn Ile Ile Thr Val Glu Val Asp
         35                  40                  45

Ala Ala Val Ile Gln Gln Ile Arg Glu Ile Phe Gln Thr Met Ala
    50                  55                  60

Ser His Phe Asn Ser Thr Arg Val Val Arg Asp Glu Ala Ile Lys Gly
 65                  70                  75                  80

Ile Arg Asp His Phe Arg Ala Ala Val Pro Thr Arg Asn Val Val Val
                 85                  90                  95

Val His Thr Gln His Ile His Thr Leu Val Gly Leu Glu His Thr His
                100                 105                 110

Leu Val Leu Gln Thr Gly Leu Phe Lys Lys Val Pro Val Asp Ile Tyr
            115                 120                 125

Val Phe Lys Ser Gly Val Phe Thr Leu Leu Gly Asp Gly Gly Phe Ile
        130                 135                 140

Asn Trp Ala Trp Gly Gly Phe Val Gln Glu Val Ala Gly Lys Arg Ile
145                 150                 155                 160

His Phe Arg Leu Pro Pro Gly Ala Leu Pro
                165                 170

<210> SEQ ID NO 307
<211> LENGTH: 172
<212> TYPE: PRT
<213> ORGANISM: Artificial Sequence
<220> FEATURE:
<223> OTHER INFORMATION: IPD103 variant

<400> SEQUENCE: 307

Met Ala Asp Pro Ala Thr Ala Ala Arg Glu Ala Glu Glu Glu Val Gln

-continued

```
                1               5                  10                 15
Glu Thr Leu Met Asp Glu Thr Glu Ala Val Gly Thr His Leu Asp Phe
                20                 25                 30

Leu Gly Ala Asp Val Lys Leu Gln Pro Arg Asn Ile Ile Thr Val Glu
                35                 40                 45

Val Asp Ala Ala Val Ile Gln Gln Ile Arg Glu Ile Phe Gln Thr
    50                 55                 60

Met Ala Arg His Phe Asn Ser Thr Arg Val Val Arg Asp Glu Ala Ile
65                  70                 75                 80

Lys Gly Ile Arg Asp His Phe Arg Ala Ala Val Pro Thr Arg Asn Val
                85                 90                 95

Val Val Val His Thr Gln His Val His Thr Leu Val Gly Leu Glu His
                100                105                110

Thr His Leu Val Leu Gln Thr Gly Leu Phe Lys Lys Val Pro Val Asp
                115                120                125

Ile Tyr Val Phe Lys Ser Gly Val Phe Thr Leu Leu Gly Asp Gly Gly
                130                135                140

Phe Ile Asn Trp Ala Trp Gly Gly Phe Val Gln Glu Val Ala Gly Lys
145                 150                155                160

Arg Ile His Phe Arg Leu Pro Pro Gly Ala Leu Pro
                165                170

<210> SEQ ID NO 308
<211> LENGTH: 171
<212> TYPE: PRT
<213> ORGANISM: Artificial Sequence
<220> FEATURE:
<223> OTHER INFORMATION: IPD103 variant

<400> SEQUENCE: 308

Met Ala Asp Lys Ala Ala Ala Ala Arg Glu Ala Glu Glu Glu Val
1               5                  10                 15

Glu Thr Thr Met Asp Glu Thr Glu Ala Val Gly Thr His Leu Asp Phe
                20                 25                 30

Val Ala Gly Leu Glu Val Gln Pro Arg Lys Val Ile Thr Val Glu Val
                35                 40                 45

Asp Ala Ala Val Ile Gln Gln Ile Arg Glu Ile Phe Arg Thr Met
    50                 55                 60

Ala Ser His Phe Asn Ser Thr Arg Val Val Arg Asp Glu Ala Ile Lys
65                  70                 75                 80

Gly Ile Arg Asp His Phe Arg Ala Ala Val Pro Thr Arg Asn Val Val
                85                 90                 95

Val Ile His Thr Gln His Val His Thr Leu Val Gly Leu Glu His Thr
                100                105                110

His Leu Val Leu Gln Thr Gly Leu Phe Lys Lys Val Pro Val Asp Ile
                115                120                125

Tyr Val Phe Lys Ser Gly Val Phe Thr Leu Leu Gly Asp Gly Gly Phe
                130                135                140

Ile Asn Trp Ala Trp Gly Gly Phe Val Asp Gln Val Val Gly Lys Arg
145                 150                155                160

Ile His Phe Arg Leu Pro Pro Gly Ala Leu Pro
                165                170

<210> SEQ ID NO 309
<211> LENGTH: 170
<212> TYPE: PRT
```

<213> ORGANISM: Artificial Sequence
<220> FEATURE:
<223> OTHER INFORMATION: IPD103 variant

<400> SEQUENCE: 309

Met Ala Asp Pro Ala Ala Ala Arg Glu Ala Glu Glu Val Glu
1               5                   10                  15

Thr Thr Met Asp Glu Thr Glu Ala Val Gly Thr His Leu Asp Phe Val
            20                  25                  30

Ala Gly Leu Glu Val Gln Pro Arg Asn Ile Ile Thr Val Glu Val Asp
        35                  40                  45

Ala Ala Ala Val Ile Gln Gln Ile Ser Glu Ile Phe Arg Thr Met Ala
    50                  55                  60

Ser His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val Val
                85                  90                  95

Val His Thr Gln His Ile His Thr Leu Glu Gly Leu Glu His Thr His
            100                 105                 110

Leu Val Leu Gln Thr Gly Ile Phe Lys Lys Val Pro Val Asp Ile Tyr
        115                 120                 125

Val Phe Lys Ser Gly Val Phe Thr Leu Leu Gly Asp Gly Gly Phe Ile
    130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 310
<211> LENGTH: 172
<212> TYPE: PRT
<213> ORGANISM: Artificial Sequence
<220> FEATURE:
<223> OTHER INFORMATION: IPD103 variant

<400> SEQUENCE: 310

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
            100                 105                 110

Thr Asn Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Asp Gln Val Val Gly Lys
145                 150                 155                 160

```
Arg Ile His Phe Arg Leu Pro Pro Gly Ala Leu Pro
                165                 170
```

<210> SEQ ID NO 311
<211> LENGTH: 172
<212> TYPE: PRT
<213> ORGANISM: Artificial Sequence
<220> FEATURE:
<223> OTHER INFORMATION: IPD103 variant

<400> SEQUENCE: 311

```
Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
            20                  25                  30

Phe Val Ala Gly Leu Glu Val Gln Pro Arg Lys Val Ile Thr Val Glu
                35                  40                  45

Val Asp Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Glu Gly Leu Glu His
            100                 105                 110

Thr His Leu Val Leu Gln Thr Gly Leu Phe Lys Lys Val Pro Val Asp
                115                 120                 125

Ile Tyr Val Phe Lys Ser Gly Val Phe Thr Leu Leu Gly Asp Gly Gly
            130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170
```

<210> SEQ ID NO 312
<211> LENGTH: 171
<212> TYPE: PRT
<213> ORGANISM: Artificial Sequence
<220> FEATURE:
<223> OTHER INFORMATION: IPD103 variant

<400> SEQUENCE: 312

```
Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
                35                  40                  45

Asp Ala Ala Val Ile Gln Gln Ile Arg Glu Ile Phe Arg Thr Met
            50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Val Gly Leu Glu His Thr
            100                 105                 110

His Leu Val Leu Gln Thr Gly Ile Phe Lys Lys Val Pro Val Asp Ile
                115                 120                 125
```

Tyr Val Phe Lys Ser Gly Val Phe Thr Asn Leu Gly Asp Gly Gly Phe
            130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 313
<211> LENGTH: 172
<212> TYPE: PRT
<213> ORGANISM: Artificial Sequence
<220> FEATURE:
<223> OTHER INFORMATION: IPD103 variant

<400> SEQUENCE: 313

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Arg Asn Ile Ile Thr Val Glu
            35                  40                  45

Val Asp Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
            85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 314
<211> LENGTH: 172
<212> TYPE: PRT
<213> ORGANISM: Artificial Sequence
<220> FEATURE:
<223> OTHER INFORMATION: IPD103 variant

<400> SEQUENCE: 314

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Arg Asn Ile Ile Thr Val Glu
            35                  40                  45

Val Asp Ala Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val

```
                    85                  90                  95
Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Leu Leu Gly Asp Gly Gly
        130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 315
<211> LENGTH: 171
<212> TYPE: PRT
<213> ORGANISM: Artificial Sequence
<220> FEATURE:
<223> OTHER INFORMATION: IPD103 variant

<400> SEQUENCE: 315

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Ala Val Ile Gln Gln Ile Arg Glu Ile Phe Arg Thr Met
        50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
                100                 105                 110

His Leu Val Leu Gln Thr Gly Leu Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 316
<211> LENGTH: 173
<212> TYPE: PRT
<213> ORGANISM: Artificial Sequence
<220> FEATURE:
<223> OTHER INFORMATION: IPD103 variant

<400> SEQUENCE: 316

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
                20                  25                  30

Phe Leu Gly Ala Asp Val Lys Leu Gln Pro Arg Asn Ile Ile Thr Val
            35                  40                  45
```

```
Glu Val Asp Ala Ala Val Ile Gln Gln Ile Arg Glu Ile Phe Arg
    50                  55                  60
Thr Met Ala Ser His Phe Asn Ser Thr Arg Val Val Arg Asp Glu Ala
65                  70                  75                  80
Ile Lys Gly Ile Arg Asp His Phe Arg Ala Ala Val Pro Thr Arg Asn
                85                  90                  95
Val Val Val His Thr Gln His Ile His Thr Leu Glu Gly Leu Glu
            100                 105                 110
His Thr His Leu Val Leu Gln Thr Gly Leu Phe Lys Lys Val Pro Val
                115                 120                 125
Asp Ile Tyr Val Phe Lys Ser Gly Val Phe Thr Leu Leu Gly Asp Gly
            130                 135                 140
Gly Phe Ile Asn Trp Ala Trp Gly Gly Phe Val Gln Glu Val Ala Gly
145                 150                 155                 160
Lys Arg Ile His Phe Arg Leu Pro Pro Gly Ala Leu Pro
                165                 170
```

<210> SEQ ID NO 317
<211> LENGTH: 170
<212> TYPE: PRT
<213> ORGANISM: Artificial Sequence
<220> FEATURE:
<223> OTHER INFORMATION: IPD103 variant

<400> SEQUENCE: 317

```
Met Ala Asp Pro Ala Thr Ala Ala Arg Glu Ala Glu Glu Val Glu
1               5                   10                  15
Thr Thr Met Asp Glu Thr Glu Ala Val Gly Thr His Leu Asp Phe Val
                20                  25                  30
Ala Gly Leu Glu Val Gln Pro Arg Lys Val Ile Thr Val Glu Val Asp
            35                  40                  45
Ala Ala Ala Val Ile Gln Gln Ile Arg Glu Ile Phe Gln Thr Met Ala
        50                  55                  60
Arg His Phe Asn Ser Thr Arg Val Val Arg Asp Glu Ala Ile Lys Gly
65                  70                  75                  80
Ile Arg Asp His Phe Arg Ala Ala Val Pro Thr Arg Asn Val Val Val
                85                  90                  95
Val His Thr Gln His Ile His Thr Leu Glu Gly Leu Glu His Thr Asn
            100                 105                 110
Leu Val Leu Gln Thr Gly Leu Phe Lys Lys Val Pro Val Asp Ile Tyr
        115                 120                 125
Val Phe Lys Ser Gly Val Phe Thr Leu Leu Gly Asp Gly Gly Phe Ile
    130                 135                 140
Asn Trp Ala Trp Gly Gly Phe Val Gln Glu Val Ala Gly Lys Arg Ile
145                 150                 155                 160
His Phe Arg Leu Pro Pro Gly Ala Leu Pro
                165                 170
```

<210> SEQ ID NO 318
<211> LENGTH: 171
<212> TYPE: PRT
<213> ORGANISM: Artificial Sequence
<220> FEATURE:
<223> OTHER INFORMATION: IPD103 variant

<400> SEQUENCE: 318

```
Met Ala Asp Lys Ala Ala Ala Ala Ala Arg Glu Ala Glu Glu Glu Val
1               5                   10                  15
```

```
Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Ile His Thr Leu Gly Leu Glu His Thr
            100                 105                 110

Asn Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 319
<211> LENGTH: 171
<212> TYPE: PRT
<213> ORGANISM: Artificial Sequence
<220> FEATURE:
<223> OTHER INFORMATION: IPD103 variant

<400> SEQUENCE: 319

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 320
<211> LENGTH: 172
<212> TYPE: PRT
<213> ORGANISM: Artificial Sequence
```

```
<220> FEATURE:
<223> OTHER INFORMATION: IPD103 variant

<400> SEQUENCE: 320

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
            20                  25                  30

Phe Val Ala Gly Leu Glu Val Gln Pro Arg Lys Val Ile Thr Val Glu
            35                  40                  45

Val Asp Ala Ala Ala Val Ile Gln Gln Ile Arg Glu Ile Phe Gln Thr
        50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Glu Gly Leu Glu His
            100                 105                 110

Thr Asn Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 321
<211> LENGTH: 171
<212> TYPE: PRT
<213> ORGANISM: Artificial Sequence
<220> FEATURE:
<223> OTHER INFORMATION: IPD103 variant

<400> SEQUENCE: 321

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
            35                  40                  45

Asp Ala Ala Ala Val Ile Gln Gln Ile Arg Glu Ile Phe Arg Thr Met
        50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Ile His Thr Leu Glu Gly Leu Glu His Thr
            100                 105                 110

His Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
```

<210> SEQ ID NO 322
<211> LENGTH: 172
<212> TYPE: PRT
<213> ORGANISM: Artificial Sequence
<220> FEATURE:
<223> OTHER INFORMATION: IPD103 variant

<400> SEQUENCE: 322

```
Met Ala Asp Lys Ala Ala Ala Ala Arg Glu Ala Glu Glu Glu Val Gln
 1               5                  10                  15
Glu Thr Leu Met Asp Glu Thr Glu Ala Val Gly Thr His Leu Asp Phe
                20                  25                  30
Leu Gly Ala Asp Val Lys Leu Gln Pro Arg Asn Ile Ile Thr Val Glu
            35                  40                  45
Val Asp Ala Ala Val Ile Gln Gln Ile Arg Glu Ile Phe Arg Thr
     50                  55                  60
Met Ala Ser His Phe Asn Ser Thr Arg Val Val Arg Asp Glu Ala Ile
 65                  70                  75                  80
Lys Gly Ile Arg Asp His Phe Arg Ala Ala Val Pro Thr Arg Asn Val
                 85                  90                  95
Val Val Val His Thr Gln His Ile His Thr Leu Glu Gly Leu Glu His
            100                 105                 110
Thr Asn Leu Val Leu Gln Thr Gly Leu Phe Lys Lys Val Pro Val Asp
        115                 120                 125
Ile Tyr Val Phe Lys Ser Gly Val Phe Thr Leu Leu Gly Asp Gly Gly
    130                 135                 140
Phe Ile Asn Trp Ala Trp Gly Gly Phe Val Gln Glu Val Ala Gly Lys
145                 150                 155                 160
Arg Ile His Phe Arg Leu Pro Pro Gly Ala Leu Pro
                165                 170
```

<210> SEQ ID NO 323
<211> LENGTH: 171
<212> TYPE: PRT
<213> ORGANISM: Artificial Sequence
<220> FEATURE:
<223> OTHER INFORMATION: IPD103 variant

<400> SEQUENCE: 323

```
Met Ala Asp Lys Ala Ala Ala Ala Arg Glu Ala Glu Glu Glu Val
 1               5                  10                  15
Glu Thr Thr Met Asp Glu Thr Glu Ala Val Gly Thr His Leu Asp Phe
                20                  25                  30
Val Ala Gly Leu Glu Val Gln Pro Arg Lys Val Ile Thr Val Glu Val
            35                  40                  45
Asp Ala Ala Val Ile Gln Gln Ile Arg Glu Ile Phe Arg Thr Met
     50                  55                  60
Ala Ser His Phe Asn Ser Thr Arg Val Val Arg Asp Glu Ala Ile Lys
 65                  70                  75                  80
Gly Ile Arg Asp His Phe Arg Ala Ala Val Pro Thr Arg Asn Val Val
                 85                  90                  95
Val Val His Thr Gln His Val His Thr Leu Glu Gly Leu Glu His Thr
            100                 105                 110
Asn Leu Val Leu Gln Thr Gly Leu Phe Lys Lys Val Pro Val Asp Ile
        115                 120                 125
```

Tyr Val Phe Lys Ser Gly Val Phe Thr Leu Leu Gly Asp Gly Gly Phe
            130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
            165                 170

<210> SEQ ID NO 324
<211> LENGTH: 171
<212> TYPE: PRT
<213> ORGANISM: Artificial Sequence
<220> FEATURE:
<223> OTHER INFORMATION: IPD103 variant

<400> SEQUENCE: 324

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
            35                  40                  45

Asp Ala Ala Ala Val Ile Gln Gln Ile Arg Glu Ile Phe Arg Thr Met
50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
            85                  90                  95

Val Val His Thr Gln His Ile His Thr Leu Glu Gly Leu Glu His Thr
            100                 105                 110

His Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
            130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
            165                 170

<210> SEQ ID NO 325
<211> LENGTH: 171
<212> TYPE: PRT
<213> ORGANISM: Artificial Sequence
<220> FEATURE:
<223> OTHER INFORMATION: IPD103 variant

<400> SEQUENCE: 325

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
            35                  40                  45

Asp Ala Ala Ala Val Ile Gln Gln Ile Arg Glu Ile Phe Arg Thr Met
50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
            85                  90                  95

```
Val Ile His Thr Gln His Ile His Thr Leu Glu Gly Leu Glu His Thr
            100                 105                 110

Asn Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
            130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 326
<211> LENGTH: 171
<212> TYPE: PRT
<213> ORGANISM: Artificial Sequence
<220> FEATURE:
<223> OTHER INFORMATION: IPD103 variant

<400> SEQUENCE: 326

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
            35                  40                  45

Asp Ala Ala Val Ile Gln Gln Ile Arg Glu Ile Phe Arg Thr Met
        50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Ile His Thr Leu Glu Gly Leu Glu His Thr
            100                 105                 110

Asn Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
            130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 327
<211> LENGTH: 172
<212> TYPE: PRT
<213> ORGANISM: Artificial Sequence
<220> FEATURE:
<223> OTHER INFORMATION: IPD103 variant

<400> SEQUENCE: 327

Met Ala Asp Lys Ala Ala Ala Ala Arg Glu Ala Glu Glu Val
1               5                   10                  15

Gln Glu Thr Leu Met Asp Glu Thr Glu Ala Val Gly Thr His Leu Asp
                20                  25                  30

Phe Val Ala Gly Leu Glu Val Gln Pro Arg Lys Val Ile Thr Val Glu
            35                  40                  45

Val Asp Ala Ala Ala Val Ile Gln Gln Ile Arg Glu Ile Phe Arg Thr
```

-continued

```
               50                  55                  60
Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 328
<211> LENGTH: 172
<212> TYPE: PRT
<213> ORGANISM: Artificial Sequence
<220> FEATURE:
<223> OTHER INFORMATION: IPD103 variant

<400> SEQUENCE: 328

Met Ala Asp Lys Ala Ala Ala Ala Arg Glu Ala Glu Glu Glu Val
 1               5                  10                  15

Gln Glu Thr Leu Met Asp Glu Thr Glu Ala Val Gly Thr His Leu Asp
                20                  25                  30

Phe Val Ala Gly Leu Glu Val Gln Pro Arg Lys Val Ile Thr Val Glu
            35                  40                  45

Val Asp Ala Ala Val Ile Gln Gln Ile Arg Glu Ile Phe Gln Thr
        50                  55                  60

Met Ala Arg His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Val His Thr Gln His Val His Thr Leu Val Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Gln Glu Val Ala Gly Lys
145                 150                 155                 160

Arg Ile His Phe Arg Leu Pro Pro Gly Ala Leu Pro
                165                 170

<210> SEQ ID NO 329
<211> LENGTH: 171
<212> TYPE: PRT
<213> ORGANISM: Artificial Sequence
<220> FEATURE:
<223> OTHER INFORMATION: IPD103 variant

<400> SEQUENCE: 329

Met Ala Asp Pro Ala Thr Ala Ala Arg Glu Ala Glu Glu Glu Val Gln
 1               5                  10                  15
```

```
Glu Thr Leu Met Asp Glu Thr Glu Ala Val Gly Thr His Leu Asp Phe
             20                  25                  30

Val Ala Gly Leu Glu Val Gln Pro Arg Lys Val Ile Thr Val Glu Val
         35                  40                  45

Asp Ala Ala Val Ile Gln Gln Ile Arg Glu Ile Phe Arg Thr Met
     50                  55                  60

Ala Ser His Phe Asn Ser Thr Arg Val Val Arg Asp Glu Ala Ile Lys
 65                  70                  75                  80

Gly Ile Arg Asp His Phe Arg Ala Ala Val Pro Thr Arg Asn Val Val
                 85                  90                  95

Val Val His Thr Gln His Val His Thr Leu Glu Gly Leu Glu His Thr
            100                 105                 110

Asn Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
            130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 330
<211> LENGTH: 172
<212> TYPE: PRT
<213> ORGANISM: Artificial Sequence
<220> FEATURE:
<223> OTHER INFORMATION: IPD103 variant

<400> SEQUENCE: 330

Met Ala Asp Lys Ala Ala Ala Ala Arg Glu Ala Glu Glu Glu Val
 1               5                  10                  15

Glu Thr Thr Met Asp Glu Thr Glu Ala Val Gly Thr His Leu Asp Phe
             20                  25                  30

Leu Gly Ala Asp Val Lys Leu Gln Pro Arg Asn Ile Ile Thr Val Glu
         35                  40                  45

Val Asp Ala Ala Ala Val Ile Gln Gln Ile Arg Glu Ile Phe Arg Thr
     50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Val His Thr Gln His Ile His Thr Leu Glu Gly Leu Glu His
            100                 105                 110

Thr Asn Leu Val Leu Gln Thr Gly Leu Phe Lys Lys Val Pro Val Asp
            115                 120                 125

Ile Tyr Val Phe Lys Ser Gly Val Phe Thr Leu Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 331
<211> LENGTH: 172
<212> TYPE: PRT
<213> ORGANISM: Artificial Sequence
<220> FEATURE:
```

<223> OTHER INFORMATION: IPD103 variant

<400> SEQUENCE: 331

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 332
<211> LENGTH: 172
<212> TYPE: PRT
<213> ORGANISM: Artificial Sequence
<220> FEATURE:
<223> OTHER INFORMATION: IPD103 variant

<400> SEQUENCE: 332

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Val His Thr Leu Val Gly Leu Glu His
            100                 105                 110

Thr His Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Asp Gln Val Ala Gly Lys
145                 150                 155                 160

Arg Ile His Phe Arg Leu Pro Pro Gly Ala Leu Pro
                165                 170

<210> SEQ ID NO 333
<211> LENGTH: 172
<212> TYPE: PRT
<213> ORGANISM: Artificial Sequence
<220> FEATURE:
<223> OTHER INFORMATION: IPD103 variant

<400> SEQUENCE: 333

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
            100                 105                 110

Thr His Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 334
<211> LENGTH: 170
<212> TYPE: PRT
<213> ORGANISM: Artificial Sequence
<220> FEATURE:
<223> OTHER INFORMATION: IPD103 variant

<400> SEQUENCE: 334

Met Ala Asp Pro Ala Thr Ala Ala Arg Glu Ala Glu Glu Val Glu
1               5                   10                  15

Thr Thr Met Asp Glu Thr Glu Ala Val Gly Thr His Leu Asp Phe Val
            20                  25                  30

Ala Gly Leu Glu Val Gln Pro Arg Lys Val Ile Thr Val Glu Val Asp
        35                  40                  45

Ala Ala Val Ile Gln Gln Ile Arg Glu Ile Phe Arg Thr Met Ala
    50                  55                  60

Ser His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val
                85                  90                  95

Ile His Thr Gln His Ile His Thr Leu Glu Gly Leu Glu His Thr Asn
            100                 105                 110

Leu Val Leu Gln Thr Gly Leu Phe Lys Lys Val Pro Val Asp Ile Tyr
        115                 120                 125

Val Phe Lys Ser Gly Val Phe Thr Leu Leu Gly Asp Gly Gly Phe Ile

```
                    130               135                140
Asn Trp Ala Trp Gly Gly Phe Val Gln Glu Val Ala Gly Lys Arg Ile
145                 150                 155                 160

His Phe Arg Leu Pro Pro Gly Ala Leu Pro
                165                 170

<210> SEQ ID NO 335
<211> LENGTH: 171
<212> TYPE: PRT
<213> ORGANISM: Artificial Sequence
<220> FEATURE:
<223> OTHER INFORMATION: IPD103 variant

<400> SEQUENCE: 335

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Val Ile Thr Val Glu Val
                35                  40                  45

Asp Ala Ala Val Ile Gln Gln Ile Arg Glu Ile Phe Gln Thr Met
50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
                100                 105                 110

His Leu Val Leu Gln Thr Gly Leu Phe Lys Lys Val Pro Val Asp Ile
                115                 120                 125

Tyr Val Phe Lys Ser Gly Val Phe Thr Asn Leu Gly Asp Gly Gly Phe
                130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 336
<211> LENGTH: 171
<212> TYPE: PRT
<213> ORGANISM: Artificial Sequence
<220> FEATURE:
<223> OTHER INFORMATION: IPD103 variant
<220> FEATURE:
<221> NAME/KEY: misc_feature
<222> LOCATION: (43)..(43)
<223> OTHER INFORMATION: Xaa can be any naturally occurring amino acid

<400> SEQUENCE: 336

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Xaa Ile Thr Val Glu Val
                35                  40                  45

Asp Ala Ala Ala Val Ile Gln Gln Ile Arg Glu Ile Phe Arg Thr Met
50                  55                  60

Ala Ser His Phe Asn Ser Thr Arg Val Val Arg Asp Glu Ala Ile Lys
65                  70                  75                  80
```

Gly Ile Arg Asp His Phe Arg Ala Ala Val Pro Thr Arg Asn Val
            85                  90                  95

Val Val His Thr Gln His Ile His Thr Leu Val Gly Leu Glu His Thr
            100                 105                 110

Asn Leu Val Leu Gln Thr Gly Ile Phe Lys Lys Val Pro Val Asp Ile
        115                 120                 125

Tyr Val Phe Lys Ser Gly Val Phe Thr Ile Leu Gly Asp Gly Gly Phe
    130                 135                 140

Ile Asn Trp Ala Trp Gly Gly Phe Val Gln Glu Val Val Gly Lys Arg
145                 150                 155                 160

Ile His Phe Arg Leu Pro Pro Gly Ala Leu Pro
            165                 170

<210> SEQ ID NO 337
<211> LENGTH: 172
<212> TYPE: PRT
<213> ORGANISM: Artificial Sequence
<220> FEATURE:
<223> OTHER INFORMATION: IPD103 variant

<400> SEQUENCE: 337

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
            20                  25                  30

Phe Val Ala Gly Leu Glu Val Gln Pro Arg Lys Val Ile Thr Val Glu
        35                  40                  45

Val Asp Ala Ala Val Ile Gln Gln Ile Arg Glu Ile Phe Arg Thr
    50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
            85                  90                  95

Val Val Val His Thr Gln His Ile His Thr Leu Glu Gly Leu Glu His
            100                 105                 110

Thr Asn Leu Val Leu Gln Thr Gly Ile Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
            165                 170

<210> SEQ ID NO 338
<211> LENGTH: 171
<212> TYPE: PRT
<213> ORGANISM: Artificial Sequence
<220> FEATURE:
<223> OTHER INFORMATION: IPD103 variant

<400> SEQUENCE: 338

Met Ala Asp Pro Ala Thr Ala Arg Glu Ala Glu Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Lys Val Ile Thr Val Glu Val

```
            35                  40                  45
Asp Ala Ala Val Ile Gln Gln Ile Arg Glu Ile Phe Arg Thr Met
 50                  55                  60
Ala Ser His Phe Asn Ser Thr Arg Val Val Arg Asp Glu Ala Ile Lys
 65                  70                  75                  80
Gly Ile Arg Asp His Phe Arg Ala Ala Val Pro Thr Arg Asn Val Val
                 85                  90                  95
Val Ile His Thr Gln His Val Thr Leu Val Gly Leu Glu His Thr
                100                 105                 110
Asn Leu Val Leu Gln Thr Gly Leu Phe Lys Lys Val Pro Val Asp Ile
            115                 120                 125
Tyr Val Phe Lys Ser Gly Val Phe Thr Asn Leu Gly Asp Gly Phe
            130                 135                 140
Ile Asn Trp Ala Trp Gly Gly Phe Val Gln Val Ala Gly Lys Arg
145                 150                 155                 160
Ile His Phe Arg Leu Pro Pro Gly Ala Leu Pro
                165                 170

<210> SEQ ID NO 339
<211> LENGTH: 170
<212> TYPE: PRT
<213> ORGANISM: Artificial Sequence
<220> FEATURE:
<223> OTHER INFORMATION: IPD103 variant

<400> SEQUENCE: 339

Met Ala Asp Pro Ala Thr Ala Ala Arg Glu Ala Glu Glu Val Glu
  1               5                  10                  15
Thr Thr Met Asp Glu Thr Glu Ala Val Gly Thr His Leu Asp Phe Val
                 20                  25                  30
Ala Gly Leu Glu Val Gln Pro Arg Lys Val Ile Thr Val Glu Val Asp
             35                  40                  45
Ala Ala Ala Val Ile Gln Gln Ile Arg Glu Ile Phe Arg Thr Met Ala
         50                  55                  60
Ser His Phe Asn Ser Thr Arg Val Val Arg Asp Glu Ala Ile Lys Gly
 65                  70                  75                  80
Ile Arg Asp His Phe Arg Ala Ala Val Pro Thr Arg Asn Val Val Val
                 85                  90                  95
Val His Thr Gln His Ile His Thr Leu Val Gly Leu Glu His Thr His
                100                 105                 110
Leu Val Leu Gln Thr Gly Ile Phe Lys Lys Val Pro Val Asp Ile Tyr
            115                 120                 125
Val Phe Lys Ser Gly Val Phe Thr Leu Leu Gly Asp Gly Phe Ile
            130                 135                 140
Asn Trp Ala Trp Gly Gly Phe Val Asp Gln Val Val Gly Lys Arg Ile
145                 150                 155                 160
His Phe Arg Leu Pro Pro Gly Ala Leu Pro
                165                 170

<210> SEQ ID NO 340
<211> LENGTH: 171
<212> TYPE: PRT
<213> ORGANISM: Artificial Sequence
<220> FEATURE:
<223> OTHER INFORMATION: IPD103 variant

<400> SEQUENCE: 340
```

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
            85                  90                  95

Val Val His Thr Gln His Val His Thr Leu Glu Gly Leu Glu His Thr
        100                 105                 110

His Leu Val Leu Gln Thr Gly Ile Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
            165                 170

<210> SEQ ID NO 341
<211> LENGTH: 172
<212> TYPE: PRT
<213> ORGANISM: Artificial Sequence
<220> FEATURE:
<223> OTHER INFORMATION: IPD103 variant

<400> SEQUENCE: 341

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Val Ile Gln Gln Ile Arg Glu Ile Phe Arg Thr
    50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
            85                  90                  95

Val Val Val His Thr Gln His Ile His Thr Leu Glu Gly Leu Glu His
        100                 105                 110

Thr Asn Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
            165                 170

<210> SEQ ID NO 342
<211> LENGTH: 172

```
<212> TYPE: PRT
<213> ORGANISM: Artificial Sequence
<220> FEATURE:
<223> OTHER INFORMATION: IPD103 variant

<400> SEQUENCE: 342
```

| Met<br>1 | Ala | Asp | Lys | Ala<br>5 | Ala | Ala | Ala | Arg | Glu<br>10 | Ala | Glu | Glu | Glu | Val<br>15 |
|---|---|---|---|---|---|---|---|---|---|---|---|---|---|---|
| Gln | Glu | Thr | Leu<br>20 | Met | Asp | Glu | Thr | Glu<br>25 | Ala | Val | Gly | Thr | His<br>30 | Leu | Asp |
| Phe | Val | Ala<br>35 | Gly | Leu | Glu | Val | Gln<br>40 | Pro | Arg | Asn | Ile | Ile<br>45 | Thr | Val | Glu |
| Val | Asp<br>50 | Ala | Ala | Ala | Val | Ile<br>55 | Gln | Gln | Ile | Arg | Glu<br>60 | Ile | Phe | Arg | Thr |
| Met<br>65 | Ala | Ser | His | Phe | Asn<br>70 | Ser | Thr | Arg | Val | Val<br>75 | Arg | Asp | Glu | Ala | Ile<br>80 |
| Lys | Gly | Ile | Arg | Asp<br>85 | His | Phe | Arg | Ala | Ala<br>90 | Val | Pro | Thr | Arg | Asn<br>95 | Val |
| Val | Val | Val | His<br>100 | Thr | Gln | His | Ile | His<br>105 | Thr | Leu | Val | Gly | Leu<br>110 | Glu | His |
| Thr | His | Leu<br>115 | Val | Leu | Gln | Thr | Gly<br>120 | Leu | Phe | Lys | Lys | Val<br>125 | Pro | Val | Asp |
| Ile | Tyr<br>130 | Val | Phe | Lys | Ser | Gly<br>135 | Val | Phe | Thr | Leu | Leu<br>140 | Gly | Asp | Gly | Gly |
| Phe<br>145 | Ile | Asn | Trp | Ala | Trp<br>150 | Gly | Gly | Phe | Val | Gln<br>155 | Glu | Val | Ala | Gly | Lys<br>160 |
| Arg | Ile | His | Phe | Arg<br>165 | Leu | Pro | Pro | Gly | Ala<br>170 | Leu | Pro | | | | |

```
<210> SEQ ID NO 343
<211> LENGTH: 171
<212> TYPE: PRT
<213> ORGANISM: Artificial Sequence
<220> FEATURE:
<223> OTHER INFORMATION: IPD103 variant

<400> SEQUENCE: 343
```

| Met<br>1 | Ala | Asp | Lys | Ala<br>5 | Ala | Ala | Ala | Arg | Glu<br>10 | Ala | Glu | Glu | Glu | Val<br>15 |
|---|---|---|---|---|---|---|---|---|---|---|---|---|---|---|
| Glu | Thr | Thr | Met | Asp<br>20 | Glu | Thr | Glu | Ala | Val<br>25 | Gly | Thr | His | Leu | Asp<br>30 | Phe |
| Val | Ala | Gly<br>35 | Leu | Glu | Val | Gln | Pro<br>40 | Arg | Lys | Val | Ile | Thr<br>45 | Val | Glu | Val |
| Asp | Ala<br>50 | Ala | Ala | Val | Ile | Gln<br>55 | Gln | Ile | Arg | Glu | Ile<br>60 | Phe | Gln | Thr | Met |
| Ala<br>65 | Arg | His | Phe | Asn | Ser<br>70 | Thr | Arg | Val | Val | Arg<br>75 | Asp | Glu | Ala | Ile | Lys<br>80 |
| Gly | Ile | Arg | Asp | His<br>85 | Phe | Arg | Ala | Ala | Val<br>90 | Pro | Thr | Arg | Asn | Val<br>95 | Val |
| Val | Val | His | Thr<br>100 | Gln | His | Ile | His | Thr<br>105 | Leu | Glu | Gly | Leu | Glu<br>110 | His | Thr |
| Asn | Leu | Val<br>115 | Leu | Gln | Thr | Gly | Leu<br>120 | Phe | Lys | Lys | Val | Pro<br>125 | Val | Asp | Ile |
| Tyr | Val<br>130 | Phe | Lys | Ser | Gly | Val<br>135 | Phe | Thr | Asn | Leu | Gly<br>140 | Asp | Gly | Gly | Phe |
| Ile<br>145 | Asn | Trp | Ala | Trp | Gly<br>150 | Gly | Phe | Val | Asp | Gln<br>155 | Val | Val | Gly | Lys | Arg<br>160 |

```
Ile His Phe Arg Leu Pro Pro Gly Ala Leu Pro
            165                 170

<210> SEQ ID NO 344
<211> LENGTH: 172
<212> TYPE: PRT
<213> ORGANISM: Artificial Sequence
<220> FEATURE:
<223> OTHER INFORMATION: IPD103 variant

<400> SEQUENCE: 344

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
                20                  25                  30

Phe Val Ala Gly Leu Glu Val Gln Pro Arg Lys Val Ile Thr Val Glu
            35                  40                  45

Val Asp Ala Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Gln Glu Val Val Gly Lys
145                 150                 155                 160

Arg Ile His Phe Arg Leu Pro Pro Gly Ala Leu Pro
                165                 170

<210> SEQ ID NO 345
<211> LENGTH: 171
<212> TYPE: PRT
<213> ORGANISM: Artificial Sequence
<220> FEATURE:
<223> OTHER INFORMATION: IPD103 variant

<400> SEQUENCE: 345

Met Ala Asp Pro Ala Thr Ala Ala Arg Glu Ala Glu Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Ala Val Ile Gln Gln Ile Arg Glu Ile Phe Gln Thr Met
        50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Val Gly Leu Glu His Thr
            100                 105                 110

His Leu Val Leu Gln Thr Gly Ile Phe Lys Lys Val Pro Val Asp Ile
```

```
              115                 120                 125
Tyr Val Phe Lys Ser Gly Val Phe Thr Leu Leu Gly Asp Gly Gly Phe
            130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 346
<211> LENGTH: 173
<212> TYPE: PRT
<213> ORGANISM: Artificial Sequence
<220> FEATURE:
<223> OTHER INFORMATION: IPD103 variant

<400> SEQUENCE: 346

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Arg Asn Ile Ile Thr Val Glu
            35                  40                  45

Val Asp Ala Ala Val Ile Gln Gln Ile Arg Glu Ile Phe Arg Thr
50                  55                  60

Thr Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Ser Gln His Ile His Thr Leu Glu Gly Leu Glu His
                100                 105                 110

Thr His Leu Val Leu Gln Thr Gly Ile Phe Lys Lys Val Pro Val Asp
            115                 120                 125

Met Tyr Val Phe Lys Ser Gly Val Phe Thr Asn Leu Gly Asp Gly Gly
            130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro Arg
                165                 170

<210> SEQ ID NO 347
<211> LENGTH: 171
<212> TYPE: PRT
<213> ORGANISM: Artificial Sequence
<220> FEATURE:
<223> OTHER INFORMATION: IPD103 variant

<400> SEQUENCE: 347

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80
```

```
Gly Ile Arg Asp His Phe Arg Ala Ala Val Pro Thr Arg Asn Val Val
            85                  90                  95

Val Val His Thr Gln His Val His Thr Leu Val Gly Leu Glu His Thr
            100                 105                 110

His Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
            165                 170
```

<210> SEQ ID NO 348
<211> LENGTH: 172
<212> TYPE: PRT
<213> ORGANISM: Artificial Sequence
<220> FEATURE:
<223> OTHER INFORMATION: IPD103 variant

<400> SEQUENCE: 348

```
Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
            85                  90                  95

Val Val Ile His Thr Gln His Val His Thr Leu Val Gly Leu Glu His
            100                 105                 110

Thr Asn Leu Val Leu Gln Thr Gly Leu Phe Lys Lys Val Pro Val Asp
            115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
            165                 170
```

<210> SEQ ID NO 349
<211> LENGTH: 171
<212> TYPE: PRT
<213> ORGANISM: Artificial Sequence
<220> FEATURE:
<223> OTHER INFORMATION: IPD103 variant

<400> SEQUENCE: 349

```
Met Ala Asp Pro Ala Thr Ala Arg Glu Ala Glu Glu Val Glu
1               5                   10                  15

Thr Thr Met Asp Glu Thr Glu Ala Val Gly Thr His Leu Asp Phe Leu
            20                  25                  30

Gly Ala Asp Val Lys Leu Gln Pro Arg Asn Ile Ile Thr Val Glu Val
        35                  40                  45
```

```
Asp Ala Ala Val Ile His Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Ser Gln His Ile His Thr Leu Val Gly Leu Glu His Thr
            100                 105                 110

His Leu Val Leu Gln Thr Gly Leu Phe Lys Lys Val Pro Val Asp Met
            115                 120                 125

Tyr Val Phe Lys Ser Gly Val Phe Thr Asn Leu Gly Asp Gly Gly Phe
            130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170
```

<210> SEQ ID NO 350
<211> LENGTH: 172
<212> TYPE: PRT
<213> ORGANISM: Artificial Sequence
<220> FEATURE:
<223> OTHER INFORMATION: IPD103 variant

<400> SEQUENCE: 350

```
Met Ala Asp Pro Ala Thr Ala Ala Arg Glu Asp Glu Glu Val Gln
1               5                   10                  15

Glu Thr Leu Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
            35                  40                  45

Val Asp Ala Ala Val Ile Gln Gln Ile Arg Glu Ile Phe Arg Thr
    50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
            100                 105                 110

Thr His Leu Val Leu Gln Thr Gly Leu Phe Lys Lys Val Pro Val Asp
            115                 120                 125

Ile Tyr Val Phe Lys Ser Gly Val Phe Thr Leu Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170
```

<210> SEQ ID NO 351
<211> LENGTH: 171
<212> TYPE: PRT
<213> ORGANISM: Artificial Sequence
<220> FEATURE:
<223> OTHER INFORMATION: IPD103 variant

<400> SEQUENCE: 351

Met Ala Asp Lys Ala Ala Ala Ala Ala Arg Glu Ala Glu Glu Glu Val

-continued

```
              1               5                  10                 15
            Glu Thr Thr Met Asp Glu Thr Glu Ala Val Gly Thr His Leu Asp Phe
                            20                 25                 30
            Val Ala Gly Leu Glu Val Gln Pro Arg Asn Ile Ile Thr Val Glu Val
                            35                 40                 45
            Asp Ala Ala Val Ile Gln Gln Ile Arg Glu Ile Phe Arg Thr Met
                            50                 55                 60
            Ala Ser His Phe Asn Ser Thr Arg Val Val Arg Asp Glu Ala Ile Lys
             65                 70                 75                 80
            Gly Ile Arg Asp His Phe Arg Ala Ala Val Pro Thr Arg Asn Val Val
                                85                 90                 95
            Val Val His Thr Gln His Ile His Thr Leu Glu Gly Leu Glu His Thr
                           100                105                110
            His Leu Val Leu Gln Thr Gly Ile Phe Lys Lys Val Pro Val Asp Ile
                           115                120                125
            Tyr Val Phe Lys Ser Gly Val Phe Thr Leu Leu Gly Asp Gly Gly Phe
                           130                135                140
            Ile Asn Trp Ala Trp Gly Gly Phe Val Gln Glu Val Ala Gly Lys Arg
            145                150                155                160
            Ile His Phe Arg Leu Pro Pro Gly Ala Leu Pro
                           165                170
```

<210> SEQ ID NO 352
<211> LENGTH: 172
<212> TYPE: PRT
<213> ORGANISM: Artificial Sequence
<220> FEATURE:
<223> OTHER INFORMATION: IPD103 variant

<400> SEQUENCE: 352

```
            Met Ala Asp Lys Ala Ala Thr Ala Ala Arg Glu Ala Glu Glu Glu Val
             1               5                  10                 15
            Gln Glu Thr Leu Met Asp Glu Thr Glu Ala Val Gly Thr His Leu Asp
                            20                 25                 30
            Phe Val Ala Gly Leu Glu Val Gln Pro Arg Asn Ile Ile Thr Val Glu
                            35                 40                 45
            Val Asp Ala Ala Val Ile Gln Gln Ile Arg Glu Ile Phe Arg Thr
                            50                 55                 60
            Met Ala Ser His Phe Asn Ser Thr Arg Val Val Arg Asp Glu Ala Ile
             65                 70                 75                 80
            Lys Gly Ile Arg Asp His Phe Arg Ala Ala Val Pro Thr Arg Asn Val
                                85                 90                 95
            Val Val Val His Thr Gln His Ile His Thr Leu Glu Gly Leu Glu His
                           100                105                110
            Thr Asn Leu Val Leu Gln Thr Gly Ile Phe Lys Lys Val Pro Val Asp
                           115                120                125
            Ile Tyr Val Phe Lys Ser Gly Val Phe Thr Leu Leu Gly Asp Gly Gly
                           130                135                140
            Phe Ile Asn Trp Ala Trp Gly Gly Phe Val Gln Gln Val Val Gly Lys
            145                150                155                160
            Arg Ile His Phe Arg Leu Pro Pro Gly Ala Leu Pro
                           165                170
```

<210> SEQ ID NO 353
<211> LENGTH: 172
<212> TYPE: PRT

<213> ORGANISM: Artificial Sequence
<220> FEATURE:
<223> OTHER INFORMATION: IPD103 variant

<400> SEQUENCE: 353

```
Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Lys Val Ile Thr Val Glu
        35                  40                  45

Val Asp Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Ile His Thr Leu Glu Gly Leu Glu His
            100                 105                 110

Thr Asn Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Asp Glu Val Val Gly Lys
145                 150                 155                 160

Arg Ile His Phe Arg Leu Pro Pro Gly Ala Leu Pro
                165                 170
```

<210> SEQ ID NO 354
<211> LENGTH: 173
<212> TYPE: PRT
<213> ORGANISM: Artificial Sequence
<220> FEATURE:
<223> OTHER INFORMATION: IPD103 variant

<400> SEQUENCE: 354

```
Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
            20                  25                  30

Phe Leu Gly Ala Asp Val Lys Leu Gln Pro Arg Asn Ile Ile Thr Val
        35                  40                  45

Glu Val Asp Ala Ala Ala Val Ile Gln Gln Ile Arg Glu Ile Phe Arg
    50                  55                  60

Thr Met Ala Ser His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Ile His Thr Gln His Val His Thr Leu Val Gly Leu Glu
            100                 105                 110

His Thr His Leu Val Leu Leu Thr Gly Ile Phe Lys Lys Val Pro Val
        115                 120                 125

Asp Ile Tyr Val Phe Lys Ser Gly Val Phe Thr Asn Leu Gly Asp Gly
    130                 135                 140

Gly Phe Ile Asn Trp Ala Trp Gly Gly Phe Val Gln Glu Val Ala Gly
145                 150                 155                 160
```

```
Lys Arg Ile His Phe Arg Leu Pro Pro Gly Ala Leu Pro
            165                 170
```

<210> SEQ ID NO 355
<211> LENGTH: 172
<212> TYPE: PRT
<213> ORGANISM: Artificial Sequence
<220> FEATURE:
<223> OTHER INFORMATION: IPD103 variant

<400> SEQUENCE: 355

```
Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
            20                  25                  30

Phe Val Ala Gly Leu Glu Val Gln Pro Arg Asn Ile Ile Thr Val Glu
            35                  40                  45

Val Asp Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
            165                 170
```

<210> SEQ ID NO 356
<211> LENGTH: 171
<212> TYPE: PRT
<213> ORGANISM: Artificial Sequence
<220> FEATURE:
<223> OTHER INFORMATION: IPD103 variant

<400> SEQUENCE: 356

```
Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Leu Phe Lys Lys Val Pro Val Asp Ile
            115                 120                 125
```

```
Tyr Val Phe Lys Ser Gly Val Phe Thr Leu Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
            165                 170

<210> SEQ ID NO 357
<211> LENGTH: 172
<212> TYPE: PRT
<213> ORGANISM: Artificial Sequence
<220> FEATURE:
<223> OTHER INFORMATION: IPD103 variant

<400> SEQUENCE: 357

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Arg Asn Ile Ile Thr Val Glu
            35                  40                  45

Val Asp Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Glu Gly Leu Glu His
            100                 105                 110

Thr Asn Leu Val Leu Gln Thr Gly Leu Phe Lys Lys Val Pro Val Asp
        115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 358
<211> LENGTH: 172
<212> TYPE: PRT
<213> ORGANISM: Artificial Sequence
<220> FEATURE:
<223> OTHER INFORMATION: IPD103 variant

<400> SEQUENCE: 358

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
                20                  25                  30

Phe Val Ala Gly Leu Glu Val Gln Pro Arg Asn Ile Ile Thr Val Glu
            35                  40                  45

Val Asp Ala Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
```

```
                 85                  90                  95

Val Val Ile His Thr Gln His Ile His Thr Leu Val Gly Leu Glu His
                100                 105                 110

Thr Asn Leu Val Leu Gln Thr Gly Leu Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 359
<211> LENGTH: 172
<212> TYPE: PRT
<213> ORGANISM: Artificial Sequence
<220> FEATURE:
<223> OTHER INFORMATION: IPD103 variant

<400> SEQUENCE: 359

Met Ala Asp Lys Ala Ala Ala Ala Arg Glu Ala Glu Glu Glu Val
1               5                  10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Val Pro Thr Arg Asn Val
                85                  90                  95

Val Val Val His Thr Gln His Val His Thr Leu Glu Gly Leu Glu His
                100                 105                 110

Thr Asn Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 360
<211> LENGTH: 171
<212> TYPE: PRT
<213> ORGANISM: Artificial Sequence
<220> FEATURE:
<223> OTHER INFORMATION: IPD103 variant

<400> SEQUENCE: 360

Met Ala Asp Pro Ala Thr Ala Ala Arg Glu Ala Glu Glu Glu Val Gln
1               5                  10                  15

Glu Thr Leu Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45
```

```
Asp Ala Ala Ala Val Ile Gln Gln Ile Arg Glu Ile Phe Arg Thr Met
 50                  55                  60

Ala Ser His Phe Asn Ser Thr Arg Val Val Arg Asp Glu Ala Ile Lys
 65                  70                  75                  80

Gly Ile Arg Asp His Phe Arg Ala Ala Val Pro Thr Arg Asn Val Val
                 85                  90                  95

Val Val His Thr Gln His Ile His Thr Leu Glu Gly Leu Glu His Thr
            100                 105                 110

His Leu Val Leu Gln Thr Gly Ile Phe Lys Lys Val Pro Val Asp Ile
            115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 361
<211> LENGTH: 172
<212> TYPE: PRT
<213> ORGANISM: Artificial Sequence
<220> FEATURE:
<223> OTHER INFORMATION: IPD103 variant

<400> SEQUENCE: 361

Met Ala Asp Lys Ala Ala Ala Ala Arg Glu Ala Glu Glu Glu Val
1               5                   10                  15

Gln Glu Thr Leu Met Asp Glu Thr Ala Val Gly Thr His Leu Asp
                20                  25                  30

Phe Val Ala Gly Leu Glu Val Gln Pro Arg Lys Val Ile Thr Val Glu
                35                  40                  45

Val Asp Ala Ala Val Ile Gln Gln Ile Arg Glu Ile Phe Arg Thr
 50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                85                  90                  95

Val Val Val His Thr Gln His Ile His Thr Leu Val Gly Leu Glu His
            100                 105                 110

Thr His Leu Val Leu Gln Thr Gly Leu Phe Lys Lys Val Pro Val Asp
            115                 120                 125

Ile Tyr Val Phe Lys Ser Gly Val Phe Thr Leu Leu Gly Asp Gly Gly
    130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 362
<211> LENGTH: 170
<212> TYPE: PRT
<213> ORGANISM: Artificial Sequence
<220> FEATURE:
<223> OTHER INFORMATION: IPD103 variant

<400> SEQUENCE: 362

Met Ala Asp Pro Ala Thr Ala Ala Arg Glu Ala Glu Glu Glu Val Glu
1               5                   10                  15
```

```
Thr Thr Met Asp Glu Thr Glu Ala Val Gly Thr His Leu Asp Phe Val
            20                  25                  30

Ala Gly Leu Glu Val Gln Pro Arg Lys Val Ile Thr Val Glu Val Asp
        35                  40                  45

Ala Ala Ala Val Ile Gln Gln Ile Arg Glu Ile Phe Arg Thr Met Ala
    50                  55                  60

Ser His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val Val
                85                  90                  95

Val His Thr Gln His Ile His Thr Leu Glu Gly Leu Glu His Thr Asn
            100                 105                 110

Leu Val Leu Gln Thr Gly Leu Phe Lys Lys Val Pro Val Asp Ile Tyr
        115                 120                 125

Val Phe Lys Ser Gly Val Phe Thr Asn Leu Gly Asp Gly Gly Phe Ile
    130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 363
<211> LENGTH: 171
<212> TYPE: PRT
<213> ORGANISM: Artificial Sequence
<220> FEATURE:
<223> OTHER INFORMATION: IPD103 variant

<400> SEQUENCE: 363

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
        35                  40                  45

Asp Ala Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Ala Gln His Ile His Thr Leu Glu Gly Leu Glu His Thr
            100                 105                 110

Asn Leu Val Leu Gln Thr Gly Ile Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 364
<211> LENGTH: 173
<212> TYPE: PRT
<213> ORGANISM: Artificial Sequence
```

```
<220> FEATURE:
<223> OTHER INFORMATION: IPD103 variant

<400> SEQUENCE: 364

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
                20                  25                  30

Phe Leu Gly Ala Asp Val Lys Leu Gln Pro Arg Asn Ile Ile Thr Val
            35                  40                  45

Glu Val Asp Ala Ala Val Ile Gln Gln Ile Arg Glu Ile Phe Arg
50                  55                  60

Thr Met Ala Ser His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Ile His Thr Gln His Val His Thr Leu Val Gly Leu Glu
            100                 105                 110

His Thr His Leu Val Leu Gln Thr Gly Ile Phe Lys Lys Val Pro Val
        115                 120                 125

Asp Ile Tyr Val Phe Lys Ser Gly Val Phe Thr Leu Leu Gly Asp Gly
    130                 135                 140

Gly Phe Ile Asn Trp Ala Trp Gly Gly Phe Val Gln Glu Val Ala Gly
145                 150                 155                 160

Lys Arg Ile His Phe Arg Leu Pro Pro Gly Ala Leu Pro
                165                 170

<210> SEQ ID NO 365
<211> LENGTH: 171
<212> TYPE: PRT
<213> ORGANISM: Artificial Sequence
<220> FEATURE:
<223> OTHER INFORMATION: IPD103 variant

<400> SEQUENCE: 365

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Asn Ile Ile Thr Val Glu Val
            35                  40                  45

Asp Ala Ala Ala Val Ile Gln Gln Ile Arg Glu Ile Phe Arg Thr Met
50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Glu Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
```

<210> SEQ ID NO 366
<211> LENGTH: 171
<212> TYPE: PRT
<213> ORGANISM: Artificial Sequence
<220> FEATURE:
<223> OTHER INFORMATION: IPD103 variant

<400> SEQUENCE: 366

Ile Thr Asp Pro Ala Thr Ala Ala Arg Glu Ala Glu Glu Val Glu
1               5                   10                  15

Thr Thr Met Asp Glu Thr Glu Ala Val Gly Thr His Leu Asp Phe Leu
            20                  25                  30

Gly Ala Asp Val Lys Leu Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 367
<211> LENGTH: 173
<212> TYPE: PRT
<213> ORGANISM: Artificial Sequence
<220> FEATURE:
<223> OTHER INFORMATION: IPD103 variant

<400> SEQUENCE: 367

Met Ala Asp Lys Ala Ala Ala Ala Arg Glu Ala Glu Glu Val
1               5                   10                  15

Gln Glu Thr Leu Met Asp Glu Ser Glu Ala Val Gly Thr His Leu Asp
            20                  25                  30

Phe Val Ala Gly Leu Glu Val Gln Pro Arg Lys Val Ile Thr Leu Glu
        35                  40                  45

Val Asp Ala Ala Val Ile Gln Gln Ile Arg Glu Ile Phe Arg Thr
    50                  55                  60

Met Ala Ser Pro Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Ser Gln His Ile His Thr Leu Glu Gly Leu Glu His
            100                 105                 110

Thr Asn Phe Val Leu Gln Thr Gly Leu Phe Lys Lys Val Pro Val Asp
        115                 120                 125

```
Met Tyr Val Phe Lys Ser Gly Val Phe Thr Asn Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro Arg
                165                 170

<210> SEQ ID NO 368
<211> LENGTH: 171
<212> TYPE: PRT
<213> ORGANISM: Artificial Sequence
<220> FEATURE:
<223> OTHER INFORMATION: IPD103 variant

<400> SEQUENCE: 368

Met Ala Asp Lys Ala Ala Ala Gly Arg Glu Asp Glu Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
        35                  40                  45

Asp Ala Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 369
<211> LENGTH: 171
<212> TYPE: PRT
<213> ORGANISM: Artificial Sequence
<220> FEATURE:
<223> OTHER INFORMATION: IPD103 variant

<400> SEQUENCE: 369

Met Ala Asp Pro Ala Thr Ala Arg Glu Ala Glu Glu Glu Val Gln
1               5                   10                  15

Glu Thr Leu Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95
```

```
Val Val His Thr Gln His Val His Thr Leu Val Gly Leu Glu His Thr
            100                 105                 110

His Leu Val Leu Gln Thr Gly Leu Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 370
<211> LENGTH: 171
<212> TYPE: PRT
<213> ORGANISM: Artificial Sequence
<220> FEATURE:
<223> OTHER INFORMATION: IPD103 variant

<400> SEQUENCE: 370

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Asn Ile Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65              70                  75                  80

Gly Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

His Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 371
<211> LENGTH: 173
<212> TYPE: PRT
<213> ORGANISM: Artificial Sequence
<220> FEATURE:
<223> OTHER INFORMATION: IPD103 variant

<400> SEQUENCE: 371

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Thr His Leu Asp
            20                  25                  30

Phe Leu Gly Ala Asp Val Lys Leu Gln Pro Arg Asn Ile Ile Thr Val
        35                  40                  45

Glu Val Asp Ala Ala Ala Val Ile Gln Gln Ile Arg Glu Ile Phe Gln
```

```
                50                  55                  60
Thr Met Ala Arg His Phe Asn Ser Thr Arg Val Val Arg Asp Glu Ala
 65                  70                  75                  80

Ile Lys Gly Ile Arg Asp His Phe Arg Ala Val Pro Thr Arg Asn
                 85                  90                  95

Val Val Val Val His Thr Gln His Ile His Thr Leu Glu Gly Leu Glu
                100                 105                 110

His Thr His Leu Val Leu Gln Thr Gly Leu Phe Lys Lys Val Pro Val
                115                 120                 125

Asp Ile Tyr Val Phe Lys Ser Gly Val Phe Thr Leu Leu Gly Asp Gly
            130                 135                 140

Gly Phe Ile Asn Trp Ala Trp Gly Gly Phe Val Asp Gln Val Val Gly
145                 150                 155                 160

Lys Arg Ile His Phe Arg Leu Pro Pro Gly Ala Leu Pro
                165                 170
```

<210> SEQ ID NO 372
<211> LENGTH: 171
<212> TYPE: PRT
<213> ORGANISM: Artificial Sequence
<220> FEATURE:
<223> OTHER INFORMATION: IPD103 variant

<400> SEQUENCE: 372

```
Met Ala Asp Glu Val Ala Gly His His Gly Pro Ala Cys Glu Glu Glu
 1               5                  10                  15

Glu Glu Glu Met Leu Met Asp Glu Thr Glu Ala Val Gly Val His Ala
                20                  25                  30

Ile Asp Gly Leu Pro Val Gln Asn Arg Ser Ile Ile Thr Val Glu Val
             35                  40                  45

Asp Ala Ala Val Ile Gln Gln Ile Arg Glu Ile Phe Arg Thr Met
         50                  55                  60

Ala Ser His Phe Asn Ser Thr Arg Val Val Arg Asp Glu Ala Ile Lys
 65                  70                  75                  80

Gly Ile Arg Asp His Phe Arg Leu Ala Val Pro Thr Arg Asn Val Val
                 85                  90                  95

Val Val His Thr Gln His Val His Thr Leu Val Gly Leu Glu His Thr
                100                 105                 110

His Leu Val Leu Gln Thr Gly Ile Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170
```

<210> SEQ ID NO 373
<211> LENGTH: 172
<212> TYPE: PRT
<213> ORGANISM: Artificial Sequence
<220> FEATURE:
<223> OTHER INFORMATION: IPD103 variant

<400> SEQUENCE: 373

```
Met Ala Asp Lys Ala Ala Ala Ala Arg Glu Ala Glu Glu Glu Val
 1               5                  10                  15
```

```
Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Asp Ala Val Glu Ser
            100                 105                 110

Ser His Leu Val Leu Arg Thr Gly Leu Phe Lys Lys Val Pro Val Asp
        115                 120                 125

Ile Phe Val Phe Lys Ser Gly Val Phe Thr Asn Leu Gly Asp Gly Gly
130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170
```

<210> SEQ ID NO 374
<211> LENGTH: 169
<212> TYPE: PRT
<213> ORGANISM: Artificial Sequence
<220> FEATURE:
<223> OTHER INFORMATION: IPD103 variant

<400> SEQUENCE: 374

```
Met Ala Asp Lys Ala Ala Ala Ala Arg Glu Ala Glu Glu Val
1               5                   10                  15

Glu Thr Thr Met Asp Glu Thr Glu Ala Val Gly Val His Ala Ile Asp
            20                  25                  30

Gly Leu Pro Val Gln Asn Arg Ser Ile Ile Thr Val Glu Val Asp Ala
        35                  40                  45

Ala Ala Val Ile Gln Gln Ile Arg Glu Ile Phe Arg Thr Met Ala Ser
50                  55                  60

His Phe Asn Ser Thr Arg Val Val Arg Asp Glu Ala Ile Lys Ser Ile
65                  70                  75                  80

Arg Asp His Phe Arg Leu Ala Val Pro Thr Arg Asn Val Val Val Val
                85                  90                  95

His Thr Gln His Val His Thr Leu Asp Ala Val Glu Ser Ser His Leu
            100                 105                 110

Val Leu Arg Thr Gly Leu Phe Lys Lys Val Pro Val Asp Ile Phe Val
        115                 120                 125

Phe Lys Ser Gly Val Phe Thr Asn Leu Gly Asp Gly Gly Phe Ile Asn
130                 135                 140

Trp Ala Trp Gly Gly Phe Val Gln Glu Val Ala Gly Lys Arg Ile His
145                 150                 155                 160

Phe Arg Leu Pro Pro Gly Ala Leu Pro
                165
```

<210> SEQ ID NO 375
<211> LENGTH: 172
<212> TYPE: PRT
<213> ORGANISM: Artificial Sequence
<220> FEATURE:

<223> OTHER INFORMATION: IPD103 variant

<400> SEQUENCE: 375

Met Ala Asp Glu Val Ala Gly His His Gly Pro Ala Cys Glu Glu Glu
1               5                   10                  15

Glu Glu Thr Thr Met Asp Glu Thr Glu Ala Val Gly Thr His Leu Asp
            20                  25                  30

Phe Val Ala Gly Leu Glu Val Gln Pro Arg Lys Val Ile Thr Val Glu
        35                  40                  45

Val Asp Ala Ala Val Ile Gln Gln Ile Arg Glu Ile Phe Arg Thr
50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Val His Thr Leu Asp Ala Val Glu Ser
            100                 105                 110

Ser His Leu Val Leu Arg Thr Gly Leu Phe Lys Lys Val Pro Val Asp
        115                 120                 125

Ile Phe Val Phe Lys Ser Gly Val Phe Thr Asn Leu Gly Asp Gly Gly
130                 135                 140

Phe Ile Asn Trp Ala Trp Gly Gly Tyr Val Gln Glu Val Val Gly Lys
145                 150                 155                 160

Arg Ile His Phe Arg Leu Pro Pro Gly Ala Leu Pro
                165                 170

<210> SEQ ID NO 376
<211> LENGTH: 171
<212> TYPE: PRT
<213> ORGANISM: Artificial Sequence
<220> FEATURE:
<223> OTHER INFORMATION: IPD103 variant

<400> SEQUENCE: 376

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Ala Val Ile Gln Gln Ile Arg Glu Ile Phe Arg Thr Met
50                  55                  60

Ala Ser His Phe Asn Ser Thr Arg Val Val Arg Asp Glu Ala Ile Lys
65                  70                  75                  80

Gly Ile Arg Asp His Phe Arg Leu Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Arg Thr Gly Leu Phe Lys Lys Val Pro Val Asp Ile
        115                 120                 125

Phe Val Phe Lys Ser Gly Val Phe Thr Asn Leu Gly Asp Gly Gly Phe
130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 377
<211> LENGTH: 170
<212> TYPE: PRT
<213> ORGANISM: Artificial Sequence
<220> FEATURE:
<223> OTHER INFORMATION: IPD103 variant

<400> SEQUENCE: 377

```
Met Ala Asp Pro Ala Thr Ala Ala Arg Glu Ala Glu Glu Val Glu
1               5                   10                  15

Thr Thr Met Asp Glu Thr Glu Ala Val Gly Thr His Leu Asp Phe Val
            20                  25                  30

Ala Gly Leu Glu Val Gln Pro Arg Lys Val Ile Thr Val Glu Val Asp
        35                  40                  45

Ala Ala Ala Val Ile Gln Gln Ile Arg Glu Ile Phe Gln Thr Met Ala
    50                  55                  60

Arg His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val Val
                85                  90                  95

Ile His Thr Gln His Val His Thr Leu Asp Ala Val Glu Ser Ser His
            100                 105                 110

Leu Val Leu Arg Thr Gly Leu Phe Lys Lys Val Pro Val Asp Ile Phe
        115                 120                 125

Val Phe Lys Ser Gly Val Phe Thr Asn Leu Gly Asp Gly Gly Phe Ile
    130                 135                 140

Asn Trp Ala Trp Gly Gly Tyr Val Asp Gln Val Val Gly Lys Arg Ile
145                 150                 155                 160

His Phe Arg Leu Pro Pro Gly Ala Leu Pro
                165                 170
```

<210> SEQ ID NO 378
<211> LENGTH: 172
<212> TYPE: PRT
<213> ORGANISM: Artificial Sequence
<220> FEATURE:
<223> OTHER INFORMATION: IPD103 variant

<400> SEQUENCE: 378

```
Met Ala Asp Glu Val Ala Gly His His Gly Pro Ala Cys Glu Glu Glu
1               5                   10                  15

Glu Glu Arg Thr Met Asp Glu Thr Glu Ala Val Gly Thr His Leu Asp
            20                  25                  30

Phe Val Ala Gly Leu Glu Val Gln Pro Arg Lys Val Ile Thr Val Glu
        35                  40                  45

Val Asp Ala Ala Ala Val Ile Gln His Ile Arg Glu Ile Phe Gly Thr
    50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Val His Thr Gln His Val His Thr Leu Asp Ala Val Glu Ser
            100                 105                 110

Ser His Leu Val Leu Arg Thr Gly Leu Phe Lys Lys Val Pro Val Asp
        115                 120                 125

Ile Phe Val Phe Lys Ser Gly Val Phe Thr Asn Leu Gly Asp Gly Gly
```

Phe Ile Asn Trp Ala Trp Gly Gly Tyr Val Gln Glu Val Val Gly Lys
145                 150                 155                 160

Arg Ile His Phe Arg Leu Pro Pro Gly Ala Leu Pro
            165                 170

<210> SEQ ID NO 379
<211> LENGTH: 173
<212> TYPE: PRT
<213> ORGANISM: Artificial Sequence
<220> FEATURE:
<223> OTHER INFORMATION: IPD103 variant

<400> SEQUENCE: 379

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
                20                  25                  30

Asp Phe Val Ala Gly Leu Glu Val Gln Pro Arg Lys Val Ile Thr Val
            35                  40                  45

Glu Val Asp Ala Ala Val Ile Gln Gln Ile Arg Glu Ile Phe Arg
50                  55                  60

Thr Met Ala Ser His Phe Asn Ser Thr Arg Val Val Arg Asp Glu Ala
65                  70                  75                  80

Ile Lys Gly Ile Arg Asp His Phe Arg Leu Ala Val Pro Thr Arg Asn
                85                  90                  95

Val Val Val Val His Thr Gln His Val His Thr Leu Asp Ala Val Glu
            100                 105                 110

Ser Ser His Leu Val Leu Arg Thr Gly Leu Phe Lys Lys Val Pro Val
        115                 120                 125

Asp Ile Phe Val Phe Lys Ser Gly Val Phe Thr Asn Leu Gly Asp Gly
    130                 135                 140

Gly Phe Ile Asn Trp Ala Trp Gly Gly Tyr Gly Val Asn His Thr Ala
145                 150                 155                 160

Lys Arg Val Val Phe Ser Arg Pro Pro Gly Ala Leu Pro
                165                 170

<210> SEQ ID NO 380
<211> LENGTH: 171
<212> TYPE: PRT
<213> ORGANISM: Artificial Sequence
<220> FEATURE:
<223> OTHER INFORMATION: IPD103 variant

<400> SEQUENCE: 380

Met Ala Asp Ala Ala Ala Ala Ala Arg Glu Glu Glu Glu Glu Glu Gln
1               5                   10                  15

Glu Thr Thr Met Asp Glu Thr Glu Ala Val Gly Thr His Leu Asp Phe
                20                  25                  30

Val Ala Gly Leu Glu Val Gln Pro Arg Asn Ile Ile Thr Val Glu Val
            35                  40                  45

Asp Ala Ala Ala Val Ile Gln Gln Ile Arg Glu Ile Phe Gln Ser Met
        50                  55                  60

Ile Ser His Phe Asn Ser Thr Arg Val Val Arg Asp Glu Ala Ile Lys
65                  70                  75                  80

Gly Ile Arg Asp His Phe Arg Val Ala Val Pro Thr Arg Asn Val Val
                85                  90                  95

```
Val Ile His Thr Gln His Val His Thr Leu Glu Gly Val Glu Ser Ser
                100                 105                 110

His Leu Val Leu Gln Thr Gly Met Phe Lys Lys Val Pro Val Asp Ile
            115                 120                 125

Tyr Val Phe Lys Ser Gly Val Phe Thr Ile Leu Gly Asp Gly Gly Phe
        130                 135                 140

Ile Asn Trp Ala Trp Gly Gly Phe Gly Asp Gln Val Val Gly Lys Arg
145                 150                 155                 160

Val His Phe Arg Leu Pro Pro Gly Ala Leu Pro
                165                 170

<210> SEQ ID NO 381
<211> LENGTH: 171
<212> TYPE: PRT
<213> ORGANISM: Artificial Sequence
<220> FEATURE:
<223> OTHER INFORMATION: IPD103 variant

<400> SEQUENCE: 381

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
                100                 105                 110

His Leu Val Leu Gln Thr Gly Ile Phe Lys Lys Val Pro Val Asp Ile
            115                 120                 125

Phe Val Phe Lys Ser Gly Val Phe Thr Asn Leu Gly Asp Gly Gly Phe
        130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 382
<211> LENGTH: 173
<212> TYPE: PRT
<213> ORGANISM: Artificial Sequence
<220> FEATURE:
<223> OTHER INFORMATION: IPD103 variant

<400> SEQUENCE: 382

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
            20                  25                  30

Asp Phe Val Ala Gly Leu Glu Val Gln Pro Arg Asn Ile Ile Thr Val
        35                  40                  45

Glu Val Asp Ala Ala Ala Val Ile Gln Gln Ile Arg Glu Ile Phe Gln
    50                  55                  60
```

```
Thr Met Ala Arg His Phe Asn Ser Thr Arg Val Val Arg Asp Glu Ala
 65                  70                  75                  80

Ile Lys Gly Ile Arg Asp His Phe Arg Ala Ala Val Pro Thr Arg Asn
                 85                  90                  95

Val Val Val Ile His Thr Gln Val His Thr Leu Asp Ala Val Glu
            100                 105                 110

Ser Ser His Leu Val Leu Arg Thr Gly Leu Phe Lys Lys Val Pro Val
            115                 120                 125

Asp Ile Phe Val Phe Lys Ser Gly Val Phe Thr Asn Leu Gly Asp Gly
            130                 135                 140

Gly Phe Ile Asn Trp Ala Trp Gly Gly Phe Val Gln Glu Val Ala Gly
145                 150                 155                 160

Lys Arg Ile His Phe Arg Leu Pro Pro Gly Ala Leu Pro
                165                 170
```

<210> SEQ ID NO 383
<211> LENGTH: 171
<212> TYPE: PRT
<213> ORGANISM: Artificial Sequence
<220> FEATURE:
<223> OTHER INFORMATION: IPD103 variant

<400> SEQUENCE: 383

```
Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
            35                  40                  45

Asp Ala Ala Val Ile Gln Gln Ile Arg Glu Ile Phe Arg Thr Met
50                  55                  60

Ala Ser His Phe Asn Ser Thr Arg Val Val Arg Asp Glu Ala Ile Lys
 65                  70                  75                  80

Ser Ile Arg Asp His Phe Arg Ala Ala Val Pro Thr Arg Asn Val Val
                 85                  90                  95

Val Ile His Thr Gln His Val His Thr Leu Glu Gly Leu Glu His Thr
            100                 105                 110

Asn Leu Val Leu Gln Thr Gly Leu Phe Lys Lys Val Pro Val Asp Ile
            115                 120                 125

Tyr Val Phe Lys Ser Gly Val Phe Thr Asn Leu Gly Asp Gly Gly Phe
            130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170
```

<210> SEQ ID NO 384
<211> LENGTH: 170
<212> TYPE: PRT
<213> ORGANISM: Artificial Sequence
<220> FEATURE:
<223> OTHER INFORMATION: IPD103 variant

<400> SEQUENCE: 384

```
Met Ala Asp Glu Ala Ala Ala Ala Arg Glu Ala Glu Glu Glu Glu
1               5                   10                  15

Glu Glu Met Leu Met Asp Glu Thr Glu Ala Val Gly Val His Ala Ile
```

```
                   20                  25                  30

Asp Gly Leu Pro Val Gln Asn Arg Ser Ile Ile Thr Val Glu Val Asp
                 35                  40                  45

Ala Ala Ala Val Ile Gln Gln Ile Arg Glu Ile Phe Arg Thr Met Ala
     50                  55                  60

Ser His Phe Asn Ser Thr Arg Val Val Arg Asp Glu Ala Ile Lys Gly
 65                  70                  75                  80

Ile Arg Asp His Phe Arg Leu Ala Val Pro Thr Arg Asn Val Val
                 85                  90                  95

Ile His Thr Gln His Ile His Thr Leu Val Gly Leu Glu Ser Ser His
                100                 105                 110

Leu Ala Leu Arg Thr Gly Leu Phe Lys Lys Val Pro Val Asp Ile Tyr
            115                 120                 125

Val Phe Lys Ser Gly Val Phe Thr Leu Leu Gly Asp Gly Gly Phe Ile
        130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 385
<211> LENGTH: 172
<212> TYPE: PRT
<213> ORGANISM: Artificial Sequence
<220> FEATURE:
<223> OTHER INFORMATION: IPD103 variant

<400> SEQUENCE: 385

Met Ala Asp Lys Ala Ala Ala Ala Arg Glu Ala Glu Glu Val
 1               5                  10                  15

Glu Thr Thr Met Asp Glu Thr Glu Ala Val Gly Thr His Leu Asp Phe
                 20                  25                  30

Leu Gly Ala Asp Val Lys Leu Gln Pro Arg Asn Ile Ile Thr Val Glu
                 35                  40                  45

Val Asp Ala Ala Ala Val Ile Gln Gln Ile Arg Glu Ile Phe Gln Thr
     50                  55                  60

Met Ala Arg His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
                100                 105                 110

Thr Asn Leu Val Leu Arg Thr Gly Leu Phe Lys Lys Val Pro Val Asp
            115                 120                 125

Ile Tyr Val Phe Lys Ser Gly Val Phe Thr Leu Leu Gly Asp Gly Gly
        130                 135                 140

Phe Ile Asn Trp Ala Trp Gly Gly Phe Val Gln Glu Val Ala Gly Lys
145                 150                 155                 160

Arg Ile His Phe Arg Leu Pro Pro Gly Ala Leu Pro
                165                 170

<210> SEQ ID NO 386
<211> LENGTH: 170
<212> TYPE: PRT
<213> ORGANISM: Artificial Sequence
<220> FEATURE:
<223> OTHER INFORMATION: IPD103 variant
```

<400> SEQUENCE: 386

Met Ala Asp Glu Val Ala Gly His His Gly Pro Ala Cys Glu Glu
1               5                   10                  15

Val Glu Thr Thr Met Asp Glu Thr Glu Ala Val Gly Val His Ala Ile
            20                  25                  30

Asp Gly Leu Pro Val Gln Asn Arg Ser Ile Ile Thr Val Glu Val Asp
        35                  40                  45

Ala Ala Val Ile Gln Gln Ile Arg Glu Ile Phe Arg Thr Met Ala
    50                  55                  60

Ser His Phe Asn Ser Thr Arg Val Val Arg Asp Glu Ala Ile Lys Gly
65                  70                  75                  80

Ile Arg Asp His Phe Arg Leu Ala Val Pro Thr Arg Asn Val Val
                85                  90                  95

Val His Thr Gln His Val His Thr Leu Glu Gly Leu Glu His Thr Asn
            100                 105                 110

Leu Val Leu Gln Thr Gly Leu Phe Lys Lys Val Pro Val Asp Ile Tyr
        115                 120                 125

Val Phe Lys Ser Gly Val Phe Thr Leu Leu Gly Asp Gly Gly Phe Ile
    130                 135                 140

Asn Trp Ala Trp Gly Gly Phe Val Gln Glu Val Ala Gly Lys Arg Ile
145                 150                 155                 160

His Phe Arg Leu Pro Pro Gly Ala Leu Pro
                165                 170

<210> SEQ ID NO 387
<211> LENGTH: 171
<212> TYPE: PRT
<213> ORGANISM: Artificial Sequence
<220> FEATURE:
<223> OTHER INFORMATION: IPD103 variant

<400> SEQUENCE: 387

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Pro Arg Lys Val Ile Thr Val Glu Val
        35                  40                  45

Asp Ala Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Val Gly Leu Glu His Thr
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 388
<211> LENGTH: 171
<212> TYPE: PRT
<213> ORGANISM: Artificial Sequence
<220> FEATURE:
<223> OTHER INFORMATION: IPD103 variant

<400> SEQUENCE: 388

```
Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Ser Ile Arg Asp His Phe Arg Leu Ala Val Pro Thr Arg Asn Val Val
                85                  90                  95

Val Ile His Thr Gln His Val His Thr Leu Glu Gly Leu Glu Ser Ser
            100                 105                 110

His Leu Val Leu Arg Thr Gly Leu Phe Lys Lys Val Pro Val Asp Ile
        115                 120                 125

Phe Val Phe Lys Ser Gly Val Phe Thr Asn Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170
```

<210> SEQ ID NO 389
<211> LENGTH: 171
<212> TYPE: PRT
<213> ORGANISM: Artificial Sequence
<220> FEATURE:
<223> OTHER INFORMATION: IPD103 variant

<400> SEQUENCE: 389

```
Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Ala Ser Met
    50                  55                  60

Ile Lys His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Arg Thr Gly Leu Phe Lys Lys Val Pro Val Asp Ile
        115                 120                 125

Phe Val Phe Lys Ser Gly Val Phe Thr Asn Leu Gly Asp Gly Gly Phe
    130                 135                 140
```

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 390
<211> LENGTH: 171
<212> TYPE: PRT
<213> ORGANISM: Artificial Sequence
<220> FEATURE:
<223> OTHER INFORMATION: IPD103 variant

<400> SEQUENCE: 390

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
                20                  25                  30

Ile Asp Gly Leu Pro Val Gln Asn Arg Ser Ile Ile Thr Val Glu Val
            35                  40                  45

Asp Ala Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Ser Ile Arg Asp His Phe Arg Ala Ala Val Pro Thr Arg Asn Val Val
                85                  90                  95

Val Val His Thr Gln His Ile His Thr Leu Glu Gly Leu Glu His Thr
            100                 105                 110

Asn Leu Val Leu Gln Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Gln Glu Val Ala Gly Lys Arg
145                 150                 155                 160

Ile His Phe Arg Leu Pro Pro Gly Ala Leu Pro
                165                 170

<210> SEQ ID NO 391
<211> LENGTH: 171
<212> TYPE: PRT
<213> ORGANISM: Artificial Sequence
<220> FEATURE:
<223> OTHER INFORMATION: IPD103 variant

<400> SEQUENCE: 391

Met Ala Asp Pro Ala Thr Ala Ala Arg Glu Ala Glu Glu Val Gln
1               5                   10                  15

Glu Thr Leu Met Asp Glu Thr Glu Ala Val Gly Thr His Leu Asp Phe
                20                  25                  30

Val Ala Gly Leu Glu Val Gln Pro Arg Lys Val Ile Thr Val Glu Val
            35                  40                  45

Asp Ala Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Asp Ala Val Glu Ser Ser 100                 105                 110

His Leu Val Leu Arg Thr Gly Leu Phe Lys Lys Val Pro Val Asp Ile
            115                 120                 125

Phe Val Phe Lys Ser Gly Val Phe Thr Leu Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 392
<211> LENGTH: 171
<212> TYPE: PRT
<213> ORGANISM: Artificial Sequence
<220> FEATURE:
<223> OTHER INFORMATION: IPD103 variant

<400> SEQUENCE: 392

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Leu Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Arg Thr Gly Leu Phe Lys Lys Val Pro Val Asp Ile
        115                 120                 125

Phe Val Phe Lys Ser Gly Val Phe Thr Asn Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 393
<211> LENGTH: 172
<212> TYPE: PRT
<213> ORGANISM: Artificial Sequence
<220> FEATURE:
<223> OTHER INFORMATION: IPD103 variant

<400> SEQUENCE: 393

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
        35                  40                  45

Val Asp Ala Ala Ala Val Ile Gln Gln Ile Arg Glu Ile Phe Arg Thr
    50                  55                  60

Met Ala Ser His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
            85                  90                  95

Val Val Val His Thr Gln His Val His Thr Leu Val Gly Leu Glu His
            100                 105                 110

Thr His Leu Val Leu Gln Thr Gly Leu Phe Lys Lys Val Pro Val Asp
            115                 120                 125

Ile Tyr Val Phe Lys Ser Gly Val Phe Thr Leu Leu Gly Asp Gly Gly
            130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
            165                 170

<210> SEQ ID NO 394
<211> LENGTH: 173
<212> TYPE: PRT
<213> ORGANISM: Artificial Sequence
<220> FEATURE:
<223> OTHER INFORMATION: IPD103 variant

<400> SEQUENCE: 394

Met Ala Asp Glu Val Ala Gly His His Gly Pro Ala Cys Glu Glu
1               5                   10                  15

Glu Glu Glu Met Leu Met Asp Glu Thr Glu Ala Val Gly Thr His Leu
            20                  25                  30

Asp Phe Val Ala Gly Leu Glu Val Gln Asn Arg Ser Ile Ile Thr Val
            35                  40                  45

Glu Val Asp Ala Ala Val Ile Gln Gln Ile Arg Glu Ile Phe Arg
    50                  55                  60

Thr Met Ala Ser His Phe Asn Ser Thr Arg Val Val Arg Asp Glu Ala
65                  70                  75                  80

Ile Lys Gly Ile Arg Asp His Phe Arg Leu Ala Val Pro Thr Arg Asn
            85                  90                  95

Val Val Val Val His Thr Gln His Val His Thr Leu Asp Ala Val Glu
            100                 105                 110

Ser Ser His Leu Val Leu Arg Thr Gly Leu Phe Lys Lys Val Pro Val
            115                 120                 125

Asp Ile Phe Val Phe Lys Ser Gly Val Phe Thr Asn Leu Gly Asp Gly
    130                 135                 140

Gly Phe Ile Asn Trp Ala Trp Gly Gly Tyr Gly Val Asn His Thr Ala
145                 150                 155                 160

Lys Arg Val Val Phe Ser Arg Pro Pro Gly Ala Leu Pro
            165                 170

<210> SEQ ID NO 395
<211> LENGTH: 171
<212> TYPE: PRT
<213> ORGANISM: Artificial Sequence
<220> FEATURE:
<223> OTHER INFORMATION: IPD103 variant

<400> SEQUENCE: 395

Met Ala Asp Glu Val Ala Gly His His Gly Pro Ala Cys Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
                35                  40                  45

Asp Ala Ala Val Ile Gln Gln Ile Arg Glu Ile Phe Arg Thr Met
 50                  55                  60

Ala Ser His Phe Asn Ser Thr Arg Val Val Arg Asp Glu Ala Ile Lys
 65                  70                  75                  80

Ser Ile Arg Asp His Phe Arg Leu Ala Val Pro Thr Arg Asn Val Val
                 85                  90                  95

Val Ile His Thr Gln His Val His Thr Leu Asp Ala Val Glu Ser Ser
                100                 105                 110

His Leu Val Leu Gln Thr Gly Leu Phe Lys Lys Val Pro Val Asp Ile
                115                 120                 125

Tyr Val Phe Lys Ser Gly Val Phe Thr Asn Leu Gly Asp Gly Gly Phe
            130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 396
<211> LENGTH: 172
<212> TYPE: PRT
<213> ORGANISM: Artificial Sequence
<220> FEATURE:
<223> OTHER INFORMATION: IPD103 variant

<400> SEQUENCE: 396

Met Ala Asp Lys Ala Ala Ala Ala Arg Glu Ala Glu Glu Glu Val
 1               5                  10                  15

Glu Thr Thr Met Asp Glu Thr Glu Ala Val Gly Thr His Leu Asp Phe
                 20                  25                  30

Leu Gly Ala Asp Val Lys Leu Gln Pro Arg Asn Ile Ile Thr Val Glu
            35                  40                  45

Val Asp Ala Ala Val Ile Gln Gln Ile Arg Glu Ile Phe Arg Thr
 50                  55                  60

Met Ala Ser His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
                100                 105                 110

Thr His Leu Val Leu Gln Thr Gly Leu Phe Lys Lys Val Pro Val Asp
            115                 120                 125

Ile Tyr Val Phe Lys Ser Gly Val Phe Thr Asn Leu Gly Asp Gly Gly
            130                 135                 140

Phe Ile Asn Trp Ala Trp Gly Gly Phe Val Gln Glu Val Ala Gly Lys
145                 150                 155                 160

Arg Ile His Phe Arg Arg Pro Pro Gly Ala Leu Pro
                165                 170

<210> SEQ ID NO 397
<211> LENGTH: 171
<212> TYPE: PRT
<213> ORGANISM: Artificial Sequence
<220> FEATURE:
<223> OTHER INFORMATION: IPD103 variant

<400> SEQUENCE: 397

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Ala Ser Met
    50                  55                  60

Ile Lys His Tyr Asn Ser Thr Arg Val Val Arg Asp Glu Ala Ile Lys
65                  70                  75                  80

Ser Ile Arg Asp His Phe Arg Ala Ala Val Pro Thr Arg Asn Val Val
                85                  90                  95

Val Ile His Thr Gln His Val His Thr Leu Glu Gly Leu Glu His Thr
            100                 105                 110

Asn Leu Val Leu Gln Thr Gly Leu Phe Lys Lys Val Pro Val Asp Ile
        115                 120                 125

Phe Val Phe Lys Ser Gly Val Phe Thr Asn Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 398
<211> LENGTH: 171
<212> TYPE: PRT
<213> ORGANISM: Artificial Sequence
<220> FEATURE:
<223> OTHER INFORMATION: IPD103 variant

<400> SEQUENCE: 398

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

```
<210> SEQ ID NO 399
<211> LENGTH: 171
<212> TYPE: PRT
<213> ORGANISM: Artificial Sequence
<220> FEATURE:
<223> OTHER INFORMATION: IPD103 variant

<400> SEQUENCE: 399

Met Ala Asp Pro Ala Thr Ala Ala Arg Glu Ala Glu Glu Val Glu
1               5                   10                  15

Thr Thr Met Asp Glu Thr Glu Ala Val Gly Thr His Leu Asp Phe Leu
                20                  25                  30

Gly Ala Asp Val Lys Leu Gln Pro Arg Asn Ile Ile Thr Val Glu Val
            35                  40                  45

Asp Ala Ala Val Ile Gln Gln Ile Arg Glu Ile Phe Gln Thr Met
        50                  55                  60

Ala Arg His Phe Asn Ser Thr Arg Val Val Arg Asp Glu Ala Ile Lys
65                  70                  75                  80

Gly Ile Arg Asp His Phe Arg Leu Ala Val Pro Thr Arg Asn Val Val
                85                  90                  95

Val Ile His Thr Gln His Val His Thr Leu Asp Ala Val Glu Ser Ser
            100                 105                 110

Arg Leu Val Leu Arg Thr Gly Leu Phe Lys Lys Val Pro Val Asp Ile
        115                 120                 125

Phe Val Phe Lys Ser Gly Val Phe Thr Asn Leu Gly Asp Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 400
<211> LENGTH: 173
<212> TYPE: PRT
<213> ORGANISM: Artificial Sequence
<220> FEATURE:
<223> OTHER INFORMATION: IPD103 variant

<400> SEQUENCE: 400

Met Ala Asp Lys Ala Ala Ala Ala Arg Glu Ala Glu Glu Val
1               5                   10                  15

Gln Glu Thr Leu Met Asp Glu Thr Glu Ala Val Gly Thr His Leu Asp
                20                  25                  30

Phe Leu Gly Ala Asp Val Lys Leu Gln Pro Arg Lys Val Ile Thr Val
            35                  40                  45

Glu Val Asp Ala Ala Ala Val Ile Gln Gln Ile Arg Glu Ile Phe Arg
        50                  55                  60

Thr Met Ala Ser His Phe Asn Ser Thr Arg Val Val Arg Asp Glu Ala
65                  70                  75                  80

Ile Lys Gly Ile Arg Asp His Phe Arg Ala Val Pro Thr Arg Asn
                85                  90                  95

Val Val Val Val His Thr Gln His Val His Thr Leu Asp Ala Val Glu
            100                 105                 110

Ser Ser His Leu Val Leu Arg Thr Gly Leu Phe Lys Lys Val Pro Val
        115                 120                 125

Asp Ile Tyr Val Phe Lys Ser Gly Val Phe Thr Leu Leu Gly Asp Gly
    130                 135                 140
```

```
Gly Phe Ile Asn Trp Ala Trp Gly Gly Phe Val Asp Gln Val Val Gly
145                 150                 155                 160

Lys Arg Ile His Phe Arg Leu Pro Pro Gly Ala Leu Pro
                165                 170
```

<210> SEQ ID NO 401
<211> LENGTH: 171
<212> TYPE: PRT
<213> ORGANISM: Artificial Sequence
<220> FEATURE:
<223> OTHER INFORMATION: IPD103 variant

<400> SEQUENCE: 401

```
Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
                20                  25                  30

Ile Asp Gly Leu Pro Val Gln Asn Arg Ser Ile Ile Thr Val Glu Val
            35                  40                  45

Asp Ala Ala Val Ile Gln Gln Ile Arg Glu Ile Phe Ala Ser Met
        50                  55                  60

Ile Lys His Tyr Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Val His Thr Leu Asp Ala Val Glu Ser Ser
                100                 105                 110

His Leu Val Leu Arg Thr Gly Leu Phe Lys Lys Val Pro Val Asp Ile
            115                 120                 125

Tyr Val Phe Lys Ser Gly Val Phe Thr Leu Leu Gly Asp Gly Gly Phe
130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170
```

<210> SEQ ID NO 402
<211> LENGTH: 173
<212> TYPE: PRT
<213> ORGANISM: Artificial Sequence
<220> FEATURE:
<223> OTHER INFORMATION: IPD103 variant

<400> SEQUENCE: 402

```
Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Thr His Leu
                20                  25                  30

Asp Phe Val Ala Gly Leu Glu Val Gln Pro Arg Lys Val Ile Thr Val
            35                  40                  45

Glu Val Asp Ala Ala Ala Val Ile Gln Gln Ile Arg Glu Ile Phe Gln
        50                  55                  60

Thr Met Ala Arg His Tyr Asn Ser Thr Arg Val Val Arg Asp Glu Ala
65                  70                  75                  80

Ile Lys Ser Ile Arg Asp His Phe Arg Ala Ala Val Pro Thr Arg Asn
                85                  90                  95

Val Val Val Val His Thr Gln His Ile His Thr Leu Asp Ala Val Glu
                100                 105                 110
```

```
Ser Ser His Leu Val Leu Arg Thr Gly Leu Phe Lys Lys Val Pro Val
        115                 120                 125

Asp Ile Phe Val Phe Lys Ser Gly Val Phe Thr Asn Leu Gly Asp Gly
    130                 135                 140

Gly Phe Ile Asn Trp Ala Trp Gly Gly Phe Val Gln Glu Val Ala Gly
145                 150                 155                 160

Lys Arg Ile His Phe Arg Leu Pro Pro Gly Ala Leu Pro
                165                 170

<210> SEQ ID NO 403
<211> LENGTH: 171
<212> TYPE: PRT
<213> ORGANISM: Artificial Sequence
<220> FEATURE:
<223> OTHER INFORMATION: IPD103 variant

<400> SEQUENCE: 403

Met Ala Asp Lys Ala Ala Ala Ala Arg Glu Ala Glu Glu Glu Val
1               5                   10                  15

Glu Thr Thr Met Asp Glu Thr Glu Ala Val Gly Val His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Gly Ser Met
    50                  55                  60

Ile Asn His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Ala Val Glu Ser Ser
            100                 105                 110

His Leu Val Leu Gln Thr Gly Leu Phe Lys Lys Val Pro Val Asp Ile
        115                 120                 125

Tyr Val Phe Lys Ser Gly Val Phe Thr Leu Leu Gly Asp Gly Gly Phe
    130                 135                 140

Ile Asn Trp Ala Trp Gly Gly Phe Gly Leu Glu Leu Ala Gly Lys Arg
145                 150                 155                 160

Val His Phe Arg Arg Pro Pro Gly Ala Leu Pro
                165                 170

<210> SEQ ID NO 404
<211> LENGTH: 171
<212> TYPE: PRT
<213> ORGANISM: Artificial Sequence
<220> FEATURE:
<223> OTHER INFORMATION: IPD103 variant

<400> SEQUENCE: 404

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
```

```
                65                  70                  75                  80
Ser Ile Arg Asp His Phe Arg Leu Ala Val Pro Thr Arg Asn Val Val
                85                  90                  95

Val Val His Thr Gln His Ile His Thr Leu Glu Gly Leu Glu His Thr
            100                 105                 110

Asn Leu Val Leu Gln Thr Gly Leu Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 405
<211> LENGTH: 170
<212> TYPE: PRT
<213> ORGANISM: Artificial Sequence
<220> FEATURE:
<223> OTHER INFORMATION: IPD103 variant

<400> SEQUENCE: 405

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Val His Ala Ile
                20                  25                  30

Asp Gly Leu Pro Val Gln Asn Arg Ser Ile Ile Thr Val Glu Val Asp
            35                  40                  45

Ala Ala Ala Val Ile Gln Gln Ile Arg Glu Ile Phe Ala Ser Met Ile
        50                  55                  60

Lys His Tyr Asn Ser Thr Arg Val Val Arg Asp Glu Ala Ile Lys Ser
65                  70                  75                  80

Ile Arg Asp His Phe Arg Leu Ala Val Pro Thr Arg Asn Val Val Val
                85                  90                  95

Ile His Thr Gln His Val His Thr Leu Val Gly Leu Glu His Thr His
            100                 105                 110

Leu Val Leu Gln Thr Gly Leu Phe Lys Lys Val Pro Val Asp Ile Tyr
        115                 120                 125

Val Phe Lys Ser Gly Val Phe Thr Leu Leu Gly Asp Gly Gly Phe Ile
    130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 406
<211> LENGTH: 171
<212> TYPE: PRT
<213> ORGANISM: Artificial Sequence
<220> FEATURE:
<223> OTHER INFORMATION: IPD103 variant

<400> SEQUENCE: 406

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
                20                  25                  30
```

```
Ile Asp Gly Leu Pro Val Gln Asn Arg Ser Ile Ile Thr Val Glu Val
         35                  40                  45

Asp Ala Ala Val Ile Gln Gln Ile Arg Glu Ile Phe Arg Thr Met
 50                  55                  60

Ala Ser His Phe Asn Ser Thr Arg Val Val Arg Asp Glu Ala Ile Lys
 65                  70                  75                  80

Ser Ile Arg Asp His Phe Arg Leu Ala Val Pro Thr Arg Asn Val Val
                 85                  90                  95

Val Val His Thr Gln His Val His Thr Leu Asp Ala Val Glu Ser Ser
                100                 105                 110

His Leu Val Leu Arg Thr Gly Leu Phe Lys Lys Val Pro Val Asp Ile
            115                 120                 125

Phe Val Phe Lys Ser Gly Val Phe Thr Leu Leu Gly Asp Gly Gly Phe
        130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 407
<211> LENGTH: 173
<212> TYPE: PRT
<213> ORGANISM: Artificial Sequence
<220> FEATURE:
<223> OTHER INFORMATION: IPD103 variant

<400> SEQUENCE: 407

Met Ala Asp Glu Val Ala Gly His His Gly Pro Ala Cys Glu Glu Glu
 1               5                  10                  15

Glu Glu Glu Met Leu Met Asp Glu Thr Glu Ala Val Gly Thr His Leu
             20                  25                  30

Asp Phe Val Ala Gly Leu Glu Val Gln Pro Arg Lys Val Ile Thr Val
         35                  40                  45

Glu Val Asp Ala Ala Ala Val Ile Gln Gln Ile Arg Glu Ile Phe Arg
 50                  55                  60

Thr Met Ala Ser His Phe Asn Ser Thr Arg Val Val Arg Asp Glu Ala
 65                  70                  75                  80

Ile Lys Gly Ile Arg Asp His Phe Arg Ala Ala Val Pro Thr Arg Asn
                 85                  90                  95

Val Val Val Ile His Thr Gln His Val His Thr Leu Asp Ala Val Glu
                100                 105                 110

Ser Ser His Leu Val Leu Arg Thr Gly Leu Phe Lys Lys Val Pro Val
            115                 120                 125

Asp Ile Phe Val Phe Lys Ser Gly Val Phe Thr Leu Leu Gly Asp Gly
        130                 135                 140

Gly Phe Ile Asn Trp Ala Trp Gly Gly Tyr Val Gln Glu Val Val Gly
145                 150                 155                 160

Lys Arg Ile His Phe Arg Leu Pro Pro Gly Ala Leu Pro
                165                 170

<210> SEQ ID NO 408
<211> LENGTH: 171
<212> TYPE: PRT
<213> ORGANISM: Artificial Sequence
<220> FEATURE:
<223> OTHER INFORMATION: IPD103 variant

<400> SEQUENCE: 408
```

-continued

```
Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Pro Arg Lys Val Ile Thr Val Glu Val
        35                  40                  45

Asp Ala Ala Val Ile Gln Gln Ile Arg Glu Ile Phe Ala Ser Met
    50                  55                  60

Ile Lys His Tyr Asn Ser Thr Arg Val Val Arg Asp Glu Ala Ile Lys
65                  70                  75                  80

Gly Ile Arg Asp His Phe Arg Leu Ala Val Pro Thr Arg Asn Val Val
                85                  90                  95

Val Val His Thr Gln His Ile His Thr Leu Glu Gly Leu Glu His Thr
                100                 105                 110

Asn Leu Val Leu Arg Thr Gly Leu Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170
```

<210> SEQ ID NO 409
<211> LENGTH: 171
<212> TYPE: PRT
<213> ORGANISM: Artificial Sequence
<220> FEATURE:
<223> OTHER INFORMATION: IPD103 variant

<400> SEQUENCE: 409

```
Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
            20                  25                  30

Val Ala Gly Leu Glu Val Gln Pro Arg Lys Val Ile Thr Val Glu Val
        35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Val His Thr Gln His Ile His Thr Leu Asp Ala Val Glu Ser Ser
                100                 105                 110

His Leu Val Leu Arg Thr Gly Leu Phe Lys Lys Val Pro Val Asp Ile
            115                 120                 125

Tyr Val Phe Lys Ser Gly Val Phe Thr Leu Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170
```

<210> SEQ ID NO 410

<211> LENGTH: 171
<212> TYPE: PRT
<213> ORGANISM: Artificial Sequence
<220> FEATURE:
<223> OTHER INFORMATION: IPD103 variant

<400> SEQUENCE: 410

```
Met Ala Asp Glu Val Ala Gly His His Gly Pro Ala Cys Glu Glu Glu
1               5                   10                  15
Glu Glu Glu Met Leu Met Asp Glu Thr Glu Ala Val Gly Val His Ala
            20                  25                  30
Ile Asp Gly Leu Pro Val Gln Asn Arg Ser Ile Ile Thr Val Glu Val
        35                  40                  45
Asp Ala Ala Val Ile Gln Gln Ile Arg Glu Ile Phe Gln Thr Met
    50                  55                  60
Ala Ser His Phe Asn Ser Thr Arg Val Val Arg Asp Glu Ala Ile Lys
65                  70                  75                  80
Ser Ile Arg Asp His Phe Arg Leu Ala Val Pro Thr Arg Asn Val Val
                85                  90                  95
Val Ile His Thr Gln His Val His Thr Leu Asp Ala Val Glu Ser Ser
            100                 105                 110
His Leu Val Leu Arg Thr Gly Leu Phe Lys Lys Val Pro Val Asp Ile
        115                 120                 125
Tyr Val Phe Lys Ser Gly Val Phe Thr Asn Leu Gly Asp Gly Gly Phe
    130                 135                 140
Ile Asn Trp Ala Trp Gly Gly Tyr Gly Val Asn His Thr Ala Lys Arg
145                 150                 155                 160
Val Val Phe Ser Arg Pro Pro Gly Ala Leu Pro
                165                 170
```

<210> SEQ ID NO 411
<211> LENGTH: 174
<212> TYPE: PRT
<213> ORGANISM: Artificial Sequence
<220> FEATURE:
<223> OTHER INFORMATION: IPD103 variant

<400> SEQUENCE: 411

```
Met Ala Asp Glu Val Ala Gly His His Gly Pro Ala Cys Glu Glu Glu
1               5                   10                  15
Glu Glu Glu Met Leu Met Asp Glu Thr Glu Ala Val Gly Thr His Leu
            20                  25                  30
Asp Phe Leu Gly Ala Asp Val Lys Leu Gln Pro Arg Asn Ile Ile Thr
        35                  40                  45
Val Glu Val Asp Ala Ala Val Ile Gln Gln Ile Arg Glu Ile Phe
    50                  55                  60
Gln Thr Met Ala Arg His Phe Asn Ser Thr Arg Val Val Arg Asp Glu
65                  70                  75                  80
Ala Ile Lys Gly Ile Arg Asp His Phe Arg Ala Ala Val Pro Thr Arg
                85                  90                  95
Asn Val Val Val His Thr Gln His Ile His Thr Leu Glu Gly Leu
            100                 105                 110
Glu His Thr Asn Leu Val Leu Gln Thr Gly Leu Phe Lys Lys Val Pro
        115                 120                 125
Val Asp Ile Tyr Val Phe Lys Ser Gly Val Phe Thr Asn Leu Gly Asp
    130                 135                 140
Gly Gly Phe Ile Asn Trp Ala Trp Gly Gly Phe Val Gln Glu Val Ala
```

```
                145                 150                 155                 160
Gly Lys Arg Ile His Phe Arg Leu Pro Pro Gly Ala Leu Pro
                165                 170

<210> SEQ ID NO 412
<211> LENGTH: 171
<212> TYPE: PRT
<213> ORGANISM: Artificial Sequence
<220> FEATURE:
<223> OTHER INFORMATION: IPD103 variant

<400> SEQUENCE: 412

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
                20                  25                  30

Ile Asp Gly Leu Pro Val Gln Asn Arg Ser Ile Ile Thr Val Glu Val
            35                  40                  45

Asp Ala Ala Val Ile Gln Gln Ile Arg Glu Ile Phe Arg Thr Met
        50                  55                  60

Ala Ser His Phe Asn Ser Thr Arg Val Val Arg Asp Glu Ala Ile Lys
65                  70                  75                  80

Ser Ile Arg Asp His Phe Arg Leu Ala Val Pro Thr Arg Asn Val Val
                85                  90                  95

Val Ile His Thr Gln His Val His Thr Leu Asp Ala Val Glu Ser Ser
            100                 105                 110

His Leu Val Leu Arg Thr Gly Leu Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 413
<211> LENGTH: 171
<212> TYPE: PRT
<213> ORGANISM: Artificial Sequence
<220> FEATURE:
<223> OTHER INFORMATION: IPD103 variant

<400> SEQUENCE: 413

Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
                20                  25                  30

Ile Asp Gly Leu Pro Val Gln Asn Arg Ser Ile Ile Thr Val Glu Val
            35                  40                  45

Asp Ala Ala Val Ile Gln Gln Ile Arg Glu Ile Phe Ala Ser Met
        50                  55                  60

Ile Lys His Tyr Asn Ser Thr Arg Val Val Arg Asp Glu Ala Ile Lys
65                  70                  75                  80

Ser Ile Arg Asp His Phe Arg Leu Ala Val Pro Thr Arg Asn Val Val
                85                  90                  95

Val Ile His Thr Gln His Val His Thr Leu Asp Ala Val Glu Ser Ser
            100                 105                 110
```

His Leu Val Leu Arg Thr Gly Leu Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
                165                 170

<210> SEQ ID NO 414
<211> LENGTH: 170
<212> TYPE: PRT
<213> ORGANISM: Artificial Sequence
<220> FEATURE:
<223> OTHER INFORMATION: IPD103 variant

<400> SEQUENCE: 414

Met Ala Asp Lys Ala Ala Ala Ala Arg Glu Ala Glu Glu Glu Val
1               5                   10                  15

Gln Glu Thr Leu Met Asp Glu Thr Glu Ala Val Gly Val His Ala Ile
            20                  25                  30

Asp Gly Leu Pro Val Gln Pro Arg Asn Ile Ile Thr Val Glu Val Asp
        35                  40                  45

Ala Ala Ala Val Ile Gln Gln Ile Arg Glu Ile Phe Arg Thr Met Ala
50                  55                  60

Ser His Phe Asn Ser Thr Arg Val Val Arg Asp Glu Ala Ile Lys Gly
65                  70                  75                  80

Ile Arg Asp His Phe Arg Ala Ala Val Pro Thr Arg Asn Val Val Val
                85                  90                  95

Val His Thr Gln His Val His Thr Leu Val Gly Leu Glu His Thr His
            100                 105                 110

Leu Val Leu Gln Thr Gly Leu Phe Ile Lys Val Pro Val Asp Ile Tyr
        115                 120                 125

Val Phe Lys Ser Gly Val Phe Thr Leu Leu Gly Asp Gly Gly Phe Ile
    130                 135                 140

Asn Trp Ala Trp Gly Gly Phe Val Asp Gln Val Val Gly Lys Arg Ile
145                 150                 155                 160

His Phe Arg Leu Pro Pro Gly Ala Leu Pro
                165                 170

<210> SEQ ID NO 415
<211> LENGTH: 171
<212> TYPE: PRT
<213> ORGANISM: Artificial Sequence
<220> FEATURE:
<223> OTHER INFORMATION: IPD103 variant

<400> SEQUENCE: 415

Met Ala Asp Glu Val Ala Gly His His Gly Pro Ala Cys Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
        35                  40                  45

Asp Ala Ala Ala Val Ile Gln Gln Ile Arg Glu Ile Phe Ala Ser Met
    50                  55                  60

Ile Lys His Tyr Asn Ser Thr Arg Val Val Arg Asp Glu Ala Ile Lys
65                  70                  75                  80

```
Ser Ile Arg Asp His Phe Arg Leu Ala Val Pro Thr Arg Asn Val Val
            85                  90                  95

Val Ile His Thr Gln His Val His Thr Leu Asp Ala Val Glu Ser Ser
            100                 105                 110

His Leu Val Leu Gln Thr Gly Leu Phe Lys Lys Val Pro Val Asp Ile
            115                 120                 125

Tyr Val Phe Lys Ser Gly Val Phe Thr Leu Leu Gly Asp Gly Gly Phe
            130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
            165                 170
```

<210> SEQ ID NO 416
<211> LENGTH: 171
<212> TYPE: PRT
<213> ORGANISM: Artificial Sequence
<220> FEATURE:
<223> OTHER INFORMATION: IPD103 variant

<400> SEQUENCE: 416

```
Met Ala Asp Glu Val Ala Gly His His Gly Pro Ala Cys Glu Glu Glu
1               5                   10                  15

Glu Glu Glu Met Leu Met Asp Glu Thr Glu Ala Val Gly Val His Ala
            20                  25                  30

Ile Asp Gly Leu Pro Val Gln Asn Arg Ser Ile Ile Thr Val Glu Val
            35                  40                  45

Asp Ala Ala Val Ile Gln Gln Ile Arg Glu Ile Phe Arg Thr Met
    50                  55                  60

Ala Ser His Phe Asn Ser Thr Arg Val Val Arg Asp Glu Ala Ile Lys
65                  70                  75                  80

Ser Ile Arg Asp His Phe Arg Leu Ala Val Pro Thr Arg Asn Val Val
            85                  90                  95

Val Val His Thr Gln His Val His Thr Leu Asp Ala Val Glu Ser Ser
            100                 105                 110

His Leu Val Leu Arg Thr Gly Leu Phe Lys Lys Val Pro Val Asp Ile
            115                 120                 125

Phe Val Phe Lys Ser Gly Val Phe Thr Asn Leu Gly Asp Gly Gly Phe
            130                 135                 140

Ile Asn Trp Ala Trp Gly Gly Tyr Gly Val Asn His Thr Ala Lys Arg
145                 150                 155                 160

Val Val Phe Ser Arg Pro Pro Gly Ala Leu Pro
            165                 170
```

<210> SEQ ID NO 417
<211> LENGTH: 459
<212> TYPE: DNA
<213> ORGANISM: Artificial Sequence
<220> FEATURE:
<223> OTHER INFORMATION: IPD103 variant

<400> SEQUENCE: 417

```
atggacgaga ctgaggcggt ggggacgcac ctggacttct tgggcgcgga cgtgaagttg      60
caaccccgca acatcatcac cgtggaggtg gacgcggctg ccgtaatcca acagatcaga     120
gagatcttcc agacaatggc gcgtcacttc aactctacga gggtggtgcg ggatgaagcc     180
atcaagggca ttcgagacca cttcagggcc gccgtcccga ctcgcaacgt ggtggtcatt     240
```

```
cacactcagc acgttcacac actggtgggc ttggagcaca cccacctcgt cttgcagacc    300
ggcatcttca aaaggtccc  cgtcgacatc tatgtcttca agtccggcgt cttcaccaac    360
cttggagacg gaggcttcat caactgggca tggggtggct tcgtcgacca ggtcgtcggc    420
aagcgtatcc acttccgctt gccccccggg gcgctccct                           459
```

```
<210> SEQ ID NO 418
<211> LENGTH: 516
<212> TYPE: DNA
<213> ORGANISM: Artificial Sequence
<220> FEATURE:
<223> OTHER INFORMATION: IPD103 variant

<400> SEQUENCE: 418
atggcggaca aagcagcagc agcagctaga gaagctgaag aagaggtgga gacgacgatg     60
gacgagactg aggcggtggg gacgcacctg gacttcttgg gcgcggacgt gaagttgcaa    120
cccgggaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatcccct tccgcttgcc ccccggggcg ctccct                              516
```

```
<210> SEQ ID NO 419
<211> LENGTH: 516
<212> TYPE: DNA
<213> ORGANISM: Artificial Sequence
<220> FEATURE:
<223> OTHER INFORMATION: IPD103 variant

<400> SEQUENCE: 419
atggcggaca aagcagcagc aggagctaga gaagctgaag aagaggtgga gacgacgatg     60
gacgagactg aggcggtggg gacgcacctg gacttcttgg gcgcggacgt gaagttgcaa    120
cccacgaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

```
<210> SEQ ID NO 420
<211> LENGTH: 516
<212> TYPE: DNA
<213> ORGANISM: Artificial Sequence
<220> FEATURE:
<223> OTHER INFORMATION: IPD103 variant

<400> SEQUENCE: 420
atggcggaca aagcagcagc agcagctaga gaagctgaag aagaggtgga gacgacgatg     60
gacgagactg aggcggtggg gacgcacctg gacttcttgg gcgcggacgt gaagttgcaa    120
```

| | |
|---|---|
| ccctgaaca tcatcaccgt ggaggtggac gcggctgccg taatccaaca gatcagagag | 180 |
| atcttccaga caatggcgcg tcacttcaac tctacgaggg tggtgcggga tgaagccatc | 240 |
| aagggcattc gagaccactt cagggccgcc gtcccgactc gcaacgtggt ggtcattcac | 300 |
| actcagcacg ttcacacact ggtgggcttg gagcacaccc acctcgtctt gcagaccggc | 360 |
| atcttcaaaa aggtccccgt cgacatctat gtcttcaagt ccggcgtctt caccaacctt | 420 |
| ggagacggag gcttcatcaa ctgggcatgg ggtggcttcg tcgaccaggt cgtcggcaag | 480 |
| cgtatccact tccgcttgcc ccccggggcg ctccct | 516 |

<210> SEQ ID NO 421
<211> LENGTH: 516
<212> TYPE: DNA
<213> ORGANISM: Artificial Sequence
<220> FEATURE:
<223> OTHER INFORMATION: IPD103 variant

<400> SEQUENCE: 421

| | |
|---|---|
| atggcggaca aagcagcagc agcagctaga gaagctgaag aagaggtgga gacgacgatg | 60 |
| gacgagactg aggcggtggg gacgcacctg gacttcttgg gcgcggacgt gaagttgcaa | 120 |
| cccccctaaca tcatcaccgt ggaggtggac gcggctgccg taatccaaca gatcagagag | 180 |
| atcttccaga caatggcgcg tcacttcaac tctacgaggg tggtgcggga tgaagccatc | 240 |
| aagggcattc gagaccactt cagggccgcc gtcccgactc gcaacgtggt ggtcattcac | 300 |
| actcagcacg ttcacacact ggtgggcttg gagcacaccc acctcgtctt gcagaccggc | 360 |
| atcttcaaaa aggtccccgt cgacatctat gtcttcaagt ccggcgtctt caccaacctt | 420 |
| ggagacggag gcttcatcaa ctgggcatgg ggtggcttcg tcgaccaggt cgtcggcaag | 480 |
| cgtatccact tccgcttgcc ccccggggcg ctccct | 516 |

<210> SEQ ID NO 422
<211> LENGTH: 516
<212> TYPE: DNA
<213> ORGANISM: Artificial Sequence
<220> FEATURE:
<223> OTHER INFORMATION: IPD103 variant

<400> SEQUENCE: 422

| | |
|---|---|
| atggcggaca aagcagcagc agcagctaga gaagctgaag aagaggtgga gacgacgatg | 60 |
| gacgagactg aggcggtggg gacgcacctg gacttcttgg gcgcggacgt gaagttgcaa | 120 |
| ccctgaaca tcatcaccgt ggaggtggac gcggctgccg taatccaaca gatcagagag | 180 |
| atcttccaga caatggcgcg tcacttcaac tctacgaggg tggtgcggga tgaagccatc | 240 |
| aagggcattc gagaccactt cagggccgcc gtcccgactc gcaacgtggt ggtcattcac | 300 |
| actcagcacg ttcacacact ggtgggcttg gagcacaccc acctcgtctt gcagaccggc | 360 |
| atcttcaaaa aggtccccgt cgacatctat gtcttcaagt ccggcgtctt caccaacctt | 420 |
| ggagacggag gcttcatcaa ctgggcatgg ggtggcttcg tcgaccaggt cgtcggcaag | 480 |
| cgtatccact tccgcttgcc ccccggggcg ctccct | 516 |

<210> SEQ ID NO 423
<211> LENGTH: 516
<212> TYPE: DNA
<213> ORGANISM: Artificial Sequence
<220> FEATURE:
<223> OTHER INFORMATION: IPD103 variant

<400> SEQUENCE: 423

```
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccctataaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg agcacaccc acctcgtctt gcagaccggc    360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516
```

<210> SEQ ID NO 424
<211> LENGTH: 516
<212> TYPE: DNA
<213> ORGANISM: Artificial Sequence
<220> FEATURE:
<223> OTHER INFORMATION: IPD103 variant

<400> SEQUENCE: 424

```
atggcggaca aagcagcagc agcagcttat gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg agcacaccc acctcgtctt gcagaccggc    360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516
```

<210> SEQ ID NO 425
<211> LENGTH: 519
<212> TYPE: DNA
<213> ORGANISM: Artificial Sequence
<220> FEATURE:
<223> OTHER INFORMATION: IPD103 variant

<400> SEQUENCE: 425

```
atggcggaca aagcagcagc agcagcagct acggaagctg aagaagaggt ggagacgacg    60
atggacgaga ctgaggcggt ggggacgcac ctggacttct tgggcgcgga cgtgaagttg   120
caaccccgca acatcatcac cgtggaggtg gacgcggctg ccgtaatcca acagatcaga   180
gagatcttcc agacaatggc gcgtcacttc aactctacga gggtggtgcg ggatgaagcc   240
atcaagggca ttcgagacca cttcagggcc gccgtcccga ctcgcaacgt ggtggtcatt   300
cacactcagc acgttcacac actggtgggc ttggagcaca cccacctcgt cttgcagacc   360
ggcatcttca aaaggtccc cgtcgacatc tatgtcttca gtccggcgt cttcaccaac    420 cttggagacg gaggcttcat caactgggca tggggtggct tcgtcgacca ggtcgtcggc   480
aagcgtatcc acttccgctt gcccccggg gcgctccct                           519
```

<210> SEQ ID NO 426
<211> LENGTH: 516
<212> TYPE: DNA

<213> ORGANISM: Artificial Sequence
<220> FEATURE:
<223> OTHER INFORMATION: IPD103 variant

<400> SEQUENCE: 426

```
atggcggaca aagcagcagc agcagctgcc gaagctgaag aagaggtgga gacgacgatg    60
gacgagactg aggcggtggg gacgcacctg gacttcttgg gcgcggacgt gaagttgcaa   120
ccccgcaaca tcataccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg agcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact ccgcttgcc ccccggggcg ctccct                              516
```

<210> SEQ ID NO 427
<211> LENGTH: 519
<212> TYPE: DNA
<213> ORGANISM: Artificial Sequence
<220> FEATURE:
<223> OTHER INFORMATION: IPD103 variant

<400> SEQUENCE: 427

```
atggcggaca aagcagcagc agcagcagct atggaagctg aagaagaggt ggagacgacg    60
atggacgaga ctgaggcggt ggggacgcac ctggacttct gggcgcgga cgtgaagttg   120
caaccccgca acatcatcac cgtggaggtg gacgcggctg ccgtaatcca acagatcaga   180
gagatcttcc agacaatggc gcgtcacttc aactctacga gggtggtgcg ggatgaagcc   240
atcaagggca ttcgagacca cttcagggcc gccgtcccga ctcgcaacgt ggtggtcatt   300
cacactcagc acgttcacac actggtgggc ttggagcaca cccacctcgt cttgcagacc   360
ggcatcttca aaaggtccc cgtcgacatc tatgtcttca gtccggcgt cttcaccaac   420
cttggagacg gaggcttcat caactgggca tggggtggct cgtcgacca ggtcgtcggc   480
aagcgtatcc acttccgctt gcccccgg gcgctccct                             519
```

<210> SEQ ID NO 428
<211> LENGTH: 519
<212> TYPE: DNA
<213> ORGANISM: Artificial Sequence
<220> FEATURE:
<223> OTHER INFORMATION: IPD103 variant

<400> SEQUENCE: 428

```
atggcggaca aagcagcagc agcagcagct agtgaagctg aagaagaggt ggagacgacg    60
atggacgaga ctgaggcggt ggggacgcac ctggacttct gggcgcgga cgtgaagttg   120
caaccccgca acatcatcac cgtggaggtg gacgcggctg ccgtaatcca acagatcaga   180
gagatcttcc agacaatggc gcgtcacttc aactctacga gggtggtgcg ggatgaagcc   240
atcaagggca ttcgagacca cttcagggcc gccgtcccga ctcgcaacgt ggtggtcatt   300
cacactcagc acgttcacac actggtgggc ttggagcaca cccacctcgt cttgcagacc   360
ggcatcttca aaaggtccc cgtcgacatc tatgtcttca gtccggcgt cttcaccaac   420
cttggagacg gaggcttcat caactgggca tggggtggct cgtcgacca ggtcgtcggc   480
aagcgtatcc acttccgctt gcccccgg gcgctccct                             519
```

-continued

<210> SEQ ID NO 429
<211> LENGTH: 459
<212> TYPE: DNA
<213> ORGANISM: Artificial Sequence
<220> FEATURE:
<223> OTHER INFORMATION: IPD103 variant

<400> SEQUENCE: 429

| | | | | | |
|---|---|---|---|---|---|
| atggacgaga | ctgaggcggt | ggggacgcac | ctggacttct | tgggcgcgga | cgtgaagttg | 60 |
| caacccacga | acatcatcac | cgtggaggtg | gacgcggctg | ccgtaatcca | acagatcaga | 120 |
| gagatcttcc | agacaatggc | gcgtcacttc | aactctacga | gggtggtgcg | ggatgaagcc | 180 |
| atcaagggca | ttcgagacca | cttcagggcc | gccgtcccga | ctcgcaacgt | ggtggtcatt | 240 |
| cacactcagc | acgttcacac | actggtgggc | ttggagcaca | cccacctcgt | cttgcagacc | 300 |
| ggcatcttca | aaaaggtccc | cgtcgacatc | tatgtcttca | agtccggcgt | cttcaccaac | 360 |
| cttggagacg | gaggcttcat | caactgggca | tggggtggct | tcgtcgacca | ggtcgtcggc | 420 |
| aagcgtatcc | acttccgctt | gccccccggg | gcgctccct | | | 459 |

<210> SEQ ID NO 430
<211> LENGTH: 459
<212> TYPE: DNA
<213> ORGANISM: Artificial Sequence
<220> FEATURE:
<223> OTHER INFORMATION: IPD103 variant

<400> SEQUENCE: 430

| | | | | | |
|---|---|---|---|---|---|
| atggacgaga | ctgaggcggt | ggggacgcac | ctggacttct | tgggcgcgga | cgtgaagttg | 60 |
| caaccctgga | acatcatcac | cgtggaggtg | gacgcggctg | ccgtaatcca | acagatcaga | 120 |
| gagatcttcc | agacaatggc | gcgtcacttc | aactctacga | gggtggtgcg | ggatgaagcc | 180 |
| atcaagggca | ttcgagacca | cttcagggcc | gccgtcccga | ctcgcaacgt | ggtggtcatt | 240 |
| cacactcagc | acgttcacac | actggtgggc | ttggagcaca | cccacctcgt | cttgcagacc | 300 |
| ggcatcttca | aaaaggtccc | cgtcgacatc | tatgtcttca | agtccggcgt | cttcaccaac | 360 |
| cttggagacg | gaggcttcat | caactgggca | tggggtggct | tcgtcgacca | ggtcgtcggc | 420 |
| aagcgtatcc | acttccgctt | gccccccggg | gcgctccct | | | 459 |

<210> SEQ ID NO 431
<211> LENGTH: 459
<212> TYPE: DNA
<213> ORGANISM: Artificial Sequence
<220> FEATURE:
<223> OTHER INFORMATION: IPD103 variant

<400> SEQUENCE: 431

| | | | | | |
|---|---|---|---|---|---|
| atggacgaga | ctgaggcggt | ggggacgcac | ctggacttct | tgggcgcgga | cgtgaagttg | 60 |
| caaccctata | acatcatcac | cgtggaggtg | gacgcggctg | ccgtaatcca | acagatcaga | 120 |
| gagatcttcc | agacaatggc | gcgtcacttc | aactctacga | gggtggtgcg | ggatgaagcc | 180 |
| atcaagggca | ttcgagacca | cttcagggcc | gccgtcccga | ctcgcaacgt | ggtggtcatt | 240 |
| cacactcagc | acgttcacac | actggtgggc | ttggagcaca | cccacctcgt | cttgcagacc | 300 |
| ggcatcttca | aaaaggtccc | cgtcgacatc | tatgtcttca | agtccggcgt | cttcaccaac | 360 |
| cttggagacg | gaggcttcat | caactgggca | tggggtggct | tcgtcgacca | ggtcgtcggc | 420 |
| aagcgtatcc | acttccgctt | gccccccggg | gcgctccct | | | 459 |

<210> SEQ ID NO 432
<211> LENGTH: 513
<212> TYPE: DNA
<213> ORGANISM: Artificial Sequence
<220> FEATURE:
<223> OTHER INFORMATION: IPD103 variant

<400> SEQUENCE: 432

```
atggcggacc aagcagcagc agcttgtgaa gctgaagaag aggtggagac gacgatggac    60
gagactgagg cggtggggac gcacctggac ttcttgggcg cggacgtgaa gttgcaaccc   120
cctaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg gcatgggggt ggcttcgtcg accaggtcgt cggcaagcgt   480
atccacttcc gcttgccccc cggggcgctc cct                                513
```

<210> SEQ ID NO 433
<211> LENGTH: 513
<212> TYPE: DNA
<213> ORGANISM: Artificial Sequence
<220> FEATURE:
<223> OTHER INFORMATION: IPD103 variant

<400> SEQUENCE: 433

```
atggcggacc aagcagcagc agctgtggaa gctgaagaag aggtggagac gacgatggac    60
gagactgagg cggtggggac gcacctggac ttcttgggcg cggacgtgaa gttgcaaccc   120
cctaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg gcatgggggt ggcttcgtcg accaggtcgt cggcaagcgt   480
atccacttcc gcttgccccc cggggcgctc cct                                513
```

<210> SEQ ID NO 434
<211> LENGTH: 513
<212> TYPE: DNA
<213> ORGANISM: Artificial Sequence
<220> FEATURE:
<223> OTHER INFORMATION: IPD103 variant

<400> SEQUENCE: 434

```
atggcggacc aagcagcagc agctgacgaa gctgaagaag aggtggagac gacgatggac    60
gagactgagg cggtggggac gcacctggac ttcttgggcg cggacgtgaa gttgcaaccc   120
acgaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
```

```
gacggaggct tcatcaactg ggcatggggt ggcttcgtcg accaggtcgt cggcaagcgt    480
atccacttcc gcttgccccc cggggcgctc cct                                 513

<210> SEQ ID NO 435
<211> LENGTH: 513
<212> TYPE: DNA
<213> ORGANISM: Artificial Sequence
<220> FEATURE:
<223> OTHER INFORMATION: IPD103 variant

<400> SEQUENCE: 435
atggcggacc aagcagcagc agctcaagaa gctgaagaag aggtggagac gacgatggac    60
gagactgagg cggtggggac gcacctggac ttcttgggcg cggacgtgaa gttgcaaccc   120
ctgaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag gccgccgtc ccgactcgca acgtggtggt cattcacact    300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg ggcatggggt ggcttcgtcg accaggtcgt cggcaagcgt   480
atccacttcc gcttgccccc cggggcgctc cct                                513

<210> SEQ ID NO 436
<211> LENGTH: 513
<212> TYPE: DNA
<213> ORGANISM: Artificial Sequence
<220> FEATURE:
<223> OTHER INFORMATION: IPD103 variant

<400> SEQUENCE: 436
atggcggacc aagcagcagc agctggcgaa gctgaagaag aggtggagac gacgatggac    60
gagactgagg cggtggggac gcacctggac ttcttgggcg cggacgtgaa gttgcaaccc   120
ctgaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag gccgccgtc ccgactcgca acgtggtggt cattcacact    300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg ggcatggggt ggcttcgtcg accaggtcgt cggcaagcgt   480
atccacttcc gcttgccccc cggggcgctc cct                                513

<210> SEQ ID NO 437
<211> LENGTH: 516
<212> TYPE: DNA
<213> ORGANISM: Artificial Sequence
<220> FEATURE:
<223> OTHER INFORMATION: IPD103 variant

<400> SEQUENCE: 437
atggcggaca aagcagcagc agcagctagg gcagctgaag aagaggtgga gacgacgatg    60
gacgagactg aggcggtggg gacgcacctg gacttcttgg gcgcggacgt gaagttgcaa   120
ccctggaaca tcatcaccgt ggaggtggac gcggctgccg taatccaaca gatcagagag   180
atcttccaga caatggcgcg tcacttcaac tctacgaggg tggtgcggga tgaagccatc   240
```

```
aagggcattc gagaccactt cagggccgcc gtcccgactc gcaacgtggt ggtcattcac     300
actcagcacg ttcacacact ggtgggcttg gagcacaccc acctcgtctt gcagaccggc     360
atcttcaaaa aggtccccgt cgacatctat gtcttcaagt ccggcgtctt caccaacctt     420
ggagacggag gcttcatcaa ctgggcatgg ggtggcttcg tcgaccaggt cgtcggcaag     480
cgtatccact tccgcttgcc ccccggggcg ctccct                               516

<210> SEQ ID NO 438
<211> LENGTH: 516
<212> TYPE: DNA
<213> ORGANISM: Artificial Sequence
<220> FEATURE:
<223> OTHER INFORMATION: IPD103 variant

<400> SEQUENCE: 438
atggcggaca aagcagcagc agcagctgcc gaagctgaag aagaggtgga gacgacgatg      60
gacgagactg aggcggtggg gacgcacctg gacttcttgg gcgcggacgt gaagttgcaa     120
cccacgaaca tcatcaccgt ggaggtggac gcggctgccg taatccaaca gatcagagag     180
atcttccaga caatggcgcg tcacttcaac tctacgaggg tggtgcggga tgaagccatc     240
aagggcattc gagaccactt cagggccgcc gtcccgactc gcaacgtggt ggtcattcac     300
actcagcacg ttcacacact ggtgggcttg gagcacaccc acctcgtctt gcagaccggc     360
atcttcaaaa aggtccccgt cgacatctat gtcttcaagt ccggcgtctt caccaacctt     420
ggagacggag gcttcatcaa ctgggcatgg ggtggcttcg tcgaccaggt cgtcggcaag     480
cgtatccact tccgcttgcc ccccggggcg ctccct                               516

<210> SEQ ID NO 439
<211> LENGTH: 516
<212> TYPE: DNA
<213> ORGANISM: Artificial Sequence
<220> FEATURE:
<223> OTHER INFORMATION: IPD103 variant

<400> SEQUENCE: 439
atggcggaca aagcagcagc agcagctatg gaagctgaag aagaggtgga gacgacgatg      60
gacgagactg aggcggtggg gacgcacctg gacttcttgg gcgcggacgt gaagttgcaa     120
cccacgaaca tcatcaccgt ggaggtggac gcggctgccg taatccaaca gatcagagag     180
atcttccaga caatggcgcg tcacttcaac tctacgaggg tggtgcggga tgaagccatc     240
aagggcattc gagaccactt cagggccgcc gtcccgactc gcaacgtggt ggtcattcac     300
actcagcacg ttcacacact ggtgggcttg gagcacaccc acctcgtctt gcagaccggc     360
atcttcaaaa aggtccccgt cgacatctat gtcttcaagt ccggcgtctt caccaacctt     420
ggagacggag gcttcatcaa ctgggcatgg ggtggcttcg tcgaccaggt cgtcggcaag     480
cgtatccact tccgcttgcc ccccggggcg ctccct                               516

<210> SEQ ID NO 440
<211> LENGTH: 516
<212> TYPE: DNA
<213> ORGANISM: Artificial Sequence
<220> FEATURE:
<223> OTHER INFORMATION: IPD103 variant

<400> SEQUENCE: 440
atggcggaca aagcagcagc agcagctagt gaagctgaag aagaggtgga gacgacgatg      60
gacgagactg aggcggtggg gacgcacctg gacttcttgg gcgcggacgt gaagttgcaa     120
```

-continued

```
cccctgaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

<210> SEQ ID NO 441
<211> LENGTH: 516
<212> TYPE: DNA
<213> ORGANISM: Artificial Sequence
<220> FEATURE:
<223> OTHER INFORMATION: IPD103 variant

<400> SEQUENCE: 441

```
atggcggaca aagcagcagc agcagctgcc gaagctgaag aagaggtgga gacgacgatg    60
gacgagactg aggcggtggg gacgcacctg gacttcttgg gcgcggacgt gaagttgcaa    120
ccctggaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

<210> SEQ ID NO 442
<211> LENGTH: 516
<212> TYPE: DNA
<213> ORGANISM: Artificial Sequence
<220> FEATURE:
<223> OTHER INFORMATION: IPD103 variant

<400> SEQUENCE: 442

```
atggcggaca aagcagcagc agcagctatg gaagctgaag aagaggtgga gacgacgatg    60
gacgagactg aggcggtggg gacgcacctg gacttcttgg gcgcggacgt gaagttgcaa    120
ccctggaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

<210> SEQ ID NO 443
<211> LENGTH: 516
<212> TYPE: DNA
<213> ORGANISM: Artificial Sequence
<220> FEATURE:
<223> OTHER INFORMATION: IPD103 variant

<400> SEQUENCE: 443

```
atggcggaca aagcagcagc agcagctatg gaagctgaag aagaggtgga gacgacgatg      60
gacgagactg aggcggtggg gacgcacctg gacttcttgg gcgcggacgt gaagttgcaa     120
ccctataaca tcatcaccgt ggaggtggac gcggctgccg taatccaaca gatcagagag     180
atcttccaga caatggcgcg tcacttcaac tctacgaggg tggtgcggga tgaagccatc     240
aagggcattc gagaccactt cagggccgcc gtcccgactc gcaacgtggt ggtcattcac     300
actcagcacg ttcacacact ggtgggcttg gagcacaccc acctcgtctt gcagaccggc     360
atcttcaaaa aggtccccgt cgacatctat gtcttcaagt ccggcgtctt caccaacctt     420
ggagacggag gcttcatcaa ctgggcatgg ggtggcttcg tcgaccaggt cgtcggcaag     480
cgtatccact ccgcttgcc ccccggggcg ctccct                                516
```

<210> SEQ ID NO 444
<211> LENGTH: 516
<212> TYPE: DNA
<213> ORGANISM: Artificial Sequence
<220> FEATURE:
<223> OTHER INFORMATION: IPD103 variant

<400> SEQUENCE: 444

```
atggcggaca aagcagcagc agcagctgcc gaagctgaag aagaggtgga gacgacgatg      60
gacgagactg aggcggtggg gacgcacctg gacttcttgg gcgcggacgt gaagttgcaa     120
ccctataaca tcatcaccgt ggaggtggac gcggctgccg taatccaaca gatcagagag     180
atcttccaga caatggcgcg tcacttcaac tctacgaggg tggtgcggga tgaagccatc     240
aagggcattc gagaccactt cagggccgcc gtcccgactc gcaacgtggt ggtcattcac     300
actcagcacg ttcacacact ggtgggcttg gagcacaccc acctcgtctt gcagaccggc     360
atcttcaaaa aggtccccgt cgacatctat gtcttcaagt ccggcgtctt caccaacctt     420
ggagacggag gcttcatcaa ctgggcatgg ggtggcttcg tcgaccaggt cgtcggcaag     480
cgtatccact ccgcttgcc ccccggggcg ctccct                                516
```

<210> SEQ ID NO 445
<211> LENGTH: 153
<212> TYPE: PRT
<213> ORGANISM: Artificial Sequence
<220> FEATURE:
<223> OTHER INFORMATION: IPD103 variant

<400> SEQUENCE: 445

```
Met Asp Glu Thr Glu Ala Val Gly Thr His Leu Asp Phe Leu Gly Ala
1               5                   10                  15
Asp Val Lys Leu Gln Pro Arg Asn Ile Ile Thr Val Glu Val Asp Ala
            20                  25                  30
Ala Ala Val Ile Gln Gln Ile Arg Glu Ile Phe Gln Thr Met Ala Arg
        35                  40                  45
His Phe Asn Ser Thr Arg Val Val Arg Asp Glu Ala Ile Lys Gly Ile
    50                  55                  60
Arg Asp His Phe Arg Ala Ala Val Pro Thr Arg Asn Val Val Ile
65                  70                  75                  80
His Thr Gln His Val His Thr Leu Val Gly Leu Glu His Thr His Leu
                85                  90                  95
Val Leu Gln Thr Gly Ile Phe Lys Lys Val Pro Val Asp Ile Tyr Val
            100                 105                 110
```

```
Phe Lys Ser Gly Val Phe Thr Asn Leu Gly Asp Gly Phe Ile Asn
                115                 120                 125

Trp Ala Trp Gly Gly Phe Val Asp Gln Val Val Gly Lys Arg Ile His
    130                 135                 140

Phe Arg Leu Pro Pro Gly Ala Leu Pro
145                 150

<210> SEQ ID NO 446
<211> LENGTH: 172
<212> TYPE: PRT
<213> ORGANISM: Artificial Sequence
<220> FEATURE:
<223> OTHER INFORMATION: IPD103 variant

<400> SEQUENCE: 446

Met Ala Asp Lys Ala Ala Ala Ala Arg Glu Ala Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Gly Asn Ile Ile Thr Val Glu
            35                  40                  45

Val Asp Ala Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile Pro Phe Arg Leu Pro Pro Gly Ala Leu Pro
                165                 170

<210> SEQ ID NO 447
<211> LENGTH: 172
<212> TYPE: PRT
<213> ORGANISM: Artificial Sequence
<220> FEATURE:
<223> OTHER INFORMATION: IPD103 variant

<400> SEQUENCE: 447

Met Ala Asp Lys Ala Ala Ala Gly Ala Arg Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Thr Asn Ile Ile Thr Val Glu
            35                  40                  45

Val Asp Ala Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95
```

```
Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 448
<211> LENGTH: 172
<212> TYPE: PRT
<213> ORGANISM: Artificial Sequence
<220> FEATURE:
<223> OTHER INFORMATION: IPD103 variant

<400> SEQUENCE: 448

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Leu Asn Ile Ile Thr Val Glu
        35                  40                  45

Val Asp Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 449
<211> LENGTH: 172
<212> TYPE: PRT
<213> ORGANISM: Artificial Sequence
<220> FEATURE:
<223> OTHER INFORMATION: IPD103 variant

<400> SEQUENCE: 449

Met Ala Asp Lys Ala Ala Ala Ala Arg Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Pro Asn Ile Ile Thr Val Glu
        35                  40                  45

Val Asp Ala Ala Val Ile Gln Gln Ile Arg Glu Ile Phe Gln Thr
```

```
                50                  55                  60

Met Ala Arg His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 450
<211> LENGTH: 172
<212> TYPE: PRT
<213> ORGANISM: Artificial Sequence
<220> FEATURE:
<223> OTHER INFORMATION: IPD103 variant

<400> SEQUENCE: 450

Met Ala Asp Lys Ala Ala Ala Ala Arg Glu Ala Glu Glu Glu Val
 1               5                  10                  15

Glu Thr Thr Met Asp Glu Thr Glu Ala Val Gly Thr His Leu Asp Phe
                 20                  25                  30

Leu Gly Ala Asp Val Lys Leu Gln Pro Trp Asn Ile Ile Thr Val Glu
            35                  40                  45

Val Asp Ala Ala Val Ile Gln Gln Ile Arg Glu Ile Phe Gln Thr
        50                  55                  60

Met Ala Arg His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 451
<211> LENGTH: 172
<212> TYPE: PRT
<213> ORGANISM: Artificial Sequence
<220> FEATURE:
<223> OTHER INFORMATION: IPD103 variant

<400> SEQUENCE: 451

Met Ala Asp Lys Ala Ala Ala Ala Arg Glu Ala Glu Glu Glu Val
 1               5                  10                  15
```

```
Glu Thr Thr Met Asp Glu Thr Glu Ala Val Gly Thr His Leu Asp Phe
             20                  25                  30

Leu Gly Ala Asp Val Lys Leu Gln Pro Tyr Asn Ile Ile Thr Val Glu
         35                  40                  45

Val Asp Ala Ala Ala Val Ile Gln Gln Ile Arg Glu Ile Phe Gln Thr
     50                  55                  60

Met Ala Arg His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 452
<211> LENGTH: 172
<212> TYPE: PRT
<213> ORGANISM: Artificial Sequence
<220> FEATURE:
<223> OTHER INFORMATION: IPD103 variant

<400> SEQUENCE: 452

Met Ala Asp Lys Ala Ala Ala Ala Tyr Glu Ala Glu Glu Val
 1               5                  10                  15

Glu Thr Thr Met Asp Glu Thr Glu Ala Val Gly Thr His Leu Asp Phe
             20                  25                  30

Leu Gly Ala Asp Val Lys Leu Gln Pro Arg Asn Ile Ile Thr Val Glu
         35                  40                  45

Val Asp Ala Ala Ala Val Ile Gln Gln Ile Arg Glu Ile Phe Gln Thr
     50                  55                  60

Met Ala Arg His Phe Asn Ser Thr Arg Val Val Arg Asp Glu Ala Ile
 65                  70                  75                  80

Lys Gly Ile Arg Asp His Phe Arg Ala Ala Val Pro Thr Arg Asn Val
                 85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 453
<211> LENGTH: 173
<212> TYPE: PRT
<213> ORGANISM: Artificial Sequence
<220> FEATURE:
```

<223> OTHER INFORMATION: IPD103 variant

<400> SEQUENCE: 453

Met Ala Asp Lys Ala Ala Ala Ala Ala Thr Glu Ala Glu Glu Glu
1               5                   10                  15

Val Glu Thr Thr Met Asp Glu Thr Glu Ala Val Gly Thr His Leu Asp
            20                  25                  30

Phe Leu Gly Ala Asp Val Lys Leu Gln Pro Arg Asn Ile Ile Thr Val
            35                  40                  45

Glu Val Asp Ala Ala Ala Val Ile Gln Gln Ile Arg Glu Ile Phe Gln
50                  55                  60

Thr Met Ala Arg His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                    85                  90                  95

Val Val Val Ile His Thr Gln His Val His Thr Leu Val Gly Leu Glu
                100                 105                 110

His Thr His Leu Val Leu Gln Thr Gly Ile Phe Lys Lys Val Pro Val
            115                 120                 125

Asp Ile Tyr Val Phe Lys Ser Gly Val Phe Thr Asn Leu Gly Asp Gly
        130                 135                 140

Gly Phe Ile Asn Trp Ala Trp Gly Gly Phe Val Asp Gln Val Val Gly
145                 150                 155                 160

Lys Arg Ile His Phe Arg Leu Pro Pro Gly Ala Leu Pro
                    165                 170

<210> SEQ ID NO 454
<211> LENGTH: 172
<212> TYPE: PRT
<213> ORGANISM: Artificial Sequence
<220> FEATURE:
<223> OTHER INFORMATION: IPD103 variant

<400> SEQUENCE: 454

Met Ala Asp Lys Ala Ala Ala Ala Ala Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Arg Asn Ile Ile Thr Val Glu
            35                  40                  45

Val Asp Ala Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                    85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                    165                 170

<210> SEQ ID NO 455
<211> LENGTH: 173
<212> TYPE: PRT
<213> ORGANISM: Artificial Sequence
<220> FEATURE:
<223> OTHER INFORMATION: IPD103 variant

<400> SEQUENCE: 455

```
Met Ala Asp Lys Ala Ala Ala Ala Ala Met Glu Ala Glu Glu
1               5                   10                  15

Val Glu Thr Thr Met Asp Glu Thr Glu Ala Val Gly Thr His Leu Asp
            20                  25                  30

Phe Leu Gly Ala Asp Val Lys Leu Gln Pro Arg Asn Ile Ile Thr Val
        35                  40                  45

Glu Val Asp Ala Ala Ala Val Ile Gln Gln Ile Arg Glu Ile Phe Gln
    50                  55                  60

Thr Met Ala Arg His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Ile His Thr Gln His Val His Thr Leu Val Gly Leu Glu
            100                 105                 110

His Thr His Leu Val Leu Gln Thr Gly Ile Phe Lys Lys Val Pro Val
        115                 120                 125

Asp Ile Tyr Val Phe Lys Ser Gly Val Phe Thr Asn Leu Gly Asp Gly
    130                 135                 140

Gly Phe Ile Asn Trp Ala Trp Gly Gly Phe Val Asp Gln Val Val Gly
145                 150                 155                 160

Lys Arg Ile His Phe Arg Leu Pro Pro Gly Ala Leu Pro
                165                 170
```

<210> SEQ ID NO 456
<211> LENGTH: 173
<212> TYPE: PRT
<213> ORGANISM: Artificial Sequence
<220> FEATURE:
<223> OTHER INFORMATION: IPD103 variant

<400> SEQUENCE: 456

```
Met Ala Asp Lys Ala Ala Ala Ala Ala Ser Glu Ala Glu Glu
1               5                   10                  15

Val Glu Thr Thr Met Asp Glu Thr Glu Ala Val Gly Thr His Leu Asp
            20                  25                  30

Phe Leu Gly Ala Asp Val Lys Leu Gln Pro Arg Asn Ile Ile Thr Val
        35                  40                  45

Glu Val Asp Ala Ala Ala Val Ile Gln Gln Ile Arg Glu Ile Phe Gln
    50                  55                  60

Thr Met Ala Arg His Phe Asn Ser Thr Arg Val Val Arg Asp Glu Ala
65                  70                  75                  80

Ile Lys Gly Ile Arg Asp His Phe Arg Ala Ala Val Pro Thr Arg Asn
                85                  90                  95

Val Val Val Ile His Thr Gln His Val His Thr Leu Val Gly Leu Glu
            100                 105                 110

His Thr His Leu Val Leu Gln Thr Gly Ile Phe Lys Lys Val Pro Val
        115                 120                 125

Asp Ile Tyr Val Phe Lys Ser Gly Val Phe Thr Asn Leu Gly Asp Gly
```

Gly Phe Ile Asn Trp Ala Trp Gly Gly Phe Val Asp Gln Val Val Gly
145                 150                 155                 160

Lys Arg Ile His Phe Arg Leu Pro Pro Gly Ala Leu Pro
                165                 170

<210> SEQ ID NO 457
<211> LENGTH: 153
<212> TYPE: PRT
<213> ORGANISM: Artificial Sequence
<220> FEATURE:
<223> OTHER INFORMATION: IPD103 variant

<400> SEQUENCE: 457

Met Asp Glu Thr Glu Ala Val Gly Thr His Leu Asp Phe Leu Gly Ala
1               5                   10                  15

Asp Val Lys Leu Gln Pro Thr Asn Ile Ile Thr Val Glu Val Asp Ala
                20                  25                  30

Ala Ala Val Ile Gln Gln Ile Arg Glu Ile Phe Gln Thr Met Ala Arg
            35                  40                  45

His Phe Asn Ser Thr Arg Val Val Arg Asp Glu Ala Ile Lys Gly Ile
        50                  55                  60

Arg Asp His Phe Arg Ala Ala Val Pro Thr Arg Asn Val Val Ile
65                  70                  75                  80

His Thr Gln His Val His Thr Leu Val Gly Leu Glu His Thr His Leu
                85                  90                  95

Val Leu Gln Thr Gly Ile Phe Lys Lys Val Pro Val Asp Ile Tyr Val
            100                 105                 110

Phe Lys Ser Gly Val Phe Thr Asn Leu Gly Asp Gly Gly Phe Ile Asn
        115                 120                 125

Trp Ala Trp Gly Gly Phe Val Asp Gln Val Val Gly Lys Arg Ile His
    130                 135                 140

Phe Arg Leu Pro Pro Gly Ala Leu Pro
145                 150

<210> SEQ ID NO 458
<211> LENGTH: 153
<212> TYPE: PRT
<213> ORGANISM: Artificial Sequence
<220> FEATURE:
<223> OTHER INFORMATION: IPD103 variant

<400> SEQUENCE: 458

Met Asp Glu Thr Glu Ala Val Gly Thr His Leu Asp Phe Leu Gly Ala
1               5                   10                  15

Asp Val Lys Leu Gln Pro Trp Asn Ile Ile Thr Val Glu Val Asp Ala
                20                  25                  30

Ala Ala Val Ile Gln Gln Ile Arg Glu Ile Phe Gln Thr Met Ala Arg
            35                  40                  45

His Phe Asn Ser Thr Arg Val Val Arg Asp Glu Ala Ile Lys Gly Ile
        50                  55                  60

Arg Asp His Phe Arg Ala Ala Val Pro Thr Arg Asn Val Val Ile
65                  70                  75                  80

His Thr Gln His Val His Thr Leu Val Gly Leu Glu His Thr His Leu
                85                  90                  95

Val Leu Gln Thr Gly Ile Phe Lys Lys Val Pro Val Asp Ile Tyr Val
            100                 105                 110

```
Phe Lys Ser Gly Val Phe Thr Asn Leu Gly Asp Gly Phe Ile Asn
            115                 120                 125

Trp Ala Trp Gly Gly Phe Val Asp Gln Val Val Gly Lys Arg Ile His
        130                 135                 140

Phe Arg Leu Pro Pro Gly Ala Leu Pro
145                 150

<210> SEQ ID NO 459
<211> LENGTH: 153
<212> TYPE: PRT
<213> ORGANISM: Artificial Sequence
<220> FEATURE:
<223> OTHER INFORMATION: IPD103 variant

<400> SEQUENCE: 459

Met Asp Glu Thr Glu Ala Val Gly Thr His Leu Asp Phe Leu Gly Ala
1               5                   10                  15

Asp Val Lys Leu Gln Pro Tyr Asn Ile Ile Thr Val Glu Val Asp Ala
            20                  25                  30

Ala Ala Val Ile Gln Gln Ile Arg Glu Ile Phe Gln Thr Met Ala Arg
        35                  40                  45

His Phe Asn Ser Thr Arg Val Val Arg Asp Glu Ala Ile Lys Gly Ile
    50                  55                  60

Arg Asp His Phe Arg Ala Ala Val Pro Thr Arg Asn Val Val Ile
65                  70                  75                  80

His Thr Gln His Val His Thr Leu Val Gly Leu Glu His Thr His Leu
                85                  90                  95

Val Leu Gln Thr Gly Ile Phe Lys Lys Val Pro Val Asp Ile Tyr Val
            100                 105                 110

Phe Lys Ser Gly Val Phe Thr Asn Leu Gly Asp Gly Phe Ile Asn
        115                 120                 125

Trp Ala Trp Gly Gly Phe Val Asp Gln Val Val Gly Lys Arg Ile His
    130                 135                 140

Phe Arg Leu Pro Pro Gly Ala Leu Pro
145                 150

<210> SEQ ID NO 460
<211> LENGTH: 171
<212> TYPE: PRT
<213> ORGANISM: Artificial Sequence
<220> FEATURE:
<223> OTHER INFORMATION: IPD103 variant

<400> SEQUENCE: 460

Met Ala Asp Gln Ala Ala Ala Cys Glu Ala Glu Glu Val Glu
1               5                   10                  15

Thr Thr Met Asp Glu Thr Glu Ala Val Gly Thr His Leu Asp Phe Leu
            20                  25                  30

Gly Ala Asp Val Lys Leu Gln Pro Pro Asn Ile Ile Thr Val Glu Val
        35                  40                  45

Asp Ala Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110
```

His Leu Val Leu Gln Thr Gly Ile Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 461
<211> LENGTH: 171
<212> TYPE: PRT
<213> ORGANISM: Artificial Sequence
<220> FEATURE:
<223> OTHER INFORMATION: IPD103 variant

<400> SEQUENCE: 461

Met Ala Asp Gln Ala Ala Ala Val Glu Ala Glu Glu Val Glu
1               5                   10                  15

Thr Thr Met Asp Glu Thr Glu Ala Val Gly Thr His Leu Asp Phe Leu
            20                  25                  30

Gly Ala Asp Val Lys Leu Gln Pro Asn Ile Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 462
<211> LENGTH: 171
<212> TYPE: PRT
<213> ORGANISM: Artificial Sequence
<220> FEATURE:
<223> OTHER INFORMATION: IPD103 variant

<400> SEQUENCE: 462

Met Ala Asp Gln Ala Ala Ala Asp Glu Ala Glu Glu Val Glu
1               5                   10                  15

Thr Thr Met Asp Glu Thr Glu Ala Val Gly Thr His Leu Asp Phe Leu
            20                  25                  30

Gly Ala Asp Val Lys Leu Gln Pro Thr Asn Ile Ile Thr Val Glu Val
        35                  40                  45

Asp Ala Ala Val Ile Gln Gln Ile Arg Glu Ile Phe Gln Thr Met
    50                  55                  60

Ala Arg His Phe Asn Ser Thr Arg Val Val Arg Asp Glu Ala Ile Lys

```
                    65                  70                  75                  80
Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 463
<211> LENGTH: 171
<212> TYPE: PRT
<213> ORGANISM: Artificial Sequence
<220> FEATURE:
<223> OTHER INFORMATION: IPD103 variant

<400> SEQUENCE: 463

Met Ala Asp Gln Ala Ala Ala Ala Gln Glu Ala Glu Glu Glu Val Glu
1               5                   10                  15

Thr Thr Met Asp Glu Thr Glu Ala Val Gly Thr His Leu Asp Phe Leu
                20                  25                  30

Gly Ala Asp Val Lys Leu Gln Pro Leu Asn Ile Ile Thr Val Glu Val
            35                  40                  45

Asp Ala Ala Ala Val Ile Gln Gln Ile Arg Glu Ile Phe Gln Thr Met
        50                  55                  60

Ala Arg His Phe Asn Ser Thr Arg Val Val Arg Asp Glu Ala Ile Lys
65                  70                  75                  80

Gly Ile Arg Asp His Phe Arg Ala Ala Val Pro Thr Arg Asn Val Val
                85                  90                  95

Val Ile His Thr Gln His Val His Thr Leu Val Gly Leu Glu His Thr
            100                 105                 110

His Leu Val Leu Gln Thr Gly Ile Phe Lys Lys Val Pro Val Asp Ile
        115                 120                 125

Tyr Val Phe Lys Ser Gly Val Phe Thr Asn Leu Gly Asp Gly Gly Phe
    130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 464
<211> LENGTH: 171
<212> TYPE: PRT
<213> ORGANISM: Artificial Sequence
<220> FEATURE:
<223> OTHER INFORMATION: IPD103 variant

<400> SEQUENCE: 464

Met Ala Asp Gln Ala Ala Ala Ala Gly Glu Ala Glu Glu Glu Val Glu
1               5                   10                  15

Thr Thr Met Asp Glu Thr Glu Ala Val Gly Thr His Leu Asp Phe Leu
                20                  25                  30
```

Gly Ala Asp Val Lys Leu Gln Pro Leu Asn Ile Ile Thr Val Glu Val
            35                  40                  45

Asp Ala Ala Val Ile Gln Gln Ile Arg Glu Ile Phe Gln Thr Met
 50                  55                  60

Ala Arg His Phe Asn Ser Thr Arg Val Val Arg Asp Glu Ala Ile Lys
 65                  70                  75                  80

Gly Ile Arg Asp His Phe Arg Ala Ala Val Pro Thr Arg Asn Val Val
                 85                  90                  95

Val Ile His Thr Gln His Val His Thr Leu Val Gly Leu Glu His Thr
                100                 105                 110

His Leu Val Leu Gln Thr Gly Ile Phe Lys Lys Val Pro Val Asp Ile
            115                 120                 125

Tyr Val Phe Lys Ser Gly Val Phe Thr Asn Leu Gly Asp Gly Gly Phe
        130                 135                 140

Ile Asn Trp Ala Trp Gly Gly Phe Val Asp Gln Val Val Gly Lys Arg
145                 150                 155                 160

Ile His Phe Arg Leu Pro Pro Gly Ala Leu Pro
                165                 170

<210> SEQ ID NO 465
<211> LENGTH: 172
<212> TYPE: PRT
<213> ORGANISM: Artificial Sequence
<220> FEATURE:
<223> OTHER INFORMATION: IPD103 variant

<400> SEQUENCE: 465

Met Ala Asp Lys Ala Ala Ala Ala Arg Ala Ala Glu Glu Glu Val
 1               5                  10                  15

Glu Thr Thr Met Asp Glu Thr Glu Ala Val Gly Thr His Leu Asp Phe
            20                  25                  30

Leu Gly Ala Asp Val Lys Leu Gln Pro Trp Asn Ile Ile Thr Val Glu
        35                  40                  45

Val Asp Ala Ala Val Ile Gln Gln Ile Arg Glu Ile Phe Gln Thr
 50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 466
<211> LENGTH: 172
<212> TYPE: PRT
<213> ORGANISM: Artificial Sequence
<220> FEATURE:
<223> OTHER INFORMATION: IPD103 variant

<400> SEQUENCE: 466

Met Ala Asp Lys Ala Ala Ala Ala Glu Ala Glu Glu Val
1               5                   10                  15

Glu Thr Thr Met Asp Glu Thr Glu Ala Val Gly Thr His Leu Asp Phe
                    20                  25                  30

Leu Gly Ala Asp Val Lys Leu Gln Pro Thr Asn Ile Ile Thr Val Glu
                35                  40                  45

Val Asp Ala Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
                115                 120                 125

Ile Tyr Val Phe Lys Ser Gly Val Phe Thr Asn Leu Gly Asp Gly Gly
                130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 467
<211> LENGTH: 172
<212> TYPE: PRT
<213> ORGANISM: Artificial Sequence
<220> FEATURE:
<223> OTHER INFORMATION: IPD103 variant

<400> SEQUENCE: 467

Met Ala Asp Lys Ala Ala Ala Ala Met Glu Ala Glu Glu Val
1               5                   10                  15

Glu Thr Thr Met Asp Glu Thr Glu Ala Val Gly Thr His Leu Asp Phe
                    20                  25                  30

Leu Gly Ala Asp Val Lys Leu Gln Pro Thr Asn Ile Ile Thr Val Glu
                35                  40                  45

Val Asp Ala Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
                115                 120                 125

Ile Tyr Val Phe Lys Ser Gly Val Phe Thr Asn Leu Gly Asp Gly Gly
                130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 468

<211> LENGTH: 172
<212> TYPE: PRT
<213> ORGANISM: Artificial Sequence
<220> FEATURE:
<223> OTHER INFORMATION: IPD103 variant

<400> SEQUENCE: 468

Met Ala Asp Lys Ala Ala Ala Ala Ala Ser Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Leu Asn Ile Ile Thr Val Glu
        35                  40                  45

Val Asp Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 469
<211> LENGTH: 172
<212> TYPE: PRT
<213> ORGANISM: Artificial Sequence
<220> FEATURE:
<223> OTHER INFORMATION: IPD103 variant

<400> SEQUENCE: 469

Met Ala Asp Lys Ala Ala Ala Ala Ala Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Trp Asn Ile Ile Thr Val Glu
        35                  40                  45

Val Asp Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
        115                 120                 125

Ile Tyr Val Phe Lys Ser Gly Val Phe Thr Asn Leu Gly Asp Gly Gly
    130                 135                 140

Phe Ile Asn Trp Ala Trp Gly Gly Phe Val Asp Gln Val Val Gly Lys

```
                145                 150                 155                 160
Arg Ile His Phe Arg Leu Pro Pro Gly Ala Leu Pro
                165                 170

<210> SEQ ID NO 470
<211> LENGTH: 172
<212> TYPE: PRT
<213> ORGANISM: Artificial Sequence
<220> FEATURE:
<223> OTHER INFORMATION: IPD103 variant

<400> SEQUENCE: 470

Met Ala Asp Lys Ala Ala Ala Ala Met Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Trp Asn Ile Ile Thr Val Glu
                35                  40                  45

Val Asp Ala Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
                100                 105                 110

Thr His Leu Val Leu Gln Thr Gly Ile Phe Lys Lys Val Pro Val Asp
                115                 120                 125

Ile Tyr Val Phe Lys Ser Gly Val Phe Thr Asn Leu Gly Asp Gly Gly
                130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170

<210> SEQ ID NO 471
<211> LENGTH: 172
<212> TYPE: PRT
<213> ORGANISM: Artificial Sequence
<220> FEATURE:
<223> OTHER INFORMATION: IPD103 variant

<400> SEQUENCE: 471

Met Ala Asp Lys Ala Ala Ala Ala Met Glu Ala Glu Glu Glu Val
1               5                   10                  15

Glu Thr Thr Met Asp Glu Thr Glu Ala Val Gly Thr His Leu Asp Phe
                20                  25                  30

Leu Gly Ala Asp Val Lys Leu Gln Pro Tyr Asn Ile Ile Thr Val Glu
                35                  40                  45

Val Asp Ala Ala Ala Val Ile Gln Gln Ile Arg Glu Ile Phe Gln Thr
    50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
                100                 105                 110
```

```
Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170
```

<210> SEQ ID NO 472
<211> LENGTH: 172
<212> TYPE: PRT
<213> ORGANISM: Artificial Sequence
<220> FEATURE:
<223> OTHER INFORMATION: IPD103 variant

<400> SEQUENCE: 472

```
Met Ala Asp Lys Ala Ala Ala Ala Ala Glu Ala Glu Glu Glu Val
1               5                   10                  15

Glu Thr Thr Met Asp Glu Thr Glu Ala Val Gly Thr His Leu Asp Phe
            20                  25                  30

Leu Gly Ala Asp Val Lys Leu Gln Pro Tyr Asn Ile Ile Thr Val Glu
        35                  40                  45

Val Asp Ala Ala Ala Val Ile Gln Gln Ile Arg Glu Ile Phe Gln Thr
50                  55                  60

Met Ala Arg His Phe Asn Ser Thr Arg Val Val Arg Asp Glu Ala Ile
65                  70                  75                  80

Lys Gly Ile Arg Asp His Phe Arg Ala Ala Val Pro Thr Arg Asn Val
                85                  90                  95

Val Val Ile His Thr Gln His Val His Thr Leu Val Gly Leu Glu His
            100                 105                 110

Thr His Leu Val Leu Gln Thr Gly Ile Phe Lys Lys Val Pro Val Asp
            115                 120                 125

Ile Tyr Val Phe Lys Ser Gly Val Phe Thr Asn Leu Gly Asp Gly Gly
        130                 135                 140

Phe Ile Asn Trp Ala Trp Gly Gly Phe Val Asp Gln Val Val Gly Lys
145                 150                 155                 160

Arg Ile His Phe Arg Leu Pro Pro Gly Ala Leu Pro
                165                 170
```

<210> SEQ ID NO 473
<211> LENGTH: 40
<212> TYPE: DNA
<213> ORGANISM: Artificial Sequence
<220> FEATURE:
<223> OTHER INFORMATION: mutagenesis primer

<400> SEQUENCE: 473
agcatatggc ggacaaagca gcagcagcag ctagagaagc        40

<210> SEQ ID NO 474
<211> LENGTH: 36
<212> TYPE: DNA
<213> ORGANISM: Artificial Sequence
<220> FEATURE:
<223> OTHER INFORMATION: mutagenesis primer

<400> SEQUENCE: 474
cgactcgaga tgggtgccgg caggcaggca tattgc        36

<210> SEQ ID NO 475
<211> LENGTH: 37
<212> TYPE: DNA
<213> ORGANISM: Artificial Sequence
<220> FEATURE:
<223> OTHER INFORMATION: mutagenesis primer

<400> SEQUENCE: 475
agcatatggc ggaccaagca gcagcagcta gagaagc       37

<210> SEQ ID NO 476
<211> LENGTH: 25
<212> TYPE: DNA
<213> ORGANISM: Artificial Sequence
<220> FEATURE:
<223> OTHER INFORMATION: mutagenesis primer

<400> SEQUENCE: 476
aacatatggc cgaaccagca gcagc       25

<210> SEQ ID NO 477
<211> LENGTH: 24
<212> TYPE: DNA
<213> ORGANISM: Artificial Sequence
<220> FEATURE:
<223> OTHER INFORMATION: mutagenesis primer

<400> SEQUENCE: 477
ttctcgagtc aagggagcgc ccca       24

<210> SEQ ID NO 478
<211> LENGTH: 27
<212> TYPE: DNA
<213> ORGANISM: Artificial Sequence
<220> FEATURE:
<223> OTHER INFORMATION: mutagenesis primer

<400> SEQUENCE: 478
aacatatggc cgaccaagga gcagcag       27

<210> SEQ ID NO 479
<211> LENGTH: 23
<212> TYPE: DNA
<213> ORGANISM: Artificial Sequence
<220> FEATURE:
<223> OTHER INFORMATION: mutagenesis primer

<400> SEQUENCE: 479
ttctcgagtc aagggagcgc ccc       23

<210> SEQ ID NO 480
<211> LENGTH: 25
<212> TYPE: DNA
<213> ORGANISM: Artificial Sequence
<220> FEATURE:
<223> OTHER INFORMATION: mutagenesis primer

<400> SEQUENCE: 480
aacatatggc cgaccaagct gcagc       25

<210> SEQ ID NO 481
<211> LENGTH: 28
<212> TYPE: DNA
<213> ORGANISM: Artificial Sequence
<220> FEATURE:
<223> OTHER INFORMATION: mutagenesis primer

<400> SEQUENCE: 481
aacatatgag agagcgagag cgagagcg                               28

<210> SEQ ID NO 482
<211> LENGTH: 25
<212> TYPE: DNA
<213> ORGANISM: Artificial Sequence
<220> FEATURE:
<223> OTHER INFORMATION: mutagenesis primer

<400> SEQUENCE: 482
aacatatggc cgaaccagca gcagc                                 25

<210> SEQ ID NO 483
<211> LENGTH: 24
<212> TYPE: DNA
<213> ORGANISM: Artificial Sequence
<220> FEATURE:
<223> OTHER INFORMATION: mutagenesis primer

<400> SEQUENCE: 483
aacatatggc cgacaaagcg cctc                                  24

<210> SEQ ID NO 484
<211> LENGTH: 24
<212> TYPE: DNA
<213> ORGANISM: Artificial Sequence
<220> FEATURE:
<223> OTHER INFORMATION: mutagenesis primer

<400> SEQUENCE: 484
ttctcgagtc aagggagtgc cccg                                  24

<210> SEQ ID NO 485
<211> LENGTH: 27
<212> TYPE: DNA
<213> ORGANISM: Artificial Sequence
<220> FEATURE:
<223> OTHER INFORMATION: mutagenesis primer

<400> SEQUENCE: 485
aacatatggc cgaccaagta gcagcag                               27

<210> SEQ ID NO 486
<211> LENGTH: 25
<212> TYPE: DNA
<213> ORGANISM: Artificial Sequence
<220> FEATURE:
<223> OTHER INFORMATION: mutagenesis primer

<400> SEQUENCE: 486
aacatatggc cgacccagca acagc                                 25

<210> SEQ ID NO 487
<211> LENGTH: 33
<212> TYPE: DNA
<213> ORGANISM: Artificial Sequence
<220> FEATURE:
<223> OTHER INFORMATION: mutagenesis primer

<400> SEQUENCE: 487
aacatatgca gagagagaga gagagagaga tgg                        33

<210> SEQ ID NO 488

```
<211> LENGTH: 28
<212> TYPE: DNA
<213> ORGANISM: Artificial Sequence
<220> FEATURE:
<223> OTHER INFORMATION: mutagenesis primer

<400> SEQUENCE: 488
aacatatggc cgacaaagta gcagcagc                                28

<210> SEQ ID NO 489
<211> LENGTH: 23
<212> TYPE: DNA
<213> ORGANISM: Artificial Sequence
<220> FEATURE:
<223> OTHER INFORMATION: mutagenesis primer

<400> SEQUENCE: 489
ttctcgagtc aagggagtgc ccc                                     23

<210> SEQ ID NO 490
<211> LENGTH: 28
<212> TYPE: DNA
<213> ORGANISM: Artificial Sequence
<220> FEATURE:
<223> OTHER INFORMATION: mutagenesis primer

<400> SEQUENCE: 490
aacatatgag agagcgagag cgagagcg                                28

<210> SEQ ID NO 491
<211> LENGTH: 28
<212> TYPE: DNA
<213> ORGANISM: Artificial Sequence
<220> FEATURE:
<223> OTHER INFORMATION: mutagenesis primer

<400> SEQUENCE: 491
aacatatggc cgatgacaaa gtagcaag                                28

<210> SEQ ID NO 492
<211> LENGTH: 22
<212> TYPE: DNA
<213> ORGANISM: Artificial Sequence
<220> FEATURE:
<223> OTHER INFORMATION: mutagenesis primer

<400> SEQUENCE: 492
ttctcgagtc aagggagggc cc                                      22

<210> SEQ ID NO 493
<211> LENGTH: 27
<212> TYPE: DNA
<213> ORGANISM: Artificial Sequence
<220> FEATURE:
<223> OTHER INFORMATION: mutagenesis primer

<400> SEQUENCE: 493
aacatatggc cgatgaggta gctggtc                                 27

<210> SEQ ID NO 494
<211> LENGTH: 21
<212> TYPE: DNA
<213> ORGANISM: Artificial Sequence
<220> FEATURE:
<223> OTHER INFORMATION: mutagenesis primer

<400> SEQUENCE: 494
```

```
aacatatgga cgccgctgcc g                                              21
```

<210> SEQ ID NO 495
<211> LENGTH: 22
<212> TYPE: DNA
<213> ORGANISM: Artificial Sequence
<220> FEATURE:
<223> OTHER INFORMATION: mutagenesis primer

<400> SEQUENCE: 495

```
ttctcgagtc aagggagcgc cc                                             22
```

<210> SEQ ID NO 496
<211> LENGTH: 516
<212> TYPE: DNA
<213> ORGANISM: Artificial Sequence
<220> FEATURE:
<223> OTHER INFORMATION: IPD103 variant

<400> SEQUENCE: 496

```
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccaacagat cagagagatc   180
ttcgcgtcaa tgatcaaaca ctacaactct acgagggtgg tgcgggatga agccatcaag   240
agcattcgag accacttcag gctcgccgtc ccgactcgca acgtggtggt cattcacact   300
cagcacgttc acacactgga cgccgtggag tcctcccacc tcgtcttgcg gaccggcctg   360
ttcaaaaagg tccctgtcga catctttgtc ttcaagtccg gcgtcttcac caacctggga   420
gacggaggct tcatcaactg gcatgggggt ggctacggcg tcaaccacac cgccaagcgt   480
gtcgtcttca gccggccccc cggggcgctc ccttga                             516
```

<210> SEQ ID NO 497
<211> LENGTH: 495
<212> TYPE: DNA
<213> ORGANISM: Artificial Sequence
<220> FEATURE:
<223> OTHER INFORMATION: Mutagenesis assembly block
<220> FEATURE:
<221> NAME/KEY: misc_feature
<222> LOCATION: (132)..(133)
<223> OTHER INFORMATION: n is a, c, g, or t
<220> FEATURE:
<221> NAME/KEY: misc_feature
<222> LOCATION: (134)..(134)
<223> OTHER INFORMATION: k is g or t

<400> SEQUENCE: 497

```
gcagccatat ggcggacaaa gcagcagcag cagctagaga agctgaagaa gaggtggaga    60
cgacgatgga cgagactgag gcggtgggga cgcacctgga cttcttgggc gcggacgtga   120
agttgcaacc cnnkaacatc atcaccgtgg aggtggacgc ggctgccgta atccaacaga   180
tcagagagat cttccagaca atggcgcgtc acttcaactc tacgagggtg gtgcgggatg   240
aagccatcaa gggcattcga gaccacttca gggccgccgt cccgactcgc aacgtggtgg   300
tcattcacac tcagcacgtt cacacactgg tgggcttgga gcacccac ctcgtcttgc     360 agaccggcat cttcaaaaag gtccccgtcg acatctatgt cttcaagtcc ggcgtcttca   420
ccaaccttgg agacggaggc ttcatcaact gggcatgggg tggcttcgtc gaccaggtcg   480
tcggcaagcg tatcc                                                    495
```

<210> SEQ ID NO 498
<211> LENGTH: 30
<212> TYPE: DNA
<213> ORGANISM: Artificial Sequence
<220> FEATURE:
<223> OTHER INFORMATION: mutagenesis primer

<400> SEQUENCE: 498
ctgctgctgc tttgtccgcc atatggctgc                              30

<210> SEQ ID NO 499
<211> LENGTH: 26
<212> TYPE: DNA
<213> ORGANISM: Artificial Sequence
<220> FEATURE:
<223> OTHER INFORMATION: mutagenesis primer

<400> SEQUENCE: 499
cgaccaggtc gtcggcaagc gtatcc                                  26

<210> SEQ ID NO 500
<211> LENGTH: 51
<212> TYPE: DNA
<213> ORGANISM: Artificial Sequence
<220> FEATURE:
<223> OTHER INFORMATION: mutagensis primer
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (35)..(35)
<223> OTHER INFORMATION: k is g or t

<400> SEQUENCE: 500
agcatatggc ggacaaagca gcagcagcag ctnnkgaagc tgaagaagag g       51

<210> SEQ ID NO 501
<211> LENGTH: 32
<212> TYPE: DNA
<213> ORGANISM: Artificial Sequence
<220> FEATURE:
<223> OTHER INFORMATION: mutagensis primer

<400> SEQUENCE: 501
agcatatgga cgagactgag gcggtgggga cg                           32

<210> SEQ ID NO 502
<211> LENGTH: 48
<212> TYPE: DNA
<213> ORGANISM: Artificial Sequence
<220> FEATURE:
<223> OTHER INFORMATION: mutagensis primer
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: k is g or t

<400> SEQUENCE: 502
agcatatggc ggaccaagca gcagcagctn nkgaagctga agaagagg           48

<210> SEQ ID NO 503
<211> LENGTH: 51

<212> TYPE: DNA
<213> ORGANISM: Artificial Sequence
<220> FEATURE:
<223> OTHER INFORMATION: mutagensis primer

<400> SEQUENCE: 503
agcatatggc ggacaaagca gcagcagcag ctgctgaagc tgaagaagag g    51

<210> SEQ ID NO 504
<211> LENGTH: 51
<212> TYPE: DNA
<213> ORGANISM: Artificial Sequence
<220> FEATURE:
<223> OTHER INFORMATION: mutagensis primer

<400> SEQUENCE: 504
agcatatggc ggacaaagca gcagcagcag ctatggaagc tgaagaagag g    51

<210> SEQ ID NO 505
<211> LENGTH: 51
<212> TYPE: DNA
<213> ORGANISM: Artificial Sequence
<220> FEATURE:
<223> OTHER INFORMATION: mutagensis primer

<400> SEQUENCE: 505
agcatatggc ggacaaagca gcagcagcag ctagtgaagc tgaagaagag g    51

<210> SEQ ID NO 506
<211> LENGTH: 576
<212> TYPE: DNA
<213> ORGANISM: Artificial Sequence
<220> FEATURE:
<223> OTHER INFORMATION: IPD103 his-tagged

<400> SEQUENCE: 506
atgggcagca gccatcatca tcatcatcac agcagcggcc tggtgccgcg cggcagccat    60
atggcggacc aagcagcagc agctagagaa gctgaagaag aggtggagac gacgatggac    120
gagactgagg cggtggggac gcacctggac ttcttgggcg cggacgtgaa gttgcaaccc    180
cgcaacatca tcaccgtgga ggtggacgcc gctgccgtaa tccaacagat cagagagatc    240
ttccagacaa tggcgcgtca cttcaactct acgagggtgg tgcgggatga agccatcaag    300
ggcattcgag accacttcag gccgccgtc ccgactcgca acgtggtggt cattcacact    360
cagcacgttc acacactggt gggcttggag cacacccacc tcgtcttgca gaccggcatc    420
ttcaaaaagg tccccgtcga catctatgtc ttcaagtccg gcgtcttcac caaccttgga    480
gacggaggct tcatcaactg gcatggggt ggcttcgtcg accaggtcgt cggcaagcgt    540
atccacttcc gcttgccccc cgggcgctc ccttga    576

<210> SEQ ID NO 507
<211> LENGTH: 191
<212> TYPE: PRT
<213> ORGANISM: Artificial Sequence
<220> FEATURE:
<223> OTHER INFORMATION: IPD103 his-tagged

<400> SEQUENCE: 507

Met Gly Ser Ser His His His His His His Ser Ser Gly Leu Val Pro
1               5                   10                  15

Arg Gly Ser His Met Ala Asp Gln Ala Ala Ala Ala Arg Glu Ala Glu
            20                  25                  30

-continued

```
Glu Glu Val Glu Thr Thr Met Asp Glu Thr Glu Ala Val Gly Thr His
        35                  40                  45

Leu Asp Phe Leu Gly Ala Asp Val Lys Leu Gln Pro Arg Asn Ile Ile
    50                  55                  60

Thr Val Glu Val Asp Ala Ala Ala Val Ile Gln Gln Ile Arg Glu Ile
65                  70                  75                  80

Phe Gln Thr Met Ala Arg His Phe Asn Ser Thr Arg Val Val Arg Asp
                85                  90                  95

Glu Ala Ile Lys Gly Ile Arg Asp His Phe Arg Ala Ala Val Pro Thr
            100                 105                 110

Arg Asn Val Val Val Ile His Thr Gln His Val His Thr Leu Val Gly
        115                 120                 125

Leu Glu His Thr His Leu Val Leu Gln Thr Gly Ile Phe Lys Lys Val
    130                 135                 140

Pro Val Asp Ile Tyr Val Phe Lys Ser Gly Val Phe Thr Asn Leu Gly
145                 150                 155                 160
Asp Gly Gly Phe Ile Asn Trp Ala Trp Gly Gly Phe Val Asp Gln Val
                165                 170                 175
Val Gly Lys Arg Ile His Phe Arg Leu Pro Pro Gly Ala Leu Pro
            180                 185                 190

<210> SEQ ID NO 508
<211> LENGTH: 5
<212> TYPE: PRT
<213> ORGANISM: Artificial Sequence
<220> FEATURE:
<223> OTHER INFORMATION: fusion linker

<400> SEQUENCE: 508

Glu Glu Lys Lys Asn
1               5
```

INSECTICIDAL PROTEINS FROM PLANTS AND METHODS FOR THEIR USE

CROSS-REFERENCE TO RELATED APPLICATIONS

This application claims priority to U.S. provisional patent application Ser. No. 62/357,501 filed Jul. 1, 2016, herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "6762WOPCT_SequenceListing" created on Jun. 1, 2017, and having a size of 546 kilobytes and is filed concurrently with the specification. The sequence listing contained in this ASCII formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect isolated or recombinant nucleic acid molecules are provided encoding IPD103 polypeptides including amino acid substitutions, deletions, insertions, and fragments thereof. Provided are isolated or recombinant nucleic acid molecules capable of encoding IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect IPD103 polypeptides are encompassed. Also provided are isolated or recombinant IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, as well as amino acid substitutions, deletions, insertions, fragments thereof and combinations thereof.

In another aspect methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

In another aspect methods for detecting the nucleic acids and polypeptides of the embodiments in a sample are also included. A kit for detecting the presence of an IPD103 polypeptide or detecting the presence of a polynucleotide encoding an IPD103 polypeptide in a sample is provided. The kit may be provided along with all reagents and control samples necessary for carrying out a method for detecting the intended agent, as well as instructions for use.

In another aspect the compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD103 polypeptides.

BRIEF DESCRIPTION OF THE FIGURES

FIG. 1A-1B shows an amino acid sequence alignment, using the ALIGNX® module of the Vector NTI® suite, of the IPD103Aa polypeptide (SEQ ID NO: 2), IPD103Ab polypeptide (SEQ ID NO: 4), IPD103Ac polypeptide (SEQ ID NO: 6), IPD103Ad polypeptide (SEQ ID NO: 8), IPD103Ae polypeptide (SEQ ID NO: 10), IPD103Ba polypeptide (SEQ ID NO: 12), IPD103Bb polypeptide (SEQ ID NO: 14), IPD103Bc polypeptide (SEQ ID NO: 16), IPD103Bd polypeptide (SEQ ID NO: 18), IPD103Be polypeptide (SEQ ID NO: 20), IPD103Bf polypeptide (SEQ ID NO: 22), IPD103Bg polypeptide (SEQ ID NO: 24), IPD103Bh polypeptide (SEQ ID NO: 26), IPD103Ca polypeptide (SEQ ID NO: 34), IPD103 Da polypeptide (SEQ ID NO: 38), and IPD103Db polypeptide (SEQ ID NO: 40). The amino acid sequence diversity between the amino acid sequences is highlighted. Conservative amino acid differences are indicated by (▒) shading and non-conservative amino acid difference by (■) shading. The start site of the truncation variant M20 IPD103Aa polypeptide (SEQ ID NO: 417) of Example 6, is indicated above the IPD103Aa sequence (SEQ ID NO: 2) by a "●" above residue 20. The position of residues R10 and R42 where amino acid substitutions were made Example 16 are indicated above the IPD103Aa sequence (SEQ ID NO: 2) by a "▼" above the residue.

FIG. 2 shows the % leaf damage by CEW, ECB and FAW of individual transgenic TO maize events from constructs PHP79658, PHP79559 and PHP79660 expressing the IPD103Aa polypeptide (SEQ ID NO: 2).

FIG. 3 shows the Total Corn Ear Feeding ($cm^2$) by CEW of individual transgenic TO maize events from constructs PHP79658, PHP79559 and PHP79660 expressing the IPD103Aa polypeptide (SEQ ID NO: 2).

FIG. 4 shows a curve reflecting densitometry values of in-gel fluorescence, from the SDS-PAGE gel of Example 16, for homologous competition of 25 nM IPD103Aa$^{Alexa}$ binding to *Helicoverpa zea* (Corn Earworm) BBMVs normalized to the amount bound in the absence of unlabeled IPD103Aa (SEQ ID NO: 2). The solid line reflects the best fit of a square logistic equation to the data.

FIG. 5 shows a curve reflecting densitometry values of in-gel fluorescence, from the SDS-PAGE gel of Example 16, for homologous competition of 25 nM IPD103Aa$^{Alexa}$ binding to *Ostrinia nubilalis* (European Corn Borer) BBMVs normalized to the amount bound in the absence of unlabeled IPD103Aa (SEQ ID NO: 2). The solid line reflects the best fit of a square logistic equation to the data.

DETAILED DESCRIPTION

It is to be understood that this disclosure is not limited to the particular methodology, protocols, cell lines, genera, and reagents described, as such may vary. It is also to be understood that the terminology used herein is for the purpose of describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding IPD103 polypeptides. In particular, the nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered IPD103 polypeptides by methods known in the art, such as site directed mutagenesis, domain swapping or DNA shuffling. The IPD103 polypeptides find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica undecimpunctata* howardi)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin; (2011) *PLoS Pathogens* 7:1-13); from *Pseudomonas protegens* strain CHAO and Pf-5 (previously *fluorescens*) (Pechy-Tarr, (2008) *Environmental Microbiology* 10:2368-2386; GenBank Accession No. EU400157); from *Pseudomonas taiwanensis* (Liu, et al., (2010) *J. Agric. Food Chem.*, 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos.

6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; an IPD079 polypeptide of U.S. Ser. No. 62/201,977; an IPD082 polypeptide of U.S. Ser. No. 62/269,482, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin genes and the *B. thuringiensis* cytolytic cyt1 and cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E and Cry9F families; a Cry15 protein of Naimov, et al., (2008) *Applied and Environmental Microbiology,* 74:7145-7151; a Cry22, a Cry34Ab1 protein of U.S. Pat. Nos. 6,127,180, 6,624,145 and 6,340,593; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent Application Publication Number 2010/0005543, cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA. (2010) GM Crop Database Center for Environmental Risk Assessment (CERA), ILSI Research Foundation, Wash. D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1DA & Cry1BE (US2012/0331590); Cry1DA & Cry1Fa (US2012/0331589); Cry1AB & Cry1BE (US2012/0324606); Cry1Fa & Cry2Aa and Cry1I & Cry1E (US2012/0324605); Cry34Ab/35Ab and Cry6Aa (US20130167269); Cry34Ab/VCry35Ab & Cry3Aa (US20130167268); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus*, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus*, *Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366).

In some embodiments the IPD103 polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of IPD103 polypeptides. The protein resulting from translation of these IPD103 genes allows cells to control or kill pests that ingest it.

IPD103 Proteins and Variants and Fragments Thereof

IPD103 polypeptides are encompassed by the disclosure. "IPD103 polypeptide" and "IPD103 protein" as used herein interchangeably refers to a polypeptide having insecticidal activity including but not limited to insecticidal activity against one or more insect pests of the Lepidoptera and/or Coleoptera orders, and is sufficiently homologous to the IPD103Aa polypeptide of SEQ ID NO: 2. A variety of IPD103 polypeptides are contemplated. Sources of IPD103 polypeptides or related proteins include fern or other primitive plant species selected from but not limited to *Athyrium* species, *Platycerium* species, *Pteris* species, *Colysis* species, *Nephrolepis* species, *Polystichium* species, *Thelypteris* species, *Tectaria* species, and *Davallia* species. Alignment of the amino acid sequences of IPD103 polypeptide homologs (for example—FIG. 1), allows for the identification of residues that are highly conserved amongst the natural homologs of this family.

In some embodiments the IPD103 polypeptide is derived from a fern species in the Order Athyriales.

In some embodiments the IPD103 polypeptide is derived from a fern species in the Order Athyriales, Family Athyriaceae.

In some embodiments the IPD103 polypeptide is derived from a fern species in the Order Athyriales, Family Athyriaceae, Genus *Athyrium* selected from but not limited to *Athyrium arisanense*, *Athyrium atkinsonii*, *Athyrium biserrulatum*, *Athyrium brevifrons*, *Athyrium chingianum*, *Athyrium clarkei*, *Athyrium clivicola*, *Athyrium cryptogrammoides*, *Athyrium cumingianum*, *Athyrium cuspidatum*, *Athyrium deltoidofrons*, *Athyrium distentifolium*, *Athyrium epirachis*, *Athyrium eremicola*, *Athyrium fangii*, *Athyrium filix-femina*, *Athyrium frangulum*, *Athyrium giraldii*, *Athyrium iseanum*, *Athyrium kirisimaense*, *Athyrium kuratae*, *Athyrium masamunei*, *Athyrium melanolepis*, *Athyrium monomachi*, *Athyrium multidentatum*, *Athyrium nakanoi*, *Athyrium neglectum*, *Athyrium nigripes*, *Athyrium nikkoense*, *Athyrium niponicum*, *Athyrium nyalamense*, *Athyrium oblitescens*, *Athyrium otophorum*, *Athyrium palustre*, *Athyrium pinetorum*, *Athyrium pubicostatum*, *Athyrium reflexipinnum*, *Athyrium rhachidosorum*, *Athyrium rupestre*, *Athyrium scandicinum*, *Athyrium setuligerum*, *Athyrium sheareri*, *Athyrium silvicola*, *Athyrium sinense*, *Athyrium skinneri*, *Athyrium spinulosum*, *Athyrium strigillosum*, *Athyrium subrigescens*, *Athyrium subtriangulare*, *Athyrium supraspinescens*, *Athyrium tashiroi*, *Athyrium tozanense*, *Athyrium vidalii*, *Athyrium viridescentipes*, *Athyrium wardii*, *Athyrium×akiense*, *Athyrium×hisatsuanum*, *Athyrium× tokashikii*, *Athyrium yokoscense*, and *Athyrium yui*.

In some embodiments the IPD103 polypeptide is derived from a fern species in the Order Polypodiales.

In some embodiments the IPD103 polypeptide is derived from a fern species in the Order Polypodiales, Family Nephrolepidaceae.

In some embodiments the IPD103 polypeptide is derived from a fern species in the Order Polypodiales, Family Nephrolepidaceae, Genus *Nephrolepis* selected from but not limited to *Nephrolepis abrupta*, *Nephrolepis acutifolia*, *Nephrolepis averyi*, *Nephrolepis biserrata*, *Nephrolepis brownii*, *Nephrolepis copelandi*, *Nephrolepis cordifolia*, *Nephrolepis davalliae*, *Nephrolepis davallioides*, *Nephrolepis dicksonioides*, *Nephrolepis exaltata*, *Nephrolepis falcata*, *Nephrolepis falciformis*, *Nephrolepis hippocrepicis*, *Nephrolepis laurifolia*, *Nephrolepis lauterbachii*, *Nephrolepis medlerae*, *Nephrolepis obliterata*, *Nephrolepis pectinata*, *Nephrolepis pendula*, *Nephrolepis pseudobiserrata*, *Nephrolepis radicans*, *Nephrolepis rivularis*, and *Nephrolepis undulata*.

In some embodiments the IPD103 polypeptide is derived from a fern species in the Order Polypodiales, Family Polypodiaceae.

In some embodiments the IPD103 polypeptide is derived from a fern species in the order Polypodiales, Family Polypodiaceae, Genus *Platycerium* selected from but not limited to *Platycerium alcicorne*, *Platycerium andinum*, *Platycerium angolense*, *Platycerium bifurcatum*, *Platycerium coronarium*, *Platycerium elephantotis*, *Platycerium ellisii*, *Platycerium grande*, *Platycerium hillii*, *Platycerium holttumii*, *Platycerium madagascariense*, *Platycerium quadridichotomum*, *Platycerium ridleyi*, *Platycerium stemaria*, *Platycerium superbum*, *Platycerium veitchii*, *Platycerium*

*wallichii, Platycerium wandae, Platycerium wilhelminae-reginae,* and *Platycerium willinkii.*

In some embodiments the IPD103 polypeptide is derived from a fern species in the order Polypodiales, Family Polypodiaceae, Genus *Colysis* selected from but not limited to *Colysis ampla, Colysis digitata, Colysis diversifolia, Colysis elegans Colysis elliptica, Colysis flexiloba, Colysis hemionitidea, Colysis hemitoma, Colysis henryi, Colysis insignis, Colysis intermedia, Colysis leveillei, Colysis longpes, Colysis pedunculata, Colysis pentaphylla, Colysis pothifolia, Colysis pteropus, Colysis shintenensis, Colysis simplicifrons, Colysis triphylla, Colysis wrightii,* and *Colysis xshintenensis.*

In some embodiments the IPD103 polypeptide is derived from a fern species in the Order Polypodiales, Family Pteridaceae.

In some embodiments the IPD103 polypeptide is derived from a fern species in the Order Polypodiales, Family Pteridaceae, Genus *Pteris* selected from but not limted to *Pteris actiniopteroides, Pteris amoena, Pteris angustipinna, Pteris angustipinnula, Pteris aspericaulis, Pteris austrosinica, Pteris baksaensis, Pteris bella, Pteris biaurita, Pteris bomiensis, Pteris cadieri, Pteris changjiangensis, Pteris confertinervia, Pteris crassiuscula, Pteris cretica, Pteris cryptogrammoides, Pteris dactylina, Pteris dangiana, Pteris decrescens, Pteris deltodon, Pteris dispar, Pteris dissitifolia, Pteris ensiformis, Pteris esquirolii, Pteris excelsa, Pteris fauriei, Pteris finotii, Pteris formosana, Pteris gallinopes, Pteris gracillima, Pteris grevilleana, Pteris guangdongensis, Pteris guizhouensis, Pteris henryi, Pteris heteromorpha, Pteris hui, Pteris insignis, Pteris kidoi, Pteris kiuschinensis, Pteris kiuschiuensis, Pteris laurisilvicola, Pteris libonsis, Pteris linearis, Pteris longipes, Pteris longipinna, Pteris longipinnula, Pteris maclurei, Pteris maclurioides, Pteris medogensis, Pteris morii, Pteris multifida, Pteris nipponica, Pteris obtusiloba, Pteris occidentali-sinica, Pteris oshimensis, Pteris paucipinnula, Pteris plumbea, Pteris pseudodactylina, Pteris pseudopellucida, Pteris puberula, Pteris quadristipitis, Pteris quinquefoliata, Pteris rufopilosa, Pteris ryukyuensis, Pteris sanduensis, Pteris scabristipes, Pteris semipinnata, Pteris setulosocostulata, Pteris shimianensis, Pteris sichuanensis, Pteris sinensis, Pteris splendida, Pteris stenophylla, Pteris subquinata, Pteris taiwanensis, Pteris tibetica, Pteris tripartita, Pteris undulatipinna, Pteris venusta, Pteris viridissima, Pteris vittata, Pteris wallichiana, Pteris wangiana, Pteris xiaoyingiae, Pteris xichouensis,* and *Pteris wulaiensis.*

In some embodiments the IPD103 polypeptide is derived from a fern species in the Order Polypodiales, Family Tectariaceae.

In some embodiments the IPD103 polypeptide is derived from a fern species in the Order Polypodiales, Family Tectariaceae, Genus *Tectaria* selected from but not limited to *Tectaria acerifolia, Tectaria acrocarpa, Tectaria adenophora, Tectaria aequatoriensis, Tectaria amblyotis, Tectaria amphiblestra, Tectaria andersonii, Tectaria angelicifolia, Tectaria angulata, Tectaria antioquiana, Tectaria athyrioides, Tectaria athyriosora, Tectaria aurita, Tectaria balansae, Tectaria barberi, Tectaria barteri, Tectaria beccariana, Tectaria blumeana, Tectaria brachiata, Tectaria brauniana, Tectaria brevilobata, Tectaria brooksii, Tectaria buchtienii, Tectaria calcarea, Tectaria camerooniana, Tectaria chattagramica, Tectaria cherasica, Tectaria chimborazensis, Tectaria chinensis, Tectaria christii, Tectaria christovalensis, Tectaria cicutaria, Tectaria coadunata, Tectaria confluens, Tectaria consimilis, Tectaria cordulata, Tectaria coriandrifolia, Tectaria craspedocarpa, Tectaria crenata, Tectaria crinigera, Tectaria croftii, Tectaria curtisii, Tectaria danfuensis, Tectaria decaryana, Tectaria decastroi, Tectaria decurrens, Tectaria degeneri, Tectaria dolichosora, Tectaria draconoptera, Tectaria dubia, Tectaria durvillei, Tectaria ebenina, Tectaria estremerana, Tectaria exauriculata, Tectaria fauriei, Tectaria fengii, Tectaria fernandensis, Tectaria ferruginea, Tectaria filisquamata, Tectaria fimbriata, Tectaria fissa, Tectaria gaudichaudii, Tectaria gemmifera, Tectaria godeffroyi, Tectaria grandidentata, Tectaria griffithii* var. *singaporeana, Tectaria grossedentata, Tectaria hederifolia, Tectaria hekouensis, Tectaria heracleifolia, Tectaria herpetocaulos, Tectaria heterocarpa, Tectaria hilocarpa, Tectaria holttumii, Tectaria hookeri, Tectaria humbertiana, Tectaria hymenodes, Tectaria hymenophylla, Tectaria impressa, Tectaria incisa, Tectaria inopinata, Tectaria isomorpha, Tectaria jacobsii, Tectaria jardini, Tectaria johannis-winkleri, Tectaria keckii, Tectaria kehdingiana, Tectaria kingii, Tectaria kouniensis, Tectaria kweichowensis, Tectaria labrusca, Tectaria lacei, Tectaria laotica, Tectaria latifolia, Tectaria lawrenceana, Tectaria laxa, Tectaria leptophylla, Tectaria lifuensis, Tectaria lizarzaburui, Tectaria lobbii, Tectaria lombokensis, Tectaria macrosora, Tectaria macrota, Tectaria madagascarica, Tectaria magnifica, Tectaria manilensis, Tectaria marchionica, Tectaria media, Tectaria melanocaulis, Tectaria melanocauloides, Tectaria melanorachis, Tectaria menyanthidis, Tectaria mesodon, Tectaria mexicana, Tectaria microchlamys, Tectaria microlepis, Tectaria minuta, Tectaria moorei, Tectaria morlae, Tectaria moussetii, Tectaria murrayi, Tectaria nabirensis, Tectaria nausoriensis, Tectaria nebulosa, Tectaria nesiotica, Tectaria nicaraguensis, Tectaria nicotianifolia, Tectaria nitens, Tectaria novoguineensis, Tectaria organensis, Tectaria palmate, Tectaria pandurifolia, Tectaria pedata, Tectaria pentagonalis, Tectaria perdimorpha, Tectaria phaeocaulis, Tectaria pica, Tectaria pilosa, Tectaria plantaginea, Tectaria pleiosora, Tectaria pleiotoma, Tectaria poilanei, Tectaria polymorpha, Tectaria prolifera, Tectaria pseudosinuata, Tectariaxpteropus-minor, Tectaria pubens, Tectaria puberula, Tectaria pubescens, Tectaria quinquefida, Tectaria quitensis, Tectaria ramosii, Tectaria rara, Tectaria remotipinna, Tectaria repanda, Tectaria rheophytica, Tectaria rigida, Tectaria rivalis, Tectaria rockii, Tectaria rufescens, Tectaria rufovillosa, Tectaria sagenioides, Tectaria schmutzii, Tectaria schultzei, Tectaria seemannii, Tectaria semibipinnata, Tectaria semipinnata, Tectaria seramensis, Tectaria siifolia, Tectaria simaoensis, Tectaria simonsii, Tectaria simulans, Tectaria singaporeana, Tectaria sinuata, Tectaria squamipes, Tectaria stalactica, Tectaria stearnsii, Tectaria stenosemioides, Tectaria subcaudata, Tectaria subconfluens, Tectaria subcordata, Tectaria subdigitata, Tectaria subebenea, Tectaria subrepanda, Tectaria subsageniacea, Tectaria subtriloba, Tectaria subtriphylla, Tectaria sulitii, Tectaria suluensis, Tectaria sumatrana, Tectaria tabonensis, Tectaria taccifolia, Tectaria tahitensis, Tectaria tenerifrons, Tectaria tenuifolia, Tectaria teratocarpa, Tectaria ternata, Tectaria transiens, Tectaria translucens, Tectaria tricuspis, Tectaria trifida, Tectaria trifoliata, Tectaria triglossa, Tectaria triloba, Tectaria trimenii, Tectaria trinitensis, Tectaria tripartita, Tectaria variabilis, Tectaria vasta, Tectaria vieillardii, Tectaria villosa, Tectaria vitiensis, Tectaria vivipara, Tectaria waterlotii, Tectaria weberi, Tectaria wightii, Tectariaxamesiana, Tectariaxcynthiae, Tectaria yunnanensis, Tectaria zeylanica,* and *Tectaria zollingeri.*

In some embodiments the IPD103 polypeptide is derived from a fern species in the Order Polypodiales, Family Davalliaceae.

In some embodiments the IPD103 polypeptide is derived from a fern species in the Order Polypodiales, Family Davalliaceae Genus *Davallia* selected from but not limited to *Davallia adiantoides, Davallia amabilis, Davallia assamica, Davallia austrosinica, Davallia biflora, Davallia boryana, Davallia brachypoda, Davallia brevisora, Davallia bullata, Davallia bullata, Davallia calvescens, Davallia calvescens, Davallia canariensis, Davallia chaerophylla, Davallia chaerophylloide, Davallia chrysanthemifolia, Davallia clarkei, Davallia cumingii, Davallia cylindrica, Davallia divaricata, Davallia divaricata, Davallia divaricata* var. *orientate, Davallia domingensis, Davallia dubia, Davallia elmeri, Davallia falcata, Davallia falcinella, Davallia ferulacea, Davallia flaccida, Davallia formosana, Davallia fumarioides, Davallia goudotiana, Davallia gracilis, Davallia griffithiana, Davallia griffithiana, Davallia henryana, Davallia heterophylla, Davallia hookeriana, Davallia hymenophylloides, Davallia immersa, Davallia inaequalis* var. *minor, Davallia jamaicensis, Davallia khasiyana, Davallia kurzii, Davallia lepida, Davallia lepida, Davallia macraeana, Davallia magellanica, Davallia mariesii, Davallia membranulosa, Davallia membranulosa, Davallia millefolium, Davallia moorei, Davallia multidentata, Davallia nodosa, Davallia novae-guineae, Davallia orientalis, Davallia parallela, Davallia parkeri, Davallia parvipinnula, Davallia patens, Davallia pectinata, Davallia perdurans, Davallia pilosula, Davallia platylepis, Davallia polypodioides, Davallia polypodioides* var. *hispida, Davallia polypodioides* var. *pilosula, Davallia pseudocystopteris, Davallia puberula, Davallia pyramidata, Davallia pyxidata, Davallia repens, Davallia rhomboidea, Davallia rhomboidea, Davallia rhomboidea, Davallia sinensis, Davallia sloanei, Davallia solida, Davallia solida, Davallia stipellata, Davallia strigosa, Davallia strigosa, Davallia strigosa* var. *rhomboidea, Davallia subalpina, Davallia subsolida, Davallia teyermannii, Davallia triangularis, Davallia tripinnata, Davallia truncata, Davallia tyermanni, Davallia tyermannii, Davallia uncinella, Davallia urophylla, Davallia vestita, Davallia wilfordii* var. *contracta*, and *Davallia yunnanensis*.

In some embodiments the IPD103 polypeptide is derived from a fern species in the Order Polypodiales, Family Dryopteridaceae.

In some embodiments the IPD103 polypeptide is derived from a fern species in the Order Polypodiales, Family Dryopteridaceae, Genus *Polystichum* selected from but not limited to *Polystichum acanthophyllum, Polystichum aculeatum, Polystichum acutidens, Polystichum acutipinnulum, Polystichum adungense, Polystichum alcicome, Polystichum altum, Polystichum anomalum, Polystichum ariticulatipilosum, Polystichum assurgentipinnum, Polystichum atkinsonii, Polystichum attenuatum, Polystichum auriculum, Polystichum bakerianum, Polystichum baoxingense, Polystichum biaristatum, Polystichum bifidum, Polystichum bigemmatum, Polystichum bissectum, Polystichum bomiense, Polystichum brachypterum, Polystichum braunii, Polystichum capillipes, Polystichum castaneum, Polystichum chingiae, Polystichum christii, Polystichum chunii, Polystichum consimile, Polystichum costularisorum, Polystichum craspedosorum, Polystichum crassinervium, Polystichum cringerum, Polystichum cuneatiforme, Polystichum cyclolobum, Polystichum daguanense, Polystichum dangii, Polystichum delavayi, Polystichum deltodon, Polystichum dielsii, Polystichum diffundens, Polystichum discretum, Polystichum disjunctum, Polystichum duthiei, Polystichum elevatovenusum, Polystichum erosum, Polystichum exauriforme, Polystichum excellens, Polystichum excelsius, Polystichum fimbriatum, Polystichum formosanum, Polystichum frigidicola, Polystichum fugongense, Polystichum gongboense, Polystichum grandifrons, Polystichum guangxiense, Polystichum gymnocarpium, Polystichum habaense, Polystichum hancockii, Polystichum hecatopteron, Polystichum herbaceum, Polystichum houchangense, Polystichum huae, Polystichum ichangense, Polystichum inaense, Polystichum incisopinnulum, Polystichum integrilimbum, Polystichum integrilobum, Polystichum jinfoshaense, Polystichum jiulaodongense, Polystichum jizhushanense, Polystichum kangdingense, Polystichum kungianum, Polystichum kwangtungense, Polystichum lachenense, Polystichum lanceolatum, Polystichum langchungense, Polystichum latilepis, Polystichum lentum, Polystichum leveillei, Polystichum liui, Polystichum lonchitis, Polystichum longiaristatum, Polystichum longidens, Polystichum longpaleatum, Polystichum longpes, Polystichum longpinnulum, Polystichum longispinosum, Polystichum longissimum, Polystichum macrochlaenum, Polystichum makinoi, Polystichum manmeiense, Polystichum martinii, Polystichum mayebarae, Polystichum medogense, Polystichum mehrae, Polystichum meiguense, Polystichum melanostipes, Polystichum mollissimum, Polystichum morii, Polystichum moupinense, Polystichum muscicola, Polystichum nayongense, Polystichum neoliuii, Polystichum neolobatum, Polystichum nepalense, Polystichum nigrum, Polystichum ningshenense, Polystichum nudisorum, Polystichum obliquum, Polystichum oblongum, Polystichum oligocarpum, Polystichum omeiense, Polystichum oreodoxa, Polystichum orientalitibeticum, Polystichum otophorum, Polystichum ovatopaleaceum, Polystichum paramoupinense, Polystichum parvifoliolatum, Polystichum parvipinnulum, Polystichum pianmaense, Polystichum piceo-paleaceum, Polystichum polyblepharum, Polystichum prescottianum, Polystichum prionolepis, Polystichum pseudocastaneum, Polystichum pseudolanceolatum, Polystichum pseudomakinoi, Polystichum pseudorhomboideum, Polystichum pseudosetosum, Polystichum pseudoxiphophyllum, Polystichum punctiferum, Polystichum puteicola, Polystichum pycnopterum, Polystichum qamdoense, Polystichum retrosopaleaceum, Polystichum revolutum, Polystichum rhombiforme, Polystichum rigens, Polystichum robustum, Polystichum rufopaleaceum, Polystichum saxicola, Polystichum semifertile, Polystichum setillosum, Polystichum shandongense, Polystichum shensiense, Polystichum shimurae, Polystichum simplicipinnum, Polystichum sinense, Polystichum sinotsussimense, Polystichum sozanense, Polystichum speluncicola, Polystichum squarrosum, Polystichum stenophyllum, Polystichum stimulans, Polystichum subacutidens, Polystichum subdeltodon, Polystichum subfimbriatum, Polystichum submarginale, Polystichum submite, Polystichum subulatum, Polystichum tacticopterum, Polystichum taizhongense, Polystichum tangmaiense, Polystichum thomsonii, Polystichum tibeticum, Polystichum tonkinense, Polystichum tripteron, Polystichum tsingkanshanense, Polystichum tsussimense, Polystichum wattii, Polystichum xiphophyllum, Polystichum yadongense, Polystichum yuanum, Polystichum yunnanense*, and *Polystichum zayuense*.

In some embodiments the IPD103 polypeptide is derived from a fern species in the Order Polypodiales, Family Thelypteridaceae.

In some embodiments the IPD103 polypeptide is derived from a fern species in the Order Polypodiales, Family Thelypteridaceae, Genus *Thelypteris* selected from but not limited to *Thelypteris abrupta, Thelypteris acuminata, Thelypteris affinis, Thelypteris angulariloba, Thelypteris angustifrons, Thelypteris aurita, Thelypteris beddomei, Thelyp-

*teris boninensis, Thelypteris bukoensis, Thelypteris castanea, Thelypteris clypeolutata, Thelypteris consanguinea, Thelypteris cystopteroides, Thelypteris dayi, Thelypteris erubescens, Thelypteris esquirolii, Thelypteris flexilis, Thelypteris gemmulifera, Thelypteris glandulosa, Thelypteris globulifera, Thelypteris gracilescens, Thelypteris gracilis, Thelypteris interrupta, Thelypteris jaculosa, Thelypteris japonica, Thelypteris laxa, Thelypteris linkiana, Thelypteris liukiuensis, Thelypteris longissima, Thelypteris meniscioides, Thelypteris miyagii, Thelypteris musashiensis, Thelypteris navarrensis, Thelypteris nevadensis, Thelypteris nipponica, Thelypteris ogasawarensis, Thelypteris oligocarpa, Thelypteris omeiensis, Thelypteris opulenta, Thelypteris ovata, Thelypteris palustris, Thelypteris parasitica, Thelypteris poiteana, Thelypteris reticulata, Thelypteris rustica, Thelypteris seemannii, Thelypteris sp. b1-007, Thelypteris sp. Janssen 2679, Thelypteris subaurita, Thelypteris taiwanensis, Thelypteris truncata, Thelypteris tylodes, Thelypteris uraiensis,* and *Thelypteris viridifrons.*

"Sufficiently homologous" is used herein to refer to an amino acid sequence that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments the sequence homology is against the full length sequence of an IPD103 polypeptide. In some embodiments the IPD103 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. The term "about" when used herein in context with percent sequence identity means+/−0.5%. One of skill in the art will recognize that these values can be appropriately adjusted to determine corresponding homology of proteins taking into account amino acid similarity and the like. In some embodiments the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX® module of the Vector NTI® Program Suite (Invitrogen Corporation, Carlsbad, Calif.) with all default parameters.

As used herein, the terms "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

A "recombinant protein" is used herein to refer to a protein that is no longer in its natural environment, for example in vitro or in a recombinant bacterial or plant host cell. An IPD103 polypeptide that is substantially free of cellular material includes preparations of protein having less than about 30%, 20%, 10% or 5% (by dry weight) of non-pesticidal protein (also referred to herein as a "contaminating protein").

"Fragments" or "biologically active portions" include polypeptide fragments comprising amino acid sequences sufficiently identical to an IPD103 polypeptide and that exhibit insecticidal activity. "Fragments" or "biologically active portions" of IPD103 polypeptides includes fragments comprising amino acid sequences sufficiently identical to the amino acid sequence set forth in IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38 wherein the IPD103 polypeptide has insecticidal activity. Such biologically active portions can be prepared by recombinant techniques and evaluated for insecticidal activity. In some embodiments, the IPD103 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus relative to IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, e.g., by proteolysis, by insertion of a start codon, by deletion of the codons encoding the deleted amino acids and concomitant insertion of a start codon, and/or insertion of a stop codon. In some embodiments, the IPD103 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 amino acids from the N-terminus of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. In some embodiments, the IPD103 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. In some embodiments the truncated variant is the polypeptide of SEQ ID NO: 445.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments an IPD103 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, wherein the IPD103 polypeptide has insecticidal activity.

In some embodiments an IPD103 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of the IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments the sequence identity is across the entire length of the polypeptide calculated using ClustalW algorithm in the ALIGNX® module of the Vector NTI® Program Suite (Invitrogen Corporation, Carlsbad, Calif.) with all default parameters.

In some embodiments the IPD103 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2.

In some embodiments an IPD103 polypeptide comprises an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the native amino acid at the corresponding position of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38.

In some embodiments an IPD103 polypeptide variant comprises any one or more active amino acid substitutions of Table 5 and/or 7.

Methods for such manipulations are generally known in the art. For example, amino acid sequence variants of an IPD103 polypeptide can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of an IPD103 polypeptide to confer pesticidal activity may be improved by the use of such techniques upon the compositions of this disclosure.

For example, conservative amino acid substitutions may be made at one or more predicted nonessential amino acid residues. A "nonessential" amino acid residue is a residue that can be altered from the wild-type sequence of an IPD103 polypeptide without altering the biological activity. Nonessential amino acid residues can be identified by aligning related IPD103 homologs such as is shown in FIG. 1. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different IPD103 polypeptide coding regions can be used to create a new IPD103 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered IPD103 polypeptides. Domains may be swapped between IPD103 polypeptides resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Phylogenetic, sequence motif, and structural analyses of insecticidal protein families. A sequence and structure analysis method can be employed, which is composed of four components: phylogenetic tree construction, protein sequence motifs finding, secondary structure prediction, and alignment of protein sequences and secondary structures. Details about each component are illustrated below.

1) Phylogenetic Tree Construction

The phylogenetic analysis can be performed using the software MEGA5. Protein sequences can be subjected to ClustalW version 2 analysis (Larkin M. A et al (2007) *Bioinformatics* 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

2) Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, Calif., 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

3) Secondary Structure Prediction

PSIPRED, top ranked secondary structure prediction method (Jones D T. (1999) *J. Mol. Biol.* 292: 195-202), can be used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100. The PSIPRED results contain the predicted secondary structures (Alpha helix: H, Beta strand: E, and Coil: C) and the corresponding confidence scores for each amino acid in a given protein sequence.

4) Alignment of Protein Sequences and Secondary Structures

A script can be developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments the IPD103 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, IPD103 polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

One skilled in the art understands that the polynucleotide coding sequence can be modified to add a codon at the penultimate position following the methionine start codon to create a restriction enzyme site for recombinant cloning purposes and/or for expression purposes. In some embodiments the IPD103 polypeptide further comprises an alanine residue at the penultimate position after the translation initiator methionine.

In some embodiments the translation initiator methionine of the IPD103 polypeptide is cleaved off post translationally. One skilled in the art understands that the N-terminal translation initiator methionine can be removed by methionine aminopeptidase in many cellular expression systems.

In some embodiments the IPD103 polypeptide comprises the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments the IPD103 polypeptide comprises the amino acid sequence of SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO:

412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471 or SEQ ID NO: 472.

In some embodiments, chimeric polypeptides are provided comprising regions of at least two different IPD103 polypeptides of the disclosure.

In some embodiments, chimeric polypeptides are provided comprising regions of at least two different IPD103 polypeptides selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In some embodiments, chimeric IPD103 polypeptide are provided comprising an N-terminal Region of a first IPD103 polypeptide of the disclosure operably fused to a C-terminal Region of a second IPD103 polypeptide of the disclosure.

In some embodiments, chimeric IPD103 polypeptide are provided comprising an N-terminal Region of a first IPD103 polypeptide operably fused to a C-terminal Region of a second IPD103 polypeptide, where the first and second IPD103 polypeptide is selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In other embodiments the IPD103 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.,* 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.,* 275:9091-9094. The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273:10567-10577; Cotton, et al., (1999) *J. Am. Chem. Soc.* 121:1100-1101; Evans, et al., (1999) *J. Biol. Chem.* 274:18359-18363; Evans, et al., (1999) *J. Biol. Chem.* 274:3923-3926; Evans, et al., (1998) *Protein Sci.* 7:2256-2264; Evans, et al., (2000) *J. Biol. Chem.* 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207: 187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.,* 120:5591-5592). For the application of inteins in plant transgenes, see, Yang, et al., (*Transgene Res* 15:583-593 (2006)) and Evans, et al., (*Annu. Rev. Plant Biol.* 56:375-392 (2005)).

In another embodiment the IPD103 polypeptide may be encoded by two separate genes where the intein of the precursor protein comes from the two genes, referred to as a split-intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. Inteins that may be used for are listed at neb.com/neb/inteins.html, which can be accessed on the world-wide web using the "www" prefix). The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) *EMBO J.* 17:918-926 may be followed. In constructing the first and the second expression cassette, the 5' intein coding sequence is linked to the 3' end of the first fragment coding for the N-terminal part of the IPD103 polypeptide and the 3' intein coding sequence is linked to the 5' end of the second fragment coding for the C-terminal part of the IPD103 polypeptide.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA.* 95(16):9226-31 and Evans, et al., (2000) *J Biol Chem.* 275(13):9091-4 and of the DnaE gene from *Nostoc punctiforme* (see, Iwai, et al., (2006) *FEBS Lett.* 580(7):1853-8). Non-split inteins have been artificially split in the laboratory to create new split inteins, for example: the artificially split Ssp DnaB intein (see, Wu, et al., (1998) *Biochim Biophys Acta.* 1387:422-32) and split Sce VMA intein (see, Brenzel, et al., (2006) *Biochemistry.* 45(6):1571-8) and an artificially split fungal mini-intein (see, Elleuche, et al., (2007) *Biochem Biophys Res Commun.* 355(3):830-4). There are also intein databases available that catalogue known inteins (see for example the online-database available at: bioinformatics.weizmann.ac.ilrpietro/inteins/Intein-stable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) *Biochim Biophys Acta.* 1387: 422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) *Mol Microbiol.* 47:61-73) and hedgehog (Hog) auto-processing domains (the latter is combined with inteins when referred to as the Hog/intein superfamily or HINT family (see, Dassa, et al., (2004) *J Biol Chem.* 279:32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) *Biochemistry.* 46(1):322-30). Other such mixtures of disparate split intein partners have been shown to be unreactive one with another (see, Brenzel, et al., (2006) *Biochemistry.* 45(6):1571-8). However, it is within the ability of a person skilled in the relevant art to determine whether a particular pair of polypeptides is able to associate with each other to provide a functional intein, using routine methods and without the exercise of inventive skill.

In some embodiments the IPD103 polypeptide is a circular permuted variant. In certain embodiments the IPD103 polypeptide is a circular permuted variant of the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472, or variant thereof having an amino acid substitution, deletion, addition or combinations thereof. The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). The first in vitro application of this type of rearrangement to proteins was described by Goldenberg and Creighton (*J. Mol. Biol.* 165:407-413, 1983). In creating a circular permuted variant a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157:105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) *Critical Rev. Biotech.* 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637; the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Thus using either the experimentally derived structural information or predictive methods (e.g., Srinivisan and Rose, (1995) *Proteins: Struct., Fund. & Genetics* 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted IPD103 polypeptides with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted IPD103 polypeptides with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another embodiment fusion proteins are provided that include within its amino acid sequence an amino acid sequence comprising an IPD103 polypeptide or chimeric IPD103 polypeptide of the disclosure. Methods for design and construction of fusion proteins (and polynucleotides encoding same) are known to those of skill in the art. Polynucleotides encoding an IPD103 polypeptide may be fused to signal sequences which will direct the localization of the IPD103 polypeptide to particular compartments of a prokaryotic or eukaryotic cell and/or direct the secretion of the IPD103 polypeptide of the embodiments from a prokaryotic or eukaryotic cell. For example, in *E. coli*, one may wish to direct the expression of the protein to the periplasmic space. Examples of signal sequences or proteins (or fragments thereof) to which the IPD103 polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IPD103 polypeptide may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art. Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the IPD103 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29): 15104-9. In some embodiments the IPD103 polypeptide is fused to a heterologous signal peptide or heterologous transit peptide.

In some embodiments fusion proteins are provide comprising an IPD103 polypeptide or chimeric IPD103 polypeptide of the disclosure represented by a formula selected from the group consisting of:

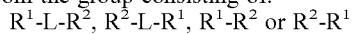

wherein $R^1$ is an IPD103 polypeptide or chimeric IPD103 polypeptide of the disclosure and $R^2$ is a protein of interest. In some embodiments $R^1$ and $R^2$ are an IPD103 polypeptide or chimeric IPD103 polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$, or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN (SEQ ID NO: 508) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding IPD103 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding IPD103 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding IPD103 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an IPD103 polypeptide is a non-genomic sequence.

A variety of polynucleotides that encode IPD103 polypeptides or related proteins are contemplated. Such polynucleotides are useful for production of IPD103 polypeptides in host cells when operably linked to a suitable promoter, transcription termination and/or polyadenylation sequences. Such polynucleotides are also useful as probes for isolating homologous or substantially homologous polynucleotides that encode IPD103 polypeptides or related proteins.

Polynucleotides Encoding IPD103 Polypeptides

One source of polynucleotides that encode IPD103 polypeptides or related proteins is a fern or other primitive plant species selected from but not limited to *Athyrium* species, *Platycerium* species, *Pteris* species, *Colysis* species, *Nephrolepis* species, *Polystichium* species, *Thelypteris* species, *Tectaria* species, and *Davallia* species, which contains an IPD103 polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, encoding an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, respectively. The polynucleotides of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37 can be used to express IPD103 polypeptides in recombinant bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode IPD103 polypeptides or related proteins. Such probes can be used to identify homologous or substantially homologous polynucleotides derived from fern or other primitive plant species selected from but not limited to *Athyrium* species, *Platycerium* species, *Pteris* species, *Colysis* species, *Neph-* rolepis species, *Polystichium* species, *Thelypteris* species, *Tectaria* species, and *Davallia* species.

In some embodiments the nucleic acid molecule encoding the IPD103 polypeptide is derived from a fern species in the Order Athyriales.

In some embodiments the nucleic acid molecule encoding the IPD103 polypeptide is derived from a fern species in the Order Athyriales, Family Athyriaceae.

In some embodiments the nucleic acid molecule encoding the IPD103 polypeptide is derived from a fern species in the Order Athyriales, Family Athyriaceae, Genus *Athyrium* selected from but not limited to *Athyrium arisanense, Athyrium atkinsonii, Athyrium biserrulatum, Athyrium brevifrons, Athyrium chingianum, Athyrium clarkei, Athyrium clivicola, Athyrium cryptogrammoides, Athyrium cumingianum, Athyrium cuspidatum, Athyrium deltoidofrons, Athyrium distentifolium, Athyrium epirachis, Athyrium eremicola, Athyrium fangii, Athyrium filix-femina, Athyrium frangulum, Athyrium giraldii, Athyrium iseanum, Athyrium kirisimaense, Athyrium kuratae, Athyrium masamunei, Athyrium melanolepis, Athyrium monomachi, Athyrium multidentatum, Athyrium nakanoi, Athyrium neglectum, Athyrium nigripes, Athyrium nikkoense, Athyrium niponicum, Athyrium nyalamense, Athyrium oblitescens, Athyrium otophorum, Athyrium palustre, Athyrium pinetorum, Athyrium pubicostatum, Athyrium reflexipinnum, Athyrium rhachidosorum, Athyrium rupestre, Athyrium scandicinum, Athyrium setuligerum, Athyrium sheareri, Athyrium silvicola, Athyrium sinense, Athyrium skinneri, Athyrium spinulosum, Athyrium strigillosum, Athyrium subrigescens, Athyrium subtriangulare, Athyrium supraspinescens, Athyrium tashiroi, Athyrium tozanense, Athyrium vidalii, Athyrium viridescentipes, Athyrium wardii, Athyrium×akiense, Athyrium× hisatsuanum, Athyrium×tokashikii, Athyrium yokoscense,* and *Athyrium yui.*

In some embodiments the nucleic acid molecule encoding the IPD103 polypeptide is derived from a fern species in the Order Polypodiales.

In some embodiments the nucleic acid molecule encoding the IPD103 polypeptide is derived from a fern species in the Order Polypodiales, Family Nephrolepidaceae.

In some embodiments the nucleic acid molecule encoding the IPD103 polypeptide is derived from a fern species in the Order Polypodiales, Family Nephrolepidaceae, Genus *Nephrolepis* selected from but not limited to *Nephrolepis abrupta, Nephrolepis acutifolia, Nephrolepis averyi, Nephrolepis biserrata, Nephrolepis brownii, Nephrolepis copelandi, Nephrolepis cordifolia, Nephrolepis davalliae, Nephrolepis davallioides, Nephrolepis dicksonioides, Nephrolepis exaltata, Nephrolepis falcata, Nephrolepis falciformis, Nephrolepis hippocrepicis, Nephrolepis laurifolia, Nephrolepis lauterbachii, Nephrolepis medlerae, Nephrolepis obliterata, Nephrolepis pectinata, Nephrolepis pendula, Nephrolepis pseudobiserrata, Nephrolepis radicans, Nephrolepis rivularis,* and *Nephrolepis undulata.*

In some embodiments the nucleic acid molecule encoding the IPD103 polypeptide is derived from a fern species in the Order Polypodiales, Family Polypodiaceae.

In some embodiments the nucleic acid molecule encoding the IPD103 polypeptide is derived from a fern species in the order Polypodiales, Family Polypodiaceae, Genus *Platycerium* selected from but not limited to *Platycerium alcicorne, Platycerium andinum, Platycerium angolense, Platycerium bifurcatum, Platycerium coronarium, Platycerium elephantotis, Platycerium ellisii, Platycerium grande, Platycerium hillii, Platycerium holttumii, Platycerium madagascariense, Platycerium quadridichotomum, Platycerium ridleyi, Platycerium stemaria, Platycerium superbum, Platycerium veitchii, Platycerium wallichii, Platycerium wandae, Platycerium wilhelminae-reginae,* and *Platycerium willinkii.*

In some embodiments the nucleic acid molecule encoding the IPD103 polypeptide is derived from a fern species in the order Polypodiales, Family Polypodiaceae, Genus *Colysis* selected from but not limited to *Colysis ampla, Colysis digitata, Colysis diversifolia, Colysis elegans Colysis elliptica, Colysis flexiloba, Colysis hemionitidea, Colysis hemitoma, Colysis henryi, Colysis insignis, Colysis intermedia, Colysis leveillei, Colysis lonopes, Colysis pedunculata, Colysis pentaphylla, Colysis pothifolia, Colysis pteropus, Colysis shintenensis, Colysis simplicifrons, Colysis triphylla, Colysis wrightii,* and *Colysis×shintenensis.*

In some embodiments the nucleic acid molecule encoding the IPD103 polypeptide is derived from a fern species in the Order Polypodiales, Family Pteridaceae.

In some embodiments the nucleic acid molecule encoding the IPD103 polypeptide is derived from a fern species in the Order Polypodiales, Family Pteridaceae, Genus *Pteris* selected from but not limted to *Pteris actiniopteroides, Pteris amoena, Pteris angustipinna, Pteris angustipinnula, Pteris aspericaulis, Pteris austrosinica, Pteris baksaensis, Pteris bella, Pteris biaurita, Pteris bomiensis, Pteris cadieri, Pteris changjiangensis, Pteris confertinervia, Pteris crassiuscula, Pteris cretica, Pteris cryptogrammoides, Pteris dactylina, Pteris dangiana, Pteris decrescens, Pteris deltodon, Pteris dispar, Pteris dissitifolia, Pteris ensiformis, Pteris esquirolii, Pteris excelsa, Pteris fauriei, Pteris finotii, Pteris formosana, Pteris gallinopes, Pteris gracillima, Pteris grevilleana, Pteris guangdongensis, Pteris guizhouensis, Pteris henryi, Pteris heteromorpha, Pteris hui, Pteris insignis, Pteris kidoi, Pteris kiuschinensis, Pteris kiuschiuensis, Pteris laurisilvicola, Pteris libonsis, Pteris linearis, Pteris longipes, Pteris longipinna, Pteris longpinnula, Pteris maclurei, Pteris maclurioides, Pteris medogensis, Pteris morii, Pteris multifida, Pteris nipponica, Pteris obtusiloba, Pteris occidentali-sinica, Pteris oshimensis, Pteris paucipinnula, Pteris plumbea, Pteris pseudodactylina, Pteris pseudopellucida, Pteris puberula, Pteris quadristipitis, Pteris quinquefoliata, Pteris rufopilosa, Pteris ryukyuensis, Pteris sanduensis, Pteris scabristipes, Pteris semipinnata, Pteris setulosocostulata, Pteris shimianensis, Pteris sichuanensis, Pteris sinensis, Pteris splendida, Pteris stenophylla, Pteris subquinata, Pteris taiwanensis, Pteris tibetica, Pteris tripartita, Pteris undulatipinna, Pteris venusta, Pteris viridissima, Pteris vittata, Pteris wallichiana, Pteris wangiana, Pteris xiaoyingiae, Pteris xichouensis,* and *Pteris xwulaiensis.*

In some embodiments the nucleic acid molecule encoding the IPD103 polypeptide is derived from a fern species in the Order Polypodiales, Family Tectariaceae.

In some embodiments the nucleic acid molecule encoding the IPD103 polypeptide is derived from a fern species in the Order Polypodiales, Family Tectariaceae, Genus *Tectaria* selected from but not limited to *Tectaria acerifolia, Tectaria acrocarpa, Tectaria adenophora, Tectaria aequatoriensis, Tectaria amblyotis, Tectaria amphiblestra, Tectaria andersonii, Tectaria angelicifolia, Tectaria angulata, Tectaria antioquiana, Tectaria athyrioides, Tectaria athyriosora, Tectaria aurita, Tectaria balansae, Tectaria barberi, Tectaria barteri, Tectaria beccariana, Tectaria blumeana, Tectaria brachiata, Tectaria brauniana, Tectaria brevilobata, Tectaria brooksii, Tectaria buchtienii, Tectaria calcarea, Tectaria camerooniana, Tectaria chattagramica, Tectaria cherasica, Tectaria chimborazensis, Tectaria chinensis, Tec-* taria christii, Tectaria christovalensis, Tectaria cicutaria, Tectaria coadunata, Tectaria confluens, Tectaria consimilis, Tectaria cordulata, Tectaria coriandrifolia, Tectaria craspedocarpa, Tectaria crenata, Tectaria crinigera, Tectaria croftii, Tectaria curtisii, Tectaria danfuensis, Tectaria decaryana, Tectaria decastroi, Tectaria decurrens, Tectaria degeneri, Tectaria dolichosora, Tectaria draconoptera, Tectaria dubia, Tectaria durvillei, Tectaria ebenina, Tectaria estremerana, Tectaria exauriculata, Tectaria fauriei, Tectaria fengii, Tectaria fernandensis, Tectaria ferruginea, Tectaria filisquamata, Tectaria fimbriata, Tectaria fissa, Tectaria gaudichaudii, Tectaria gemmifera, Tectaria godeffroyi, Tectaria grandidentata, Tectaria griffithii var. singaporeana, Tectaria grossedentata, Tectaria hederifolia, Tectaria hekouensis, Tectaria heracleifolia, Tectaria herpetocaulos, Tectaria heterocarpa, Tectaria hilocarpa, Tectaria holttumii, Tectaria hookeri, Tectaria humbertiana, Tectaria hymenodes, Tectaria hymenophylla, Tectaria impressa, Tectaria incisa, Tectaria inopinata, Tectaria isomorpha, Tectaria jacobsii, Tectaria jardini, Tectaria johannis-winkleri, Tectaria keckii, Tectaria kehdingiana, Tectaria kingii, Tectaria kouniensis, Tectaria kweichowensis, Tectaria labrusca, Tectaria lacei, Tectaria laotica, Tectaria latifolia, Tectaria lawrenceana, Tectaria laxa, Tectaria leptophylla, Tectaria lifuensis, Tectaria lizarzaburui, Tectaria lobbii, Tectaria lombokensis, Tectaria macrosora, Tectaria macrota, Tectaria madagascarica, Tectaria magnifica, Tectaria manilensis, Tectaria marchionica, Tectaria media, Tectaria melanocaulis, Tectaria melanocauloides, Tectaria melanorachis, Tectaria menyanthidis, Tectaria mesodon, Tectaria mexicana, Tectaria microchlamys, Tectaria microlepis, Tectaria minuta, Tectaria moorei, Tectaria morlae, Tectaria moussetii, Tectaria murrayi, Tectaria nabirensis, Tectaria nausoriensis, Tectaria nebulosa, Tectaria nesiotica, Tectaria nicaraguensis, Tectaria nicotianifolia, Tectaria nitens, Tectaria novoguineensis, Tectaria organensis, Tectaria palmate, Tectaria pandurifolia, Tectaria pedata, Tectaria pentagonalis, Tectaria perdimorpha, Tectaria phaeocaulis, Tectaria pica, Tectaria pilosa, Tectaria plantaginea, Tectaria pleiosora, Tectaria pleiotoma, Tectaria poilanei, Tectaria polymorpha, Tectaria prolifera, Tectaria pseudosinuata, Tectaria×pteropus-minor, Tectaria pubens, Tectaria puberula, Tectaria pubescens, Tectaria quinquefida, Tectaria quitensis, Tectaria ramosii, Tectaria rara, Tectaria remotipinna, Tectaria repanda, Tectaria rheophytica, Tectaria rigida, Tectaria rivalis, Tectaria rockii, Tectaria rufescens, Tectaria rufovillosa, Tectaria sagenioides, Tectaria schmutzii, Tectaria schultzei, Tectaria seemannii, Tectaria semibipinnata, Tectaria semipinnata, Tectaria seramensis, Tectaria siifolia, Tectaria simaoensis, Tectaria simonsii, Tectaria simulans, Tectaria singaporeana, Tectaria sinuata, Tectaria squamipes, Tectaria stalactica, Tectaria stearnsii, Tectaria stenosemioides, Tectaria subcaudata, Tectaria subconfluens, Tectaria subcordata, Tectaria subdigitata, Tectaria subebenea, Tectaria subrepanda, Tectaria subsageniacea, Tectaria subtriloba, Tectaria subtriphylla, Tectaria sulitii, Tectaria suluensis, Tectaria sumatrana, Tectaria tabonensis, Tectaria taccifolia, Tectaria tahitensis, Tectaria tenerifrons, Tectaria tenuifolia, Tectaria teratocarpa, Tectaria ternata, Tectaria transiens, Tectaria translucens, Tectaria tricuspis, Tectaria trifida, Tectaria trifoliata, Tectaria triglossa, Tectaria triloba, Tectaria trimenii, Tectaria trinitensis, Tectaria tripartita, Tectaria variabilis, Tectaria vasta, Tectaria vieillardii, Tectaria villosa, Tectaria vitiensis, Tectaria vivipara, Tectaria waterlotii, Tectaria weberi, Tectaria wightii, Tectaria× amesiana, Tectaria×cynthiae, Tectaria yunnanensis, Tectaria zeylanica, and Tectaria zollingeri.

In some embodiments the nucleic acid molecule encoding the IPD103 polypeptide is derived from a fern species in the Order Polypodiales, Family Davalliaceae.

In some embodiments the nucleic acid molecule encoding the IPD103 polypeptide is derived from a fern species in the Order Polypodiales, Family Davalliaceae Genus Davallia selected from but not limited to Davallia adiantoides, Davallia amabilis, Davallia assamica, Davallia austrosinica, Davallia biflora, Davallia boryana, Davallia brachypoda, Davallia brevisora, Davallia bullata, Davallia bullata, Davallia calvescens, Davallia calvescens, Davallia canariensis, Davallia chaerophylla, Davallia chaerophylloide, Davallia chrysanthemifolia, Davallia clarkei, Davallia cumingii, Davallia cylindrica, Davallia divaricata, Davallia divaricata, Davallia divaricata var. orientate, Davallia domingensis, Davallia dubia, Davallia elmeri, Davallia falcata, Davallia falcinella, Davallia ferulacea, Davallia flaccida, Davallia formosana, Davallia fumarioides, Davallia goudotiana, Davallia gracilis, Davallia griffithiana, Davallia griffithiana, Davallia henryana, Davallia heterophylla, Davallia hookeriana, Davallia hymenophylloides, Davallia immersa, Davallia inaequalis var. minor, Davallia jamaicensis, Davallia khasiyana, Davallia kurzii, Davallia lepida, Davallia lepida, Davallia macraeana, Davallia magellanica, Davallia mariesii, Davallia membranulosa, Davallia membranulosa, Davallia millefolium, Davallia moorei, Davallia multidentata, Davallia nodosa, Davallia novae-guineae, Davallia orientalis, Davallia parallela, Davallia parkeri, Davallia parvipinnula, Davallia patens, Davallia pectinata, Davallia perdurans, Davallia pilosula, Davallia platylepis, Davallia polypodioides, Davallia polypodioides var. hispida, Davallia polypodioides var. pilosula, Davallia pseudocystopteris, Davallia puberula, Davallia pyramidata, Davallia pyxidata, Davallia repens, Davallia rhomboidea, Davallia rhomboidea, Davallia rhomboidea, Davallia sinensis, Davallia sloanei, Davallia solida, Davallia solida, Davallia stipellata, Davallia strigosa, Davallia strigosa, Davallia strigosa var. rhomboidea, Davallia subalpina, Davallia subsolida, Davallia teyermannii, Davallia triangularis, Davallia tripinnata, Davallia truncata, Davallia tyermanni, Davallia tyermannii, Davallia uncinella, Davallia urophylla, Davallia vestita, Davallia wilfordii var. contracta, and Davallia yunnanensis.

In some embodiments the nucleic acid molecule encoding the IPD103 polypeptide is derived from a fern species in the Order Polypodiales, Family Dryopteridaceae.

In some embodiments the nucleic acid molecule encoding the IPD103 polypeptide is derived from a fern species in the Order Polypodiales, Family Dryopteridaceae, Genus *Polystichum* selected from but not limited to *Polystichum acanthophyllum, Polystichum aculeatum, Polystichum acutidens, Polystichum acutipinnulum, Polystichum adungense, Polystichum alcicorne, Polystichum altum, Polystichum anomalum, Polystichum ariticulatipilosum, Polystichum assurgentipinnum, Polystichum atkinsonii, Polystichum attenuatum, Polystichum auriculum, Polystichum bakerianum, Polystichum baoxingense, Polystichum biaristatum, Polystichum bifidum, Polystichum bigemmatum, Polystichum bissectum, Polystichum bomiense, Polystichum brachypterum, Polystichum braunii, Polystichum capillipes, Polystichum castaneum, Polystichum chingiae, Polystichum christii, Polystichum chunii, Polystichum consimile, Polystichum costularisorum, Polystichum craspedosorum, Polystichum crassinervium, Polystichum cringerum, Polystichum cuneatiforme, Polystichum cyclolobum, Polystichum daguanense, Polystichum dangii, Polystichum delavayi, Polystichum deltodon, Polystichum dielsii, Polystichum diffundens, Poly-* stichum discretum, Polystichum disjunctum, Polystichum duthiei, Polystichum elevatovenusum, Polystichum erosum, Polystichum exauriforme, Polystichum excellens, Polystichum excelsius, Polystichum fimbriatum, Polystichum formosanum, Polystichum frigidicola, Polystichum fugongense, Polystichum gongboense, Polystichum grandifrons, Polystichum guangxiense, Polystichum gymnocarpium, Polystichum habaense, Polystichum hancockii, Polystichum hecatopteron, Polystichum herbaceum, Polystichum houchangense, Polystichum huae, Polystichum ichangense, Polystichum inaense, Polystichum incisopinnulum, Polystichum integrilimbum, Polystichum integrilobum, Polystichum jinfoshaense, Polystichum jiulaodongense, Polystichum jizhushanense, Polystichum kangdingense, Polystichum kungianum, Polystichum kwangtungense, Polystichum lachenense, Polystichum lanceolatum, Polystichum langchungense, Polystichum latilepis, Polystichum lentum, Polystichum leveillei, Polystichum liui, Polystichum lonchitis, Polystichum longiaristatum, Polystichum longidens, Polystichum longpaleatum, Polystichum longipes, Polystichum longpinnulum, Polystichum longispinosum, Polystichum longissimum, Polystichum macrochlaenum, Polystichum makinoi, Polystichum manmeiense, Polystichum martinii, Polystichum mayebarae, Polystichum medogense, Polystichum mehrae, Polystichum meiguense, Polystichum melanostipes, Polystichum mollissimum, Polystichum morii, Polystichum moupinense, Polystichum muscicola, Polystichum nayongense, Polystichum neoliuii, Polystichum neolobatum, Polystichum nepalense, Polystichum nigrum, Polystichum ningshenense, Polystichum nudisorum, Polystichum obliquum, Polystichum oblongum, Polystichum oligocarpum, Polystichum omeiense, Polystichum oreodoxa, Polystichum orientalitibeticum, Polystichum otophorum, Polystichum ovato-paleaceum, Polystichum paramoupinense, Polystichum parvifoliolatum, Polystichum parvipinnulum, Polystichum pianmaense, Polystichum piceo-paleaceum, Polystichum polyblepharum, Polystichum prescottianum, Polystichum prionolepis, Polystichum pseudocastaneum, Polystichum pseudolanceolatum, Polystichum pseudomakinoi, Polystichum pseudorhomboideum, Polystichum pseudosetosum, Polystichum pseudoxiphophyllum, Polystichum punctiferum, Polystichum puteicola, Polystichum pycnopterum, Polystichum qamdoense, Polystichum retrosopaleaceum, Polystichum revolutum, Polystichum rhombiforme, Polystichum rigens, Polystichum robustum, Polystichum rufopaleaceum, Polystichum saxicola, Polystichum semifertile, Polystichum setillosum, Polystichum shandongense, Polystichum shensiense, Polystichum shimurae, Polystichum simplicipinnum, Polystichum sinense, Polystichum sinotsus-simense, Polystichum sozanense, Polystichum speluncicola, Polystichum squarrosum, Polystichum stenophyllum, Polystichum stimulans, Polystichum subacutidens, Polystichum subdeltodon, Polystichum subfimbriatum, Polystichum submarginale, Polystichum submite, Polystichum subulatum, Polystichum tacticopterum, Polystichum taizhongense, Polystichum tangmaiense, Polystichum thomsonii, Polystichum tibeticum, Polystichum tonkinense, Polystichum tripteron, Polystichum tsingkanshanense, Polystichum tsus-simense, Polystichum wattii, Polystichum xiphophyllum, Polystichum yadongense, Polystichum yuanum, Polystichum yunnanense, and Polystichum zayuense.

In some embodiments the nucleic acid molecule encoding the IPD103 polypeptide is derived from a fern species in the Order Polypodiales, Family Thelypteridaceae.

In some embodiments the nucleic acid molecule encoding the IPD103 polypeptide is derived from a fern species in the Order Polypodiales, Family Thelypteridaceae, Genus Thelypteris selected from but not limited to Thelypteris abrupta, Thelypteris acuminata, Thelypteris affinis, Thelypteris angulariloba, Thelypteris angustifrons, Thelypteris aurita, Thelypteris beddomei, Thelypteris boninensis, Thelypteris bukoensis, Thelypteris castanea, Thelypteris clypeolutata, Thelypteris consanguinea, Thelypteris cystopteroides, Thelypteris dayi, Thelypteris erubescens, Thelypteris esquirolii, Thelypteris flexilis, Thelypteris gemmulifera, Thelypteris glandulosa, Thelypteris globulifera, Thelypteris gracilescens, Thelypteris gracilis, Thelypteris interrupta, Thelypteris jaculosa, Thelypteris japonica, Thelypteris laxa, Thelypteris linkiana, Thelypteris liukiuensis, Thelypteris longissima, Thelypteris meniscioides, Thelypteris miyagii, Thelypteris musashiensis, Thelypteris navarrensis, Thelypteris nevadensis, Thelypteris nipponica, Thelypteris ogasawarensis, Thelypteris oligocarpa, Thelypteris omeiensis, Thelypteris opulenta, Thelypteris ovata, Thelypteris palustris, Thelypteris parasitica, Thelypteris poiteana, Thelypteris reticulata, Thelypteris rustica, Thelypteris seemannii, Thelypteris sp. b1-007, Thelypteris sp. Janssen 2679, Thelypteris subaurita, Thelypteris taiwanensis, Thelypteris truncata, Thelypteris tylodes, Thelypteris uraiensis, and Thelypteris viridifrons.

Polynucleotides that encode IPD103 polypeptides can also be synthesized de novo from an IPD103 polypeptide sequence. The sequence of the polynucleotide gene can be deduced from an IPD103 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD103 polypeptide sequences that can be used to obtain corresponding nucleotide encoding sequences include, but are not limited to the IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38. Furthermore, synthetic IPD103 polynucleotide sequences of the disclosure can be designed so that they will be expressed in plants.

In some embodiments the nucleic acid molecule encoding an IPD103 polypeptide is a polynucleotide having the sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the IPD103 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an IPD103 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, wherein the IPD103 polypeptide has insecticidal activity.

In some embodiments the nucleic acid molecule encodes an IPD103 polypeptide comprising an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the native amino acid at the corresponding position of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38.

In some embodiments the nucleic acid molecule encodes an IPD103 polypeptide variant comprising any one or more amino acid substitutions of Table 5 or 7.

Also provided are nucleic acid molecules that encode transcription and/or translation products that are subsequently spliced to ultimately produce functional IPD103 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD103 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365, 377 and 6,531,316). Thus, in some embodiments the polynucleotides do not directly encode a full-length IPD103 polypeptide, but rather encode a fragment or fragments of an IPD103 polypeptide. These polynucleotides can be used to express a functional IPD103 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD103 polypeptides are also encompassed by the embodiments. "Fragment" as used herein refers to a portion of the nucleic acid sequence encoding an IPD103 polypeptide. A fragment of a nucleic acid sequence may encode a biologically active portion of an IPD103 polypeptide or it may be a fragment that can be used as a hybridization probe or PCR primer using methods disclosed below. Nucleic acid molecules that are fragments of a nucleic acid sequence encoding an IPD103 polypeptide comprise at least about 150, 180, 210, 240, 270, 300, 330 or 360, contiguous nucleotides or up to the number of nucleotides present in a full-length nucleic acid sequence encoding an IPD103 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD103 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of the full-length IPD103Aa polypeptide (SEQ ID NO: 2). In some embodiments, the insecticidal activity is against a Lepidopteran species. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*: Southern corn rootworm or spotted cucumber beetle; *Diabrotica undecimpunctata* howardi, and the Mexican corn rootworm, *D. virgifera zeae*. In one embodiment, the insecticidal activity is against a *Diabrotica* species.

In some embodiments the IPD103 polypeptide is encoded by a nucleic acid sequence sufficiently homologous to the nucleic acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37. "Sufficiently homologous" is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins encoded by two nucleic acid sequences by taking into account degeneracy, amino acid similarity, reading frame positioning, and the like. In some embodiments the sequence homology is against the full length sequence of the polynucleotide encoding an IPD103 polypeptide or against the full length sequence of an IPD103 polypeptide.

In some embodiments the nucleic acid encodes an IPD103 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. In some embodiments the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two amino acid sequences or of two nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of SEQ ID NO: 1). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

In some embodiments the IPD103 polynucleotide encodes an IPD103 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2.

In some embodiments polynucleotides are provided encoding chimeric polypeptides comprising regions of at least two different IPD103 polypeptides of the disclosure.

In some embodiments polynucleotides are provided encoding chimeric polypeptides comprising regions of at least two different IPD103 polypeptides selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In some embodiments polynucleotides are provided encoding chimeric polypeptides comprising an N-terminal Region of a first IPD103 polypeptide of the disclosure operably fused to a C-terminal Region of a second IPD103 polypeptide of the disclosure.

In some embodiments polynucleotides are provided encoding chimeric polypeptides comprising an N-terminal Region of a first IPD103 polypeptide operably fused to a C-terminal Region of a second IPD103 polypeptide, where the IPD103 polypeptide is selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In some embodiments an IPD103 polynucleotide encodes the IPD103 polypeptide comprising an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

The embodiments also encompass nucleic acid molecules encoding IPD103 polypeptide variants. "Variants" of the IPD103 polypeptide encoding nucleic acid sequences include those sequences that encode the IPD103 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the IPD103 polypeptides disclosed as discussed below.

The present disclosure provides isolated or recombinant polynucleotides that encode any of the IPD103 polypeptides disclosed herein. Those having ordinary skill in the art will readily appreciate that due to the degeneracy of the genetic code, a multitude of nucleotide sequences encoding IPD103 polypeptides of the present disclosure exist.

The skilled artisan will further appreciate that changes can be introduced by mutation of the nucleic acid sequences thereby leading to changes in the amino acid sequence of the encoded IPD103 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known, including those developed by the inventors and their co-workers. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene,* 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology (Eckstein and Lilley, eds.,* Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); *Zoller and Smith,* (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); *Nakamaye and Eckstein,* (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA,* 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US Patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from a bacterial source, including but not limited to a *Pseudomonas* species. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential IPD103 polypeptides from fern or other primitive plants, the fern or other primitive plant cell lysates can be screened with antibodies generated against an IPD103 polypeptides and/or IPD103 polypeptides using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of IPD103 polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to IPD103 polypeptides) with sequence information of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28 and their homologs. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radio-isotopes, a fluorescent compound, an enzyme or an enzyme co-factor. Probes for hybridization can be made by labeling synthetic oligonucleotides based on the known IPD103 polypeptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding an IPD103 polypeptide of the disclosure or a fragment or variant thereof. Methods for the preparation of probes for hybridization are generally known in the art and are disclosed in Sambrook and Russell, (2001), supra, herein incorporated by reference.

For example, an entire nucleic acid sequence, encoding an IPD103 polypeptide, disclosed herein or one or more portions thereof may be used as a probe capable of specifically hybridizing to corresponding nucleic acid sequences encoding IPD103 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length Compositions Compositions comprising at least one IPD103 polypeptide or IPD103 chimeric polypeptide of the disclosure are also embraced.

Antibodies

Antibodies to an IPD103 polypeptide of the embodiments or to variants or fragments thereof are also encompassed. The antibodies of the disclosure include polyclonal and monoclonal antibodies as well as fragments thereof which retain their ability to bind to an IPD103 polypeptide found in the insect gut. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, *A Laboratory Manual*, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD103 polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD103 polypeptide as antigens.

A kit for detecting the presence of an IPD103 polypeptide or detecting the presence of a nucleotide sequence encoding an IPD103 polypeptide in a sample is provided. In one embodiment, the kit provides antibody-based reagents for detecting the presence of an IPD103 polypeptide in a tissue sample. In another embodiment, the kit provides labeled nucleic acid probes useful for detecting the presence of one or more polynucleotides encoding an IPD103 polypeptide. The kit is provided along with appropriate reagents and controls for carrying out a detection method, as well as instructions for use of the kit.

Receptor Identification and Isolation

Receptors to the IPD103 polypeptide of the embodiments or to variants or fragments thereof are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the IPD103 polypeptide using the brush-border membrane vesicles from susceptible insects. In addition to the radioactive labeling method listed in the cited literatures, an IPD103 polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled IPD103 polypeptide can be incubated with blotted membrane of BBMV and labeled IPD103 polypeptide can be identified with the labeled reporters. Identification of protein band(s) that interact with the IPD103 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD103 polypeptide. Receptor function for insecticidal activity by the IPD103 polypeptide can be verified by accomplished by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD103 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an IPD103 polypeptide of the embodiments.

In some embodiments the DNA construct comprises a polynucleotide encoding a chimeric IPD103 polypeptide of the embodiments.

In some embodiments the DNA construct comprises a polynucleotide encoding a fusion protein comprising an IPD103 polypeptide of the embodiments.

In some embodiments the DNA construct comprises a polynucleotide comprising a first coding sequence encoding the N-terminal Region of a first IPD103 polypeptide of the disclosure and a second coding sequence encoding the C-terminal Region of a second IPD103 polypeptide of the disclosure.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA ed. Cech* (*Liss*, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea* maize usage table can be also found at kazusa.or.jp//cgi-bin/show.cgi?species=4577, which can be accessed using the www prefix.

A *Glycine max* usage table can be found at kazusa.or.jp//cgi-bin/show.cgi?species=3847&aa=1&style=N, which can be accessed using the www prefix.

In some embodiments the recombinant nucleic acid molecule encoding an IPD103 polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate cotranslational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger cotranslational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. *Plant Cell* 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research*, 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase Oryza sativa-Superoxide dismutase Oryza sativa-soluble starch synthase Oryza sativa-NADP-dependent Malic acid enzyme Oryza sativa-Phospho-2-dehydro-3-deoxyheptonate Aldolase 2 Oryza sativa-L-Ascorbate peroxidase 5 Oryza sativa-Phosphoglucan water dikinase, Zea Mays ssRUBISCO, Zea Mays-beta-glucosidase, Zea Mays-Malate dehydrogenase, Zea Mays Thioredoxin M-type US Patent Application Publication 2012/0304336).

The IPD103 polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize ln 2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced an IPD103 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7): 792-803; Hansen, et al., (1997) *Mol. Gen Genet.* 254(3): 337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5): 773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20): 9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al, (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al, (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a 3-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed roIC and rolD root-inducing genes of *Agrobacterium rhizogenes* (see, Plant Science (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptll (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end 1 and end2 genes are disclosed; herein incorporated by reference. In dicots, seed specific promoters include but are not limited to seed coat promoter from *Arabidopsis*, pBAN; and the early seed promoters from *Arabidopsis* p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al, (1986) *Science* 233:478-481 and U.S. patent application Ser. Nos. 10/004,357 and 10/427,692); phosphinothricin (DeBlock, et al, (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, *University of Heidelberg*; Reines, et aL, (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104;

Bonin, (1993) Ph.D. Thesis, *University of Heidelberg;* Gossen, et aL, (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Bio/technology* 6:923-926) and Lec1 transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al, (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the IPD103 polynucleotide or variants and fragments thereof directly into the plant or the introduction of the IPD103 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107: 775-784, all of which are herein incorporated by reference. Alternatively, the IPD103 polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one can identify and proliferate the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired IPD103 polypeptide. It is also recognized that such a viral polyprotein, comprising at least a portion of the amino acid sequence of an IPD103 of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931; herein incorporated by reference.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea*

*americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus* caryophyllus), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe×dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD103 polypeptide.

Methods to Introduce Genome Editing Technologies into Plants

In some embodiments, the disclosed IPD103 polynucleotide compositions can be introduced into the genome of a plant using genome editing technologies, or previously introduced IPD103 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD103 polynucleotide has previously been introduced into a genome, genome editing technologies may be used to alter or modify the introduced polynucleotide sequence. Site specific modifications that can be introduced into the disclosed IPD103 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IPD103 polynucleotide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments the polynucleotides encoding the IPD103 polypeptide disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens* strain CHA0 and Pf-5 (previously *fluorescens*) (Pechy-Tarr, (2008) *Environmental Microbiology* 10:2368-2386: GenBank Accession No. EU400157); from *Pseudomonas taiwanensis* (Liu, et al., (2010) *J. Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp.

(Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379, 946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; an IPD079 polypeptide of U.S. Ser. No. 62/201,977; an IPD082 polypeptide of U.S. Ser. No. 62/269,482, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin genes and the *B. thuringiensis* cytolytic Cyt1 and Cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Wash. D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus*, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus*, *Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion.

2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876; 6,040,497; 5,804,425; 5,633,435; 5,145,783; 4,971,908; 5,312,910; 5,188,642; 5,094,945; 4,940,835; 5,866,775; 6,225,114; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-52 and Acc1-53 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) *Biochem. J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6/288,306; 6/282,83 and 5/767, 373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtl) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic

Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi1 ps, and various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), Primula Δ6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391, 348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that, confers male fertility to be transcribed.

(A) Introduction of a deacetylase gene under the control of a tapetum-specific promoter and with the application of the chemical N—Ac-PPT (WO 2001/29237).

(B) Introduction of various stamen-specific promoters (WO 1992/13956, WO 1992/13957).

(C) Introduction of the barnase and the barstar gene (Paul, et al., (1992) *Plant Mol. Biol.*
19:611-622).

For additional examples of nuclear male and female sterility systems and genes, see also, U.S. Pat. Nos. 5,859, 341; 6,297,426; 5,478,369; 5,824,524; 5,850,014 and 6,265, 640, all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417, 428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. Nos. 6,177, 275 and 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/0257633).

(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1 996/1 441 4 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.

(A) Altering the level of xylan present in the cell wall of a plant by modulating expression of xylan synthase (U.S. Pat. No. 8,173,866).

In some embodiment the stacked trait may be a trait or event that has received regulatory approval including but not limited to the events with regulatory approval that are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications (isaaa.org/gmapprovaldatabase/default.asp, which can be accessed using the www prefix).

Gene Silencing

In some embodiments the stacked trait may be in the form of silencing of one or more polynucleotides of interest resulting in suppression of one or more target pest polypeptides. In some embodiments the silencing is achieved through the use of a suppression DNA construct.

In some embodiments one or more polynucleotide encoding the polypeptides of the IPD103 polypeptide or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment. The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) Plant J. 16:651-659 and Gura, (2000) Nature 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA (PCT Publication WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication WO 1999/61632).

The use of poly-T and poly-A sequences to generate the stem in the stem-loop structure has also been described (PCT Publication WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 2002/00904.

RNA interference refers to the process of sequence-specific post-transcriptional gene silencing in animals mediated by short interfering RNAs (siRNAs) (Fire, et al., (1998) Nature 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) Trends Genet. 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein, et al., (2001) Nature 409:363). Short interfering RNAs derived from dicer activity are typically about 21 to about 23 nucleotides in length and comprise about 19 base pair duplexes (Elbashir, et al., (2001) Genes Dev. 15:188). Dicer has also been implicated in the excision of 21- and 22-nucleotide small temporal RNAs (stRNAs) from precursor RNA of conserved structure that are implicated in translational control (Hutvagner, et al., (2001) Science 293:834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) Genes Dev. 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) Science 297:1818-1819; Volpe, et al., (2002) Science 297:1833-1837; Jenuwein, (2002) Science 297:2215-2218 and Hall, et al., (2002) Science 297:2232-2237). As such, miRNA molecules of the disclosure can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US Patent Application Publication 2009/0188008.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the disclosure have an improved loading of RNAi into the phloem of the plant than would be observed with the expression of the silencing element construct alone and, thus provide better control of phloem feeding insects by an RNAi approach. In specific embodiments, the plants, plant parts and plant cells of the disclosure can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell or phloem when compared to an appropriate control. In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and *Lygus* can be found in US Patent Application Publication 2011/0301223 and US Patent Application Publication 2009/0192117.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+−ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR and PATS. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the IPD103 polypeptide and desirably provide for improved protection of the pesticide from environmental degradation and inactivation.

Alternatively, the IPD103 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IPD103 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants, or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient or an agro-chemical composition that contains at least one of the IPD103 polypeptide produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, lndoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2, 2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, 1provalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, loxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, lodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl) methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-Amethyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rosslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermüller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata* howardi Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); Sitodiplosis mosellana Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schaffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug);

*Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, Calocoris *norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); Nysius ericae Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean platapsid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743, 477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant IPD103 polypeptide or IPD103 chimeric polypeptide of the disclosure. In some embodiments methods are provided for killing an insect pest, comprising contacting the insect pest with an insecticidally-effective amount of a recombinant pesticidal protein of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or a variant thereof.

In some embodiments methods are provided for controlling an insect pest population, comprising contacting the insect pest population, either simultaneously or sequentially, with an insecticidally-effective amount of a recombinant IPD103 polypeptide or IPD103 chimeric polypeptide of the disclosure. In some embodiments methods are provided for controlling an insect pest population, comprising contacting the insect pest population with an insecticidally-effective amount of a recombinant IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or a variant thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of a recombinant IPD103 polypeptide or chimeric IPD103 polypeptide of the disclosure. In some embodiments methods are provided for controlling an insect pest population resistant to a pesticidal protein, comprising contacting the insect pest population with an insecticidally-effective amount of a recombinant IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or a variant thereof.

In some embodiments methods are provided for protecting a plant from an insect pest, comprising expressing in the plant or cell thereof at least one recombinant polynucleotide encoding an IPD103 polypeptide or chimeric IPD103 polypeptide. In some embodiments methods are provided for protecting a plant from an insect pest, comprising expressing in the plant or cell thereof a recombinant polynucleotide encoding IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the IPD103 polypeptides of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management comprises the presentation of at least one of the IPD103 polypeptide insecticidal proteins to insects in the order Lepidoptera and/or Coleoptera.

In some embodiments the methods of controlling Lepidoptera and/or Coleoptera insect infestation in a transgenic plant and promoting insect resistance management comprises the presentation of at least one of the IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof, insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant an IPD103 polypeptide and a Cry protein or other insecticidal protein to insects in the order Lepidoptera and/or Coleoptera having different modes of action.

In some embodiments the methods, of controlling Lepidoptera and/or Coleoptera insect infestation in a transgenic plant and promoting insect resistance management, comprise expression in the transgenic plant an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof and a Cry protein or other insecticidal protein to insects in the order Lepidoptera and/or Coleoptera, where the IPD103 polypeptide and Cry protein have different modes of action.

Also provided are methods of reducing likelihood of emergence of Lepidoptera and/or Coleoptera insect resistance to transgenic plants expressing in the plants insecticidal proteins to control the insect species, comprising expression of an IPD103 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD103 polypeptide and a Cry protein. Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof and a Cry protein or other insecticidally active protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD103 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variant thereof does not compete with binding sites for Cry proteins in such insects.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing an IPD103 polypeptide disclosed herein. Expression of the IPD103 polypeptide results in a reduced ability of a pest to infest or feed on the plant, thus improving plant yield.

Methods of Processing

Further provided are methods of processing a plant, plant part or seed to obtain a food or feed product from a plant, plant part or seed comprising an IPD103 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding an IPD103 polypeptide which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds The following examples are offered by way of illustration and not by way of limitation.

EXPERIMENTALS

Example 1—Identification of Insecticidal Proteins Active Against Corn Earworm, European Corn Borer Fall Armyworm, Soybean Looper, and Velvet Bean Caterpillar from the Fern, *Athyrium niponicum* 'Red Beauty'

An insecticidal protein, IPD103Aa (SEQ ID NO: 2), was identified by protein purification, mass spectroscopy (MS) and PCR cloning from the commercial cultivar *Athyrium niponicum* 'Red Beauty', designated herein as NY15. Insecticidal activity against lepidopteran pests was observed from a protein extract from *Athyrium niponicum*, 'Red Beauty' with an artificial diet-based assay.

NY15 plant material was flash frozen in liquid nitrogen and stored at −80° C. The frozen sample was removed from storage and ground to a fine powder at liquid nitrogen temperatures with a GenoGrinder® 2010 (SPEX SamplePrep®, Metuchen, N.J.). To extract protein, 5 mL Extraction Buffer (50 mM Tris, pH 8.0, 150 mM Potassium Chloride, 2.5 mM EDTA, 1.5% Polyvinylpolypyridone and "Complete, EDTA-free" protease inhibitor cocktail (Roche, Indianapolis, Ind.) was added per gram of fresh weight of NY15. The extracted material was clarified by centrifugation at 20,000 g for 10 min. The remaining cell pellet was re-extracted with ½ the volume of Extraction Buffer, centrifuged and the supernatants combined, filtered and desalted into 20 mM Tris, pH 8, using a Sephadex™ G25 (GE Healthcare, Piscataway, N.J.) column and concentrated on 10 kDa molecular weight cutoff centrifugal concentrators (Sartorius Stedim, Goettingen, Germany).

Bioassays against Soybean Looper (SBL) (*Pseudoplusia includens*), Corn Earworm (CEW) (*Helicoverpa zea*) and European Corn Borer (ECB) (*Ostrinia nubialis*) were conducted using the desalted protein extract overlaid onto agar based Lepidoptera diet (Southland Products Inc., Lake Village, Ark.) in 96-well format. The sample was allowed to dry on top of the diet. A variable number of neonate insects (2-5) were placed individually into each well of the treated plate. The assay was run for four days at 27° C. and then scored for insect mortality, and various stages of stunting of insect growth. The scores were recorded numerically as dead (3), severely stunted (2) (little or no growth but alive and equivalent to a $1^{st}$ instar larvae), stunted (1) (growth to second instar but not equivalent to controls), or normal (0). The crude NY15 extract scored 1 against CEW in each of 4 replicates of the diet-based assay.

For protein purification, extract of NY15 was generated as described above and the supernatant desalted into 20 mM Tris, pH 8, before loading onto a 15 mL Capto™ Q column (GE Healthcare) that was equilibrated in the same buffer. A linear 10 column volume gradient from 0 M to 0.3 M NaCl in 50 mM Tris, pH 8.0 was applied. Eluted 1 mL fractions were assayed against CEW in the bioassay described above. Activity against CEW was detected in fractions eluting at ~7 to 11 mS/cm conductivity. These fractions were pooled and desalted into 20 mM Tris, pH 8.7 and loaded onto a 1 ml Mono Q™ column (GE Healthcare) equilibrated in the same buffer. A linear 20 CV gradient to 40% Elution Buffer (20 mM Tris+0.35 M NaCl, pH 8.7) was applied and 1 mL fractions were collected. Activity against CEW was detected in fractions eluting at ~8.5-13.3 mS/cm$^2$ conductivity. Active fractions were pooled and desalted into 25 mM BisTris, pH 7.2 and loaded on a 4 mL Mono P™ column (GE Healthcare). An isocratic gradient of 100% Polybuffer 74 was applied and 1 mL eluate fractions assayed against CEW. The fractions were submitted directly as well as after concentrating with 10 kDa MWCO units. There were three regions of activity associated with the Mono P™ run, where Mono P™ fractions C2-3, C7-8 and D12 all showed activity against CEW. The first two regions were active at 1× and 4× concentration while fraction D12 showed activity only after 4× concentration. Denaturing electrophoresis of the Mono P™ fractions on LDS polyacrylamide gels indicated that the abundance of a protein band at approximately 20 kDa correlated directly with the three regions of eluted CEW activity.

Protein sequencing and identification were performed by MS analysis after protein digestion. Proteins for MS identification were obtained from running sample on an LDS-PAGE gel stained with Coomassie™ Brilliant Blue G-250 stain. The bands of interest were excised from the gel, de-stained, reduced with dithiothreitol and then alkylated with iodoacetamide. Following overnight digestion with trypsin, the samples were subjected to nano-liquid chromatography/electrospray tandem mass spectrometry (nano-LC/ESI-MS/MS) on a Thermo Q Exactive™ Orbitrap™ mass spectrometer (Thermo Fisher Scientific®, 81 Wyman Street, Waltham, Mass. 02454) interfaced with an Eksigent™ NanoLC™ Ultra 1-D Plus nano-lc system (AB Sciex™, 500 Old Connecticut Path, Framingham, Mass. 01701). Protein identification was done by database searches using Mascot® (Matrix Science, 10 Perrins Lane, London NW3 1QY UK). The searches were conducted against an in-house transcriptome database containing transcripts from the *Athyrium niponicum* 'Red Beauty', NY15 source plant and the public protein database Swiss-Prot using the Mascot search engine (Matrix Science). The amino acid sequences for all three gel bands aligned with the predicted protein from a NY15.

Example 2—Transcriptomic Sequencing of *Athyrium niponicum* 'Red Beauty' and Cloning of IPD103Aa A transcriptome for *Athyrium niponicum* 'Red Beauty' (NY15) was prepared as follows. Total RNA was isolated from frozen tissues with an RNeasy® kit (Qiagen®). Sequencing libraries from the resulting total RNAs were prepared using the TruSeq™ mRNA-Seq kit and protocol from Illumina®, Inc. (San Diego, Calif.). Briefly, mRNAs were isolated via attachment to oligo(dT) beads, fragmented to a mean size of 180 nt, reverse transcribed into cDNA by random hexamer prime, end repaired, 3' A-tailed, and ligated with Illumina® indexed TruSeq™ adapters. Ligated cDNA fragments were PCR amplified using Illumina® TruSeq™ primers and purified PCR products were checked for quality and quantity on the Agilent Bioanalyzer® DNA 7500 chip. Post quality and quantity assessment, 100 ng of the transcript library was normalized by treatment with Duplex Specific Nuclease (DSN) (Evrogen®, Moscow, Russia). Normalization was accomplished by addition of 200 mM Hepes buffer, followed by heat denaturation and five hour anneal at 68° C. Annealed library was treated with 2 µl of DSN enzyme for 25 minutes, purified by Qiagen® MinElute® columns according to manufacturer protocols, and amplified twelve cycles using Illumina® adapter specific primers. Final products were purified with Ampure® XP beads (Beckman Genomics, Danvers, Mass.) and checked for quality and quantity on the Agilent Bioanalyzer® DNA 7500 chip.

Normalized transcript libraries were sequenced according to manufacturer protocols on the Illumina® HiSeq® 2500. Libraries were pooled, hybridized and sequenced three per flowcell lane using onboard clustering methods followed by sequencing to a target depth of sixty million 75 bp paired end reads per normalized library.

Peptide sequences identified for IPD103Aa (SEQ ID NO: 2) by LCMS sequencing (described in Example 2) were searched against protein sequences predicted by open reading frames (ORFs) from the transcriptome assemblies for NY15. The peptides gave a perfect match to a transcript corresponding to IPD103Aa (SEQ ID NO: 2). The coding sequence was used to design the following primers: AGCATATGGCGGACAAAGCAGCAGCAGCAGCTAG AGAAGC (SEQ ID NO: 473) and CGACTCGAGATGGGTGCCGGCAGGCAGGCATAT-TGC (SEQ ID NO: 474) to clone the IPD103Aa polynucleotide sequence (SEQ ID NO: 1). This clone was produced by polymerase chain reaction using the Kappa HiFi™ polymerase (Kapa Bioscience, Wilmington, Mass.) and the cDNA prepared from the total RNA from *Athyrium niponicum* 'Red Beauty' using the SuperScript® II kit (Thermo Fischer Scientific, Waltham, Mass.) as the template. PCR products were gel purified, digested with NdeI and XhoI restriction enzymes (New England Biolabs) and ligated into pET14b (Novagen®) also digested with the same enzymes. Colonies were sequenced to confirm the clone.

Example 3—Purification of IPD103Aa Expressed in *E. coli*

The polynucleotide of SEQ ID NO: 1, encoding IPD103Aa (SEQ ID NO: 2) was subcloned into the pET14b vector (Novagen®) using the NdeI/XhoI restriction sites in frame with the coding sequence for an N-terminal 6xHis tag followed by a thrombin cleavage site (SEQ ID NO: 40). Chemically competent OverExpress® C41(DE3) SOLOs cells (Lucigen®) were transformed with pET plasmid DNA, containing the IPD103Aa gene for recombinant protein expression. The transformed *E. coli* cells were grown overnight at 37° C. with ampicillin selection and then inoculated to a fresh 2xYT medium (1:25) and further grown to an optical density of about 0.8. Protein expression was induced by adding 0.3 mM IPTG and cells were further grown at 16° C. for 16 hours. The *E. coli* expressed proteins were purified by immobilized metal ion chromatography using HisPur™ Cobalt resin (Clonetech, Mountain View, Calif.) according to the manufacturer's protocols. The purified fractions were desalted using PD-10 columns (GE Life Sciences, Pittsburgh, USA) pre-equilibrated with PBS buffer. The eluted protein was used in diet bioassays to evaluate the protein activity on larvae of a diversity of Lepidoptera.

Example 4—Identification of IPD103Aa Homologs and their Purification after Expression in *E. coli*

Gene identities may be determined by conducting BLAST™ (Basic Local Alignment Search Tool; Altschul, et al., (1993) *J. Mol. Biol.* 215:403-410; see also ncbi.nlm.nih-.gov/BLAST/, which can be accessed using the www prefix) searches under default parameters for similarity to sequences. The polynucleotide sequence for IPD103Aa (SEQ ID NO: 1) was analyzed. Gene identities conducted by BLAST™ in a DUPONT PIONEER internal plant transcriptomes database identified multiple homologs of IPD103Aa protein (SEQ ID NO: 2). The IPD103Aa homologs and the organism they were identified from are shown in Table 1.

TABLE 1

| Gene Name | Source | Organism | DNA Seq | AA Seq |
|---|---|---|---|---|
| IPD103Aa | NY15 | *Athyrium niponicum* 'Red Beauty' | SEQ ID NO: 1 | SEQ ID NO: 2 |
| IPD103Ab | NY15 | *Athyrium niponicum* 'Red Beauty' | SEQ ID NO: 3 | SEQ ID NO: 4 |
| IPD103Ac | PS9092AF | *Platycerium wandae* | SEQ ID NO: 5 | SEQ ID NO: 6 |
| IPD103Ad | PS12349 | *Pteris ensiformis* 'Evergemiensis' | SEQ ID NO: 7 | SEQ ID NO: 8 |
| IPD103Ae | PS12349 | *Pteris ensiformis* 'Evergemiensis' | SEQ ID NO: 9 | SEQ ID NO: 10 |
| IPD103Ba | PS9092AF | *Platycerium wandae* | SEQ ID NO: 11 | SEQ ID NO: 12 |
| IPD103Bb | PS9092AF | *Platycerium wandae* | SEQ ID NO: 13 | SEQ ID NO: 14 |
| IPD103Bc | PS12409 | *Athyrium filix-femina* | SEQ ID NO: 15 | SEQ ID NO: 16 |
| IPD103Bd | PS7897CF | *Colysis wrightii* | SEQ ID NO: 17 | SEQ ID NO: 18 |
| IPD103Be | PS8837CF | *Nephrolepis falcata* | SEQ ID NO: 19 | SEQ ID NO: 20 |
| IPD103Bf | PS11699 | *Nephrolepis cordifolia* | SEQ ID NO: 21 | SEQ ID NO: 22 |
| IPD103Bg | PS13327 | *Polystichum tsus-simense* | SEQ ID NO: 23 | SEQ ID NO: 24 |
| IPD103Bh | PS13327 | *Polystichum tsus-simense* | SEQ ID NO: 25 | SEQ ID NO: 26 |
| IPD103Bi | PS12861 | *Thelypteris palustris* | SEQ ID NO: 27 | SEQ ID NO: 28 |
| IPD103Bj | PS12410 | *Athyrium filix-femina* | SEQ ID NO: 29 | SEQ ID NO: 30 |
| IPD103Bk | PS12337 | *Nephrolepis cordifolia* | SEQ ID NO: 31 | SEQ ID NO: 32 |
| IPD103Ca | PS9092AF | *Platycerium wandae* | SEQ ID NO: 33 | SEQ ID NO: 34 |
| IPD103Da | PS9539 | *Tectaria milnei* | SEQ ID NO: 35 | SEQ ID NO: 36 |
| IPD103Db | PS12356 | *Davallia tyermannii* | SEQ ID NO: 37 | SEQ ID NO: 38 | cDNAs were generated from source organisms with identified homologs from the internal database by reverse transcription from total RNA. Homologs were PCR amplified from their respective cDNA's using primers designed to the coding sequences of each homolog (Table 2). The PCR products were digested with NdeI/XhoI (New England Biolabs, Ipswich, Mass.) and ligated into a pET14b (Novagen) plasmid digested by the same enzymes. Cloned PCR products were confirmed by sequencing. The amino acid sequence identity of the IPD103Aa homologs as calculated using the Needleman-Wunsch algorithm, as implemented in the Needle program (EMBOSS tool suite) are shown in Table 3.

TABLE 2

| Gene Name | Forward Primer SEQ ID | Forward Primer | Reverse Primer SEQ ID | Reverse Primer |
|---|---|---|---|---|
| IPD103Aa | SEQ ID NO: 473 | AGCATATGGCGGACAAAGC AGCAGCAGCAGCTAGAGAA GC | SEQ ID NO: 474 | CGACTCGAGATGGGTGCCG GCAGGCAGGCATATTGC |
| IPD103Ab | SEQ ID NO: 475 | AGCATATGGCGGACCAAGC AGCAGCAGCTAGAGAAGC | SEQ ID NO: 474 | CGACTCGAGATGGGTGCCG GCAGGCAGGCATATTGC |
| IPD103Ac | SEQ ID NO: 476 | AACATATGGCCGAACCAGC AGCAGC | SEQ ID NO: 477 | TTCTCGAGTCAAGGGAGCG CCCCA |
| IPD103Ad | SEQ ID NO: 478 | AACATATGGCCGACCAAGG AGCAGCAG | SEQ ID NO: 479 | TTCTCGAGTCAAGGGAGCG CCCC |
| IPD103Ae | SEQ ID NO: 480 | AACATATGGCCGACCAAGC TGCAGC | SEQ ID NO: 479 | TTCTCGAGTCAAGGGAGCG CCCC |
| IPD103Ba | SEQ ID NO: 481 | AACATATGAGAGAGCGAGA GCGAGAGCG | SEQ ID NO: 477 | TTCTCGAGTCAAGGGAGCG CCCCA |
| IPD103Bb | SEQ ID NO: 482 | AACATATGGCCGAACCAGC AGCAGC | SEQ ID NO: 477 | TTCTCGAGTCAAGGGAGCG CCCCA |
| IPD103Bc | SEQ ID NO: 483 | AACATATGGCCGACAAAGC GCCTC | SEQ ID NO: 484 | TTCTCGAGTCAAGGGAGTG CCCCG |
| IPD103Bd | SEQ ID NO: 485 | AACATATGGCCGACCAAGT AGCAGCAG | SEQ ID NO: 479 | TTCTCGAGTCAAGGGAGCG CCCC |
| IPD103Be | SEQ ID NO: 486 | AACATATGGCCGACCCAGC AACAGC | SEQ ID NO: 479 | TTCTCGAGTCAAGGGAGCG CCCC |
| IPD103Bf | SEQ ID NO: 487 | AACATATGCAGAGAGAGAG AGAGAGAGATGG | SEQ ID NO: 479 | TTCTCGAGTCAAGGGAGCG CCCC |
| IPD103Bg | SEQ ID NO: 488 | AACATATGGCCGACAAAGT AGCAGCAGC | SEQ ID NO: 479 | TTCTCGAGTCAAGGGAGCG CCCC |
| IPD103Bh | SEQ ID NO: 488 | AACATATGGCCGACAAAGT AGCAGCAGC | SEQ ID NO: 479 | TTCTCGAGTCAAGGGAGCG CCCC |
| IPD103Bi | SEQ ID NO: 488 | AACATATGGCCGACAAAGT AGCAGCAGC | SEQ ID NO: 489 | TTCTCGAGTCAAGGGAGTG CCCC |
| IPD103Ca | SEQ ID NO: 490 | AACATATGAGAGAGCGAGA GCGAGAGCG | SEQ ID NO: 477 | TTCTCGAGTCAAGGGAGCG CCCCA |
| IPD103Cb | SEQ ID NO: 491 | AACATATGGCCGATGACAA AGTAGCAAG | SEQ ID NO: 492 | TTCTCGAGTCAAGGGAGGG CCC |
| IPD103Da | SEQ ID NO: 493 | AACATATGGCCGATGAGGT AGCTGGTC | SEQ ID NO: 479 | TTCTCGAGTCAAGGGAGCG CCCC |
| IPD103Db | SEQ ID NO: 494 | AACATATGGACGCCGCTGC CG | SEQ ID NO: 495 | TTCTCGAGTCAAGGGAGCG CCC |

Table 3 provides a matrix of percent identity of IPD103 homolog proteins. The Needleman-Wunsch algorithm, as implemented in the Needle program (EMBOSS tool suite), was used to calculate pairwise identities.

TABLE 3

| | IPD103Ab SEQ ID NO: 4 | IPD103Ac SEQ ID NO: 6 | IPD103Ad SEQ ID NO: 8 | IPD103Ae SEQ ID NO: 10 | IPD103Ba SEQ ID NO: 12 | IPD103Bb SEQ ID NO: 14 | IPD103Bc SEQ ID NO: 16 | IPD103Bd SEQ ID NO: 18 | IPD103Be SEQ ID NO: 20 |
|---|---|---|---|---|---|---|---|---|---|
| IPD103Aa SEQ ID NO: 2 | 98.8 | 98.3 | 93.6 | 93.6 | 82.0 | 86.6 | 89.5 | 93.0 | 85.5 |
| IPD103Ab SEQ ID NO: 4 | — | 98.8 | 94.7 | 94.7 | 81.4 | 86.0 | 89.0 | 94.2 | 86.0 |
| IPD103Ac SEQ ID NO: 6 | — | — | 93.6 | 93.6 | 82.5 | 87.2 | 88.4 | 93.0 | 86.0 |
| IPD103Ad SEQ ID NO: 8 | — | — | — | 99.4 | 78.6 | 83.0 | 86.0 | 92.9 | 83.0 |
| IPD103Ae SEQ ID NO: 10 | — | — | — | — | 78.6 | 83.0 | 86.5 | 92.9 | 83.6 |
| IPD103Ba SEQ ID NO: 12 | — | — | — | — | — | 92.9 | 79.7 | 83.5 | 82.5 |
| IPD103Bb SEQ ID NO: 14 | — | — | — | — | — | — | 84.2 | 87.7 | 86.6 |
| IPD103Bc SEQ ID NO: 16 | — | — | — | — | — | — | — | 86.0 | 84.3 |
| IPD103Bd SEQ ID NO: 18 | — | — | — | — | — | — | — | — | 87.7 |
| IPD103Be SEQ ID NO: 20 | — | — | — | — | — | — | — | — | — |
| IPD103Bf SEQ ID NO: 22 | — | — | — | — | — | — | — | — | — |
| IPD103Bg SEQ ID NO: 24 | — | — | — | — | — | — | — | — | — |
| IPD103Bh SEQ ID NO: 26 | — | — | — | — | — | — | — | — | — |
| IPD103Bi SEQ ID NO: 28 | — | — | — | — | — | — | — | — | — |
| IPD103Bj SEQ ID NO: 30 | — | — | — | — | — | — | — | — | — |
| IPD103Bk SEQ ID NO: 32 | — | — | — | — | — | — | — | — | — |
| IPD103Ca SEQ ID NO: 34 | — | — | — | — | — | — | — | — | — |
| IPD103Da SEQ ID NO: 36 | — | — | — | — | — | — | — | — | — |

| | IPD103Bf SEQ ID NO: 22 | IPD103Bg SEQ ID NO: 24 | IPD103Bh SEQ ID NO: 26 | IPD103Bi SEQ ID NO: 28 | IPD103Bj SEQ ID NO: 30 | IPD103Bk SEQ ID NO: 32 | IPD103Ca SEQ ID NO: 34 | IPD103Da SEQ ID NO: 36 | IPD103Db SEQ ID NO: 38 |
|---|---|---|---|---|---|---|---|---|---|
| IPD103Aa SEQ ID NO: 2 | 86.1 | 87.4 | 87.4 | 85.0 | 89.0 | 90.1 | 81.4 | 72.0 | 61.8 |
| IPD103Ab SEQ ID NO: 4 | 86.1 | 86.3 | 86.3 | 84.4 | 88.4 | 90.1 | 80.9 | 72.2 | 62.2 |
| IPD103Ac SEQ ID NO: 6 | 85.0 | 85.7 | 85.7 | 83.8 | 87.8 | 89.0 | 82.0 | 71.6 | 62.2 |
| IPD103Ad SEQ ID NO: 8 | 84.9 | 83.9 | 83.9 | 83.8 | 85.4 | 88.9 | 78.0 | 71.8 | 62.0 |
| IPD103Ae SEQ ID NO: 10 | 84.9 | 83.3 | 83.3 | 83.8 | 86.0 | 88.9 | 78.0 | 71.1 | 62.4 |
| IPD103Ba SEQ ID NO: 12 | 87.9 | 76.2 | 76.2 | 73.9 | 79.1 | 84.6 | 98.9 | 64.1 | 57.9 |
| IPD103Bb SEQ ID NO: 14 | 85.5 | 80.5 | 80.5 | 79.2 | 83.6 | 89.5 | 94.0 | 67.1 | 61.0 |
| IPD103Bc SEQ ID NO: 16 | 81.6 | 92.5 | 92.5 | 82.1 | 99.4 | 85.4 | 79.1 | 71.8 | 59.3 |
| IPD103Bd SEQ ID NO: 18 | 86.6 | 84.5 | 84.5 | 82.1 | 85.4 | 90.6 | 82.4 | 71.1 | 62.6 |
| IPD103Be SEQ ID NO: 20 | 85.6 | 81.1 | 81.1 | 77.6 | 83.7 | 89.5 | 81.4 | 69.9 | 59.9 |
| IPD103Bf SEQ ID NO: 22 | — | 79.7 | 79.7 | 77.3 | 81.0 | 95.5 | 87.4 | 67.4 | 61.7 |
| IPD103Bg SEQ ID NO: 24 | — | — | 99.4 | 80.6 | 93.1 | 83.3 | 75.7 | 71.5 | 58.1 |
| IPD103Bh SEQ ID NO: 26 | — | — | — | 80.6 | 93.1 | 83.3 | 75.7 | 71.5 | 58.1 |
| IPD103Bi SEQ ID NO: 28 | — | — | — | — | 81.5 | 84.8 | 78.6 | 71.3 | 58.7 |
| IPD103Bj SEQ ID NO: 30 | — | — | — | — | — | 84.8 | 78.6 | 71.3 | 58.7 |
| IPD103Bk SEQ ID NO: 32 | — | — | — | — | — | — | 84.1 | 70.5 | 64.5 |

TABLE 3-continued

| | | | | | | | | | |
|---|---|---|---|---|---|---|---|---|---|
| IPD103Ca SEQ ID NO: 34 | — | — | — | — | — | — | — | 63.0 | 57.4 |
| IPD103Da SEQ ID NO: 36 | — | — | — | — | — | — | — | — | 51.2 |

Example 5—Lepidoptera Assays with Purified Tapped Proteins Expressed in *E. coli*

Bioassays against the five pest species, Corn earworm (CEW) (*Helicoverpa zea*), European corn borer (ECB) (*Ostrinia nubialis*), fall armyworm (FAW) (*Spodoptera frugiperda* JE Smith), Soybean looper (SBL) (*Pseudoplusia includens*), and velvet bean caterpillar (VBC) (*Anticarsia gemmatalis* Hübner) were conducted using a dilution series of purified N-6×His-IPD103Aa (SEQ ID NO: 40) or N-6× His IPD103Ab (SEQ ID NO: 507) polypeptides incorporated into an agar-based Lepidoptera diet (Southland Products Inc., Lake Village, Ark.) in a 96-well plate format. Four replicates were used per sample. Two to five neonate insects were placed into each well of the treated plate. After four days of incubation at 27° C. larvae were scored for mortality or severity of stunting. The scores were recorded numerically as dead (3), severely stunted (2) (little or no growth but alive and equivalent to a 1st instar larvae), stunted (1) (growth to second instar but not equivalent to controls), or normal (0). Results from bioassays of a dilution series of N-6×His-tagged IPD103Aa (SEQ ID NO: 40) and N-6×His IPD103Ab (SEQ ID NO: 507) against the Lepidoptera pests are shown in Table 4. Values represent the mean larval inhibition score of 4 replicate assays.

TABLE 4

| | Dose (ppm) | CEW | ECB | FAW | SBL | VBC |
|---|---|---|---|---|---|---|
| NT-6xHis | 1350 | 3 | 2 | 2 | 3 | 3 |
| IPD103Aa | 675 | 2.25 | 2 | 2 | 2 | 2 |
| SEQ ID NO: 40 | 338 | 2 | 2 | 2 | 1.5 | 2 |
| | 169 | 2 | 2 | 2 | 2 | 2 |
| | 84 | 2 | 2 | 0.75 | 2 | 2 |
| | 42 | 2 | 1.5 | 0 | 1 | 1 |
| | 21 | 1.5 | 1.5 | 0 | 0 | 0 |
| | 11 | 0.25 | 1 | 0 | 0 | 0 |
| Buffer Control | 0 | 0 | 0 | 0 | 0 | 0 |
| NT-6xHis | 925 | 2.5 | 2 | 2 | 2 | 3 |
| IPD103Ab SEQ | 463 | 2 | 2 | 2 | 2 | 2.25 |
| ID NO: 507 | 231 | 2 | 2 | 1.25 | 2 | 2 |
| | 116 | 2 | 2 | 1.25 | 2 | 2 |
| | 58 | 2 | 2 | 1 | 2 | 2 |
| | 29 | 1.25 | 2 | 0 | 1 | 0.5 |
| | 14 | 0.75 | 2 | 0 | 0 | 0 |
| | 7 | 0.25 | 2 | 0 | 0 | 0 |
| Buffer Control | 0 | 0 | 0 | 0 | 0 | 0 |

Example 6—IPD103Aa and M20 Truncated IPD103Aa Variants with Multiple Amino Acid Substitutions at R10 and R42

To create variants of IPD103Aa (SEQ ID NO: 2) at amino acid residue R10 and R42, multiple amino acid changes were created by NNK mutagenesis. For mutations at Arg 42, a synthetic DNA (SEQ ID NO: 497) was generated compromising 5 nucleotides upstream of pET14 NdeI site and nucleotides 1-487 of IPD103Aa (SEQ ID NO: 1) where nt 124 and 125 were synthesized as either A, C, G or T and nt 126 was synthesized as either G or T to create a library of amino acid changes at the Arg42 position. The pET14b plasmid with the IPD103Aa gene (SEQ ID NO: 1) inserted in the NdeI/XhoI sites was amplified using the primers IPD103 start rev Gibson (SEQ ID NO: 498) and IPD103—for Gibson (SEQ ID NO: 499) using the Advantage® HF 2 PCR Kit (Clontech Laboratories, Inc. Mountain View, Calif.) to produce a plasmid that contained a 26 and a 30 nucleotide overlap sequence at either end that matched with the synthesized IPD103Aa R42 NNK gene (SEQ ID NO: 497). The IPD103Aa R42 NNK library was generated using the Gibson reaction (New England Biolabs, Ipswich Mass.) to combine the amplified pET14b IPD103Aa vector with the synthetic DNA. Clones were confirmed by DNA sequencing to identify the amino acid substitution at the Arg42 position.

For mutations at the Arg 10 residue, the primers IPD103Aa R10 NNK—for (SEQ ID NO: 500) and IPD103Aa_Rev primer (SEQ ID NO: 474) were used to amplify the IPD103Aa using the Advantage@ HF 2 PCR Kit (Clontech Laboratories, Inc. Mountain View, Calif.). The PCR products were digested with NdeI/XhoI (New England Biolabs, Ipswich Mass.) and ligated into a pET14b (Novagen®) plasmid digested by the same enzymes to create the IPD103Aa R10 NNK library. The same reaction was performed on the IPD103Aa R42W (SEQ ID NO: 422) backbone to create a construct with mutations at R10 with R42W. Clones were confirmed by DNA sequencing to identify the amino acid substitution at the Arg10 position.

Combinations of the mutations at R10 and R42 were created in the IPD103Aa (SEQ ID NO: 1), IPD103Ab (SEQ ID NO: 4) backbone and the R42 mutations were created in the M20 start site IPD103Aa (SEQ ID NO: 417) backbone. To create the IPD103Aa M20 start site sequence (SEQ ID NO: 417) and produce Arg42 mutations in the IPD103Aa M20 start site sequence (SEQ ID NO: 417), the IPD103Aa M(20)DETE start (SEQ ID NO: 501) primer was used with the IPD103Aa_Rev primer (SEQ ID NO: 474) to amplify the IPD103Aa (SEQ ID NO: 2), IPD103Aa R42T (SEQ ID NO: 419), IPD103Aa R42W (SEQ ID NO: 422), and IPD103Aa R42Y (SEQ ID NO: 423) sequences with the Advantage@ HF 2 PCR Kit (Clontech Laboratories, Inc. Mountain View, Calif.). The PCR products were digested with NdeI/XhoI (New England Biolabs, Ipswich Mass.) and ligated into a pET14b (Novagen) plasmid digested by the same enzymes. Clones were confirmed by DNA sequencing. To create the mutations on the IPD103Ab (SEQ ID NO: 3) backbone the primer, IPD103Ab R10 NNK for (SEQ ID NO: 502) and IPD103Aa_Rev primer (SEQ ID NO: 474) were used to amplify the IPD103Aa R42P (SEQ ID NO: 421), IPD103Aa R42T (SEQ ID NO: 419), and IPD103Aa R42L (SEQ ID NO: 420) sequences with the Advantage® HF 2 PCR Kit (Clontech Laboratories, Inc. Mountain View, Calif.). The PCR products were digested with NdeI/XhoI (New England Biolabs, Ipswich Mass.) and ligated into a pET14b (Novagen) plasmid digested by the same enzymes. Clones were confirmed by DNA sequencing. Specific mutations at R10 were combined with the IPD103Aa R42T (SEQ ID NO: 419), R42L (SEQ ID NO: 420), R42W (SEQ ID NO: 422) and R42Y (SEQ ID NO: 423) by amplifying the sequence using either the IPD103Aa R10A—for primer (SEQ ID NO: 503), IPD103Aa R10M—for primer (SEQ ID NO: 504), or the IPD103Aa R10S—for primer (SEQ ID NO: 505) with the IPD103Aa_Rev primer (SEQ ID NO: 474). The PCR products were digested with NdeI/XhoI (New England Biolabs, Ipswich Mass.) and ligated using (NEB) into a pET14b (Novagen) plasmid digested by the same enzymes. Clones were confirmed by DNA sequencing.

Sequence confirmed IPD103Aa R10 and R42 mutants were transformed into chemically competent OverExpress® C41 (DE3) SOLOs E. coli cells (Lucigen) for recombinant protein expression. The transformed E. coli cells were grown overnight at 37° C. with ampicillin selection and then inoculated to a fresh 2×YT medium (1:25) and further grown to an optical density of about 0.8. Protein expression was induced by adding 0.3 mM IPTG and cells were further grown at 16° C. for 16 hours. The E. coli expressed proteins were purified by immobilized metal ion chromatography using HisPur™ Cobalt resin (Thermo Fischer Scientific, Waltham, Mass.) according to the manufacturer's protocols. The purified fractions were desalted using PD-10 desalting columns (GE Life Sciences, Pittsburgh, Pa.) pre-equilibrated with PBS buffer. The eluted protein was run in diet assay to evaluate the insecticidal protein effects on larvae of a diversity of Lepidoptera. Bioassays were run against six pest species: Soybean Looper (SBL) (*Pseudoplusia includens*), Corn Earworm (CEW) (*Helicoverpa zea*), European Corn Borer (ECB) (*Ostrinia nubialis*), Fall Armyworm (FAW) (*Spodoptera frugiperda*), Velvetbean Caterpillar (VBC) (*Anticarsia gemmatalis*) and Black Cutworm (BCW) (*Agrotis ipsilon*) and were conducted using the purified protein at a concentration greater than 22 ug/cm$^2$ overlaid onto an agar-based Lepidoptera diet (Southland Products Inc., Lake Village, Ark.) in a 96-well plate format. Samples were allowed to dry on top of the diet and one to five neonate insects were placed into each well of the treated plate. After three days of incubation at 27° C. larvae were scored for mortality or severity of stunting. The scores were recorded numerically as dead (3), severely stunted (2) (little or no growth but alive and equivalent to a 1st instar larvae), stunted (1) (growth to second instar but not equivalent to controls), or normal (0). Activity is recorded as a "+" if an average score of 1 or greater was recorded at concentrations of purified protein greater than 22 μg/cm$^2$. Bioassay results are summarized in Table 5.

TABLE 5

| Backbone | R10 | R42 | Polypeptide | CEW | ECB | FAW | SBL | VBC | BCW | Additional amino acid change |
|---|---|---|---|---|---|---|---|---|---|---|
| M20 Start | | | SEQ ID NO: 445 | + | + | + | + | + | − | |
| IPD103Aa | | Gly | SEQ ID NO: 446 | − | + | + | − | − | nd | H163P |
| IPD103Aa | | Thr | SEQ ID NO: 447 | − | − | − | − | − | nd | A8G |
| IPD103Aa | | Leu | SEQ ID NO: 448 | + | + | − | − | + | nd | |
| IPD103Aa | | Pro | SEQ ID NO: 449 | + | − | − | − | − | nd | |
| IPD103Aa | | Trp | SEQ ID NO: 450 | + | + | − | − | + | nd | |
| IPD103Aa | | Tyr | SEQ ID NO: 451 | + | + | − | + | + | nd | |
| IPD103Aa | Tyr | | SEQ ID NO: 452 | + | + | + | + | + | + | K123E |
| IPD103Aa | Thr | | SEQ ID NO: 453 | + | + | + | + | + | − | |
| IPD103Aa | Ala | | SEQ ID NO: 454 | + | + | + | + | + | + | |
| IPD103Aa | Met | | SEQ ID NO: 455 | + | + | + | + | + | − | |
| IPD103Aa | Ser | | SEQ ID NO: 456 | + | + | + | + | + | − | |
| M20 start | | Thr | SEQ ID NO: 457 | + | + | + | + | + | nd | |
| M20 start | | Trp | SEQ ID NO: 458 | + | + | + | + | + | nd | |
| M20 start | | Tyr | SEQ ID NO: 459 | + | + | + | + | + | nd | |
| IPD103Ab | Cys | Pro | SEQ ID NO: 460 | + | + | + | + | + | nd | |
| IPD103Ab | Val | Pro | SEQ ID NO: 461 | + | + | − | + | + | nd | |
| IPD103Ab | Asp | Thr | SEQ ID NO: 462 | + | + | − | + | + | nd | |
| IPD103Ab | Gln | Leu | SEQ ID NO: 463 | + | + | + | + | + | nd | |
| IPD103Aa | Gly | Trp | SEQ ID NO: 464 | + | + | + | + | + | nd | |
| IPD103Aa | Ala | Thr | SEQ ID NO: 465 | + | + | + | + | + | nd | |
| IPD103Aa | Met | Thr | SEQ ID NO: 466 | + | + | + | + | + | nd | |
| IPD103Aa | Gly | Leu | SEQ ID NO: 467 | + | + | + | + | + | nd | |
| IPD103Aa | Ser | Leu | SEQ ID NO: 468 | + | + | + | + | + | nd | |
| IPD103Aa | Ala | Trp | SEQ ID NO: 469 | + | + | + | + | + | nd | |
| IPD103Aa | Met | Trp | SEQ ID NO: 470 | + | + | + | + | + | nd | |
| IPD103Aa | Met | Tyr | SEQ ID NO: 471 | + | + | + | + | + | nd | |
| IPD103Aa | Ala | Tyr | SEQ ID NO: 472 | + | + | + | + | + | nd | | nd—not determined

Example 7—Purification and Bioassay of IPD103 Homologs Expressed in *E. coli*

The genes encoding IPD103 homologs were subcloned into the pET14b vector (Novagen) using the NdeI/XhoI restriction sites in frame with an N-terminal 6×His tag followed by a thrombin cleavage site with the IPD103 homolog native stop codon. Chemically competent OverExpress® C41 (DE3) SOLOs cells (Lucigen) were transformed with pET14b plasmid DNA, containing the IPD103Aa homolog gene for recombinant protein expression. The transformed *E. coli* cells were grown overnight at 37° C. with ampicillin selection and then inoculated to a fresh 2×YT medium (1:100) and further grown to an optical density of about 0.8-1.2. Protein expression was induced by adding 1.0 mM IPTG and cells were further grown at 16° C. for 16 hours. The *E. coli* expressed proteins were purified by immobilized metal ion chromatography (IMAC) using Talon® Cobalt resin (Clonetech, Mountain View, Calif.) according to the manufacturer's protocols. The purified 1.5 mL fractions eluted in 250 mM imidazole were dialyzed into PBS buffer using 6K MWCO Flextubes (IBI, Peosta, Iowa) on a stir plate at 4 C overnight. The dialyzed protein was run in the diet assay to evaluate the insecticidal protein effects on larvae of a selection of Lepidoptera. The activity of a series of homologs of IPD103Aa is summarized in Table 6.

TABLE 6

| Homolog ID | AA Seq | CEW | ECB | FAW | SBL | VBC |
|---|---|---|---|---|---|---|
| IPD103Ab | SEQ ID NO: 4 | + | + | + | + | + |
| IPD103Ac | SEQ ID NO: 6 | + | + | + | + | + |
| IPD103Ad | SEQ ID NO: 8 | + | + | + | + | + |
| IPD103Ae | SEQ ID NO: 10 | + | + | + | + | + |
| IPD103Ba | SEQ ID NO: 12 | + | + | + | + | + |
| IPD103Bb | SEQ ID NO: 14 | + | + | + | − | + |
| IPD103Bc | SEQ ID NO: 16 | + | + | + | − | + |
| IPD103Bd | SEQ ID NO: 18 | + | + | + | + | + |
| IPD103Be | SEQ ID NO: 20 | + | + | + | + | + |
| IPD103Bf | SEQ ID NO: 22 | + | + | + | + | + |
| IPD103Bg | SEQ ID NO: 24 | + | + | + | + | + |
| IPD103Bh | SEQ ID NO: 26 | + | − | + | − | + |
| IPD103Bi | SEQ ID NO: 28 | + | + | + | + | + |
| IPD103Ca | SEQ ID NO: 34 | + | + | + | + | + |
| IPD103Da | SEQ ID NO: 36 | + | + | + | + | + |

Example 8—IPD103Aa Variants with Multiple Amino Acid Substitutions

To create variants of IPD103Aa (SEQ ID NO: 2) with multiple amino acid changes, variant libraries were generated by family shuffling (Chia-Chun J. Chang et al, 1999, *Nature Biotechnology* 17, 793-797) the polynucleotide sequences of SEQ ID NO: 1, SEQ ID NO: 19, and SEQ ID NO: 37, encoding IPD103Aa (SEQ ID NO: 12), IPD103Be (SEQ ID NO: 20), and IPD103 Da (SEQ ID NO: 38). Three libraries were constructed for generating IPD103 variants. In a first library (Libraryl 1), the native polynucleotide sequence of IPD103Aa (SEQ ID NO: 1) and the native polynucleotide sequence of IPD103Be (SEQ ID NO: 19) were used as library parents. In a second library, the native polynucleotide sequence of IPD103Be (SEQ ID NO: 19) and the polynucleotide sequence of SEQ ID NO: 496, encoding the IPD103 Da polypeptide, with codons optimized to increase the similarity to SEQ ID NO: 1 were used as library parents. In a third library, native polynucleotide sequences of IPD103Aa (SEQ ID NO: 1) and IPD103Be (SEQ ID NO: 19) and the codon-optimized polynucleotide sequence of IPD103 Da (SEQ ID NO: 496) were used as library parents. The second and third libraries were picked and screened together (Library123).

After transforming the library variants into *E. coli* cells, the colonies were picked and cultured in 24-well plates for protein expression. Cell lysates were generated by B-PER® Protein Extraction Reagent (Thermo Scientific, Rockford, Ill.) and screened for CEW and/or FAW insecticidal activity. The active variants were sequenced and the amino acid substitutions were identified. From library 11, 460 variants were screened and 110 active unique variants were sequence identified. From library 123, 552 variants were screened and 78 active unique variants were sequence identified.

The percent identity of the variant proteins compared to IPD103Aa (SEQ ID NO: 2), variant designation, nucleotide sequences, and amino acid sequences of the resulting active IPD103Aa polypeptide variants are summarized in Table 7. Table 8 summarizes the % identity of the active variants compared to IPD103Aa (SEQ ID NO: 2), the number of variants with each % identity, and the variant identification.

TABLE 7

| % Identity to IPD103Aa (SEQ ID NO: 2) | Variant | Polynucleotide | Polypeptide |
|---|---|---|---|
| 92 | IPD103-11Reary-01 | SEQ ID NO: 41 | SEQ ID NO: 229 |
| 90 | IPD103-11Reary-04 | SEQ ID NO: 42 | SEQ ID NO: 230 |
| 92 | IPD103-11Reary-05 | SEQ ID NO: 43 | SEQ ID NO: 231 |
| 92 | IPD103-11Reary-06 | SEQ ID NO: 44 | SEQ ID NO: 232 |
| 89 | IPD103-11Reary-08 | SEQ ID NO: 45 | SEQ ID NO: 233 |
| 94 | IPD103-11Reary-09 | SEQ ID NO: 46 | SEQ ID NO: 234 |
| 92 | IPD103-11Reary-10 | SEQ ID NO: 47 | SEQ ID NO: 235 |
| 91 | IPD103-11Reary-11 | SEQ ID NO: 48 | SEQ ID NO: 236 |
| 94 | IPD103-11Reary-13 | SEQ ID NO: 49 | SEQ ID NO: 237 |
| 98 | IPD103-11Reary-14 | SEQ ID NO: 50 | SEQ ID NO: 238 |
| 90 | IPD103-11Reary-15 | SEQ ID NO: 51 | SEQ ID NO: 239 |
| 95 | IPD103-11Reary-16 | SEQ ID NO: 52 | SEQ ID NO: 240 |
| 93 | IPD103-11Reary-17 | SEQ ID NO: 53 | SEQ ID NO: 241 |
| 92 | IPD103-11Reary-18 | SEQ ID NO: 54 | SEQ ID NO: 242 |
| 89 | IPD103-11Reary-19 | SEQ ID NO: 55 | SEQ ID NO: 243 |
| 90 | IPD103-11Reary-20 | SEQ ID NO: 56 | SEQ ID NO: 244 |
| 91 | IPD103-11Reary-21 | SEQ ID NO: 57 | SEQ ID NO: 245 |
| 94 | IPD103-11Reary-22 | SEQ ID NO: 58 | SEQ ID NO: 246 |
| 91 | IPD103-11Reary-24 | SEQ ID NO: 59 | SEQ ID NO: 247 |
| 98 | IPD103-11Reary-25 | SEQ ID NO: 60 | SEQ ID NO: 248 |
| 88 | IPD103-11Reary-26 | SEQ ID NO: 61 | SEQ ID NO: 249 |
| 95 | IPD103-11Reary-29 | SEQ ID NO: 62 | SEQ ID NO: 250 |
| 89 | IPD103-11Reary-31 | SEQ ID NO: 63 | SEQ ID NO: 251 |
| 90 | IPD103-11Reary-32 | SEQ ID NO: 64 | SEQ ID NO: 252 |
| 94 | IPD103-11Reary-33 | SEQ ID NO: 65 | SEQ ID NO: 253 |
| 95 | IPD103-11Reary-34 | SEQ ID NO: 66 | SEQ ID NO: 254 |
| 92 | IPD103-11Reary-35 | SEQ ID NO: 67 | SEQ ID NO: 255 |
| 92 | IPD103-11Reary-36 | SEQ ID NO: 68 | SEQ ID NO: 256 |
| 96 | IPD103-11Reary-37 | SEQ ID NO: 69 | SEQ ID NO: 257 |
| 87 | IPD103-11Reary-38 | SEQ ID NO: 70 | SEQ ID NO: 258 |
| 88 | IPD103-11Reary-39 | SEQ ID NO: 71 | SEQ ID NO: 259 |
| 92 | IPD103-11Reary-40 | SEQ ID NO: 72 | SEQ ID NO: 260 |
| 86 | IPD103-11Reary-41 | SEQ ID NO: 73 | SEQ ID NO: 261 |
| 92 | IPD103-11Reary-42 | SEQ ID NO: 74 | SEQ ID NO: 262 |
| 94 | IPD103-11Reary-43 | SEQ ID NO: 75 | SEQ ID NO: 263 |
| 91 | IPD103-11Reary-44 | SEQ ID NO: 76 | SEQ ID NO: 264 |
| 94 | IPD103-11Reary-45 | SEQ ID NO: 77 | SEQ ID NO: 265 |
| 89 | IPD103-11Reary-46 | SEQ ID NO: 78 | SEQ ID NO: 266 |
| 89 | IPD103-123Reary-01 | SEQ ID NO: 79 | SEQ ID NO: 267 |
| 89 | IPD103-123Reary-02 | SEQ ID NO: 80 | SEQ ID NO: 268 |
| 94 | IPD103-123Reary-05 | SEQ ID NO: 81 | SEQ ID NO: 269 |
| 88 | IPD103-123Reary-06 | SEQ ID NO: 82 | SEQ ID NO: 270 |
| 92 | IPD103-123Reary-07 | SEQ ID NO: 83 | SEQ ID NO: 271 |
| 76 | IPD103-123Reary-08 | SEQ ID NO: 84 | SEQ ID NO: 272 |
| 82 | IPD103-123Reary-09 | SEQ ID NO: 85 | SEQ ID NO: 273 |
| 89 | IPD103-123Reary-10 | SEQ ID NO: 86 | SEQ ID NO: 274 |
| 90 | IPD103-123Reary-11 | SEQ ID NO: 87 | SEQ ID NO: 275 |
| 93 | IPD103-123Reary-12 | SEQ ID NO: 88 | SEQ ID NO: 276 |
| 87 | IPD103-123Reary-13 | SEQ ID NO: 89 | SEQ ID NO: 277 |
| 89 | IPD103-123Reary-14 | SEQ ID NO: 90 | SEQ ID NO: 278 |
| 84 | IPD103-123Reary-15 | SEQ ID NO: 91 | SEQ ID NO: 279 |
| 90 | IPD103-123Reary-16 | SEQ ID NO: 92 | SEQ ID NO: 280 |
| 81 | IPD103-123Reary-17 | SEQ ID NO: 93 | SEQ ID NO: 281 |
| 88 | IPD103-123Reary-18 | SEQ ID NO: 94 | SEQ ID NO: 282 |
| 81 | IPD103-123Reary-19 | SEQ ID NO: 95 | SEQ ID NO: 283 |
| 78 | IPD103-123Reary-21 | SEQ ID NO: 96 | SEQ ID NO: 284 |
| 85 | IPD103-123Reary-22 | SEQ ID NO: 97 | SEQ ID NO: 285 |
| 77 | IPD103-123Reary-23 | SEQ ID NO: 98 | SEQ ID NO: 286 |
| 75 | IPD103-123Reary-24 | SEQ ID NO: 99 | SEQ ID NO: 287 |
| 82 | IPD103-123Reary-25 | SEQ ID NO: 100 | SEQ ID NO: 288 |
| 92 | IPD103-123Reary-26 | SEQ ID NO: 101 | SEQ ID NO: 289 |
| 79 | IPD103-123Reary-28 | SEQ ID NO: 102 | SEQ ID NO: 290 |
| 90 | IPD103-123Reary-30 | SEQ ID NO: 103 | SEQ ID NO: 291 |
| 91 | IPD103-123Reary-31 | SEQ ID NO: 104 | SEQ ID NO: 292 |
| 84 | IPD103-123Reary-32 | SEQ ID NO: 105 | SEQ ID NO: 293 |
| 93 | IPD103-123Reary-33 | SEQ ID NO: 106 | SEQ ID NO: 294 |
| 85 | IPD103-123Reary-34 | SEQ ID NO: 107 | SEQ ID NO: 295 |
| 87 | IPD103-123Reary-35 | SEQ ID NO: 108 | SEQ ID NO: 296 |
| 88 | IPD103-123Reary-37 | SEQ ID NO: 109 | SEQ ID NO: 297 |
| 89 | IPD103-123Reary-38 | SEQ ID NO: 110 | SEQ ID NO: 298 |
| 75 | IPD103-123Reary-40 | SEQ ID NO: 111 | SEQ ID NO: 299 |
| 87 | IPD103lib11reary-01 | SEQ ID NO: 112 | SEQ ID NO: 300 |
| 89 | IPD103lib11reary-03 | SEQ ID NO: 113 | SEQ ID NO: 301 |
| 95 | IPD103lib11reary-07 | SEQ ID NO: 114 | SEQ ID NO: 302 |

TABLE 7-continued

| % Identity to IPD103Aa (SEQ ID NO: 2) | Variant | Polynucleotide | Polypeptide |
|---|---|---|---|
| 93 | IPD103lib11reary-08 | SEQ ID NO: 115 | SEQ ID NO: 303 |
| 89 | IPD103lib11reary-09 | SEQ ID NO: 116 | SEQ ID NO: 304 |
| 90 | IPD103lib11reary-10 | SEQ ID NO: 117 | SEQ ID NO: 305 |
| 89 | IPD103lib11reary-11 | SEQ ID NO: 118 | SEQ ID NO: 306 |
| 93 | IPD103lib11reary-12 | SEQ ID NO: 119 | SEQ ID NO: 307 |
| 93 | IPD103lib11reary-13 | SEQ ID NO: 120 | SEQ ID NO: 308 |
| 90 | IPD103lib11reary-14 | SEQ ID NO: 121 | SEQ ID NO: 309 |
| 96 | IPD103lib11reary-15 | SEQ ID NO: 122 | SEQ ID NO: 310 |
| 92 | IPD103lib11reary-16 | SEQ ID NO: 123 | SEQ ID NO: 311 |
| 91 | IPD103lib11reary-17 | SEQ ID NO: 124 | SEQ ID NO: 312 |
| 97 | IPD103lib11reary-18 | SEQ ID NO: 125 | SEQ ID NO: 313 |
| 98 | IPD103lib11reary-19 | SEQ ID NO: 126 | SEQ ID NO: 314 |
| 90 | IPD103lib11reary-20 | SEQ ID NO: 127 | SEQ ID NO: 315 |
| 94 | IPD103lib11reary-21 | SEQ ID NO: 128 | SEQ ID NO: 316 |
| 87 | IPD103lib11reary-22 | SEQ ID NO: 129 | SEQ ID NO: 317 |
| 92 | IPD103lib11reary-23 | SEQ ID NO: 130 | SEQ ID NO: 318 |
| 92 | IPD103lib11reary-25 | SEQ ID NO: 131 | SEQ ID NO: 319 |
| 92 | IPD103lib11reary-27 | SEQ ID NO: 132 | SEQ ID NO: 320 |
| 90 | IPD103lib11reary-28 | SEQ ID NO: 133 | SEQ ID NO: 321 |
| 91 | IPD103lib11reary-29 | SEQ ID NO: 134 | SEQ ID NO: 322 |
| 89 | IPD103lib11reary-30 | SEQ ID NO: 135 | SEQ ID NO: 323 |
| 92 | IPD103lib11reary-31 | SEQ ID NO: 136 | SEQ ID NO: 324 |
| 91 | IPD103lib11reary-32 | SEQ ID NO: 137 | SEQ ID NO: 325 |
| 89 | IPD103lib11reary-33 | SEQ ID NO: 138 | SEQ ID NO: 326 |
| 93 | IPD103lib11reary-34 | SEQ ID NO: 139 | SEQ ID NO: 327 |
| 92 | IPD103lib11reary-35 | SEQ ID NO: 140 | SEQ ID NO: 328 |
| 88 | IPD103lib11reary-38 | SEQ ID NO: 141 | SEQ ID NO: 329 |
| 94 | IPD103lib11reary-39 | SEQ ID NO: 142 | SEQ ID NO: 330 |
| 96 | IPD103lib11reary-40 | SEQ ID NO: 143 | SEQ ID NO: 331 |
| 98 | IPD103lib11reary-41 | SEQ ID NO: 144 | SEQ ID NO: 332 |
| 91 | IPD103lib11reary-42 | SEQ ID NO: 145 | SEQ ID NO: 333 |
| 86 | IPD103lib11reary-43 | SEQ ID NO: 146 | SEQ ID NO: 334 |
| 95 | IPD103lib11reary-44 | SEQ ID NO: 147 | SEQ ID NO: 335 |
| 91 | IPD103lib11reary-45 | SEQ ID NO: 148 | SEQ ID NO: 336 |
| 89 | IPD103lib11reary-46 | SEQ ID NO: 149 | SEQ ID NO: 337 |
| 88 | IPD103lib11reary-47 | SEQ ID NO: 150 | SEQ ID NO: 338 |
| 89 | IPD103lib11reary-48 | SEQ ID NO: 151 | SEQ ID NO: 339 |
| 90 | IPD103lib11reary-49 | SEQ ID NO: 152 | SEQ ID NO: 340 |
| 95 | IPD103lib11reary-50 | SEQ ID NO: 153 | SEQ ID NO: 341 |
| 91 | IPD103lib11reary-51 | SEQ ID NO: 154 | SEQ ID NO: 342 |
| 92 | IPD103lib11reary-52 | SEQ ID NO: 155 | SEQ ID NO: 343 |
| 91 | IPD103lib11reary-53 | SEQ ID NO: 156 | SEQ ID NO: 344 |
| 89 | IPD103lib11reary-54 | SEQ ID NO: 157 | SEQ ID NO: 345 |
| 96 | IPD103lib11reary-55 | SEQ ID NO: 158 | SEQ ID NO: 346 |
| 92 | IPD103lib11reary-56 | SEQ ID NO: 159 | SEQ ID NO: 347 |
| 93 | IPD103lib11reary-58 | SEQ ID NO: 160 | SEQ ID NO: 348 |
| 92 | IPD103lib11reary-59 | SEQ ID NO: 161 | SEQ ID NO: 349 |
| 90 | IPD103lib11reary-62 | SEQ ID NO: 162 | SEQ ID NO: 350 |
| 91 | IPD103lib11reary-63 | SEQ ID NO: 163 | SEQ ID NO: 351 |
| 91 | IPD103lib11reary-64 | SEQ ID NO: 164 | SEQ ID NO: 352 |
| 95 | IPD103lib11reary-65 | SEQ ID NO: 165 | SEQ ID NO: 353 |
| 96 | IPD103lib11reary-66 | SEQ ID NO: 166 | SEQ ID NO: 354 |
| 94 | IPD103lib11reary-67 | SEQ ID NO: 167 | SEQ ID NO: 355 |
| 93 | IPD103lib11reary-68 | SEQ ID NO: 168 | SEQ ID NO: 356 |
| 95 | IPD103lib11reary-69 | SEQ ID NO: 169 | SEQ ID NO: 357 |
| 93 | IPD103lib11reary-70 | SEQ ID NO: 170 | SEQ ID NO: 358 |
| 96 | IPD103lib11reary-73 | SEQ ID NO: 171 | SEQ ID NO: 359 |
| 89 | IPD103lib11reary-74 | SEQ ID NO: 172 | SEQ ID NO: 360 |
| 89 | IPD103lib11reary-75 | SEQ ID NO: 173 | SEQ ID NO: 361 |
| 88 | IPD103lib11reary-76 | SEQ ID NO: 174 | SEQ ID NO: 362 |
| 88 | IPD103lib11reary-78 | SEQ ID NO: 175 | SEQ ID NO: 363 |
| 96 | IPD103lib11reary-79 | SEQ ID NO: 176 | SEQ ID NO: 364 |
| 91 | IPD103lib11reary-80 | SEQ ID NO: 177 | SEQ ID NO: 365 |
| 91 | IPD103lib11reary-82 | SEQ ID NO: 178 | SEQ ID NO: 366 |
| 85 | IPD103lib11reary-83 | SEQ ID NO: 179 | SEQ ID NO: 367 |
| 93 | IPD103lib11reary-85 | SEQ ID NO: 180 | SEQ ID NO: 368 |
| 89 | IPD103lib11reary-86 | SEQ ID NO: 181 | SEQ ID NO: 369 |
| 94 | IPD103lib11reary-87 | SEQ ID NO: 182 | SEQ ID NO: 370 |
| 96 | IPD103lib11reary-88 | SEQ ID NO: 183 | SEQ ID NO: 371 |
| 78 | IPD103lib123reary-01 | SEQ ID NO: 184 | SEQ ID NO: 372 |
| 94 | IPD103lib123reary-05 | SEQ ID NO: 185 | SEQ ID NO: 373 |
| 85 | IPD103lib123reary-07 | SEQ ID NO: 186 | SEQ ID NO: 374 |
| 82 | IPD103lib123reary-11 | SEQ ID NO: 187 | SEQ ID NO: 375 |
| 75 | IPD103lib123reary-14 | SEQ ID NO: 188 | SEQ ID NO: 376 |
| 87 | IPD103lib123reary-15 | SEQ ID NO: 189 | SEQ ID NO: 377 |
| 81 | IPD103lib123reary-16 | SEQ ID NO: 190 | SEQ ID NO: 378 |
| 76 | IPD103lib123reary-17 | SEQ ID NO: 191 | SEQ ID NO: 379 |
| 88 | IPD103lib123reary-18 | SEQ ID NO: 192 | SEQ ID NO: 380 |
| 80 | IPD103lib123reary-19 | SEQ ID NO: 193 | SEQ ID NO: 381 |
| 84 | IPD103lib123reary-23 | SEQ ID NO: 194 | SEQ ID NO: 382 |
| 90 | IPD103lib123reary-27 | SEQ ID NO: 195 | SEQ ID NO: 383 |
| 86 | IPD103lib123reary-28 | SEQ ID NO: 196 | SEQ ID NO: 384 |
| 96 | IPD103lib123reary-29 | SEQ ID NO: 197 | SEQ ID NO: 385 |
| 83 | IPD103lib123reary-30 | SEQ ID NO: 198 | SEQ ID NO: 386 |
| 86 | IPD103lib123reary-31 | SEQ ID NO: 199 | SEQ ID NO: 387 |
| 76 | IPD103lib123reary-32 | SEQ ID NO: 200 | SEQ ID NO: 388 |
| 74 | IPD103lib123reary-34 | SEQ ID NO: 201 | SEQ ID NO: 389 |
| 82 | IPD103lib123reary-37 | SEQ ID NO: 202 | SEQ ID NO: 390 |
| 79 | IPD103lib123reary-38 | SEQ ID NO: 203 | SEQ ID NO: 391 |
| 75 | IPD103lib123reary-39 | SEQ ID NO: 204 | SEQ ID NO: 392 |
| 97 | IPD103lib123reary-40 | SEQ ID NO: 205 | SEQ ID NO: 393 |
| 76 | IPD103lib123reary-41 | SEQ ID NO: 206 | SEQ ID NO: 394 |
| 76 | IPD103lib123reary-42 | SEQ ID NO: 207 | SEQ ID NO: 395 |
| 96 | IPD103lib123reary-45 | SEQ ID NO: 208 | SEQ ID NO: 396 |
| 76 | IPD103lib123reary-46 | SEQ ID NO: 209 | SEQ ID NO: 397 |
| 78 | IPD103lib123reary-47 | SEQ ID NO: 210 | SEQ ID NO: 398 |
| 91 | IPD103lib123reary-48 | SEQ ID NO: 211 | SEQ ID NO: 399 |
| 92 | IPD103lib123reary-49 | SEQ ID NO: 212 | SEQ ID NO: 400 |
| 73 | IPD103lib123reary-52 | SEQ ID NO: 213 | SEQ ID NO: 401 |
| 81 | IPD103lib123reary-54 | SEQ ID NO: 214 | SEQ ID NO: 402 |
| 85 | IPD103lib123reary-55 | SEQ ID NO: 215 | SEQ ID NO: 403 |
| 76 | IPD103lib123reary-58 | SEQ ID NO: 216 | SEQ ID NO: 404 |
| 87 | IPD103lib123reary-59 | SEQ ID NO: 217 | SEQ ID NO: 405 |
| 73 | IPD103lib123reary-60 | SEQ ID NO: 218 | SEQ ID NO: 406 |
| 81 | IPD103lib123reary-62 | SEQ ID NO: 219 | SEQ ID NO: 407 |
| 74 | IPD103lib123reary-63 | SEQ ID NO: 220 | SEQ ID NO: 408 |
| 88 | IPD103lib123reary-65 | SEQ ID NO: 221 | SEQ ID NO: 409 |
| 76 | IPD103lib123reary-67 | SEQ ID NO: 222 | SEQ ID NO: 410 |
| 90 | IPD103lib123reary-68 | SEQ ID NO: 223 | SEQ ID NO: 411 |
| 75 | IPD103lib123reary-69 | SEQ ID NO: 224 | SEQ ID NO: 412 |
| 73 | IPD103lib123reary-70 | SEQ ID NO: 225 | SEQ ID NO: 413 |
| 90 | IPD103lib123reary-72 | SEQ ID NO: 226 | SEQ ID NO: 414 |
| 73 | IPD103lib123reary-73 | SEQ ID NO: 227 | SEQ ID NO: 415 |
| 74 | IPD103lib123reary-77 | SEQ ID NO: 228 | SEQ ID NO: 416 |

TABLE 8

| % Identity to IPD103Aa (SEQ ID NO: 2) | # of Unique Sequences | Variants |
|---|---|---|
| 98 | 4 | IPD103lib11reary-19, IPD103lib11reary-41, IPD103-11Reary-14, IPD103-11Reary-25 |
| 97 | 2 | IPD103lib123reary-40, IPD103lib11reary-18 |
| 96 | 10 | IPD103lib123reary-29, IPD103lib123reary-45, IPD103lib11reary-15, IPD103lib11reary-40, IPD103lib11reary-55, IPD103lib11reary-66, IPD103lib11reary-73, IPD103lib11reary-79, IPD103lib11reary-88, IPD103-11Reary-37 |
| 95 | 8 | IPD103lib11reary-07, IPD103lib11reary-44, IPD103lib11reary-50, IPD103lib11reary-65, IPD103lib11reary-69, IPD103-11Reary-16, IPD103-11Reary-29, IPD103-11Reary-34 |

TABLE 8-continued

| % Identity to IPD103Aa (SEQ ID NO: 2) | # of Unique Sequences | Variants |
|---|---|---|
| 94 | 12 | IPD103lib123reary-05, IPD103lib11reary-21, IPD103lib11reary-39, IPD103lib11reary-67, IPD103lib11reary-87, IPD103-11Reary-09, IPD103-11Reary-13, IPD103-11Reary-22, IPD103-11Reary-33, IPD103-11Reary-43, IPD103-11Reary-45, IPD103-123Reary-05 |
| 93 | 11 | IPD103lib11reary-08, IPD103lib11reary-12, IPD103lib11reary-13, IPD103lib11reary-34, IPD103lib11reary-58, IPD103lib11reary-68, IPD103lib11reary-70, IPD103lib11reary-85, IPD103-11Reary-17, IPD103-123Reary-12, IPD103-123Reary-33 |
| 92 | 21 | IPD103lib123reary-49, IPD103lib11reary-16, IPD103lib11reary-23, IPD103lib11reary-25, IPD103lib11reary-27, IPD103lib11reary-31, IPD103lib11reary-35, IPD103lib11reary-52, IPD103lib11reary-56, IPD103lib11reary-59, IPD103-11Reary-01, IPD103-11Reary-05, IPD103-11Reary-06, IPD103-11Reary-10, IPD103-11Reary-18, IPD103-11Reary-35, IPD103-11Reary-36, IPD103-11Reary-40, IPD103-11Reary-42, IPD103-123Reary-07, IPD103-123Reary-26 |
| 91 | 17 | IPD103lib123reary-48, IPD103lib11reary-17, IPD103lib11reary-29, IPD103lib11reary-32, IPD103lib11reary-42, IPD103lib11reary-45, IPD103lib11reary-51, IPD103lib11reary-53, IPD103lib11reary-63, IPD103lib11reary-64, IPD103lib11reary-80, IPD103lib11reary-82, IPD103-11Reary-11, IPD103-11Reary-21, IPD103-11Reary-24, IPD103-11Reary-44, IPD103-123Reary-31 |
| 90 | 16 | IPD103lib123reary-27, IPD103lib123reary-68, IPD103lib123reary-72, IPD103lib11reary-10, IPD103lib11reary-14, IPD103lib11reary-20, IPD103lib11reary-28, IPD103lib11reary-49, IPD103lib11reary-62, IPD103-11Reary-04, IPD103-11Reary-15, IPD103-11Reary-20, IPD103-11Reary-32, IPD103-123Reary-11, IPD103-123Reary-16, IPD103-123Reary-30 |
| 89 | 20 | IPD103lib11reary-03, IPD103lib11reary-09, IPD103lib11reary-11, IPD103lib11reary-30, IPD103lib11reary-33, IPD103lib11reary-46, IPD103lib11reary-48, IPD103lib11reary-54, IPD103lib11reary-74, IPD103lib11reary-75, IPD103lib11reary-86, IPD103-11Reary-08, IPD103-11Reary-19, IPD103-11Reary-31, IPD103-11Reary-46, IPD103-123Reary-01, IPD103-123Reary-02, IPD103-123Reary-10, IPD103-123Reary-14, IPD103-123Reary-38 |
| 88 | 11 | IPD103lib123reary-18, IPD103lib123reary-65, IPD103lib11reary-38, IPD103lib11reary-47, IPD103lib11reary-76, IPD103lib11reary-78, IPD103-11Reary-26, IPD103-11Reary-39, IPD103-123Reary-06, IPD103-123Reary-18, IPD103-123Reary-37 |
| 87 | 7 | IPD103lib123reary-15, IPD103lib123reary-59, IPD103lib11reary-01, IPD103lib11reary-22, IPD103-11Reary-38, IPD103-123Reary-13, IPD103-123Reary-35 |
| 86 | 4 | IPD103lib123reary-28, IPD103lib123reary-31, IPD103lib11reary-43, IPD103-11Reary-41 |
| 85 | 5 | IPD103lib123reary-55, IPD103lib123reary-07, IPD103lib11reary-83, IPD103-123Reary-22, IPD103-123Reary-34 |
| 84 | 3 | IPD103lib123reary-23, IPD103-123Reary-15, IPD103-123Reary-32 |
| 83 | 1 | IPD103lib123reary-30 |
| 82 | 4 | IPD103lib123reary-11, IPD103lib123reary-37, IPD103-123Reary-09, IPD103-123Reary-25 |
| 81 | 5 | IPD103lib123reary-16, IPD103lib123reary-54, IPD103lib123reary-62, IPD103-123Reary-17, IPD103-123Reary-19 |
| 80 | 1 | IPD103lib123reary-19 |
| 79 | 2 | IPD103lib123reary-38, IPD103-123Reary-28 |
| 78 | 3 | IPD103lib123reary-47, IPD103lib123reary-01, IPD103-123Reary-21 |
| 77 | 1 | IPD103-123Reary-23 |
| 76 | 8 | IPD103lib123reary-17, IPD103lib123reary-32, IPD103lib123reary-41, IPD103lib123reary-42, IPD103lib123reary-46, IPD103lib123reary-58, IPD103lib123reary-67, IPD103-123Reary-08 |
| 75 | 5 | IPD103lib123reary-14, IPD103lib123reary-39, IPD103lib123reary-69, IPD103-123Reary-24, IPD103-123Reary-40 |
| 74 | 3 | IPD103lib123reary-34, IPD103lib123reary-63, IPD103lib123reary-77 |
| 73 | 4 | IPD103lib123reary-52, IPD103lib123reary-60, IPD103lib123reary-70, IPD103lib123reary-73 |

Example 9—Vector Constructs for Expression of IPD103 Polypeptides in Plants

For testing in maize, expression vectors PHP79658, PHP70659, and PHP7600 were constructed to include a transgene cassette containing one of three different gene designs encoding IPD103Aa (SEQ ID NO: 2), the MMV ENH:MMV ENH:BYDV promoter (U.S. Ser. No. 62/260,819), linked to the PINII terminator (US-2014-0130205).

Example 10—Expression and Insect Bioassay on Transient Leaf Tissues

To confirm activity of IPD103Aa (SEQ ID NO: 2) and IPD103Ab (SEQ ID NO: 4) the corresponding genes were cloned into a transient expression system under control of the viral promoter dMMV or AtUBQ10 promoter (Dey, et. al., (1999) *Plant Mol. Biol.* 40:771-782; PCT Patent Publication WO2011133387; Norris S R et al (1993) *Plant Mol Biol.* 21(5):895-906)). The constructs were infiltrated into leaves. The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, the unifoliate stage of bush bean (common bean, *Phaseolus vulgaris*) or soybean (*Glycine max*), were agro-infiltrated with normalized bacterial cell cultures of test and control strains. Leaf discs were excised from each plantlet and infested with neonates of Soy Bean Looper (SBL) (*Pseudoplusia includens*), Corn Earworm, (CEW) (*Helicoverpa zea*), [FAW], Velvet Bean Caterpillar (VBC) (*Anticarsia gemmatalis*) or European Corn Borer (ECB) (*Ostrinia nubialis*). Leaf discs from a control were generated with *Agrobacterium* containing only empty expression vector. Leaf discs from a non-infiltrated plant were used as a second control. The consumption of green leaf tissue was scored after two (CEW, VBC), three (SBL) or four (ECB) days after infestation and given scores of 0 to 9 as indicated by Table 9. The transiently expressed IPD103Aa (SEQ ID NO: 2) and homologs protected bush bean leaf discs from consumption by the infested insects while total green tissue consumption was observed for the negative control and untreated tissue. Transient protein expression of IPD103Aa (SEQ ID NO: 2) and IPD103Ab (SEQ ID NO: 4) were confirmed by a mass spectrometry-based protein identification method using extracted protein lysates from infiltrated leave tissues (Patterson, (1998) 10(22):1-24, Current Protocol in Molecular Biology published by John Wiley & Son Inc). As shown in Table 10, IPD103Aa (SEQ ID NO: 2) and all the homologs tested resulted in protection of bush bean against leaf feeding damage from a diversity of Lepidoptera. A selection of IPD103 R10 mutants described in Table 5 were also transiently expressed in bush bean and shown to be active against Lepidoptera (Table 11). Larval feeding damage to soybean leaves transiently expressing insecticidal genes under the control of the viral promoter dMMV (Dey, et. al., (1999) *Plant Mol. Biol.* 40:771-782) was assessed using a scale described in Table 9. The effect of expression of IPD103 proteins was compared to non-agro-infiltrated controls and controls expressing DsRed2 fluorescence marker (Clontech, Mountain View, Calif.). Activity of selected IPD103 polypeptides, transiently expressed in bush bean, against leaf feeding damage from a selection of Lepidoptera is shown in Table 10. The average score and standard error (SE) for 6 replicate measurements are shown.

Activity of selected IPD103Aa R10 variants, transiently expressed in bush bean, against leaf feeding damage from a selection of Lepidoptera is shown in Table 11.

Activity of selected IPD103Aa polypeptides, transiently expressed in Soybean, against leaf feeding damage from a selection of Lepidoptera is shown in Table 12 The average leaf feeding score and standard deviation (StdDev) for 12 replicates/treatment is shown.

TABLE 9

| Leaf Feeding Score | % Consumed |
|---|---|
| 1 | 86-100 |
| 2 | 71-85 |
| 3 | 61-70 |
| 4 | 51-60 |
| 5 | 36-50 |
| 6 | 11-35 |
| 7 | 11-36 |
| 8 | 1-3 |
| 9 | 0 |

TABLE 10

| Gene | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|
| IPD103Aa SEQ ID NO: 2 | CEW | 7.7 | 0.3 | ECB | 5.2 | 1.1 | FAW | 4.7 | 0.4 |
| IPD103Ac SEQ ID NO: 6 | | 7.5 | 0.3 | | 6.7 | 0.7 | | 4.8 | 0.7 |
| IPD103Ad SEQ ID NO: 8 | | 8.2 | 0.3 | | 3.2 | 1.2 | | 4.5 | 0.3 |
| IPD103Ae SEQ ID NO: 10 | | 7.3 | 0.3 | | 2.0 | 0.7 | | 3.8 | 0.7 |
| IPD103Ba SEQ ID NO: 12 | | 6.0 | 0.4 | | 1.8 | 0.5 | | 3.2 | 0.2 |
| IPD103Bb SEQ ID NO: 14 | | 6.3 | 0.4 | | 5.8 | 0.2 | | 3.7 | 0.2 |
| IPD103Bc SEQ ID NO: 16 | | 7.0 | 0.6 | | 3.2 | 1.4 | | 3.7 | 0.2 |
| IPD103Bd SEQ ID NO: 18 | | 7.7 | 0.3 | | 7.5 | 0.3 | | 5.7 | 0.3 |
| IPD103Be SEQ ID NO: 20 | | 7.7 | 0.3 | | 5.8 | 0.8 | | 5.5 | 0.4 |
| IPD103Bf SEQ ID NO: 22 | | 7.3 | 0.6 | | 6.2 | 0.7 | | 4.3 | 0.6 |
| IPD103Bg SEQ ID NO: 24 | | 8.0 | 0.4 | | 4.2 | 1.2 | | 4.2 | 0.6 |
| IPD103Bh SEQ ID NO: 26 | | 8.0 | 0.4 | | 6.5 | 1.2 | | 6.0 | 0.8 |
| IPD103Ca SEQ ID NO: 34 | | 6.0 | 0.8 | | 3.8 | 1.5 | | 3.0 | 0.4 |
| IPD103Da SEQ ID NO: 36 | | 6.3 | 0.3 | | 3.3 | 1.1 | | 3.5 | 0.3 |
| Negative Control | | 3.7 | 1.1 | | 2.3 | 1.3 | | 2.2 | 0.2 |
| Untreated | | 3.5 | 0.4 | | 1.2 | 0.2 | | 2.8 | 0.3 |
| IPD103Aa SEQ ID NO: 2 | SBL | 6.0 | 0.4 | VBC | 8.0 | 0.0 | | | |
| IPD103Ac SEQ ID NO: 6 | | 5.2 | 0.2 | | 8.0 | 0.0 | | | |
| IPD103Ad SEQ ID NO: 8 | | 6.0 | 0.3 | | 8.2 | 0.2 | | | |
| IPD103Ae SEQ ID NO: 10 | | 6.0 | 0.4 | | 8.2 | 0.2 | | | |
| IPD103Ba SEQ ID NO: 12 | | 4.3 | 0.3 | | 5.7 | 0.7 | | | |
| IPD103Bb SEQ ID NO: 14 | | 3.8 | 0.3 | | 6.7 | 0.4 | | | |
| IPD103Bc SEQ ID NO: 16 | | 5.3 | 0.9 | | 6.5 | 0.2 | | | |
| IPD103Bd SEQ ID NO: 18 | | 6.0 | 0.4 | | 8.0 | 0.0 | | | |
| IPD103Be SEQ ID NO: 20 | | 5.3 | 0.2 | | 7.8 | 0.2 | | | |
| IPD103Bf SEQ ID NO: 22 | | 4.5 | 0.3 | | 7.7 | 0.2 | | | |
| IPD103Bg SEQ ID NO: 24 | | 5.7 | 0.6 | | 7.8 | 0.2 | | | |
| IPD103Bh SEQ ID NO: 26 | | 5.3 | 0.4 | | 8.5 | 0.2 | | | |
| IPD103Ca SEQ ID NO: 34 | | 3.8 | 0.4 | | 4.8 | 1.3 | | | |
| IPD103Da SEQ ID NO: 36 | | 4.5 | 0.5 | | 7.2 | 0.5 | | | |
| Negative Control | | 3.3 | 0.3 | | 1.0 | 0.0 | | | |
| Untreated | | 4.0 | 0.7 | | 2.7 | 1.1 | | | |

TABLE 11

| | SEQ ID | SBL | FAW | CEW | ECB |
|---|---|---|---|---|---|
| IPD103-R10Y | SEQ ID NO: 452 | − | + | + | − |
| IPD103-R10T | SEQ ID NO: 453 | + | + | + | + |
| IPD103-R10A | SEQ ID NO: 454 | + | + | + | + |
| IPD103-R10M | SEQ ID NO: 455 | + | + | + | + |
| IPD103-R10S | SEQ ID NO: 456 | + | + | + | + |
| IPD103lib11reary-54 | SEQ ID NO: 345 | + | + | + | + |
| IPD103Be | SEQ ID NO: 20 | + | + | + | + |
| IPD103Aa | SEQ ID NO: 2 | + | − | + | + |
| Empty | | − | − | − | − |

TABLE 12

| SEQ ID NO | | CEW Avg. Score | CEW Std. DEV | SBL Avg. Score | | VBC Avg. Score | |
|---|---|---|---|---|---|---|---|
| IPD103Aa | SEQ ID NO: 2 | 7.8 | 0.5 | 7.8 | 0.8 | 7.2 | 0.7 |
| IPD103Bc | SEQ ID NO: 16 | 7.8 | 0.7 | 6.3 | 0.7 | 6.0 | 1.3 |
| IPD103Bd | SEQ ID NO: 18 | 8.2 | 0.4 | 7.8 | 0.6 | 6.8 | 1.8 |
| IPD103Be | SEQ ID NO: 20 | 6.8 | 0.6 | 6.7 | 0.8 | 6.4 | 1.2 |
| IPD103Bh | SEQ ID NO: 26 | 8.0 | 0.4 | 7.8 | 0.6 | 6.7 | 2.1 |
| IPD103Da | SEQ ID NO: 36 | 2.0 | 1.6 | 4.4 | 1.6 | 1.3 | 0.7 |
| DsRed control | | 1.0 | 0.0 | 1.3 | 0.5 | 1.0 | 0.0 |
| Neg. control | | 1.0 | 0.0 | 1.7 | 1.5 | 1.2 | 0.4 |

Example 11—Agrobacterium-Mediated Transformation of Maize and Regeneration of Transgenic Plants For Agrobacterium-mediated transformation of maize with IPD103Aa nucleotide sequences the method of Zhao was used (U.S. Pat. No. 5,981,840 and PCT Patent Publication Number WO 1998/32326; the contents of which are hereby incorporated by reference). Briefly, immature embryos were isolated from maize and the embryos contacted with a suspension of Agrobacterium under conditions whereby the bacteria are capable of transferring the PHP79658, PHP70659, and PHP7600 vectors to at least one cell of at least one of the immature embryos (step 1: the infection step). In this step the immature embryos were immersed in an Agrobacterium suspension for the initiation of inoculation. The embryos were co-cultured for a time with the Agrobacterium (step 2: the co-cultivation step). The immature embryos were cultured on solid medium following the infection step. Following this co-cultivation period an optional "resting" step is contemplated. In this resting step, the embryos were incubated in the presence of at least one antibiotic known to inhibit the growth of Agrobacterium without the addition of a selective agent for plant transformation (step 3: resting step). The immature embryos were cultured on solid medium with antibiotic, but without a selecting agent, for elimination of Agrobacterium and for a resting phase for the infected cells. Next, inoculated embryos were cultured on medium containing a selective agent and growing transformed callus is recovered (step 4: the selection step). The immature embryos were cultured on solid medium with a selective agent resulting in the selective growth of transformed cells. The callus was then regenerated into plants (step 5: the regeneration step), and calli grown on selective medium or cultured on solid medium to regenerate the plants.

For detection of the IPD103 proteins in leaf tissue 4 lyophilized leaf punches/sample were pulverized and resuspended in 1004 PBS containing 0.1% Tween 20 (PBST), 1% beta-mercaoptoethanol containing 1 tablet/7 mL complete Mini proteinase inhibitor (Roche 1183615301). The suspension was sonicated for 2 min and then centrifuged at 4° C., 20,000 g for 15 min. To a supernatant aliquot 1/3 volume of 3×NuPAGE® LDS Sample Buffer (Invitrogen™ (CA, USA), 1% B-ME containing 1 tablet/7 mL complete Mini proteinase inhibitor was added. The reaction was heated at 80° C. for 10 min and then centrifuged. A supernatant sample was loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane was incubated in PBST containing 5% skim milk powder for 2 hours before overnight incubation in affinity-purified rabbit anti-IPD103Aa polyclonal antibody in PBST overnight. The membrane was rinsed three times with PBST and then incubated in PBST for 15 min and then two times 5 min before incubating for 2 hours in PBST with goat anti-rabbit-HRP for 3 hours. The detected proteins were visualized using ECL Western Blotting Reagents (GE Healthcare cat # RPN2106) and visualized using a luminescent image analyzer (ImageQuant LAS 4000, GE Healthcare Transgenic maize plants positive for expression of the insecticidal proteins are tested for pesticidal activity using standard bioassays known in the art. Such methods include, for example, whole plant bioassays.

Example 12—Particle Bombardment Transformation and Regeneration of Transgenic Maize Plants Immature maize embryos from greenhouse donor plants are bombarded with a plasmid containing a nucleotide sequence encoding the insecticidal protein. The ears are husked and surface sterilized in 30% Clorox® bleach plus 0.5% Micro detergent for 20 minutes and rinsed two times with sterile water. The immature embryos are excised and placed embryo axis side down (scutellum side up), 25 embryos per plate, on 560Y medium for 4 hours and then aligned within the 2.5 cm target zone in preparation for bombardment. A plasmid vector DNA comprising the nucleotide sequence encoding the insecticidal protein operably linked to a promoter is precipitated onto 1.1 μm (average diameter) tungsten pellets using a $CaCl_2$ precipitation procedure as follows: 100 μl prepared tungsten particles in water; 10 μl (1 pg) DNA in Tris EDTA buffer (1 μg total DNA); 100 μl 2.5 M $CaCl_2$ and 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment. The sample plates are bombarded at level #4 in a particle gun. All samples receive a single shot at 650 PSI, with a total of ten aliquots taken from each tube of prepared particles/DNA Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of an IPD103 polypeptide by assays known in the art, such as, for example, immunoassays and Western blotting.

Transgenic maize plants positive for expression of the insecticidal proteins are tested for pesticidal activity using standard bioassays known in the art. Such methods include, for example, root excision bioassays and whole plant bioassays. See, e.g., US Patent Application Publication Number US 2003/0120054 and International Publication Number WO 2003/018810.

Bombardment medium (560Y) comprises 4.0 g/l N6 basal salts (SIGMA C-1416), 1.0 ml/l Eriksson's Vitamin Mix (1000.times.SIGMA-151 1), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite (added after bringing to volume with D-I $H_2O$) and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000.times.SIGMA-151 1), 0.5 mg/l thiamine HCl, 30.0 g/l sucrose and 2.0 mg/I 2,4-D (brought to volume with D-I $H_2O$ following adjustment to pH 5.8 with KOH); 3.0 g/l Gelrite (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 1 1 1 17-074), 5.0 ml/l MS vitamins stock solution (0.100 g nicotinic acid, 0.02 g/l thiamine HCL, 0.10 g/l pyridoxine HCL, and 0.40 WI glycine brought to volume with polished D-I $H_2O$) (Murashige and Skoog, (1962) Physiol. Plant. 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 1 1 1 17-074), 5.0 m1/1 MS vitamins stock solution (0.100 WI nicotinic acid, 0.02 WI thiamine HCL, 0.10 g/l pyridoxine HCL and 0.40 WI glycine brought to volume with polished D-I $H_2O$), 0.1 WI myoinositol and 40.0 WI sucrose (brought to volume with polished D-I $H_2O$ after adjusting pH to 5.6) and 6 g/l bacto-agar (added after bringing to volume with polished D-I $H_2O$), sterilized and cooled to 60° C.

Example 13—Insect Control Efficacy of Stable Transformed Corn Plants Against a Spectrum of Lepidopteran Insects Leaf discs were excised from transformed maize plants and tested for insecticidal activity of IPD103Aa polypeptides against the European Corn Borer (ECB) (*Ostrinia nubilalis*), Corn Earworm, (CEW) (*Helicoverpa zea*), and Fall Armyworm (*Spodoptera frugiperda*). The constructs, PHP79658, PHP79559 and PHP79660 for the expression of three IPD103Aa gene designs were used to generate transgenic maize events to test for efficacy against feeding damage caused by lepidopteran pests provided by expression of these polypeptides. FIG. 2 demonstrates that strong protection from leaf feeding by a broad spectrum of Lepidoptera pests was conferred by expression of IPD103Aa genes.

Example 14—Greenhouse Efficacy of IPD103 Polypeptide Events

Figure 4:
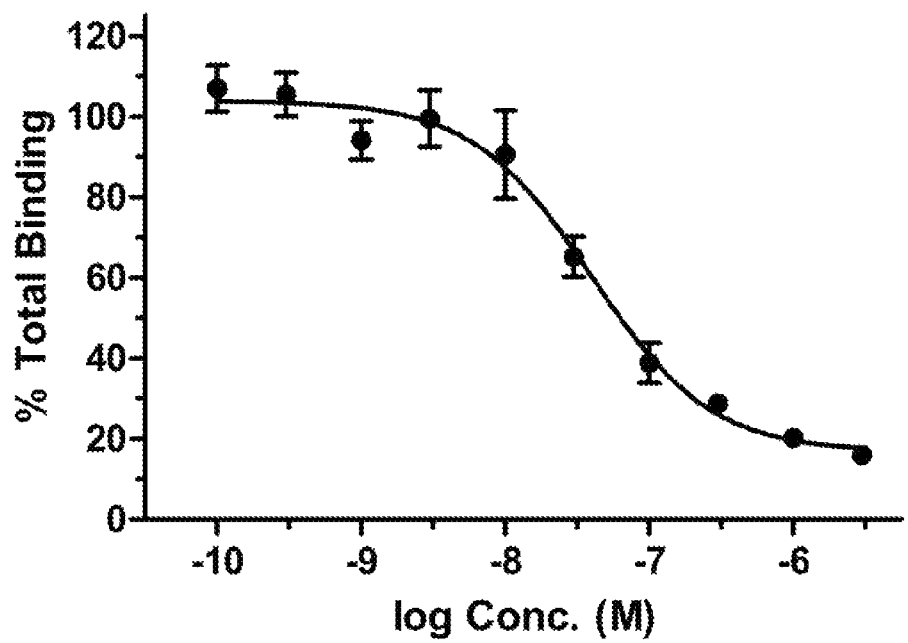

TO greenhouse efficacy results for events generated from PHP79658, PHP79659 and PHP79660 constructs are shown in FIG. 4. Efficacy for events derived from all 3 constructs was observed relative to negative control events (Empty) as measured by corn ear protection from corn earworm (CEW). Ear protection was measured, using a grid, as the number of square centimeters (CEWSCM) of ear feeding damage. FIG. 4 shows that a large proportion of events from PHP79658, PHP79659 and PHP79660 performed better than the negative control and have earworm injury scores of 2 $cm^2$ or less

Example 15—Transformation and Regeneration of Soybean (*Glycine max*)

Transgenic soybean lines are generated by the method of particle gun bombardment (Klein et al., *Nature* (London) 327:70-73 (1987); U.S. Pat. No. 4,945,050) using a BIO-RAD Biolistic PDS1000/He instrument and either plasmid or fragment DNA. The following stock solutions and media are used for transformation and regeneration of soybean plants: Stock solutions:
  Sulfate 100× Stock:
    37.0 g $MgSO_4.7H_2O$, 1.69 g $MnSO_4.H_2O$, 0.86 g $ZnSO_4.7H_2O$, 0.0025 g $CuSO_4.5H_2O$
  Halides 100× Stock:
    30.0 g $CaCl_2.2H_2O$, 0.083 g KI, 0.0025 g $CoCl_2.6H_2O$
  P, B, Mo 100× Stock:
    18.5 g $KH_2PO_4$, 0.62 g $H_3BO_3$, 0.025 g $Na_2MoO_4.2H_2O$
  Fe EDTA 100× Stock:
    3.724 g $Na_2EDTA$, 2.784 g $FeSO_4.7H_2O$
  2,4-D Stock:
    10 mg/mL Vitamin
  B5 vitamins, 1000× Stock:
    100.0 g myo-inositol, 1.0 g nicotinic acid, 1.0 g pyridoxine HCl, 10 g thiamine.HCL.
Media (Per Liter):
  SB199 Solid Medium:
    1 package MS salts (Gibco/BRL—Cat. No. 11117-066), 1 mL B5 vitamins 1000× stock, 30 g Sucrose, 4 ml 2, 4-D (40 mg/L final concentration), pH 7.0, 2 g Gelrite SB1 Solid Medium:
    1 package MS salts (Gibco/BRL—Cat. No. 11117-066), 1 mL B5 vitamins 1000× stock, 31.5 g Glucose, 2 mL 2, 4-D (20 mg/L final concentration), pH 5.7, 8 g TC agar SB196:
    10 mL of each of the above stock solutions I-4, 1 mL B5 Vitamin stock, 0.463 g (NH4)2 SO4, 2.83 g KNO3, 1 mL 2,4 D stock, 1 g asparagine, 10 g Sucrose, pH 5.7 SB71-4:
    Gamborg's B5 salts, 20 g sucrose, 5 g TC agar, pH 5.7. SB103:
    1 pk. Murashige & Skoog salts mixture, 1 mL B5 Vitamin stock, 750 mg MgCl2 hexahydrate, 60 g maltose, 2 g gelrite, pH 5.7.
  SB166:
    SB103 supplemented with 5 g per liter activated charcoal.
Soybean Embryogenic Suspension Culture Initiation:
  Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2, 1-liter bottles of sterile distilled water and those less than 3 mm are placed on individual microscope slides. The small end of the seed is cut and the cotyledons pressed out of the seed coat. Cotyledons are transferred to plates containing SB199 medium (25-30 cotyledons per plate) for 2 weeks, then transferred to SB1 for 2-4 weeks. Plates are wrapped with fiber tape. After this time, secondary embryos are cut and placed into SB196 liquid medium for 7 days.

Culture Conditions:

Soybean embryogenic suspension cultures (cv. 93Y21) were maintained in 50 mL liquid medium SB196 on a rotary shaker, 100-150 rpm, 26° C. on 16:8 h day/night photoperiod at light intensity of 80-100 ρE/m2/s. Cultures are subcultured every 7-14 days by inoculating up to ½ dime size quantity of tissue (clumps bulked together) into 50 mL of fresh liquid SB196.

Preparation of DNA for Bombardment:

In particle gun bombardment procedures it is possible to use purified 1) entire plasmid DNA; or 2) DNA fragments containing only the recombinant DNA expression cassette(s) of interest. For every seventeen bombardment transformations, 85 μL of suspension is prepared containing 1 to 90 picograms (pg) of plasmid DNA per base pair of each DNA plasmid. DNA plasmids or fragments are co-precipitated onto gold particles as follows. The DNAs in suspension are added to 50 μL of a 10-60 mg/mL 0.6 μm gold particle suspension and then combined with 50 μL $CaCl_2$ (2.5 M) and 20 μL spermidine (0.1 M). The mixture is vortexed for 5 sec, spun in a microfuge for 5 sec, and the supernatant removed. The DNA-coated particles are then washed once with 150λ of 100% ethanol, vortexed and spun in a microfuge again, then resuspended in 85 μL of anhydrous ethanol. Five μL of the DNA-coated gold particles are then loaded on each macrocarrier disk.

Tissue Preparation and Bombardment with DNA:

Approximately 100 mg of two-week-old suspension culture is placed in an empty 60 mm×15 mm petri plate and the residual liquid removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Following bombardment, the tissue from each plate is divided between two flasks, placed back into liquid media, and cultured as described above.

Selection of Transformed Embryos and Plant Regeneration:

After bombardment, tissue from each bombarded plate is divided and placed into two flasks of SB196 liquid culture maintenance medium per plate of bombarded tissue. Seven days post bombardment, the liquid medium in each flask is replaced with fresh SB196 culture maintenance medium supplemented with 100 ng/mL selective agent (selection medium). For selection of transformed soybean cells the selective agent used can be a sulfonylurea (SU) compound with the chemical name, 2-chloro-N-((4-methoxy-6 methyl-1,3,5-triazine-2-yl)aminocarbonyl) benzenesulfonamide (common names: DPX-W4189 and Chlorsulfuron). Chlorsulfuron is the active ingredient in the DuPont sulfonylurea herbicide, GLEAN®. The selection medium containing SU is replaced every two weeks for 8 weeks. After the 8 week selection period, islands of green, transformed tissue are observed growing from untransformed, necrotic embryogenic clusters. These putative transgenic events are isolated and kept in SB196 liquid medium with SU at 100 ng/mL for another 5 weeks with media changes every 1-2 weeks to generate new, clonally propagated, transformed embryogenic suspension cultures. Embryos spend a total of around 13 weeks in contact with SU. Suspension cultures are subcultured and maintained as clusters of immature embryos and also regenerated into whole plants by maturation and germination of individual somatic embryos.

Somatic embryos became suitable for germination after four weeks on maturation medium (1 week on SB166 followed by 3 weeks on SB103). They are then removed from the maturation medium and dried in empty petri dishes for up to seven days. The dried embryos are then planted in SB71-4 medium where they are allowed to germinate under the same light and temperature conditions as described above. Germinated embryos are transferred to potting medium and grown to maturity for seed production.

Example 16—Testing Cross-Resistance of Cry1Ab and Cry1F-Selected European Corn Borer To determine if Cry1Ab or Cry1F-resistant insects were cross-resistant to N-6xHis-IPD103Aa (SEQ ID NO: 40), European corn borer (ECB, *Ostrinia nubilalis*) larvae susceptible or resistant to Cry1Ab (Crespo A. et al., Pest Manag Sci 65: 1071-1081, 2009) or Cry1F (Siegfried B. et al., Pest Manag Sci 70: 725-733, 2014), were treated with N-6×His-IPD103Aa (SEQ ID NO: 40). The laboratory Cry1F-selected strain (Cry1F-R) originated from a combination of five field populations collected in 2007 and was selected for resistance using increasing amounts of lyophilized leaf tissue of Cry1F-expressing maize (Alves, A, US 2012/0148497 A1, 2012).

Larval susceptibility of ECB strains resistant to Cry1Ab (Cry1Ab-res) or Cry1F (Cry1F-res) and susceptible strains (SS) to the insecticidal proteins was determined using a diet incorporated bioassay method. Briefly, 25 μL of a sample was mixed with 75 μL of artificial diet per well in a 96-well plate. Each bioassay included eight concentrations of the sample as well as the negative buffer control, four replications for each concentration, and eight individuals for each replicate. One ECB neonate larva (<24 h after hatch) was placed in each assay well. Once infested, the plates were sealed with Mylar and ventilation holes were added to each well using #1 or #2 insect pins. Plates were incubated at 27° C., 50% RH, and a photoperiod of 16:8 hours (L:D). Mortality and larval growth inhibition (defined as inhibition if larva did not enter second instar within 6 days) by each sample were scored after a 6 day exposure. Concentrations resulting in 50% mortality (LC50) or inhibition of 50% of the individuals (1050) were calculated based on Probit analysis. The resistance ratio (RR)=(LC50 of resistant ECB)/(LC50 of susceptible ECB) was >300 fold to Cry1Ab for the Cry1A-res colony and >1000 to Cry1F for the Cry1F-res colony. Table 13 shows that the Cry1A- or Cry1F-resistant ECB were not cross-resistant to N-6×His-IPD103Aa (SEQ ID NO: 40).

TABLE 13

N-6xHis-IPD103Aa (SEQ ID NO: 40) activity against ECB resistant to Cry1A or Cry1F

| ECB colony | LC/IC | ppm | Lower 95% CL | Upper 95% CL | Resistance Ratio |
|---|---|---|---|---|---|
| SS | LC50 | 128.7 | 97.1 | 187.5 | |
| | IC50 | 40.8 | 33.2 | 50 | |
| Cry1A-res | LC50 | >256 (38% mortality) | | | >2 |
| | IC50 | 194.5 | 143.3 | 314.9 | 4.8 |
| Cry1F-res | LC50 | | ~256 | | ~2 |
| | IC50 | 168.8 | 117.7 | 293.2 | 4.1 |

Example 17—Testing Cross-Resistance of Cry1A-Selected Diamondback Moth

A diet overlay assay similar to the method described by Kain et al. (J. Econ. Entomol. 97: 2073-2078, 2004) was used to determine the susceptibility of diamondback moth (DBM, *Plutella xylostella*) to N-6×His-IPD103Aa (SEQ ID NO: 40). Eight concentrations of N-6×His-IPD103Aa (SEQ ID NO: 40) plus a control and three cups (replications) for each concentration were included in each bioassay with the resistant (Cry1A-res) or susceptible DBM colony. An aliquot of 0.2 mL of IPD103Aa solution was applied to and evenly distributed over the diet surface (surface area 7 cm$^2$) of 30-mL plastic cups with 5 ml of artificial diet. Ten DBM neonates were transferred into each cup. Cups were covered with lids and held at 27° C., 50% RH, and a photoperiod of 16:8 (L:D) h and mortality or growth inhibition assessed after 5 days. Concentrations for 50% mortality (LC50) or inhibition of 50% of the individuals (IC50) were calculated based on Probit analysis. The RR was ~100 fold with Cry1A.88 for the Cry1A-res colony. Table 14 shows that the Cry1A resistant DBM were not cross-resistant to N-6×His-IPD103Aa (SEQ ID NO: 40).

TABLE 14

| DBM strain | LC/IC | µg/cm$^2$ | Lower 95% CL | Upper 95% CL | Resistance Ratio |
|---|---|---|---|---|---|
| SS | LC50 | 2.9 | 2.1 | 4.0 | |
| | IC50 | 1.7 | 1.3 | 2.2 | |
| Cry1A-res | LC50 | 4.6 | 3.6 | 6.0 | 1.6 |
| | IC50 | 1.7 | 1.2 | 2.2 | 1 |

Example 18—Site of Action of IPD103Aa

IPD103Aa (SEQ ID NO: 2) was evaluated for stability in the presence of midgut fluid extracts from *Helicoverpa zea* (Corn Earworm) and *Ostrinia nubilalis* (European Corn Borer) to determine if the full length state represents proforms of the proteins and whether midgut proteolysis is required for activation to a toxic state in vivo.

The direct binding of the IPD103Aa (SEQ ID NO: 2) to *Helicoverpa zea* (Corn Earworm) brush border membrane vesicles was tested for target site identification. FIG. 4 shows the average densitometry values for bound Alexa-IPD103Aa (SEQ ID NO: 2) in the presence of different concentrations of unlabeled IPD103Aa (SEQ ID NO: 2) normalized to the amount bound in the absence of unlabeled IPD103Aa (SEQ ID NO: 2). The solid line reflects the best fit of a square logistic equation to the data. The data are best fit by a sigmoidal dose response equation having EC50 values of 38 nM.

Figure 5:
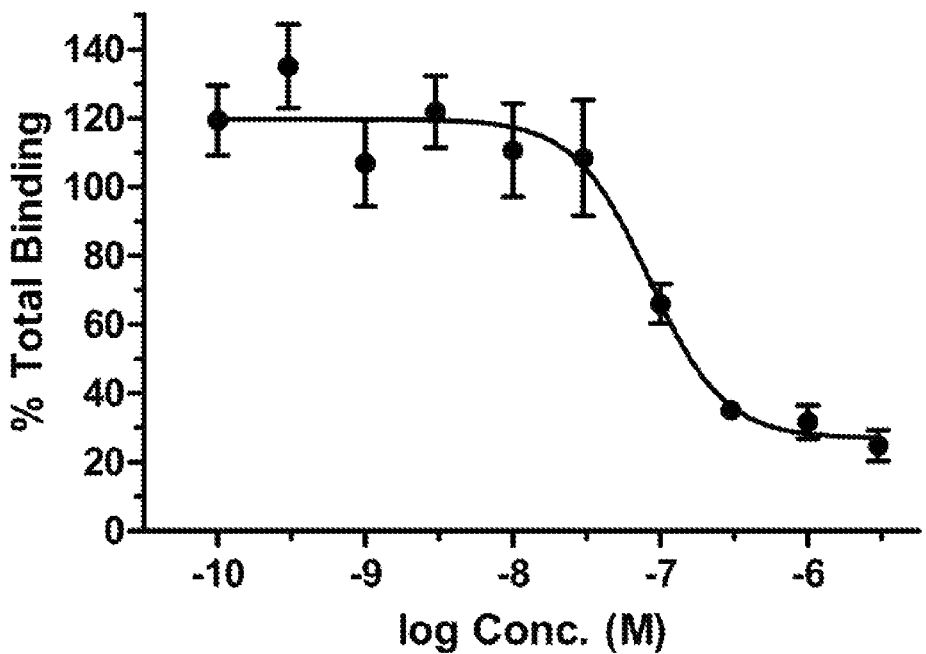

The direct binding of the IPD103Aa (SEQ ID NO: 2) to *Ostrinia nubilalis* (European Corn Borer) brush border membrane vesicles was tested for target site identification. FIG. 5 shows the average densitometry values for bound Alexa-IPD103Aa (SEQ ID NO: 2) in the presence of different concentrations of unlabeled IPD103Aa (SEQ ID NO: 2) normalized to the amount bound in the absence of unlabeled IPD103Aa (SEQ ID NO: 2). The solid line reflects the best fit of a square logistic equation to the data. The data are best fit by a sigmoidal dose response equation having EC50 values of 83 nM.

Example 19—Saturation Mutagenesis of IPD103Aa Variant

Saturation mutagenesis was performed at selected codons of the IPD103 polynucleotide of SEQ ID: 157 encoding the IPD103 variant IPD103lib11reary-54 of SEQ ID: 345 (Example 8—Table 7). Mutants were generated by site directed mutagenesis (QuikChange® Lightning Multi Site Directed Mutagenesis Kit, Agilent Technologies). After transforming the resulting library variants into *E. coli* cells, colonies were sequence identified. Unique clones were picked and cultured in 96-well plates for protein expression. Cell lysates were generated by B-PER® Protein Extraction Reagent from Thermo Scientific (3747 N Meridian Rd, Rockford, Ill. USA 61101) and screened for CEW insecticidal activity. Table 15 summarizes the amino acid substitutions identified at each mutagenized position of IPD103lib11reary-54 (SEQ ID: 345) and amino acid substitutions that retained insecticidal activity.

TABLE 15

| AA | Position | Identified substitutions | Active substitutions |
|---|---|---|---|
| A | 002 | G, V, L, I, P, S, T, C, N, Q, D, E, K, R | G, V, L, I, P, S, T, C, N, Q, E, K, R |
| D | 003 | G, A, V, L, I, W, F, P, S, T, C, E, R | G, A, V, L, I, W, F, P, S, T, C, E, R |
| P | 004 | G, A, L, W, S, Y, Q, D, E, K, R, H | G, A, L, W, S, Y, Q, D, E, K, R, H |
| A | 005 | G, V, L, P, S, C, Q, D, E, K, R | G, V, L, P, S, C, Q, D, E, K, R |
| T | 006 | G, A, V, L, I, P, S, N, Q, D, E, K, R | G, A, V, L, I, P, S, N, Q, D, E, K, R |
| A | 007 | G, V, L, W, F, P, T, C, D, K, R | G, V, L, W, F, P, T, C, D, K, R |
| A | 008 | G, L, W, P, S, T, Y, N, D, E, K, R | G, L, W, P, S, T, Y, N, D, E, K, R |
| R | 009 | G, A, V, L, I, W, F, P, S, T, N, D, E | G, A, V, L, I, W, F, P, S, T, N, D, E |
| E | 010 | G, A, V, L, M, W, S, K, R | G, A, V, L, M, W, S, K, R |
| A | 011 | G, V, W, P, S, T, C, Y, E, K, R, H | G, V, W, P, S, T, C, Y, E, K, R, H |
| E | 012 | G, V, L, W, P, S, T, Y, K, R, H | G, V, L, W, P, S, T, Y, K, R, H |
| E | 013 | G, V, L, I, M, W, F, S, D, K, R | G, V, L, I, M, W, F, S, D, K, R |
| E | 014 | G, A, V, L, F, S, T, C, Y, N, Q, R | G, A, V, L, F, S, T, C, Y, N, Q, R |
| V | 015 | G, A, L, I, S, Q, D, E, K, R | G, A, L, I, S, Q, D, E, K, R |

TABLE 15-continued

| AA | Position | Identified substitutions | Active substitutions |
|---|---|---|---|
| Q | 016 | G, A, V, L, I, W, F, P, S, T, D, R, H | G, A, V, L, I, W, F, P, S, T, D, R, H |
| E | 017 | G, A, V, L, M, S, T, C, D, K, R | G, A, V, L, M, S, T, C, D, K, R |
| T | 018 | G, V, L, I, M, W, P, S, C, Q, D, E, R | G, V, L, I, M, W, P, S, C, Q, D, E, R |
| L | 019 | G, A, W, F, P, S, T, C, Y, N, Q, E, K, R | G, W, F, P, S, T, C, Y, N, Q, E, K, R |
| M | 020 | A, V, L, I, W, F, P, S, T, Q., D, E, K, R, H | S, T |
| D | 021 | G, A, V, L, W, F, S, C, N, Q, K, R, H | G, A, V, C, N, H |
| E | 022 | G, A, V, L, M, W, P, S, Y, D, R, H | G, A, M, P, S, D |
| T | 023 | G, A, V, L, I, M, W, P, S, N, Q, E, K, R, H | V, I, S |
| E | 024 | G, V, L, M, W, P, C, Y, Q, K, R | V, M, W, P, C, Q |
| A | 025 | G, V, I, M, W, C, Y, E, R | G, V, I, M, C, E, R |
| V | 026 | G, A, L, I, M, W, S, T, Q, D, E, K, R, H | Q |
| G | 027 | A, V, L, I, M, W, P, S, C, D, K, R | |
| T | 028 | G, A, V, L, I, M, W, F, C, Q, E, K, R | A, V, I, M, C, Q, E |
| H | 029 | G, A, V, L, M, W, P, S, T, Y, N, Q, D, E, R | V, S |
| L | 030 | G, A, I, W, P, S, T, C, N, Q, D, E, K, R, H | I, P |
| D | 031 | G, A, V, L, M, F, S, T, E, R, H | S |
| F | 032 | G, A, V, L, I, M, W, P, T, N, Q, E, R, H | G, A, V, L, I, M, W, T, N, Q, E, H |
| V | 033 | G, L, M, W, F, P, S, T, C, Q, D, E, R, H | G, L, M, W, P, S, T, C, Q, E, R, H |
| A | 034 | G, V, L, I, M, W, F, S, T, C, Y, Q, E, K, R, H | G, V, L, M, S, T, C, Y, Q, E, K, R, H |
| G | 035 | A, V, L, I, M, P, S, T, N, Q, D, K, R, H | A, M, P, S, T, N, D |
| L | 036 | G, A, M, W, P, S, T, C, Q, D, E, R | A, M |
| E | 037 | G, A, V, L, M, S, N, D, K, R | G, A, V, L, M, S, N, D, K, R |
| V | 038 | G, L, M, W, S, T, Q, E, K, R, H | L, K |
| Q | 039 | G, A, L, P, S, C, Y, N, D, E, R | A, L, C, Y, N, D, E, R |
| P | 040 | G, A, V, I, M, F, S, T, C, Q, D, E, K, R | A |
| R | 041 | G, A, V, L, I, M, W, F, P, S, T, C, N, D, E | A, V, L, I, M, F, P, S, T, N, E |
| K | 042 | G, A, V, L, M, F, P, S, T, C, Y, Q, E, R, H | G, A, V, S, T, Q, E, R |
| V | 043 | G, L, I, M, W, P, S, T, E, K, R | M, T |
| I | 044 | G, A, V, L, M, W, P, S, T, Y, E, K, R | V, M |
| T | 045 | G, A, V, L, I, W, P, S, C, Q, E, K, R | A, S, E |
| V | 046 | G, A, L, F, S, C, Y, Q, E, K, R, H | L, Q, H |
| E | 047 | G, V, L, M, W, F, S, N, K, R | |
| V | 048 | A, L, I, M, W, P, S, D, E, R, H | A, L, I, M |
| D | 049 | G, A, V, L, M, W, F, P, S, Q, R, H | |
| A | 050 | G, V, L, M, W, P, S, E, K, R | G, V, L, M, W, P, S |
| A | 051 | G, V, L, M, W, S, T, C, Q, D, E, K, R | G, V, T, C, Q |
| A | 052 | G, V, L, I, M, P, S, T, C, N, Q, D, R | G, V, L, M, P, S, T, N, Q, D |
| V | 053 | G, L, W, F, S, C, Y, Q, E, K, R, H | L |
| I | 054 | G, A, V, L, W, S, T, C, Y, E, R, H | A, V, L, W, Y |

TABLE 15-continued

| AA | Position | Identified substitutions | Active substitutions |
|---|---|---|---|
| Q | 055 | G, V, L, I, W, P, S, C, Y, E, K, R, H | G, V, L, I, S, C, Y, E, K, H |
| Q | 056 | G, A, V, L, W, P, S, T, N, E, K, R | G, A, L, S, T, N, E, K, R |
| I | 057 | G, A, V, L, M, W, P, S, T, Y, N, D, R | V, L, T |
| R | 058 | G, A, L, M, W, P, S, T, C, Y, Q, D, K | G, A, L, M, W, P, S, T, C, Y, Q, D, K |
| E | 059 | G, A, L, M, P, S, Y, N, D, K, R | G, A, L, M, S, Y, N, D, K, R |
| I | 060 | G, A, V, L, M, W, S, T, N, Q, E, R, H | V, L, M, W, T, N, Q, E |
| F | 061 | G, A, V, L, M, W, S, Q, E, R | A, L, M, S |
| Q | 062 | G, A, V, L, M, F, P, S, T, R | G, A, V, L, M, F, S, T, R |
| T | 063 | G, A, V, L, P, S, Y, N, D, E, K, R, H | G, A, V, L, S, Y, N, D, E, K, R, H |
| M | 064 | G, A, L, I, W, P, S, T, N, Q, E, K, R | A, L, I |
| A | 065 | G, V, L, M, W, F, S, T, Q, D, E, R, H | G, V, L, M, W, F, S, T, Q, D, E, R, H |
| R | 066 | G, A, V, L, I, P, S, T, C, N, D, K, H | G, A, V, I, P, S, T, C, N, D, K, H |
| H | 067 | G, A, V, L, W, F, S, C, N, K, R | G, W, F, N, K |
| F | 068 | G, A, V, L, W, S, T, N, Q, K, R, H | A, V, L, S, T, Q, H |
| N | 069 | G, A, V, L, M, W, F, S, Y, Q, D, E, K, R | G, A, V, L, F, Y, Q, D |
| S | 070 | G, W, F, T, C, Y, N, Q, K, R | G, F, T, C, Y, N, Q, K, R |
| T | 071 | G, A, V, L, I, M, W, F, P, S, Q, E, K, R | A, L, I, S, Q, E, K, R |
| R | 072 | G, A, V, L, M, F, S, T, Y, Q, D, K, H | G, A, V, L, M, F, S, T, Y, Q, D, K, H |
| V | 073 | G, A, L, I, M, F, P, S, T, N, E, R | A, L, I, S, T |
| V | 074 | G, A, L, I, W, P, S, T, N, E, K, R, H | G, L, I, W, P, S, T, E, K, H |
| R | 075 | G, A, V, I, M, W, F, P, S, T, C, N, D, E, K | P |
| D | 076 | G, A, V, L, I, M, W, P, S, Y, N, E, R | G, A, W, P, S, Y, N |
| E | 077 | G, V, L, M, W, F, P, S, C, Y, N, Q, D, K, R, H | V, M, C, Y, N, Q, K, R, H |
| A | 078 | G, L, I, M, F, S, T, C, N, K, R, H | S, C, N |
| I | 079 | G, A, V, L, P, S, T, C, Y, N, D, E, K, R, H | G, V, P, Y, E |
| K | 080 | G, A, V, L, M, W, P, S, T, C, N, D, E, R | A, V, M, S, T, C, R |
| G | 081 | A, V, L, F, S, C, Y, N, D, E, R | A, V, L, S, C, N, D, R |
| I | 082 | G, A, V, L, M, S, Y, N, D, E, K, R | L, M |
| R | 083 | A, V, I, M, W, F, P, T, C, Q, D, K, H | K |
| D | 084 | G, A, V, L, I, M, P, S, C, E, R, H | |
| H | 085 | A, V, L, I, W, F, S, C, Y, N, Q, D, K, R | |
| F | 086 | G, A, V, L, I, P, S, T, C, Y, N, D, K, R | C |
| R | 087 | G, A, V, L, W, P, S, Q, E, K, H | V, L, Q |
| A | 088 | G, V, L, I, M, P, S, T, C, Y, N, Q, D, E, R, H | V, T, C, Y |
| A | 089 | G, V, L, I, M, F, P, S, C, Y, D, K, R, H | S |
| V | 090 | G, A, L, I, M, P, S, D, R | I, M |
| P | 091 | G, V, L, M, W, F, S, T, C, E, K, R, H | |
| T | 092 | G, A, V, L, I, W, S, Y, Q, E, R, H | V, L, S |
| R | 093 | G, A, V, L, M, F, P, S, T, C, D, E, K | P, S |

TABLE 15-continued

| AA | Position | Identified substitutions | Active substitutions |
|---|---|---|---|
| N | 094 | G, A, V, L, M, W, P, T, Y, Q, D, E, R, H | |
| V | 095 | G, A, L, I, W, P, S, T, C, N, Q, D, K, R, H | I, T, C, R |
| V | 096 | G, L, M, W, P, S, T, Y, N, Q, R, H | L |
| V | 097 | G, A, L, W, F, P, T, Y, E, R | A |
| V | 098 | G, A, L, M, W, S, Y, Q, E, K, R | A |
| H | 099 | G, A, V, L, I, M, W, F, T, Y, N, D, E, R | G, A, V, I, T, Y, N, R |
| T | 100 | G, A, V, L, M, W, P, S, C, N, Q, K, R, H | G, A, V, P, S, C, N, Q, H |
| Q | 101 | G, A, V, L, I, S, T, D, E, K, R | L, I, T, D, E, K, R |
| H | 102 | G, A, L, M, P, S, T, N, Q, D, E, R | A, S, N, Q, E, R |
| V | 103 | G, A, L, M, W, F, P, S, T, N, D, E, R | G, A, L, M, W, F, P, S, T, R |
| H | 104 | G, A, L, M, P, S, C, D, K, R | G, A, L, M, S, C, D, K, R |
| T | 105 | G, A, V, L, I, M, F, P, S, C, Y, Q, D, R | A, L, M, S, C, Y, Q |
| L | 106 | I, F, P, S, T, Y, D, R, H | I, F |
| V | 107 | L, I, M, W, P, S, T, Y, D, E, K, R, H | L, I, M, P, S, T, Y, D, E, K, R, H |
| G | 108 | V, L, M, P, S, T, C, Q, D, K | S, Q, D |
| L | 109 | I, M, W, F, P, S, T, Y, N, Q, D, E, K, R | I, M, W, F, P, S, T, Y, N, Q, D, E, K, R |
| E | 110 | G, A, V, L, I, W, F, S, T, Q, K, R | A, V, L, I, S, T, Q, K, R |
| H | 111 | G, A, V, L, W, F, P, S, T, Y, N, Q, D, R | G, A, V, L, W, F, P, S, T, Y, N, Q, D, R |
| T | 112 | G, A, V, L, M, W, P, S, Q, R | G, A, V, L, M, W, P, S, Q, R |
| H | 113 | G, A, V, L, M, W, F, P, S, N, Q, D, R | G, V, L, M, F, S, N, Q, R |
| L | 114 | G, A, V, I, M, W, P, S, N, Q, E, K, R, H | V, I, M, P, Q |
| V | 115 | G, A, L, W, P, S, R, H | G, A, L, W, P, S, R, H |
| L | 116 | G, A, V, M, S, C, Y, Q, R, H | V, M |
| Q | 117 | G, A, V, L, W, P, S, T, E, K, R, H | G, A, V, L, S, T, E, K, R, H |
| T | 118 | G, A, L, W, P, C, Y, Q, E, K, R | A, C |
| G | 119 | A, V, L, I, M, W, F, S, C, Y, N, D, E, R, H | A, V, M, S, N, D, E, H |
| I | 120 | G, A, V, L, M, W, F, S, T, Q, D, E, K, R | G, A, V, L, M, W, F, S, T, Q, E, K, R |
| F | 121 | G, V, L, M, W, P, S, Y, Q, D, E, K, R | G, V, L, M, W, S, Y, Q, E, K |
| K | 122 | G, V, P, S, T, C, Y, N, Q, R | G, P, S, T, C, N, R |
| K | 123 | G, A, V, L, M, W, P, S, T, C, Y, E, R | G, A, W, P, T, Y |
| V | 124 | G, A, W, T, C, N, Q, D, E, R | A, W, T, C, N, Q, R |
| P | 125 | G, A, V, L, W, S, T, Y, Q, E, R | G, A, V, L, W, S, T, Y, Q, E, R |
| V | 126 | G, A, I, F, P, S, T, Y, Q, E | A, I, F, S, T |
| D | 127 | G, A, V, L, M, W, P, S, C, Q, R, H | A, V, L, M, W, S, C, Q, R, H |
| I | 128 | A, V, L, M, W, P, S, Q, D, E, K, R | V, L, M |
| Y | 129 | G, A, V, L, I, M, W, F, P, S, T, D, R, H | |
| V | 130 | G, A, L, M, W, F, S, T, Y, D, E, R | A, L |
| F | 131 | G, V, L, W, S, T, E, R | |
| K | 132 | G, A, V, L, M, P, S, C, Q, E, R, H | G, A, V, L, P, S, C, Q, E, R |

TABLE 15-continued

| AA | Position | Identified substitutions | Active substitutions |
|---|---|---|---|
| S | 133 | G, A, L, M, W, P, T, C, Y, Q, D, K, R | G, L, M, P, T, C, Q, D, K, R |
| G | 134 | A, V, L, M, W, P, C, Y, Q, E, R | |
| V | 135 | G, A, L, M, P, S, T, Q, E, K, R | G, A, L, M, P, S, T, Q, E, K, R |
| F | 136 | G, A, V, I, M, P, S, T, C, Y, N, Q, K, R | I, M, C, Y, R |
| T | 137 | G, A, V, L, W, P, S, E, R | S |
| L | 138 | G, A, V, M, W, P, S, Q, D, K, R | V, M, S, Q |
| L | 139 | G, A, V, W, F, P, S, T, C, Y, Q, E, K, R, H | A, V |
| G | 140 | A, L, M, W, P, T, C, Q, D, R | |
| D | 141 | G, V, L, M, W, S, T, N, R | G, V, M, S, T, N, R |
| G | 142 | A, V, L, P, T, C, E, K, R | A, V |
| G | 143 | A, V, L, W, S, Q, E, R | A, W, S, Q, E |
| F | 144 | G, A, V, L, W, P, S, Q, D, K, R | G, A, V, L, W, P, S, Q, K, R |
| I | 145 | G, A, V, M, W, C, Q, E, R, H | G, A, V, M, W, C, Q, E, R, H |
| N | 146 | G, L, M, W, P, S, T, E, K, R | |
| W | 147 | G, V, M, P, S, C, | E, R |
| A | 148 | G, V, L, I, M, W, P, S, Y, Q, K, R | G, S |
| W | 149 | G, A, V, L, F, S, T, N, E | |
| G | 150 | A, V, L, I, W, S, T, Y, Q, E, K, R | I, Q |
| G | 151 | V, L, M, W, S, D, E, R | S |
| F | 152 | G, A, V, L, M, W, P, S, T, C, Q, D, R, H | W |
| V | 153 | G, A, L, I, M, W, P, S, N, E, K, R | A, L, I, P |
| Q | 154 | G, V, L, W, F, P, S, T, N, D, E, K, R, H | G, V, L, W, F, P, S, T, N, D, E, K, R, H |
| E | 155 | G, V, L, M, F, P, S, N, Q, K, R | G, V, L, M, F, S, N, Q, K, R |
| V | 156 | G, A, L, M, F, P, S, Q, E, K, R | A, L, M, F, S, Q, E, K, R |
| A | 157 | G, V, L, I, M, W, P, S, T, N, Q, E, K, R, H | G, V, L, I, M, W, S, T, N, Q, E, K, R, H |
| G | 158 | A, V, W, P, T, C, E, K, R | A, V, W, P, T, C, E, K, R |
| K | 159 | G, A, V, L, I, W, P, S, T, Y, Q, R, H | G, A, V, L, P, S, T, Y, Q, R, H |
| R | 160 | G, A, V, L, I, M, F, S, T, C, Y, E, K | I, M, Y, K |
| I | 161 | G, A, V, L, M, W, F, P, S, T, Y, Q, D, E, R | A, V, L |
| H | 162 | G, A, L, I, W, F, P, S, T, C, Y, Q, K, R | G, A, L, I, W, F, S, T, C, Y, Q, K, R |
| F | 163 | A, L, S, T, C, Y, D, E | |
| R | 164 | G, V, L, I, M, W, F, P, S, T, Y, N, D | V, L, I, M, S, T, N, D |
| L | 165 | G, V, I, M, W, F, P, S, N, Q, E, K, R | G, V, I, M, W, F, P, S, N, Q, E, K, R |
| P | 166 | G, A, V, L, I, M, W, S, T, C, Y, N, Q, D, E, K, R, H | A, T, C, Q |
| P | 167 | G, A, V, L, M, W, S, T, C, Y, N, D, R, H | A, N, D |
| G | 168 | A, V, L, M, W, P, S, T, Q, R, H | |
| A | 169 | G, V, L, M, W, F, S, T, C, N, Q, R, H | G, S, T, C, Q |

TABLE 15-continued

| AA | Position | Identified substitutions | Active substitutions |
|---|---|---|---|
| L | 170 | A, V, I, M, P, S, T, Y, Q, R, H | A, V, I, M, S, T, Y, Q, R, H |
| P | 171 | G, A, V, M, W, S, T, C, E, R | G, A, V, M, W, S, T, C, E, R |

Example 20 Identification of Amino Acid Positions Affecting the Protein Stability and Function of IPD103

Additional mutagenesis was performed on selected positions within IPD103lib11reary-54 (SEQ ID:157). Protein was purified from the single mutants and screened for activity on CEW. Table 16 summarizes additional amino acid substitutions identified, amino acid substitutions allowing retention of insecticidal activity, and amino acid substitutions resulting in reduced protein yields from *E. coli*.

TABLE 16

| AA | Position | Identified substitutions | Active substitutions | Reduced Expression substitutions |
|---|---|---|---|---|
| A | 002 | F, H, M, W, Y | F, H, M, W, Y | |
| A | 011 | D, F, L, M, N, Q | D, F, L, M, N, Q | |
| T | 018 | A, F, H, K, N, Y | A, H, K, N | |
| M | 020 | C, G, N, Y | | |
| D | 021 | E, I, M, P, T, Y | E, P, T | M |
| G | 027 | E, F, H, N, Q, T, Y | | F |
| D | 031 | I, K, P, Q | | |
| A | 034 | D, N, P | D, N, P | |
| A | 065 | C, I, K, N, P, Y | C, I, N, Y | K, P |
| R | 066 | E, F, M, Q, S, W, Y | E, F, M, S, W, Y | |
| F | 068 | C, D, E, I, M, P, Y | C, I, M | |
| S | 070 | A, D, E, H, I, L, M, P, V | A, D, E, H, L, M, V | I, P |
| N | 094 | C, F, I, K, S | | I, K |
| H | 104 | E, Q, T, W, Y | E, Q, T, W | |
| G | 140 | E, F, H, I, K, N, S, V, Y | S | I, N, V |
| W | 147 | A, D, F, H, I, K, L, N, Q, T, Y | F | D, K |
| W | 149 | C, D, H, I, K, M, P, Q, Y | | C, D, H, K, M, Q |
| Q | 154 | A, C, I, M | A | C, I, M |
| E | 155 | A, C, D, I, T, W | A, C, D, I, T, W | |
| G | 168 | C, D, E, F, I, K, N, Y | F | |

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed is:

1. A recombinant insecticidal polypeptide comprising an amino acid sequence having at least 72% sequence identity to SEQ ID NO: 2, wherein the insecticidal polypeptide is joined to a heterologous signal sequence or a transit sequence.

2. The recombinant insecticidal polypeptide of claim 1, wherein the amino acid sequence has at least 80% sequence identity to SEQ ID NO: 2.

3. A composition comprising at least one recombinant insecticidal polypeptide of claim 1.

4. A recombinant polynucleotide encoding the insecticidal polypeptide of claim 1.

5. The recombinant polynucleotide of claim 4, wherein the polynucleotide has codons optimized for expression in an agriculturally important crop.

6. The recombinant polynucleotide of claim 4, wherein the polynucleotide is a cDNA.

7. A DNA construct comprising the recombinant polynucleotide of claim 4 operably linked to a heterologous regulatory element.

8. A transgenic plant comprising the polynucleotide of claim 4.

9. A transgenic plant comprising the DNA construct of claim 7.

10. A method of inhibiting growth or killing an insect pest or pest population, comprising contacting the insect pest with the insecticidal polypeptide of claim 1.

11. A method of inhibiting growth or killing an insect pest or pest population comprising expressing in a plant the polynucleotide of claim 1.

12. A method for controlling pest infestation comprising providing in the diet of the pest the transgenic plant of claim 9 or a part thereof.

13. A method for improving the yield of a crop comprising growing the transgenic plant of claim 9, wherein the yield of the crop is increased in the presence of an insect pest relative to the crop not comprising said transgenic plant.

14. The method of claim 10, 11, 12 or 13, wherein the insect pest or pest population is resistant to at least one Cry insecticidal protein.

* * * * *